US006913926B2

(12) United States Patent
Prezant et al.

(10) Patent No.: US 6,913,926 B2
(45) Date of Patent: Jul. 5, 2005

(54) METHOD OF REGULATING BIOLOGICAL ACTIVITY OF PITUITARY TUMOR TRANSFORMING GENE (PTTG)1 USING PTTG2

(75) Inventors: Toni Rita Prezant, West Hills, CA (US); Anthony P. Heaney, Los Angeles, CA (US); Shlomo Melmed, Los Angeles, CA (US)

(73) Assignee: Cedars-Sinai Medical Center, Los Angeles, CA (US)

(*) Notice: Subject to any disclaimer, the term of this patent is extended or adjusted under 35 U.S.C. 154(b) by 0 days.

(21) Appl. No.: 09/854,326

(22) Filed: May 11, 2001

(65) Prior Publication Data

US 2003/0186902 A1 Oct. 2, 2003

Related U.S. Application Data

(63) Continuation-in-part of application No. 09/777,422, filed on Feb. 5, 2001, which is a continuation-in-part of application No. 09/730,469, filed on Dec. 4, 2000, which is a continuation-in-part of application No. 09/687,911, filed on Oct. 13, 2000, which is a continuation-in-part of application No. 09/569,956, filed on May 12, 2000, which is a continuation-in-part of application No. 08/894,251, filed as application No. PCT/US97/21463 on Nov. 21, 1997, now Pat. No. 6,455,305.
(60) Provisional application No. 60/031,338, filed on Nov. 21, 1996.

(51) Int. Cl.[7] .................. C12N 15/63; C12N 15/00; A01N 63/00; C07H 21/04
(52) U.S. Cl. .................. 435/455; 435/320.1; 424/93.2; 424/93.21; 536/23.5; 536/24.1
(58) Field of Search ............................. 435/320.1, 455, 435/325; 424/93.2, 93.21; 536/23.5, 24.1; 574/44

(56) References Cited

U.S. PATENT DOCUMENTS

| | | | |
|---|---|---|---|
| 5,474,897 A | 12/1995 | Weiss et al. |
| 5,844,107 A | 12/1998 | Hanson et al. |
| 5,877,302 A | 3/1999 | Hanson et al. |
| 5,972,900 A | 10/1999 | Ferkol, Jr. et al. |
| 5,972,901 A | 10/1999 | Ferkol, Jr. et al. |
| 6,072,041 A | 6/2000 | Davis et al. |
| 6,077,835 A | 6/2000 | Hanson et al. |

FOREIGN PATENT DOCUMENTS

| | | |
|---|---|---|
| JP | 7322892 A2 | 12/1995 |
| JP | 9173053 A2 | 7/1997 |
| WO | WO 93/25712 | 12/1993 |
| WO | WO 95/25809 | 9/1995 |
| WO | WO 98/22587 | 5/1998 |
| WO | WO 90/09442 | 8/1998 |
| WO | WO 98/39412 | 9/1998 |

OTHER PUBLICATIONS

Rudinger, 1976, Peptide Hormones, Edited by Parsons, University Park Press, Baltimore, p. 1–7.*
Kaye et al., 1990, Proc. Natl. Acad. Sci. USA, vol. 87, pp. 6922–6926.*
Skolnick et al., 2000, Trends in Biotech, vol. 18, p. 34–39.*
Eck et al., Goodman & Gilman's The Pharmacological Basis of Therapeutics, 1996, McGraw–Hill, New York, p. 77–101.*
Deonarain, M., 1998, Exp. Opin. Ther. Patents, vol. 8, No. 1, p. 53–69.*
Verma et al., 1997, Nature, vol. 389, p. 239–242.*
Gorecki, D., 2001, Expert Opin. Emerging Drugs, vol. 6, No. 2, p. 187–198.*
PCT International Search Report—PCT/US 97/21463, Nov. 22, 1997.
Marra, M., et al., "The WashU–HHMI Mouse EST Project, AC W81747", EMBL Database, Jun. 27, 1996, Heidelberg, XP002066845.
Hillier, L., et al., The WashU–Merck EST project, AC AA007646, EMBL Database, Jul. 28, 1996, Heidelberg, XP002066846.
Holton, T., et al., "ACQ57612", EMBL Database, Sep. 5, 1994, Heidelberg, XP002066847.
Nippon Telegraph and Telephone Corp.: "ACQ75553", EMBL Database, Aug. 4, 1995, Heidelberg, XP002066848.
Gonsky, R., et al., "Transforming DNA Sequences Present in Human Prolactin–Secreting Pituitary Tumors", Molec. Endocrin., 5(11): 1687–1695, Nov. 1991.
Pei, L., et al., "Isolates and Characterization of a Pituitary Tumor–Transforming Gene (PTTG)", Molec. Endocrin., 11(4):433–441, Apr. 1997.
Shimon, L., et al., "Genetic Basis of Endocrine Disease", J. Clin. Endocrin. And Metab., 82(6): 1675–1681, Jun. 1997.
Chen, L., et al., "Identification of the human pituitary tumor transforming gene (hPTTG) family: molecular structure, expression, and chromosomal localization.", 1: Gene May 2, 2000, 248(102): 41–50. Abstract Only.

(Continued)

Primary Examiner—Shin-Lin Chen
(74) Attorney, Agent, or Firm—Pillsbury Winthrop LLP

(57) ABSTRACT

Disclosed is a method of inhibiting neoplastic cellular proliferation and/or transformation of mammalian breast or ovarian cells, including cells of human origin, in vitro or in vivo. The inventive method involves the use of a pituitary tumor transforming gene (PTTG)2 peptide, which has the ability to regulate endogenous PTTG1 expression and/or function in a dominant negative manner. In some embodiments, the invention is directed to gene-based treatments that deliver PTTG2-encoding polynucleotides to mammalian cells, whether in vitro or in vivo, to inhibit the endogenous expression of PTTG1. Other embodiments are directed to peptide-based treatments that deliver PTTG2 peptide molecules to the cells, which inhibit endogenous PTTG1 expression and/or PTTG1 function. Kits useful in practicing the inventive method are also disclosed.

16 Claims, 43 Drawing Sheets

OTHER PUBLICATIONS

Heaney, A.P., "Expression of pituitary–tumor transforming gene in colorectal tumours", 1: Lancet Feb. 26, 2000; 355(9205):716–9.

Heaney, A.P., "Early involvement of Estrogen–induced pituitary tumor transforming gene and fibroblast growth factor expression in prolactinoma pathogenesis", 1: Nat Med Nov. 1999; 5(11): 1317–21.

Suhardja, A.S., et al., "Molecular pathogenesis of pituitary adenomas a review.", Acta Neurochir (Wien) 1999: 141(7): 729–36. Abstract only.

Ren, R., et al., "Identification of a ten–amine acid proline–rich SH3 binding site.", Science Feb. 19, 1993; 259(5098): 1157–61. Abstract only.

Liu, X., et al., "The v–SRC SH3 domain binds phosphatidylinositol 3'–kinase.", Mol Cell Biol Sep. 1993; 13(9): 5225–32. Abstract only.

Gout, L., et al., "The CTPase dynamin binds to and is activated by a subset of SH3 domains." Cel Oct. 8, 1993; 75(1): 25–36.

Yu, H., et al., "Solution structure of the SH3 domain of Src and identification of its ligan–binding site." Science Dec. 4, 1992; 258(5088): 1665–8. Abstract only.

Lee, L.A., et al., "Cloning and expression of human cDNA encoding human homologue of pituitary tumor transforming gene.", Biochem Mol. Biol Int May 1999; 47(5): 891–7. Abstract only.

Zou, H., et al., "Identification of a vertebrate sister–chromatid separation inhibitor involved in transformation and tumorigenesis.", Science Jul 16, 1999; 285(5426): 418–22. Abstract only.

Zhang, X., et al., "Pituitary tumor transforming gene (PTTG) expression in pituitary adenomas." J Clin Endocrinol Metab Feb. 1999; 84(2): 761–7.

Prezant, T.R., et al., "An intronless homolog of human proto–oncogene hPTTG is expressed in pituitary tumors: evidence hPTTG family.", J. Clin. Endocrinol Metab Mar. 1999; 84(3): 1149–52.

Fujimoto, N., et al., "Establishment of an estrogen responsive rat pituitary cell sub–line MtTe–2." Endocr J Jun. 1999; 46(3): 389–96. Abstract only.

Ramos–Morales, F., et al., "Cell cycle regulated expression and phosphorylation of hpttg proto–oncogene product.", Oncogene Jan. 20, 2000; 19(3): 403–9. Abstract only.

McCabe C.J., et al., "PTTG—a new pituitary tumour transforming gene.", J. Endocrinol Aug. 1999; 162(2): 163–6. Abstract only.

Kakar, S.S., "Molecular cloning, genomic organization, and identification of the promoter for the human pituitary tumor transforming gene (PTTG).", Gene Nov. 29, 1999; 240(2): 317–24. Abstract only.

Dominguez, A., et al., "hpttg, a human homologue of a rat pttg, is overexpressed in hematopoietic neoplasms. Evidence for a transcriptional function of hPTTG.", Oncogene Oct. 29, 1998; 17(17): 2187–93. Abstract only.

Pet, L., "Pituitary tumor–transforming gene protein associates with ribosomal protein S10 and a novel human homologue of DnaJ in testicular cells.", J Biol Chem Jan. 29, 1999; 274(5): 3151–8.

Saez, C., et al., "hpttg is over–expressed in pituitary adenomas and other primary epithelial neoplasias.", Oncogene Sep. 23, 1999; 18(39): 5473–6. Abstract only.

Pei, L., "Genomic Organization and identification of an enhancer element containing binding sites for multiple proteins in rat pituitary tumor–transforming gene.", J Biol Chem Feb. 27, 1998; 273(9): 5219–25.

Wang, Z., et al., "Characterization of the murine pituitary tumor transforming gene (PTTG) and its promoter.", Endocrinology Feb. 2000; 141(2): 763–71.

Zhang, X., et al., "Structure, expression, and function of human pituitary tumor–transforming gene (PTTG).", Mol Endocrinol Jan. 1999; 13(1): 156–66.

Heaney, Anthony, P., et al., "Pituitary tumor transforming gene: a novel factor in pituitary tumour formation," Balliere's Clinical Endocrinology and Metabolism, vol. 13, No. 3, pp. 367–380, 1999.

Freeman, G. J. et al., *Engagement of the PD–1 Immunoinhibitory receptor by a Novel B7 family Member Leads to Negative Regulation of Lymphocyte Activation, J. Exp Med,* 192(7):1027–1034 (Oct. 2, 2000). Abstract only.

George, J. et al., *Adoptive Transfer of beta (2)–Glycoprotein 1–Reactive Lymphocytes Enhances Early Atherosclerosis in LDL Receptor–Deficient Mice, Circulation,* 102(15):1822–1827 (Oct. 10, 2000). Abstract only.

Griffin, J. M. et al., *CD4 (+) T–Cell Activation and Induction of Autoimmune Hepatitis following Trichloroetheylene Treatment in MRL+/+Mice, Toxicol Sci,* 57(2):345–352 (Oct. 2000). Abstract only.

Grom, A. A. et al., *T–cell and T–cell receptor abnormalities in the immunopathogenesis of juvenile theumatoid arthritis, Curr Opin Rheumatol,* 12(5):420–4 (Sep. 2000). Abstract only.

Han, W. R. et al., *Prolonged allograft survival in anti–CD4 antibody transgenic mice: lack of residual helper T cells compared with other CD4–deficient mice,* 70(1):168–74 (Jul. 15, 2000). Abstract only.

Hotchkiss, R. S. et al., *Rapid onset of intestinal epthelial and lymphocyte apoptotic cell death in patients with trauma and shock, Crit Care Med,* 28(9):3207–17 (Sep. 2000). Abstract only.

Karandikar, N. J. et al., *CTLA–4 downregulates eptitope spreading and mediates remission in relapsing experimental autoimmune encephalomyelitis, J. Neuroimmunol,* 109(2): 173–80 (Sep. 2000). Abstract only.

Kenyon, N. J. et al., *Enhanced cytokine generation by peripheral blood mononuclear cells in allergic and asthma subjects, Ann Allergy Asthma Immunol,* 85(2):115–20 (Aug. 2000). Abstract only.

Kerlero de Rosbo, N et al., *Rhesus monkeys are highly susceptible to experimental autoimmune encephalomyelitis induced by myelin oligodendrocyte glycoprotein: characterisation of immunodominant T– and B–cell epitopes, J. Neuroimmunol,* 110(1–2):83–96. (Oct. 2, 2000). Abstract only.

Krieger, N. R. et al., *Rat pancreatic islet and skin xenograft survival in CD4 and CD8 knockout mice, J. Autoimmun,* 10(3):309–15 (Jun. 1997). Abstract only.

McCabe, C. J. et al., *PTTG—a new pituitary tumour transferring gene, Journal of Endocrinology,* vol. 162, pp. 163–166 (1999).

Nakajima, A. et al., *Involvement of CD70–CD27 interactions in the induction of experimental autoimmune encephalomyelitis, J. Neuroimmunol,* 109(2): 188–96 (Sep. 22, 2000). Abstract only.

Nickoloff, B. J. et al., *Is psoriasis a T–cell disease?, Exp. Dermatol,* 9(5):359–75 (Oct. 2000). Abstract only.

Odaka, C. et al., Angiotensin–converting enzyme inhibitor captopril prevents activation–induced apoptosis by interfering with T cell activation signals, Clin Exp Immunol, 121(3):515–22 (Sep. 2000). Abstract only.

Oliver, J. M. et al., Immunologically mediated signaling in basophils and mast cells: finding therapeutic targets for allergic diseases in the human FcvarepsilonR1 signaling pathway, Immunopharmacology, 48(3):269–281 (Jul. 25, 2000). Abstract only.

Ott, V. L. et al., Activating and inhibitory signaling in mast cells: New opportunities for therapeutic intervention?, J. Allergy Clin Immunol, 106(3 Pt 1):429:440 (Sep. 2000). Abstract only.

Simeonovic, C. J. et al., Differences in the contribution of CD4+ T Cells to proislet and islet allograft rejection correlate with constitutive class II MHC alloantigen expression, Cell Transplant, 5(5):525–41 (Sep.–Oct. 1996). Abstract only.

Uchida, T. et al., Roles of CD4+ and CD8+ T cells in discordant skin xenograft rejection, Transplantation, 68(11):1721–7 (Dec. 1999). Abstract only.

Wang, H. B. et al., Tumor necrosis factor receptor–1 is critically involved in the development of experimental autoimmune myasthenia gravis, Int Immunol, 12(10):1381–1388 (Oct. 2000). Abstract only.

Wang, Z. et al., Pituitary tumor transforming gene (PTTG) transforming and transactivation activity, J Biol Chem, 275(11)L7459–61 (Mar. 17, 2000).

Yi, S. et al., CD8+ T cells are capable of rejecting pancreatic islet xenografts, Transplantation, 70(6):896–906 (Sep. 27, 2000). Abstract only.

Dubik, D. et al., Mechanism of estrogen activation of c–myc oncogen expression, Oncogene, 7(8): 1587–94 (Aug. 1992). Abstract only.

Farrell WE, Molecular Pathogenesis of Pituitary Tumors, Front Neuroendocrinol, 21 (3):174–198 (Jul. 2000). Abstract only.

Levin, Ellis R., Cellular Functions of the Plasma Membrane Estrogen Receptor, TEM vol. 10, No. 9, pp. 374–377 (1999).

Pei L, Activation of mitogen–activated kinase cascade regulates pituitary tumor–transforming gene transactivation function, J. Biol Chem [epub ahead of print] (Jul. 21, 2000) Abstract only.

Petz, Larry N, et al, SP1 Binding Sites and an Estrogen Response element Half–site Are Involved in Regulation of the Human Progesterone Receptor A Promoter, Molecular Endocrinology, 14:972–985 (2000).

Porter, W., et al., Functional Synergy between the Transcription Factor Sp1 and the Estrogen Receptor, Molecular Endocrinology, 11:1569–1580 (1997).

Ramos–Morales F., et al., Cell cycle regulated expression and phosphorylation of hpttg proto–oncogene product, Oncogene 19 (3):403–9 (Jan. 20, 2000) Abstract only.

Shepel LA, et al., Relationship of polymorphisms near the rat prolactin, N–ras, and retinoblastoma genes with susceptibility to estrogen–induced pituitary tumors, Cancer Res, 50 (24):7920–5 (Dec. 15, 1990) Abstract only.

Sutherland, R. L, et al., Estrogen and progestin regulation of cell cycle progression, J. Mammary Gland Biol Neoplasia 3 (1):63–72 (Jan., 1998) Abstract only.

Wang, Zhiyong, et al., Characterization of the Murine Pituitary Tumor Transforming gene (PTTG) and Its Promoter, Endocrinology, 141:763–771 (2000).

Wu–Peng, Sharon X., et al., Delineation of Sites Mediating Estrogen Regulation of the Rat Creatine Kinase B Gene, Molecular, Endocrinology 6:231–240 (1992).

Auerbach, R. et al., Assays for Angiogenesis: A Review, Pharmac. Ther., 51:1–11 (1991).

Bikfalvi, A. et al., Biological Roles of Fibroblast Growth Factor–2, Endocrine Reviews, 18(1):26–45 (1997).

Darland, D.C. and D'Amore, P., Blood vessel maturation: vascular development comes of age, Journal of Clinical Investigation, 103(2): 157–158 (1999).

Ferrara, N. and Davis–Smith, T., The Biology of Vascular Endothelial Growth Factor, Endocrine Reviews, 18(1):4–25 (1997).

Folkman, J. and Shing, Y., Angiogenesis, Journal of Biological Chemistry, 267(16):10931–10934 (1992).

Hanahan, D. and Folkman, J., Patterns and Emerging Mechanisms of the Angiogenic Switch during Tumorigenesis, Cell, 86:353–364 (1996).

Horak, E. R. et al., Angiogenesis, assessed by platelet/endothelial cell adhesion molecule antibodies, as indicator of node metastases and survival in breast cancer, The Lancet, 340:1120–1124 (1992).

Jain, R. K. et al., Quantitative angiogenesis assays: progress and problems, Nature Medicine, 3:1203–1208 (1997).

Linderholm, B. et al., Vascular Endothelial Growth Factor is of High Prognostic Value in Node–Negative Breast Carcinoma, Journal of Clinical Oncology, 16(9):3121–3128 (1998).

Relf, M. et al., Expression of the Angiogenic Factors Vascular Endothelial Cell Growth Factor, Acidic and Basic Fibroblast Growth Factor, Tumor Growth Factor β–1, Platelet–derived Endothelial Cell Growth Factor, Placenta Growth Factor, and Pleiotrophin in Human Primary Breast Cancer and Its Relation to Angiogenesis, Cancer Research, 57:963–969 (1997).

Seghezzi, G. et al., Fibroblast Growth Factor–2 (FGF–2) Induces Vascular Endothelial Growth Factor (VEGF) Expression in the Endothelial Cells of Forming Capillaries: An Autocrine Mechanism Contributing to Angiogenesis, Journal of Cell Biology, 141(7):1659–1673 (1998).

Takahashi, Y. et al., Expression of Vascular Endothelial Growth Factor and Its Receptor, KDR, Correlates with Vascularity, Metastasis, and Proliferation of Human Colon Cancer, Cancer Research, 55:3964–3968 (1995).

Weidner, N. et al., Tumor Angiogenesis: A New Significant Independent Prognostic Indicator in Early–Stage Breast Carcinoma, Journal of the National Cancer Institute, 84(24):1875–1887 (1992).

Chen, Leilei et al., Identification of the human pituitary tumor transforming gene (hPTTG) family: molecular structure, expression, and chromosomal localization, Gene, vol. 248, pp. 41–50 (2000).

Dominguez. Africa et al., hpttg, a human homologue of rat pttg, is overexpressed in hematopoietic neoplasmas. Evidence for a transcriptional activation function of Hpttg, Oncogene, vol. 17, pp. 2187–2195 (1998).

XP–002186233. Ishikawa, Hiroki, et al., Human pituitary tumor–transforming gene induces angiogenesis. Journal of Clinical Endocrinology & Metabolism, vol. 86, No. 2, pp. 867–874 (Feb. 2001). Abstract only.

* cited by examiner

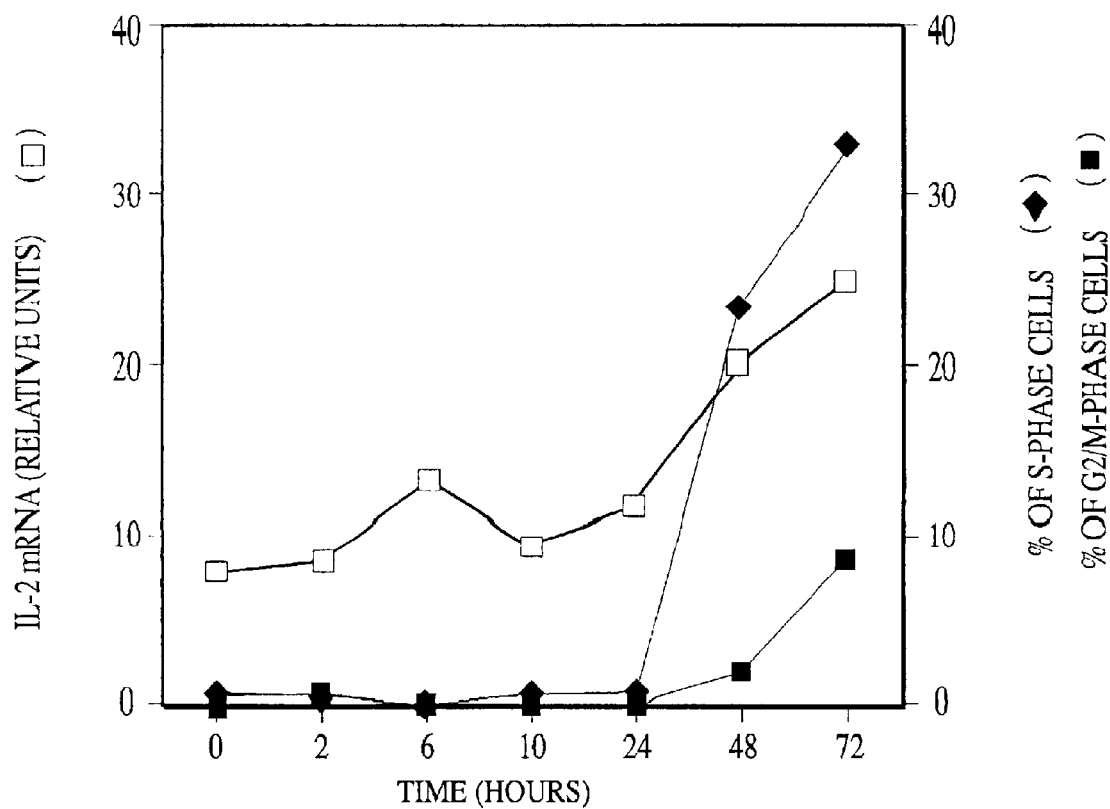
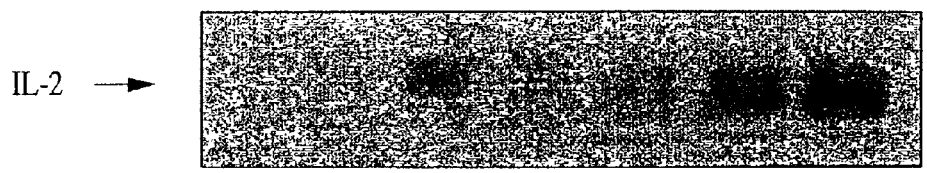
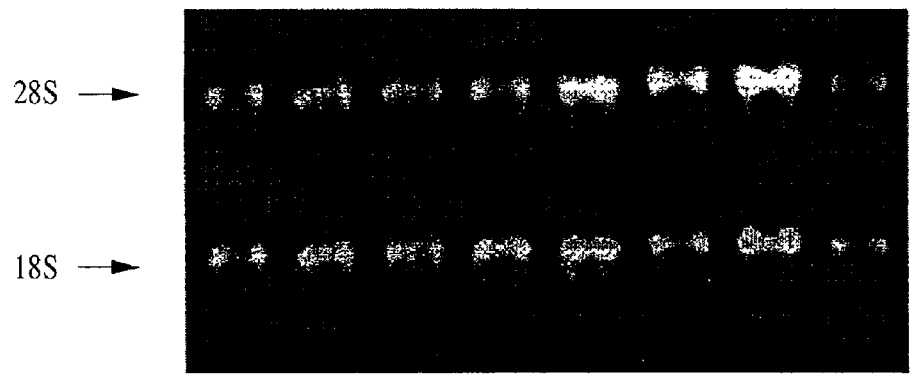
FIG. 7

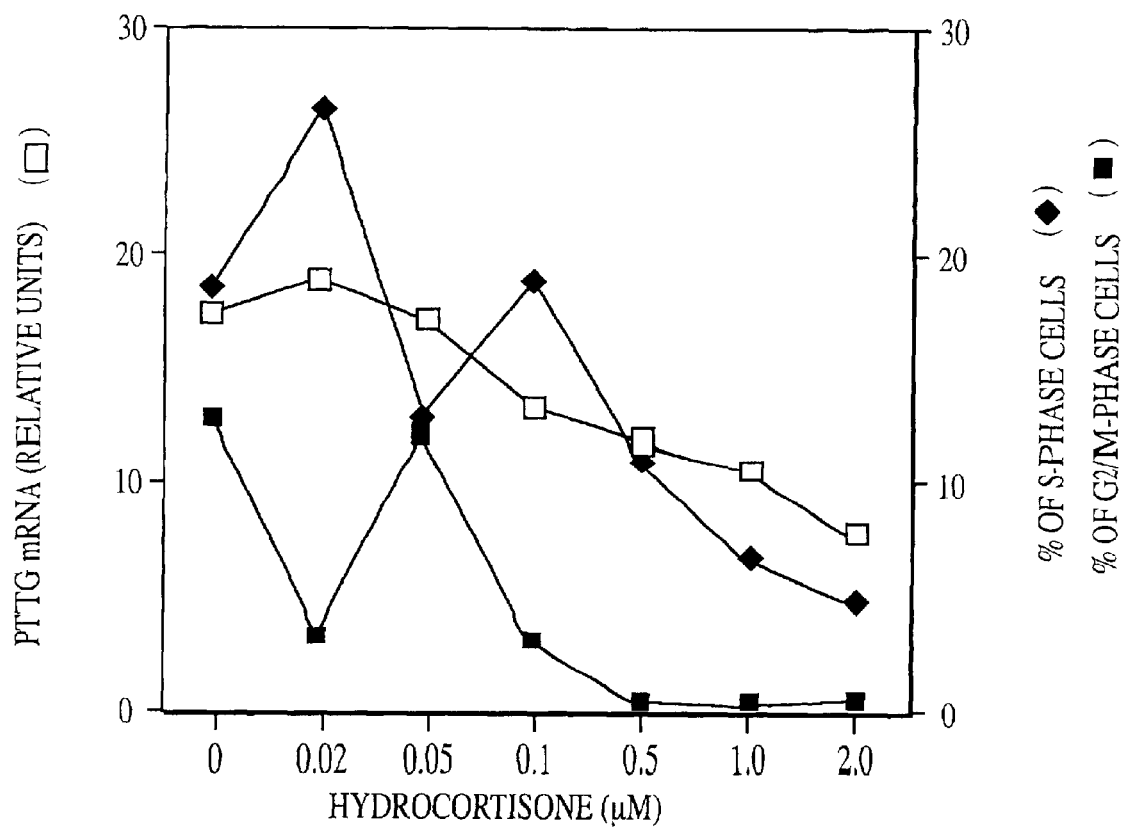
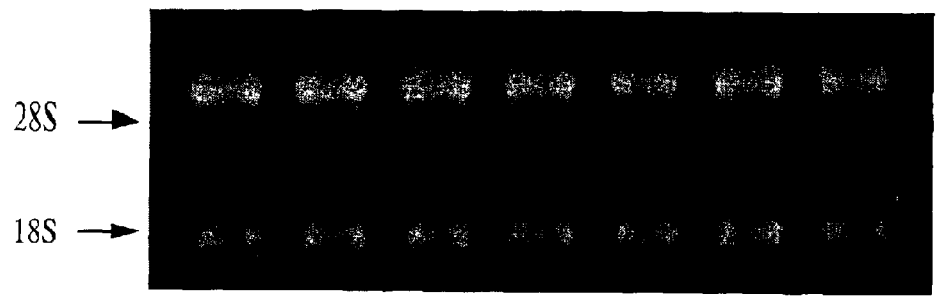
FIG. 9

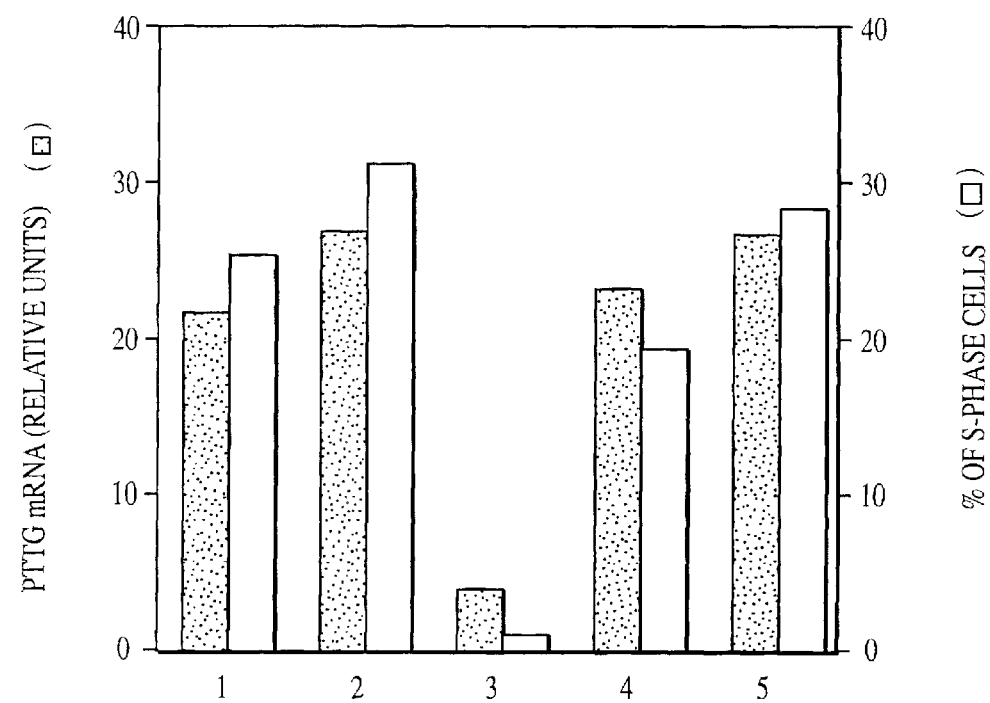
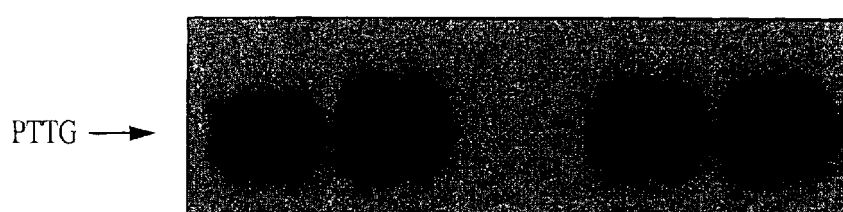
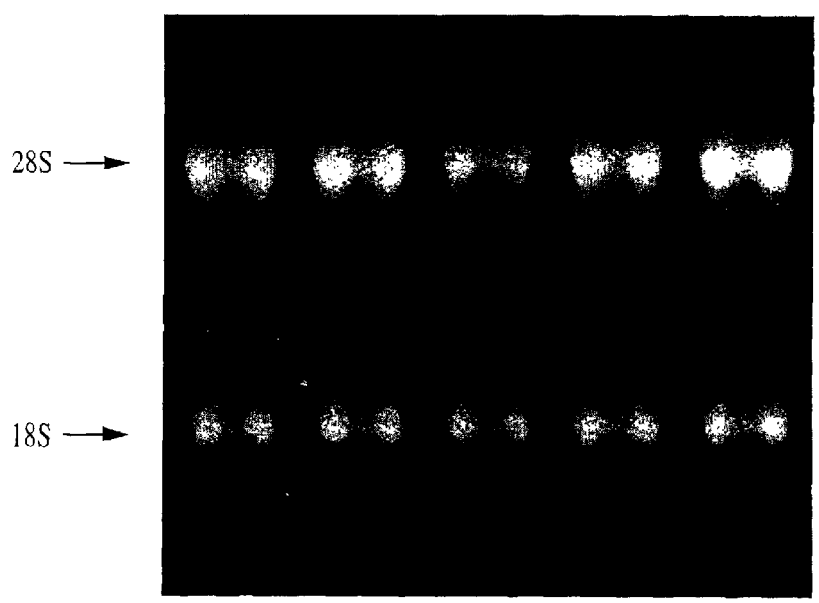
FIG. 11

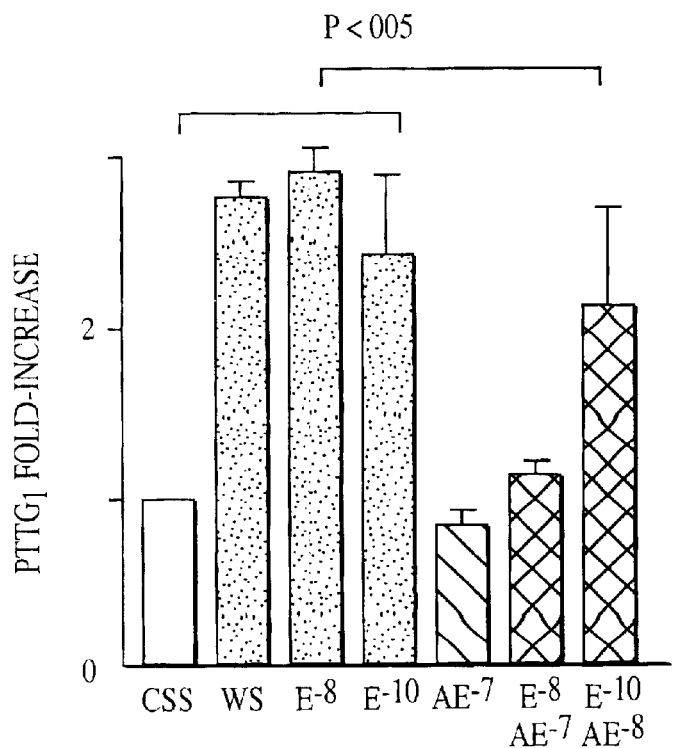
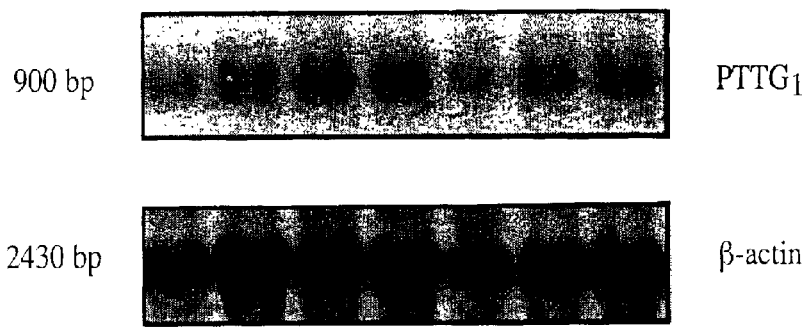
FIG. 15A
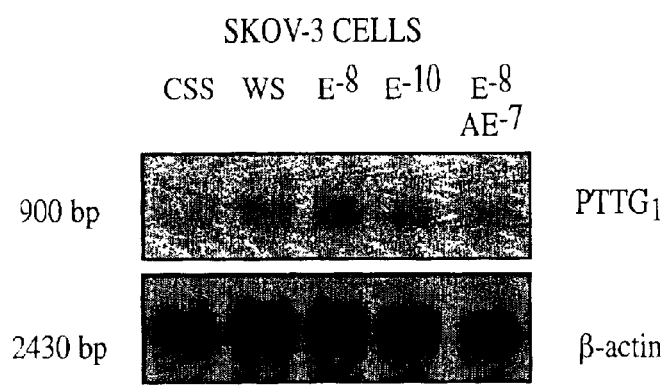
FIG. 15B

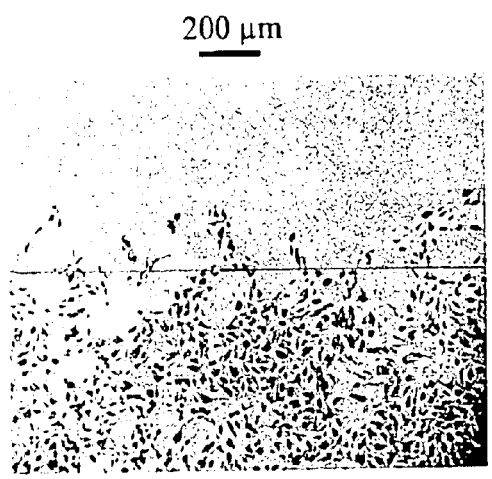 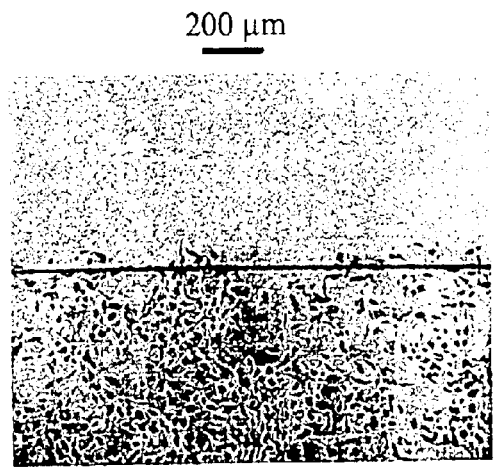
FIG. 20A-1    FIG. 20A-2

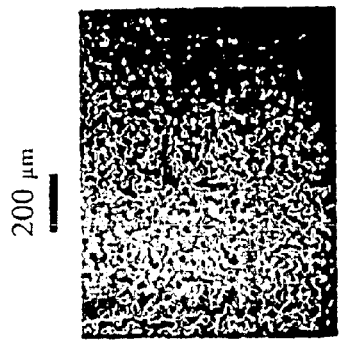
FIG. 21A-1
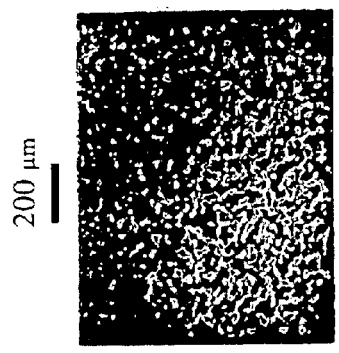
FIG. 21A-2
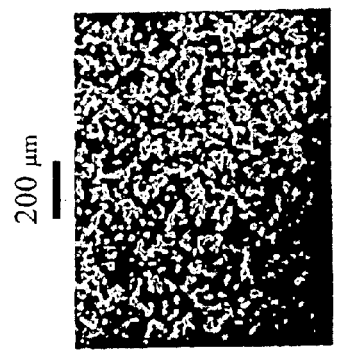
FIG. 21A-3
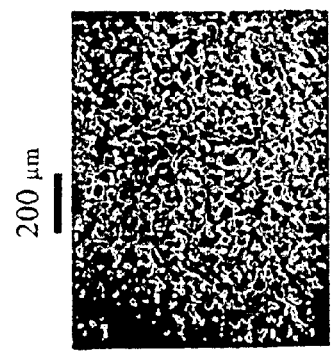
FIG. 21A-4
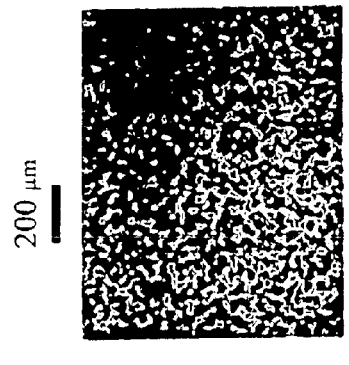
FIG. 21A-5
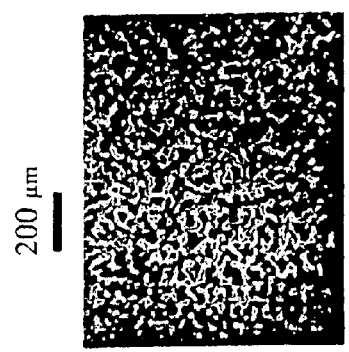
FIG. 21A-6
FIG. 21A-7
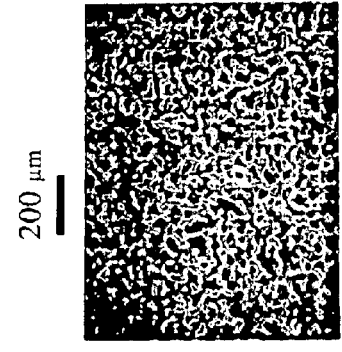
FIG. 21A-8

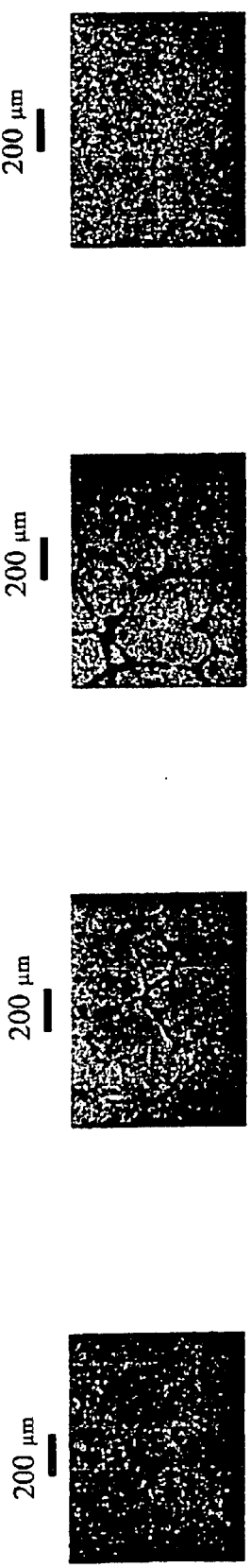

```
         MATLIYVDKE NGEPGTRVVA KDGLKLGSGP SIKALDGRSQ VSTPRFGKTF DAPPALPKAT
hPTTG1  1 ********** ********** ********** ********** ********** **********
hPTTG2  1 ******** I***** V****E*R* ******I *L****** *S******
hPTTG3  1 **F*D  *E****IL*AT *E**R*  ********KL* ISC* TS******
mPTTG   1 ****F***D  *E****R*LAS *E*******T*V --******KL* ****V***V* N*-*V***S
rPTTG   1 ****F****D *E****S*LAS *E********V --*****KL*  ****V*V*V* G*-*GL***S

RKALGTVNRA TEKSVKTKGP LKQKQPSFSA KKMTEKTVKA KSSVLASDDA YPEIEKFPF
hPTTG1 61 ********** ********** ********** ********** ********** **********
hPTTG2 61 ********** ********** R********* ********T* ****P***** **********
hPTTG3 61 ******** ****** ****** ******** *NP*G ********
mPTTG  58 ******V  APM**GK* *QP*TLTG I****ST*T Q***P*P*P L*******
rPTTG  58 ******V  *P**SSK* *QS****TL*V I**ST*T QG*AP*P* ********

NPLDFESFDL PEEHQIAHLP LSGVPLMILD EERELEKLFQ LGPPSPVKMP SPPWESNLLQ
hPTTG1 121 ********** ********** ********** ********** ********** **********
hPTTG2 121 *L****** R* E***** G***** ****** *CFA
hPTTG3 121 *G** ******** *N****IT*N **GLH N***L*T* ***K**
mPTTG  118 ********** ****SL**** ********** ****G****LH ****L*T*   FLS***DP*Y
rPTTG  118 D********* ********SL* *N********* ****G****LH *D****LQK* FL****DP*P

SPSSILSTLD VELPPVCCDI DI        (SEQ.ID.NO.:4)
hPTTG1 181 ********** C                    (SEQ.ID.NO.:64)
hPTTG2 181 VSFKHSVDPG                     (SEQ.ID.NO.:67)
hPTTG3 181 LL** ******S        (SEQ.ID.NO.:14)
mPTTG  175 **P*A***** **********Y*A **     (SEQ.ID.NO.:2)
rPTTG  178 *P*A***A** **********Y*A **
```

FIG. 24

METHOD OF REGULATING BIOLOGICAL ACTIVITY OF PITUITARY TUMOR TRANSFORMING GENE (PTTG)1 USING PTTG2

This application is a continuation-in-part of U.S. Ser. No. 09/777,422, filed Feb. 5, 2001, which is a continuation-in-part of U.S. Ser. No. 09/730,469, filed Dec. 4, 2000, which is a continuation-in-part of U.S. Ser. No. 09/687,911, filed on Oct. 13, 2000, which is a continuation-in-part of U.S. Ser. No. 09/569,956, filed on May 12, 2000, which is a continuation-in-part of U.S. Ser. No. 08/894,251, filed on Jul. 23, 1999, which issued as U.S. Pat. No. 6,455,305, on Sep. 24, 2002, and which was a national stage application, under 35 U.S.C. § 371, of international application PCT/US97/21463, filed Nov. 21, 1997, which claims the priority of the filing date of U.S. Provisional Application Ser. No. 60/031,338, filed Nov. 21, 1996.

The U.S. Government has a paid-up license in this invention and the right in limited circumstances to require the patent owner to license others on reasonable terms as provided for by the terms of Contract CA75979, awarded by the National Cancer Institute of the National Institutes of Health.

BACKGROUND OF THE INVENTION

Throughout the application various publications are referenced in parentheses. The disclosures of these publications in their entireties are hereby incorporated by reference in the application in order to more fully describe the state of the art to which this invention pertains.

1. Field of the Invention

The present invention relates to a method of inhibiting neoplastic cellular proliferation and/or transformation of mammalian cells, in vitro and in vivo.

2. Related Art

Pituitary Tumor Transforming Gene (PTTG) is highly expressed in pituitary tumors and neoplasms from the hematopoietic system and colon. (Zhang, X. et al., *Structure, expression, and function of human pituitary tumor-transforming gene (PTTG)*, Mol. Endocrinol. 13: 156–66 [1999a]; Zhang, X. et al., *Pituitary tumor transforming gene (PTTG) expression in pituitary adenomas*, J. Clin. Endocrinol. Metab. 84:761–67 [1999b]; Heaney, A. P. et al., *Pituitary tumor transforming gene in colorectal tumors*, Lancet 355:712–15[2000]; Dominguez, A. et al., *hpttg, a human homologue of rat pttg, is overexpressed in hematopoietic neoplasms. Evidence for a transcriptional activation function of hPTTG*, Oncogene 17:2187–93 [1998]; Saez, C. et al., *hpttg is over-expressed in pituitary adenomas and other primary epithelial neoplasias*, Oncogene 18:5473–6 [1999]). PTTG1 is expressed at low levels in most normal human tissues. (Chen, L. et al., *Identification of the human pituitary tumor transforming gene (hPTTG) family: molecular structure, expression, and chromosomal localization*, Gene. 248:41–50 [2000]; Heaney, A. P. et al. [2000]).

Levels of PTTG expression positively correlate with pituitary and colorectal tumor invasiveness (Zhang, X. et al. [1999b]; Heaney, A. P. et al. [2000]) and are induced by estrogen. (Heaney, A. P. et al., *Early involvement of estrogen-induced pituitary tumor transforming gene and fibroblast growth factor expression in prolactinoma pathogenesis*, Nat. Med. 5:1317–21 [1999]). In tumor cells, PTTG mRNA and protein expressions are cell cycle-dependent and peak at G2/M phase. (Yu, R. et al., *Pituitary Tumor Transforming Gene (PTTG) Regulates Placental JEG-3 Cell Division and Survival. Evidence from Live Cell Imaging*, Mol. Endocrinol. 14:1137–1146 [2000]). The mechanism of PTTG action is not very clear. PTTG upregulates basic fibroblast growth factor secretion (Zhang, X. et al. [1999a]), and transactivates DNA transcription (Dominguez, A. et al. [1998]; Wang, Z. et al., *Pituitary tumor transforming gene (PTTG) transactivating and transforming activity*, J. Biol. Chem. 275:7459–61[2000]).

PTTG encodes a securin protein the expression of which causes cell transformation, induces the production of basic fibroblast growth factor (bFGF), is regulated in vitro and in vivo by estrogen, and inhibits chromatid separation. (Pei, L., and Melmed S., *Isolation and characterization of a pituitary tumor transforming gene*, Mol. Endocrinol. 11:433–441 [1997]; Zhang, X., et al., *Structure, expression, and function of human pituitary tumor-transforming gene (PTTG)*, Mol. Endocrinol. 13:156–166 [1999a]; Heaney, A. P., et al., *Early involvement of estrogen-induced pituitary tumor transforming gene and fibroblast growth factor expression in prolactinoma pathogenesis*, Nature Med. 5:1317–1321 [1999]; Zou, H., et al., *Identification of a vertebrate sister-chromatid separation inhibitor involved in transformation and tumorigenesis*, Science 285:418–422 [1999]).

By dysregulating chromatid separation, PTTG overexpression also leads to aneuploidy, i.e., cells having one or a few chromosomes above or below the normal chromosome number. (Zou et al. [1999]; Yu, R. et al. [2000]). At the end of metaphase, securin is degraded by an anaphase-promoting complex, releasing tonic inhibition of separin, which in turn mediates degradation of cohesins, the proteins that hold sister chromatids together. Overexpression of a nondegradable PTTG disrupts sister chromatid separation (Zou et al. [1999]) and overexpression of PTTG causes apoptosis and inhibits mitosis (Yu, R. et al. [2000]). The securin function of PTTG suggests that PTTG may also be expressed in normal proliferating cells. In adult animals and humans, PTTG mRNA is most abundant in testis (Zhang, X. et al. [1999a]); Wang, Z. et al. [2000]), an organ containing rapidly proliferating gametes.

A PTTG gene family contains at least three genes that share a high degree of sequence homology, including human PTTG1, located on chromosome 5q33. (Prezant, T. R., et al., *An intronless homolog of human proto-oncogene hPTTG is expressed in pituitary tumors: evidence for hPTTG family*, J. Clin. Endocrinol. Metab. 84:1149–52 [1999]). Murine PTTG shares 66% nucleotide base sequence homology with human PTTG1 and also exhibits transforming ability. (Wang, Z. and Melmed, S., *Characterization of the murine pituitary tumor transforming gone (PTTG) and its promoter*, Endocrinology [In Press; 2000]). A proline-rich region was identified near the protein C-terminus that is critical for PTTG1's transforming activity. (Zhang, X., et al. [1999a]), as demonstrated by the inhibitory effect on in vitro transformation, in vivo tumorigenesis, and transactivation, when point mutations were introduced into the proline-rich region. Proline-rich domains may function as SH3 binding sites to mediate signal transduction of protein-tyrosine kinase. (Pawson, T., *Protein modules and signaling networks*, Nature 373:573–580 [1995]; Kuriyan, J., and Cowburn, D., *Modular peptide recognition domains in eukaryotic signaling*, Annu, Rev. Biophys. Biomol. Struct. 26:259–288 [1997]).

Breast and ovarian cancers are a model of hormone dependent malignancy. Estrogens and progesterone, acting via specific nuclear receptors, are necessary for normal development of mammary gland and ovarian tissue and their differentiated function. In addition to classical estrogenic ligand-estrogen receptor (ER) interactions, and subsequent ER binding to estrogen-response elements to regulate gene transcription, it is now apparent that transcriptional modulation can be mediated through the membranal ER. (Levin E. R., *Cellular functions of the plasma membrane estrogen receptor*, TEM 10:374–77 [1999]). This action requires modification of cytosolic signal transduction pathways such as extracellular-signal-regulated kinase/mitogen-activated protein kinase pathways (ERK/MAPK).

In breast and ovarian cancers, the molecular mechanisms through which these signal transduction effects are mediated are not well defined, although c-myc and cyclin D1 have been identified as major downstream targets of estrogen and progestin-stimulated cell cycle progression. In addition to regulating cyclin abundance, recruitment of specific CDK inhibitors, such as p21 is impaired by estrogen, and additional, as yet undefined estrogen-regulated components are likely to be regulators of mammary epithelial cell proliferation and differentiation. (Sutherland, R. L., et al., *Estrogen and progestin regulate cell cycle progression*, J. Mammary Gland Biol. Neoplasia 3:63–72 [1998]).

Several studies have described the involvement of SP1 and half-site EREs in conferring estrogen-responsiveness of several genes, including creatine kinase B, c-myc, the retinoic acid receptor α, heat shock protein 27. (Wu-Peng X. et al., *Delineation of sites mediating estrogen regulation of the rat creatine kinase B gene*, Mol. Endocrinol. 6:231–240 [1992]; Dubik, D. and Shiu, R., *Mechanism of estrogen activation of c-myc oncogene expression*, Oncogene 7:1587–1594 [1992]). This cooperative interaction of a half-site ERE and an SP1 site has recently been described for the progesterone receptor (Petx, L. and Nardulli, A. M., *Sp1 binding sites and an estrogen response element half-site are involved in regulation of the human progesterone receptor A promoter*, Mol. Endocrinol. 14:972–85 [2000]). In the context of complex promoters, EREs are generally found in multiple copies or encased among binding motifs for other transcription factors (Porter, W. et al., *Functional synergy between the transcription factor Sp1 and the estrogen receptor*, Mol. Endo. 11:1569–80 [1997]). It has been demonstrated that the SP1 sites on the murine and human PTTG-promoter are crucial for its transactivation activity, and mutational disruption of the SP1 element or competition with a known SP1 oligo resulted in up to 90% loss of PTTG-promoter activity. (Wang, Z. and Melmed, S., *SP1 activates the pituitary tumor transforming gene (PTTG) promoter during cellular transformation* J Biol Chem [2000]; Kakar, S. S., *Molecular cloning, genomic organization, and identification of the promoter for the human pituitary tumor transforming gene (PTTG)*, Gene 240: 317–324 [1999]).

In many solid tumors, tumor vascularity may inversely correlate with prognosis, and both bFGF and VEGF expression have been reported to predict prognosis (Takahashi, Y. et al., *Expression of vascular endothelial growth factor and its receptor, KDR, correlates with vascularity, metastasis, and proliferation of human colon cancer*, Cancer Res 55:3964–68 [1995]). Quantification of angiogenesis in breast cancer can be used as an independent prognostic factor. (Weidner, N. et al., *Tumor angiogenesis: a new significant and independent prognostic factor in early-stage breast carcinoma*, J. Natl. Cancer Inst. 84:1875–1887 [1992]; Horak, E. R. et al., *Angiogenesis, assessed by platelet/endothelial cell adhesion molecule antibodies, as indicator of node metastesses and survival in breast cancer*, Lancet 340:1120–1124 [1992]). Not only are tumor growth, progression, and metastasis dependent on access to vasculature, but it is also apparent that during the transition from mid-late dysplasia, as in the case of cervical intraepithelial neoplasia II (CIN II) to CIN III, an "angiogenic switch" is activated and changes in tissue angiogenic phenotype probably precede the histological tissue transition. (Hanahan, D. and Folkman, J., *Patterns and emerging mechanisms of the angiogenic switch during tumorigenesis*. Cell. 86:353–64 [1996]).

The sequence of events in angiogenesis leading to formation of new blood vessels from pre-existing vessels is highly regulated (Jain, R K et al., *Quantitative angiogenesis assays: progress and problems*, Nat Med. 3:1203–1208 [1997]; Darland D C and D'Amore P A, *Blood vessel maturation: vascular development comes of age*, J Clin Invest. 103:157–158 [1999]), and involves dissolution of vessel basement membranes, and formation of new lumen and pericytes by vascular endothelial cells. During tumor-associated angiogenesis, sustained production of angiogenic factors by cancer cells, or indirect macrophage stimulation, causes disregulated immature vessel growth (Folkman, J. and Shing, Y., *Angiogenesis*, J Biol Chem. 267:10931–10934[1992]). A number of in vitro and in vivo assays have been useful for studying angiogenesis (e.g., Jain, R K et al. [1997]; Auerbach, R. et al., *Assays for angiogenesis: a review*, Pharmacol Ther. 51:1–11 [1991]).

Several cytokines and growth factors, including basic fibroblast growth factor (bFGF) and vascular endothelial growth factor (VEGF) modulate angiogenesis in vivo with a paracrine mode of action. (Bikfalvi, A. et al., *Biological roles of fibroblast growth factor-2*, Endocr. Rev. 18:26–45 [1997]; Ferrara, N. and Davis-Smyth, T., *The biology of vascular endothelial growth factor*, Endocr Rev 18:4–25 [1997]). bFGF and VEGF levels in cytosolic fractions are significantly associated with intratumoral vascularization. (*Expression of the angiogenic factors vascular endothelial cell growth factor, acidic and basic fibroblast growth factor, tumor growth factor-1, platlet-derived endothelial cell growth factor, placenta growth factor, and pleiotrophin in human primary breast cancer and its relation to angiogenesis*, Cancer Res. 57:963–69 [1997]; Linderholm, B. et al., *Vascular endothelial growth factor is of high prognostic value in node-negative breast carcinoma*, J. Clin. Oncol. 16:3121–28 [1998]). bFGF and VEGF have synergistic effects on angiogenesis, and bFGF modulates endothelial expression of VEGF through both autocrine and paracrine actions (Seghezzi, G. et al., *Fibroblast growth factor-2 (FGF-2) induces vascular endothelial growth factor (VEGF) expression in the endothelial cells of forming capillaries: An autocrine mechanism contributing to angiogenesis*, J. Cell. Biol. 141(7):1659–73 [1998]).

PTTG regulates bFGF mRNA and protein secretion, and this function requires a preserved C-terminus P-X-X-P motif. (Zhang, X. et al. [1999a]). It has also been reported that rat pituitary pttg is regulated in vivo and in vitro by estrogen, and the maximal induction of rat pituitary pttg mRNA in vivo occurred early in pituitary transformation (normal cell to hypertrophic/hyperplastic cell), coincident with bFGF and, vascular endothelial growth factor (VEGF) induction, and pituitary angiogenesis. (Heaney, A. P. et al. [1999]).

There remains a need for a therapeutic treatment for estrogen-sensitive neoplasms, such as breast and ovarian cancers, which can inhibit neoplastic cellular proliferation and/or transformation associated with PTTG overexpression. This and other benefits are provided by the present invention as described herein.

SUMMARY OF THE INVENTION

The present invention relates to compositions and methods useful for inhibiting neoplastic cellular proliferation and/or transformation of mammalian cells, whether in vitro or in vivo.

The inventive method relies on the discovery that pituitary tumor transforming gene (PTTG)2 protein regulates transactivating activity by PTTG1 and that, surprisingly, PTTG2 peptide molecules have the ability to downregulate PTTG1 expression and/or PTTG1 function in a dominant negative manner.

Included are PTTG2 gene-based embodiments of the method of inhibiting neoplastic cellular proliferation and/or transformation of a mammalian cell, which involve delivering to a mammalian cell that endogenously overexpresses PTTG1, a composition that includes an expression vector comprising a promoter and a polynucleotide that includes a first DNA segment encoding a mammalian PTTG2 peptide. The polynucleotide is operatively linked to the promoter in a transcriptional unit, and the DNA segment encoding a mammalian PTTG2 peptide encodes a PTTG2 peptide that consists essentially of human PTTG2 ("hPTTG2"; amino acid residues 1-191 of SEQ. ID. NO.:64) or a functional fragment of hPTTG2, which includes at least amino acid residues 1–180 of (SEQ. ID. NO.:64). The DNA segment encoding a mammalian PTTG2 peptide can also encode a mammalian PTTG2 peptide having at least about 95% sequence homology with hPTTG2 or a functional fragment. In accordance with the inventive method, the expression vector is preferably complexed with a cellular uptake-enhancing agent, in an amount and under conditions sufficient to enter the cell, such that the PTTG2 peptide is expressed in the cell from the polynucleotide, thereby inhibiting PTTG1-mediated neoplastic cellular proliferation and/or transformation of the cell.

Other embodiments of the present inventive method of inhibiting neoplastic cellular proliferation and/or transformation of a mammalian cell are directed to peptide-based treatments that deliver PTTG2 peptides to the cell. These embodiments involve delivering to the mammalian cell a composition comprising a PTTG2 peptide. As described above, the PTTG2 peptide is a human PTTG2 (amino acid residues 1–191 of SEQ. ID. NO.:64) or a functional fragment of hPTTG2, which fragment includes at least amino acid residues 1–180 of (SEQ. ID. NO.:64). The PTTG2 peptide can also be a mammalian PTTG2 peptide having at least about 95% sequence homology with hPTTG2 or a functional fragment. The PTTG2 peptide is complexed with a cellular uptake-enhancing agent, in an amount and under conditions sufficient to enter the cell, thereby inhibiting PTTG1-mediated neoplastic cellular proliferation and/or transformation of the cell.

Useful kits are also provided for facilitating the practice of the inventive methods.

The present invention is further described by related applications U.S. Ser. No. 09/777,422, filed Feb. 5, 2001; U.S. Ser. No. 09/730,469, filed Dec. 4, 2000; U.S. Ser. No. 09/687,911, filed on Oct. 13, 2000; U.S. Ser. No. 09/569,956, filed on May 12, 2000; U.S. Ser. No. 08/894,251, filed Jul. 23, 1999; international application PCT/US97/21463, filed Nov. 21, 1997; and U.S. provisional application No. 60/031,338, filed Nov. 21, 1996, the disclosures all of which are incorporated by reference.

BRIEF DESCRIPTION OF THE DRAWINGS

FIG. 7 shows IL-2 mRNA expression in normal adult human T cells treated with mitogen anti-CD3 antibody. T-cells were isolated and stimulated with anti-CD3 antibody for 72 hours. IL-2 mRNA (middle panel) was measured with northern blotting and percentage of cells in S or G2/M phase was determined by FACS.

FIG. 9 demonstrates PTTG mRNA expression and hydrocortisone. PHA (5 μg/mL)-stimulated normal adult human T cells were treated with hydrocortisone for 72 hours. PTTG mRNA was measured with northern blotting (middle panel) and percentage of cells in S or G2/M phase was determined by FACS.

FIG. 11 illustrates PTTG mRNA expression in leukemia cells. PTTG mRNA values and cell cycle of cycling human leukemia HL-60 (1), Jurkat T cells (2), resting (3), PHA (5 μg/mL)-stimulated, (4) anti-CD3-stimulated, and (5) normal adult human T cells were determined.

FIG. 14 shows representative Northern (upper panel) and western (lower panel) blot analysis comparing.

FIG. 15 demonstrates regulation of PTTG1 in vitro by estrogen. (FIG. 15a) MCF-7 cells and (FIG. 15b) SKOV-3 cells transiently transfected with full-length PTTG-promoter were incubated in medium containing serum pre-treated with charcoal stripped serum (CSS) (clear bars), prior to addition of medium containing 10% fetal bovine serum (WS) (filled bars), or medium containing CSS and added estrogen (hatched bars) (Diethylstilbestrol $10^{-8}$ to $10^{-10}$ M) (E), with/without the anti-estrogen (hatched bars) (ICI-182780 $10^{-7}$ to $10^{-8}$ M) (AE). PTTG1 mRNA was normalized for β-actin. Each bar represents mean±SEM of six dishes from three separate experiments. Statistical analysis was by ANOVA.

FIG. 20 demonstrates migration of HUVECs in wound assay. The wounded monolayer of HUVEC was exposed for 16 hours to respective aliquots of conditioned media. Migrated cells were then fixed, stained and photographed. (A) Representative micrographs of migrated HUVECs in WT-hPTTG-CM are shown. 1, conditioned media alone; 2, conditioned media+100 ng/ml anti-bFGF antibody. (B) Quantification of migrated HUVECs. The number of cells within 0.1×2.5-mm area in three fields was counted using the original mark made by razor blade as origin. The results shown are the average number of cells±SD per field of three separate experiments. 1, control; 2, WT-hPTTG-CM; 3, M-hPTTG-CM; 4, C-CM; 5, N-CM; open circle, 1 ng/ml bFGF in DMEM; open triangle, serum-free DMEM; closed circle, conditioned medium alone; closed triangle, conditioned medium+100 ng/ml anti-bFGF antibody; closed square, conditioned medium+100 ng/ml pre-immune goat IgG.

FIG. 21A shows migration of HUVECs in a modified Boyden chamber assay. The sample conditioned medium was placed in the lower chamber and HUVECs were added in the upper chamber of a modified Boyden chamber. After 24 hours incubation, non-migrating cells were removed and cells migrated through membrane pores (8 μm) were stained with Giemsa and photographed. Micrographs of migrated HUVECs from representative membranes under each experimental condition. 1, serum-free DMEM; 2, 1 ng/ml bFGF in DMEM; 3, WT-hPTTG-CM; 4, WT-hPTTG-CM+ 100 ng/ml anti-bFGF antibody; 5, WT-hPTTG-CM+100 ng/ml pre-immune goat IgG; 6, M-hPTTG-CM; 7, C-CM; 8, N-CM.

FIG. 22 demonstrates tube-formation of HUVECs on Matrigel. 5×10$^4$ of HUVECs suspended in sample conditioned media and plated on GFR Matrigel thickly coated 24-well culture plates. After 24 hours incubation, cells were photographed under phase-contrast microscopy. FIG. 22A shows micrographs of tube-forming HUVECs. Representative photographs for each experimental condition are shown. 1, serum-free DMEM; 2, 1 ng/ml bFGF in DMEM; 3, WT-hPTTG-CM; 4, WT-hPTTG-CM+100 ng/ml anti-bFGF antibody; 5, WT-hPTTG-CM+100 ng/ml pre-immune goat IgG; 6, M-hPTTG-CM; 7, C-CM; 8, N-CM.

FIG. 24 shows conservation of the PTTG gene family. The encoded PTTG proteins are aligned to show homology. PXXP motifs and highly conserved regions are underlined. Asterisks indicate identical amino acids, dashes are introduced to maintain alignment. Abbreviations: h—human, m—mouse, r—rat.

FIG. 30 shows the chromosomal localization of PTTG genes. In FIG. 30D, Northern blot analysis of cell lines: HL-60, JEG3, KG1, LL24 and MB231, probed with PTTG (top) or 18S cDNA (bottom).

FIG. 32 shows inhibition of transactivation by overexpression of PTTG2.

DETAILED DESCRIPTION OF THE PREFERRED EMBODIMENTS

Figure 1:
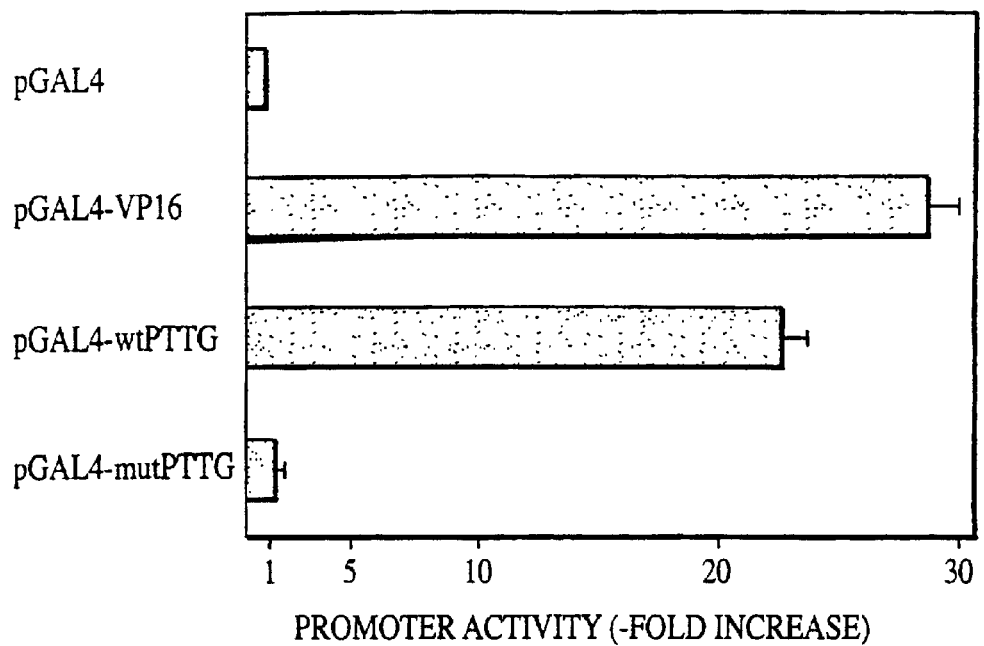
FIG. 1 illustrates transcriptional activation in transfected NIH-3T3 cells, as mediated by pGAL4, pGAL4-VP16, pGAL4-wtPTTG, or pGAL4-mutPTTG 48 hours after transfection. Cell lysate proteins were assayed for luciferase and β-gal expression. pGAL4 was used as a negative control and pGAL4-VP16 as a positive control.

The present invention relates to a method of inhibiting PTTG1-mediated neoplastic cellular proliferation and/or transformation of a mammalian cell, including, but not limited to, cells originating in colon, breast (i.e., mammary), or ovarian tissues. The cells include epithelial cells, vascular cells, leukocyte cells and any other mammalian cell type.

For the purposes of the inventive methods, the mammalian cell is a cell of human or non-human origin, originating from, or in, any mammalian animal, e.g., a non-human primate, rat, mouse, rabbit, guinea pig, hamster, bovine, porcine, ovine, equine, canine, feline, pachyderm, and the like. The mammalian cell can be situated in vivo, i.e., within a mammalian animal subject or human subject, or in vitro, i.e., the cell can be a cultured cell.

For the purposes of the invention, "neoplastic cellular proliferation" includes neoplastic (malignant or benign), hyperplastic, cytologically dysplastic and/or premalignant cellular growth or proliferation in a mammalian subject or cell culture. Hyperplastic cellular growth or proliferation includes abnormal multiplication or increase in the numbers of normal cells in a normal arrangement in a tissue, for example, as is common in benign prostatic hyperplasia. Cytologically dysplastic and/or premalignant cellular growth or proliferation include increases in cellular numbers of karyotypically abnormal but non-malignant cells within a tissue. Examples include some benign prostatic hyperplasias/dysplasia and cervical hyperplasias/dysplasias.

Neoplastic cellular growth and/or proliferation, i.e., growth of abnormally organized tissue, includes malignant and non-malignant neoplasms. Malignant neoplasms include primary, recurrent, and/or or metastatic cancerous tumors originating in any tissues, for example, carcinomas, sarcomas, lymphomas, mesotheliomas, melanomas, gliomas, nephroblastomas, glioblastomas, oligodendrogliomas, astrocytomas, ependymomas, primitive neuroectodermal tumors, atypical meningiomas, malignant meningiomas, or neuroblastomas, originating in the pituitary, hypothalamus, lung, kidney, adrenal, ureter, bladder, urethra, breast, prostate, testis, skull, brain, spine, thorax, peritoneum, ovary, uterus, stomach, liver, bowel, colon, rectum, bone, lymphatic system, skin, or in any other organ or tissue of the subject.

In accordance with some gene-based embodiments of the inventive method of inhibiting neoplastic cellular proliferation and/or transformation, an inventive composition is delivered to the cell, which composition comprises a PTTG carboxy-terminal-related polynucleotide. A "PTTG carboxy-terminal-related" polynucleotide is a polynucleotide having a contiguous sequence of bases (e.g., adenine [A], thymine [T], uracil [U], guanine [G], and/or cytosine [C]) defining a sequence specific to the 3' coding region of PTTG, and in particular of PTTG1. The 3'-end or terminal extends from approximately the mid-point of a cDNA coding sequence encoding a native PTTG to its end at a stop codon. The PTTG carboxy-terminal-related polynucleotide can be a sequence encoding a carboxy-terminal portion of a mammalian PTTG protein (i.e., a PTTG-C peptide), as described more fully below, or encoding a PTTG-specific fragment thereof, or a degenerate coding sequence, or a sequence complementary to any of these.

In some preferred embodiments, the inventive composition includes a nucleic acid construct, such as a plasmid or viral expression vector, which comprises the polynucleotide in a sense or antisense orientation, and from which PTTG-specific mRNA transcript can be expressed in the cell. In another preferred embodiment, the nucleic acid construct contains a polynucleotide encoding a mammalian PTTG carboxy-terminal (PTTG-C) peptide, which can be any PTTG-C peptide or functional fragment thereof as described herein. In particular "PTTG-C" is used interchangeably herein with "PTTG1-C". In still another preferred embodiment, the nucleic acid construct contains a polynucleotide, in a sense orientation, that encodes a mammalian PTTG2 peptide, as described herein.

The composition can also contain one or more helper plasmids or viruses, if appropriate. The plasmid or viral expression vector is a nucleic acid construct that includes a promoter region operatively linked to the polynucleotide in a transcriptional unit.

As used herein, a promoter region refers to a segment of DNA that controls transcription of a DNA to which it is operatively linked. The promoter region includes specific sequences that are sufficient for RNA polymerase recognition, binding and transcription initiation. In addition, the promoter region includes sequences that modulate this recognition, binding and transcription initiation activity of RNA polymerase. These sequences may be cis acting or may be responsive to trans acting factors. Promoters, depending upon the nature of the regulation, may be constitutive or regulated. Exemplary promoters contemplated for use in the practice of the present invention include the SV40 early promoter, the cytomegalovirus (CMV) promoter, the mouse mammary tumor virus (MMTV) steroid-inducible promoter, Moloney murine leukemia virus (MMLV) promoter, and the like.

As used herein, "expression" refers to the process by which polynucleic acids are transcribed into mRNA and translated into peptides, polypeptides, or proteins. If the polynucleic acid is derived from genomic DNA, expression may, if an appropriate eukaryotic host cell or organism is selected, include splicing of the mRNA.

As used herein, the term "operatively linked" refers to the functional relationship of DNA with regulatory and effector nucleotide sequences, such as promoters, enhancers, transcriptional and translational stop sites, and other signal sequences. For example, operative linkage of DNA to a promoter refers to the physical and functional relationship between the DNA and the promoter such that the transcription of such DNA is initiated from the promoter by an RNA polymerase that specifically recognizes, binds to and transcribes the DNA. Thus, "operatively linked" means that, within a transcriptional unit, the promoter sequence, is located upstream (i.e., 5' in relation thereto) from the coding sequence and the coding sequence, is 3' to the promoter, or alternatively is in a sequence of genes or open reading frames 3' to the promoter and expression is coordinately regulated thereby. Both the promoter and coding sequences are oriented in a 5' to 3' manner, such that transcription can take place in vitro in the presence of all essential enzymes, transcription factors, co-factors, activators, and reactants, under favorable physical conditions, e.g., suitable pH and temperature. This does not mean that, in any particular cell, conditions will favor transcription. For example, transcription from a tissue-specific promoter is generally not favored in heterologous cell types from different tissues.

The term "nucleic acid" encompasses ribonucleic acid (RNA) or deoxyribonucleic acid (DNA), which DNA can be complementary DNA (cDNA) or genomic DNA, e.g. a gene encoding a PTTG protein. "Polynucleotides" encompass nucleic acids containing a "backbone" formed by phosphodiester linkages between ribosyl or deoxyribosyl moieties. Polynucleotides also include nucleic acid analogs, for example polynucleotides having alternative linkages as known in the art. Examples include phosphorothioate linkages (e.g., phosphorothioate oligodeoxynucleotides;

S-oligonucleotides), mixed phosphorothioate and phosphodiester linkages (e.g., S-O-oligodeoxynucleotides and phosphodiester/phosphorothioate 2'-O-methyl-oligoribonucleotides; Zhou, W. et al., *Mixed backbone oligonucleotides as second-generation antisense agents with reduced phosphthioate-related side effects*, Bioorg. Med. Chem. Lett. 8(22):3269–74 [1998]), methylphosphonate-phosphodiester modifications (MP-O-oligonucleotides; Zhao, Q. et al, *Comparison of cellular binding and uptake of antisense phosphodiester, phosphorothioate, and mixed phosphorothioate and methylphosphonate oligomncleotides*, Antisense Res. Dev. 3(1):53–66 [1993]), or morpholino oligonucleotides (e.g., Schmajuk, G. et al., *Antisense oligonucleotides with different backbones. Modification of splicing pathways and efficacy of uptake*, J. Biol. Chem. 274(31):21783–89 [1999]).

Also included among polynucleotides are nucleic acid analogs having a pseudopeptide or polyamide backbone comprising N-(2-aminoethyl)glycine moieties, i.e., peptide nucleic acids (PNA). (E.g., Nielsen, P. E., *Peptide nucleic acids: on the road to new gene therapeutic drugs*, Pharmacol. Toxicol. 86(1):3–7 [2000]; Soomets, U. et al., *Antisense properties of peptide nucleic acids*, Front. Biosci. 4:D782–86 [1999]; Tyler, B. M. et al., *Peptide nucleic acids targeted to the neurotensin receptor and administered i.p. cross the blood-brain barrier and specifically reduce gene expression*, Proc. Natl. Acad. Sci. USA 96(12):7053–58 [1999]).

Polynucleotides include sense or antisense polynucleotides. "Polynucleotides" also encompasses "oligonucleotides".

A polynucleotide sequence complementary to a PTTG-specific polynucleotide sequence, as used herein, is one binding specifically with a PTTG-specific nucleotide base sequence. The phrase "binding specifically" encompasses the ability of a polynucleotide sequence to recognize a complementary base sequence and to form double-helical segments therewith via the formation of hydrogen bonds between the complementary base pairs. Thus, a complementary sequence includes, for example, an antisense sequence with respect to a sense sequence or coding sequence.

In some embodiments of the PTTG-C-related polynucleotide or in embodiments of the PTTG-2-encoding polynucleotide, the polynucleotide is in a sense orientation within the transcriptional unit, such that mRNA transcript can be produced, which when translated results in a translation product, such as a PTTG1 protein, a PTTG carboxy-terminal peptide (PTTG-C), or a PTTG2 peptide.

In other embodiments, the PTTG-C-related polynucleotide is in an antisense orientation such that transcription results in a transcript complementary to and hybridizable with a naturally-occurring sense PTTG mRNA molecule under physiological conditions, inhibiting or blocking translation therefrom. Thus, antisense oligonucleotides inactivate target mRNA sequences by either binding thereto and inducing degradation of the mRNA by, for example, RNase I digestion, or inhibiting translation of mRNA target sequence by interfering with the binding of translation-regulating factors or ribosomes, or by inclusion of other chemical structures, such as ribozyme sequences or reactive chemical groups which either degrade or chemically modify the target mRNA. For example, an antisense oligonucleotide targeted to a PTTG carboxy-terminal-related polynucleotide segment of mRNA or genomic DNA is effective in inhibiting expression of PTTG1.

Gene-based therapy strategies employing antisense oligonucleotides are well known in the art. (E.g., Rait, A. et al., *3'-End conjugates of minimally phosphorothioate-protected oligonucleotides with 1-O-hexadecylglycerol: synthesis and anti-ras activity in radiation-resistant cells*, Bioconjug Chem., 11(2):153–60 [2000]; Stenton, G. R. et al., *Aerosolized syk antisense suppresses syk expression, mediator release from macrophages, and pulmonary inflammation*, J. Immunol., 164(7):3790–7 [2000]; Suzuki, J. et al., *Antisense Bcl-x oligonucleotide induces apoptosis and prevents arterial neointimal formation in murine cardiac allografts*, Cardiovas. Res., 45(3):783–7 [2000]; Kim, J. W. et al., *Antisense oligodeoxynucleotide of glyceraldehyde-3-phosphate dehyrdogenase gene inhibits cell proliferation and induces apoptosis in human cervical carcinoma cell line*, Antisense Nucleic Acid Drug Dev., 9(6):507–13 [1999]; Han, D. C. et al., *Therapy with antisense TGF-betaI oligodeoxynucleotides reduces kidney weight and matrix mRNAs in diabetic mice*, Am. J. Physiol. Renal Physiol., 278(4):F628-F634 [2000]; Scala, S. et al., *Adenovirus-mediated suppression of HMGI (Y) protein synthesis as potential therapy of human malignant neoplasias*, Proc. Natl. Acad. Sci. USA., 97(8):4256–4261 [2000]; Arteaga, C. L., et al., *Tissue-targeted antisense c-fos retroviral vector inhibits established breast cancer xenografts in nude mice*, Cancer Res., 56(5):1098–1103 [1996]; Muller, M. et al., *Antisense phosphorothioate oligodeoxynucleotide down-regulation of the insulin-like growth factor I receptor in ovarian cancer cells*, Int. J. Cancer, 77(4):567–71 [1998]; Engelhard, H. H., *Antisense Oligodeoxynucleotide Technology: Potential Use for the Treatment of Malignant Brain Tumors*, Cancer Control, 5(2):163–170 [1998]; Alvarez-Salas, L. M. et al., *Growth inhibition of cervical tumor cells by antisense oligodeoxynucleotides directed to the human papillomavirus type 16 E6 gene*, Antisense Nucleic Acid Drug Dev., 9(5):441–50 [1999]; Im, S. A., et al., *Antiangiogenesis treatment for gliomas: transfer of antisense-vascular endothelial growth factor inhibits tumor growth in vivo*, Cancer Res., 59(4):895–900 [1999]; Maeshima, Y. et al., *Antisense oligonucleotides to proliferating cell nuclear antigen and Ki-67 inhibit human mesangial cell proliferation*, J. Am. Soc. Nephrol., 7(10):2219–29 [1996]; Chen, D. S. et al., *Retroviral Vector-mediated transfer of an antisense cyclin G1 construct inhibits osteosarcoma tumor growth in nude mice*, Hum. Gene Ther, 8(14): 1667–74 [1997]; Hirao, T. et al., *Antisense epidermal growth factor receptor delivered by adenoviral vector blocks tumor growth in human gastric cancer*, Cancer Gene Ther. 6(5):423–7 [1999]; Wang, X. Y. et al., *Antisense inhibition of protein kinase Calpha reverses the transformed phenotype in human lung carcinoma cells*, Exp. Cell Res., 250(1):253–63 [1999]; Sacco, M. G. et al., *In vitro and in vivo antisense-mediated growth inhibition of a mammary adenocarcinoma from MMTV-neu transgenic mice*, Gene Ther., 5(3);388–93 [1998]; Leonetti, C. et al., *Antitumor effect of c-myc antisense phosphorothioate oligodeoxynucleotides on human melanoma cells in vitro and in mice*, J. Natl. Cancer Inst., 88(7):419–29 [1996]; Laird, A. D. et al., *Inhibition of tumor growth in liver epthelial cells transfected with a transforming growth factor alpha antisense gene*, Cancer Res. 54(15):4224–32 (Aug. 1, 1994); Yazaki, T. et al., *Treatment of glioblastoma U-87 by systemic administration of an antisense protein kinase C-alpha phosphorothioate oligodeoxynucleotide*, Mol. Pharmacol., 50(2):236–42 [1996]; Ho, P. T. et al., *Antisense oligonucleotides as therapeutics for malignant diseases*, Semin. Oncol., 24(2):187–202 [1997]; Muller, M. et al., *Antisense phosphorothioate oligodeoxynucleotide down-regulation of the insulin-like growth factor I receptor in ovarian cancer cells,*

Int. J. Cancer, 77(4):567–71 [1998]; Elez, R. et al., *Polo-like kinasel, a new target for antisense tumor therapy*, Biochem. Biophys. Res. Commun., 269(2):352–6 [2000]; Monia, B. P. et al., *Antitumor activity of a phosphorothioate antisense oligodeoxynucleotide targeted against C-raf kinase*, Nat. Med., 2(6):668–75 [1996]).

In other embodiments of the inventive method, the inventive composition comprises a PTTG carboxy-terminal-related polynucleotide that is not contained in an expression vector, for example, a synthetic antisense oligonucleotide, such as a phosphorothioate oligodeoxynucleotide. Synthetic antisense oligonucleotides, or other antisense chemical structures designed to recognize and selectively bind to mRNA, are constructed to be complementary to portions of the PTTG coding strand, for example, to coding sequences shown in SEQ ID NOS:1, 3, 10, 15, 18, or 19 (Tables 1–6 below). By preventing translational expression of at least part of the PTTG 3' coding region, an antisense PTTG carboxy-terminal-related polynucleotide is useful, in accordance with the inventive method, to prevent expression of PTTG protein that is functional in mediating neoplastic cellular proliferation and/or transformation.

In preferred embodiments of the method of inhibiting neoplastic cellular proliferation and/or transformation, the composition also comprises an uptake-enhancing agent as further described herein. Inventive compositions, containing the uptake-enhancing agent complexed with a PTTG-specific polynucleotide, are designed to be capable of passing through the cell membrane in order to enter the cytoplasm of the cell by virtue of physical and chemical properties. In addition, the composition can be designed for delivery only to certain selected cell populations by targeting the composition to be recognized by specific cellular uptake mechanisms which take up the PTTG-specific polynucleotides only within select cell populations. For example, the composition can include a receptor agonist to bind to a receptor found only in a certain cell type.

The inventive compositions can also optionally contain one or more pharmaceutically acceptable carrier(s). As used herein, the term "acceptable carrier" encompasses any of the standard pharmaceutical carriers. The carrier can be an organic or inorganic carrier or excipient, such as water and emulsions such as an oil/water or water/oil emulsion, and various types of wetting agents. The active ingredient(s) can optionally be compounded in a composition formulated, for example, with non-toxic, pharmaceutically acceptable carriers for infusions, tablets, pellets, capsules, solutions, emulsions, suspensions, and any other form suitable for use. Such carriers also include glucose, lactose, gum acacia, gelatin, mannitol, starch paste, magnesium trisilicate, talc, corn starch, keratin, colloidal silica, potato starch, urea, medium chain length triglycerides, dextrans, normal saline, phosphate buffered saline and other carriers suitable for use in manufacturing preparations, in solid, semisolid, or liquid form. In addition auxiliary, stabilizing, thickening and coloring agents and perfumes can be used as appropriate.

PTTG-specific polynucleotides, including PTTG carboxy-terminal-related polynucleotides or PTTG2-encoding polynucleotides, are determined by base sequence similarity or homology to known mammalian PTTG-specific nucleotide sequences, for example PTTG1, PTTG2, PTTG3, or PTTG4 sequences. Base sequence homology is determined by conducting a base sequence similarity search of a genomics data base, such as the GenBank database of the National Center for Biotechnology Information (NCBI; www.ncbi.nlm.nih.gov/BLAST/), using a computerized algorithm, such as PowerBLAST, QBLAST, PSI-BLAST, PHI-BLAST, gapped or ungapped BLAST, or the "Align" program through the Baylor College of Medicine server (www.hgsc.bcm.tmc.edu/seq_data). (E.g., Altchul, S. F., et al., *Gapped BLAST and PSI-BLAST: a new generation of protein database search programs*, Nucleic Acids Res. 25(17):3389–402 [1997]; Zhang, J., & Madden, T. L., *PowerBLAST: a new network BLAST application for interactive or automated sequence analysis and annotation*, Genome Res. 7(6):649–56 [1997]; Madden, T. L., et al., *Applications of network BLAST server*, Methods Enzymol. 266:131–41 [1996]; Altschul, S. F., et al., *Basic local alignment search tool*, J. Mol. Biol. 215(3):403–10 [1990]).

Preferably, a PTTG-specific polynucleotide sequence is at least 5 to 30 contiguous nucleotides long, more preferably at least 6 to 15 contiguous nucleotides long, and most preferably at least 7 to 10 contiguous nucleotides long. Preferably, the inventive PTTG carboxy-terminal-related polynucleotide is at least about 45 contiguous nucleotides long.

Preferred examples of PTTG-specific coding sequences include the sequence for human PTTG1 (hPTTG1 or PTTG1). The PTTG1 peptide is encoded by the open reading frame at nucleotide positions 95 through 700 of human PTTG1 gene sequence SEQ. ID.NO.:3 (Table 1 below).

TABLE 1 hPTTG1 gene sequence.

| | | | | | |
|---|---|---|---|---|---|
| 1 | ATGGCCGCGA | GTTGTGGTTT | AAACCAGGAG | TGCCGCGCGT | CCGTTCACCG (SEQ. ID. NO.:3) |
| 51 | CGGCCTCAGA | TGAATGCGGC | TGTTAAGACC | TGCAATAATC | CAGAATGGCT |
| 101 | ACTCTGATCT | ATGTTGATAA | GGAAAATGGA | GAACCAGGCA | CCCGTGTGGT |
| 151 | TGCTAAGGAT | GGGCTGAAGC | TGGGGTCTGG | ACCTTCAATC | AAAGCCTTAG |
| 201 | ATGGGAGATC | TCAAGTTTCA | ACACCACGTT | TTGGCAAAAC | GTTCGATGCC |
| 251 | CCACCAGCCT | TACCTAAAGC | TACTAGAAAG | GCTTTGGGAA | CTGTCAACAG |
| 301 | AGCTACAGAA | AAGTCTGTAA | AGACCAAGGG | ACCCCTCAAA | CAAAAACAGC |
| 351 | CAAGCTTTTC | TGCCAAAAAG | ATGACTGAGA | AGACTGTTAA | AGCAAAAAGC |
| 401 | TCTGTTCCTG | CCTCAGATGA | TGCCTATCCA | GAAATAGAAA | AATTCTTTCC |

TABLE 1-continued hPTTG1 gene sequence.

```
451 CTTCAATCCT CTAGACTTTG AGAGTTTTGA CCTGCCTGAA GAGCACCAGA
501 TTGCGCACCT CCCCTTGAGT GGAGTGCCTC TCATGATCCT TGACGAGGAG
551 AGAGAGCTTG AAAAGCTGTT TCAGCTGGGC CCCCCTTCAC CTGTGAAGAT
601 GCCCTCTCCA CCATGGGAAT CCAATCTGTT GCAGTCTCCT TCAAGCATTC
651 TGTCGACCCT GGATGTTGAA TTGCCACCTG TTTGCTGTGA CATAGATATT
701 TAAATTTCTT AGTGCTTCAG AGTTTGTGTG TATTTGTATT AATAAAGCAT
751 TCTTTAACAG ATAAAAAAAA AAAAAAAA.
```

The 3' coding region of PTTG1 includes the following 168-nucleotide sequence, which corresponds to nucleotide positions 533 through 700 of SEQ. ID. NO.:3, shown in Table 2 below.

TABLE 2

Portion of 3' coding region of hPTTG1

```
  1 ATGATCCTTG ACGAGGAGAG AGAGCTTGAA AAGCTGTTTC AGCTGGGCCC  (SEQ.ID. NO.:10)
 51 CCCTTCACCT GTGAAGATGC CCTCTCCACC ATGGGAATCC AATCTGTTGC
101 AGTCTCCTTC AAGCATTCTG TCGACCCTGG ATGTTGAATT GCCACCTGTT
151 TGCTGTGACA TAGATATT.
```

Another useful example of a PTTG-specific coding sequence is a sequence that encodes a rat PTTG peptide, including nucleotide positions 293 through 889 of SEQ. ID. NO.:1 (Table 3 below).

TABLE 3

Rat PTTG1 sequence (SEQ. ID. NO.:1)
```
AATTCGGCAC GAGCCAACCT TGAGCATCTG ATCCTCTTGG CTTCTCCTTC CTATCGCTGA  60
GCTGGTAGGC TGGAGACAGT TGTTTGGGTG CCAACATCAA CAAACGATTT CTGTAGTTTA 120
GCGTTTATGA CCCTGGCGTG AAGATTTAAG GTCTGGATTA AGCCTGTTGA CTTCTCCAGC 180
TACTTCTAAA TTTTTGTGCA TAGGTGCTCT GGTCTCTGTT GCTGCTTAGT TCTTCCAGCC 240
TTCCTCAATG CCAGTTTTAT AATATGCAGG TCTCTCCCCT CAGTAATCCA GG ATG      295
GCT ACT CTG ATC TTT GTT GAT AAG GAT AAC GAA GAG CCA GGC AGC CGT   343
TTG GCA TCT AAG GAT GGA TTG AAG CTG GGC TCT GGT GTC AAA GCC TTA   391
GAT GGG AAA TTG CAG GTT TCA ACG CCA CGA GTC GGC AAA GTG TTC GGT   439
GCC CCA GGC TTG CCT AAA GCC AGC AGG AAG GCT CTG GGA ACT GTC AAC   487
AGA GTT ACT GAA AAG CCA GTG AAG AGT AGT AAA CCC CTG CAA TCG AAA   535
CAG CCG ACT CTG AGT GTG AAA AAG ATC ACC GAG AAG TCT ACT AAG ACA   583
CAA GGC TCT GCT CCT GCT CCT GAT GAT GCC TAC CCA GAA ATA GAA AAG   631
TTC TTC CCC TTC GAT CCT CTA GAT TTT GAG AGT TTT GAC CTG CCT GAA   679
GAG CAC CAG ATC TCA CTT CTC CCC TTG AAT GGA GTG CCT CTC ATG ATC   727
```

TABLE 3-continued

| Rat PTTG1 sequence | |
|---|---|
| CTG AAT GAA GAG AGG GGG CTT GAG AAG CTG CTG CAC CTG GAC CCC CCT | 775 |
| TCC CCT CTG CAG AAG CCC TTC CTA CCG TGG GAA TCT GAT CCG TTG CCG | 823 |
| TCT CCT CCC AGC GCC CTC TCC GCT CTG GAT GTT GAA TTG CCG CCT GTT | 871 |
| TGT TAC GAT GCA GAT ATT TAAACGTCTT ACTCCTTTAT AGTTTATGTA | 919 |
| AGTTGTATTA ATAAAGCATT TGTGTGTAAA AAAAAAAAAA AAAACTCGAG AGTAC | 974 |

The 3' coding region of rat PTTG includes the following 168-nucleotide sequence, which corresponds to nucleotide positions 722 through 889 of SEQ. ID. NO.:1, shown in Table 4 below.

TABLE 4

| Portion of 3' coding region of rat PTTG. | |
|---|---|
| (SEQ ID NO:18) | |
| ATG ATC CTG AAT GAA GAG AGG GGG CTT GAG AAG CTG CTG CAC CTG GAC | 48 |
| CCC CCT TCC CCT CTG CAG AAG CCC TTC CTA CCG TGG GAA TCT GAT CCG | 96 |
| TTG CCG TCT CCT CCC AGC GCC CTC TCC GCT CTG GAT GTT GAA TTG CCG | 144 |
| CCT GTT TGT TAC GAT GCA GAT ATT. | 168 |

Another useful example of a PTTG-specific coding sequence is a sequence that encodes a murine PTTG1 peptide, including nucleotide positions 304 through 891 of SEQ. ID. NO.:15 (Table 5 below).

TABLE 5

| Murine PTTG1 sequence. |
|---|
| (SEQ. ID. NO.:15) |
| 1 TCTTGAACTT GTTATGTAGC AGGAGGCCAA ATTTGAGCAT CCTCTTGGCT TCTCTTTATA |
| 61 GCAGAGATTG TAGGCTGGAG ACAGTTTTGA TGGGTGCCAA CATAAACTGA TTTCTGTAAG |
| 121 AGTTGAGTGT TTTATGACCC TGGCGTGCAG ATTTAGGATC TGGATTAAGC CTGTTGACTT |
| 181 CTCCAGCTAC TTATAAATTT TTGTGCATAG GTGCCCTGGG TAAAGCTTGG TCTCTGTTAC |
| 241 TGCGTAGTTT TTCCAGCCGT CTCAATGCCA ATATTCAGGC TCTCTCCCTT AGAGTAATCC |
| 301 AGAATGGCTA CTCTTATCTT TGTTGATAAG GATAATGAAG AACCCGGCCG CCGTTTGGCA |
| 361 TCTAAGGATG GGTTGAAGCT GGGCACTGGT GTCAAGGCCT TAGATGGGAA ATTGCAGGTT |
| 421 TCAACGCCTC GAGTCGGCAA AGTGTTCAAT GCTCCAGCCG TGCCTAAAGC CAGCAGAAAG |
| 481 GCTTTGGGGA CAGTCAACAG AGTTGCCGAA AAGCCTATGA AGACTGGCAA ACCCCTCCAA |
| 541 CCAAAACAGC CGACCTTGAC TGGGAAAAAG ATCACCGAGA AGTCTACTAA GACACAAAGC |
| 601 TCTGTTCCTG CTCCTGATGA TGCCTACCCA GAAATAGAAA AGTTCTTCCC TTTCAATCCT |
| 661 CTAGATTTTG ACCTGCCTGA GGAGCACCAG ATCTCACTTC TCCCCTTGAA TGGCGTGCCT |
| 721 CTCATCACCC TGAATGAAGA GAGAGGGCTG GAGAAGCTGC TGCATCTGGG CCCCCCTAGC |
| 781 CCTCTGAAGA CACCCTTTCT ATCATGGGAA TCTGATCCGC TGTACTCTCC TCCCAGTGCC |

TABLE 5-continued

Murine PTTG1 sequence.

841 CTCTCCACTC TGGATGTTGA ATTGCCGCCT GTTTGTTACG ATGCAGATAT TTAAACTTCT

901 TACTTCTTTG TAGTTTCTGT ATGTATGTTG TATTAATAAA GCATT.

The 3' coding region of murine PTTG1 includes the following 168-nucleotide sequence, which corresponds to nucleotide positions 724 through 891 of SEQ. ID. NO.:15, shown in Table 6 below.

TABLE 6

Portion of 3' coding region of murine *PTTG1*.

| | | | | | |
|---|---|---|---|---|---|
| ATCACCCTGA | ATGAAGAGAG | AGGGCTGGAG | AAGCTGCTGC | ATCTGGGCCC | CCCTAGCCCT   60 (SEQ ID. NO.:19). |
| CTGAAGACAC | CCTTTCTATC | ATGGGAATCT | GATCCGCTGT | ACTCTCCTCC | CAGTGCCCTC  120 |
| TCCACTCTGG | ATGTTGAATT | GCCGCCTGTT | TGTTACGATG | CAGATATT   | 168 |

Inventive PTTG-C-related polynucleotides having nucleotides sequences of SEQ. ID.NOS.:10, 18, or 19, degenerate coding sequences, or sequences complementary to any of these, are merely illustrative of useful PTTG carboxy-terminal-related polynucleotides. Other useful PTTG carboxy-terminal-related polynucleotides are functional fragments of any of SEQ. ID. NOS.:10, 18, or 19 at least about 45 contiguous nucleotides long, degenerate coding sequences, or sequences complementary to any of these, the presence of which in the cell can function to downregulate endogenous PTTG expression and/or PTTG function, which functionality can be determined by routine screening.

A human PTTG2 gene sequence (SEQ. ID. NO.:62; GenBank Accession AF116538.2) is shown in Table 6a below, as determined from genomic DNA (obtained by chromosome walking). Thus, another example of PTTG-specific coding sequence is the coding sequence for human PTTG2 protein, which begins at the transcription start site at nucleotide positions 383 through 385 of (SEQ. ID. NO.:62) and extends through the stop codon at nucleotide positions 956 through 958 of (SEQ. ID. NO.:62). This hPTTG2 coding sequence is underlined in Table 6a and defined herein as SEQ. ID. NO.:63.

TABLE 6a

Human PTTG2 gene sequence

|   |   |   |   |   |   |
|---|---|---|---|---|---|
|   1 | ataaattaga | aaatgcaata | acggcagaaa | tctttcttta | ttggttgctc (SEQ. ID. NO.:62) |
|  51 | tgcccttac  | ctaagtggtt | tttgaccatt | taacaatgtg | taagagttgg |
| 101 | gttttacctc | cattttatgg | atgtggaaat | agggcttgga | tgttagctaa |
| 151 | cttgcccaaa | tcttacagct | aacagaaagt | ggtactcccg | agattcctac |
| 201 | ccaggtttgt | ctgacctcag | gcctgtgctc | tttatatgag | ttcatgctaa |
| 251 | ctctcagatg | atgtgctagg | cacaaaaatt | agatattaca | ccaatttcca |
| 301 | ctatagttaa | cattctatct | aaatataaag | tgggaccacg | gtcttagatg |
| 351 | aatgtggctg | ttgagagcgg | caataatcca | ga<u>atggctac</u> | <u>tctgatctac</u> |
| 401 | <u>gttgataagg</u> | <u>aaattggaga</u> | <u>accaggcacc</u> | <u>cgtgtggctg</u> | <u>ccaaggatgt</u> |
| 451 | <u>gctgaagctg</u> | <u>gagtctagac</u> | <u>cttcaatcaa</u> | <u>agcattagat</u> | <u>gggatatctc</u> |
| 501 | <u>aagttttaac</u> | <u>accacgtttt</u> | <u>ggcaaaacat</u> | <u>acgatgctcc</u> | <u>atcagcctta</u> |
| 551 | <u>cctaaagcta</u> | <u>ccagaaaggc</u> | <u>tttgggcact</u> | <u>gtcaacagag</u> | <u>ctacagaaaa</u> |
| 601 | <u>gtcagtaaag</u> | <u>accaatggac</u> | <u>ccagaaaaca</u> | <u>aaaacagcca</u> | <u>agcttttctg</u> |
| 651 | <u>ccaaaaagat</u> | <u>gaccgagaag</u> | <u>actgttaaaa</u> | <u>caaaaagttc</u> | <u>tgttcctgcc</u> |
| 701 | <u>tcagatgacg</u> | <u>cctatccaga</u> | <u>aatagaaaaa</u> | <u>ttctttccct</u> | <u>tcaatcttct</u> |
| 751 | <u>agactttgag</u> | <u>agttttgacc</u> | <u>tgcctgaaga</u> | <u>gcgccagatt</u> | <u>gcacacctcc</u> |

TABLE 6a-continued

Human PTTG2 gene sequence

```
 801 ccttgagtgg agtgcctctc atgatccttg atgaggaggg agagcttgaa 851 aagctgtttc agctgggccc cccttcacct gtgaaaatgc cctctccacc 901 atgggaatgc aatctgtttg cagtctcctt caagcattct gtcgaccctg 951 gatgttgaat tgccagctgt ttgctatgac atagatattt aaatttctta 1001 gtgctttgga gtttgtgtgt acttgtatta ataaagcatt atttgtttaa 1051 caacataata aatacataaa tataaagtgg gtcatattcc tctttatgtg 1101 catctgtctc agctgtccct tgtttctata tttcttccat actacagccc 1151 gtactctttg gggatatgtc aacatgattt acttctgtag agaaacagga 1201 gacaggaaat agcaaaggat aaaggagaaa a//
```

As used herein, the term "degenerate" refers to codons that differ in at least one nucleotide from a reference nucleic acid, e.g., SEQ ID NOS:1, 3, 10, 15, 18, 19, 62, or 63, but encode the same amino acids as the reference nucleic acid. For example, codons specified by the triplets "UCU", "UCC", "UCA", and "UCG" are degenerate with respect to each other since all four of these codons encode the amino acid serine. Thus, for example, a polynucleotide that encodes the same amino acid sequence as SEQ. ID. NO.:64, is said to have a degenerate sequence with respect to hPTTG2 coding sequence SEQ. ID. NO.:63.

Other useful PTTG-C-related polynucleotides include nucleic acids or other polynucleotides, that differ in sequence from the sequences shown in SEQ ID NO:1, SEQ. ID. NO.:3, SEQ. ID. NO.:10, SEQ. ID. NO.:15, SEQ. ID. NO.:18, or SEQ. ID. NO.:19, but which when expressed in a cell, result in the same phenotype. Phenotypically similar nucleic acids are also referred to as "functionally equivalent nucleic acids". As used herein, the phrase "functionally equivalent nucleic acids" encompasses nucleic acids characterized by slight and non-consequential sequence variations that will function in substantially the same manner, compared to any of the detailed nucleotide sequences disclosed herein, to produce PTTG protein functional with respect to inducing neoplastic cellular proliferation and/or transformation, or PTTG-C peptide(s) functional with respect to inhibition of neoplastic cellular proliferation and/ or transformation, and/or polypeptide products functional with respect to immunogenicity. Such polynucleotides can have substantially the same coding sequences as the reference sequences, encoding the amino acid sequence as set forth in SEQ. ID. NO.:2, SEQ. ID. NO.:4, SEQ. ID. NO.:9, SEQ. ID. NO:14, SEQ. ID. NO.:16, or SEQ. ID. NO.:17 or a larger amino acid sequence including SEQ. ID. NO.:2, SEQ. ID. NO.:4, SEQ. ID. NO.:9, SEQ. ID. NO.:14, SEQ. ID. NO.:16, or SEQ. ID. NO.:17.

Other useful PTTG2-encoding polynucleotides include nucleic acids or other polynucleotides, that encode: (A) a peptide consisting essentially of amino acid residues 1–191 of (SEQ. ID. NO.:64) or a functional fragment thereof comprising at least amino acid residues 1–180 of (SEQ. ID. NO.:64); or (B) a mammalian PTTG2 peptide having at least about 95% sequence homology with any of (A), and which when expressed in a cell, result in the same phenotype with respect to inhibition of neoplastic cellular proliferation and/ or transformation. This includes polynucleotides that encode peptides consisting essentially of consecutive amino acid residues 1–180 of SEQ. ID. NO.:64, 1–181 of SEQ. ID. NO.:64, 1–182 of SEQ. ID. NO.:64, 1–183 of SEQ. ID. NO.:64, 1–184 of SEQ. ID. NO.:64, 1–185 of SEQ. ID. NO.:64, 1–186 of SEQ. ID. NO.:64, 1–187 of SEQ. ID. NO.:64, 1–188 of SEQ. ID. NO.:64, 1–189 of SEQ. ID. NO.:64, and 1–190 of SEQ. ID. NO.:64.

As employed herein, the term "substantially the same nucleotide sequence" refers to DNA having sufficient identity to the reference polynucleotide, such that it will hybridize to the reference nucleotide under moderately stringent hybridization conditions. In other embodiments, DNA having "substantially the same nucleotide sequence" as the reference nucleotide sequence has at least about 60% identity with respect to the reference nucleotide sequence. DNA having at least 70%, more preferably at least 90%, yet more preferably at least about 95% identity to the reference nucleotide sequence is preferred.

In preferred embodiments, functionally equivalent nucleic acids encode polypeptides or peptide fragments that are the same as those disclosed herein or that have conservative amino acid variations, or that encode larger polypeptides that include SEQ. ID. NO.:2, SEQ. ID. NO.:4, SEQ. ID. NO.:9, or SEQ. ID. NO.:14, SEQ. ID. NO.:16, SEQ. ID. NO.:17 or SEQ. ID. NO.:64, or fragments of any of these that are biologically functional fragments with respect to inhibiting neoplastic cellular proliferation and/or transformation, in accordance with embodiments of the inventive method. For example, conservative variations include substitution of a non-polar residue with another non-polar residue, or substitution of a charged residue with a similarly charged residue. These variations include those recognized by skilled artisans as those that do not substantially alter the tertiary structure of the protein.

Useful polynucleotides can be produced by a variety of methods well-known in the art, e.g., by employing PCR and other similar amplification techniques, using oligonucleotide primers specific to various regions of SEQ ID NOS:1, 3, 10, 15, 18, 19, 62, 63, or to functionally equivalent polynucleotide sequences. Other synthetic methods for producing polynucleotides or oligonucleotides of various lengths are also well known.

In accordance with embodiments of the inventive method, preferred polynucleotides hybridize under moderately stringent, preferably high stringency, conditions to substantially the entire sequence, or substantial portions (i.e., typically at least 15–30 nucleotide) of the nucleic acid sequence set forth in SEQ ID NOS:1, 3, 10, 15, 18, 19, 62, 63, 65, 66, or 68, or to complementary sequences.

The phrase "stringent hybridization" is used herein to refer to conditions under which annealed hybrids, or at least partially annealed hybrids, of polynucleic acids or other polynucleotides are stable. As known to those of skill in the art, the stability of hybrids is reflected in the melting temperature ($T_m$) of the hybrids. In general, the stability of a hybrid is a function of sodium ion concentration and temperature. Typically, the hybridization reaction is performed under conditions of relatively low stringency, followed by washes of varying, but higher, stringency. Reference to hybridization stringency relates to such washing conditions.

As used herein, the phrase "moderately stringent hybridization" refers to conditions that permit target-DNA to bind a complementary nucleic acid that has about 60% sequence identity or homology, preferably about 75% identity, more preferably about 85% identity to the target DNA; with greater than about 90% identity to target-DNA being especially preferred. Preferably, moderately stringent conditions are conditions equivalent to hybridization in 50% formamide, 5×Denhart's solution, 5×SSPE, 0.2% SDS at 42° C., followed by washing in 0.2×SSPE, 0.2% SDS, at 65° C.

The phrase "high stringency hybridization" refers to conditions that permit hybridization of only those nucleic acid sequences that form stable hybrids in 0.018 M NaCl at 65° C. (i.e., if a hybrid is not stable in 0.018 M NaCl at 65° C., it will not be stable under high stringency conditions, as contemplated herein). High stringency conditions can be provided, for example, by hybridization in 50% formamide, 5× Denhart's solution, 5×SSPE, 0.2% SDS at 42° C., followed by washing in 0.1×SSPE, and 0.1% SDS at 65° C.

The phrase "low stringency hybridization" refers to conditions equivalent to hybridization in 10% formamide, 5× Denhart's solution, 6×SSPE, 0.2% SDS at 42° C., followed by washing in 1×SSPE, 0.2% SDS, at 50° C. Denhart's solution and SSPE (see, e.g., Sambrook et al., *Molecular Cloning, A Laboratory Manual*, Cold Spring Harbor Laboratory Press [1989]) are well known to those of skill in the art as are other suitable hybridization buffers.

The PTTG carboxy-terminal-related or PTTG-encoding polynucleotide can be, but is not necessarily, of homologous origin with respect to the cell, due to the relatively high degree of sequence homology among mammalian PTTG sequences. PTTG carboxy-terminal-related polynucleotides or PTTG2-encoding polynucleotides of heterologous mammalian origin with respect to the cell are also useful. Thus, for example, in accordance with the inventive method, a human PTTG-C-encoding or PTTG2-encoding sequence functions to down regulate endogenous PTTG expression and/or PTTG function in cells of non-human mammalian origin, such as murine or rat cells, and vice versa.

In preferred embodiments of the method of inhibiting neoplastic cellular proliferation and/or transformation of a mammalian cell, the polynucleotide is complexed with a cellular uptake-enhancing agent, in an amount and under conditions sufficient to enter the cell. An "uptake-enhancing" agent, as utilized herein, means a composition of matter for enhancing the uptake of exogenous polynucleotides, such as DNA segment(s), nucleic acid analogs, or nucleic acid constructs, into a eukaryotic cell, preferably a mammalian cell, and more preferably a human cell. The enhancement is measured relative to the polynucleotide uptake in the absence of the uptake-enhancing agent, in the process of transfecting or transducing the cell. Complexation with uptake-enhancing agent(s) generally augments the uptake of a polynucleotide into the cell and/or reduces its breakdown by nucleases during its passage through the cytoplasm.

In accordance with preferred embodiments of the inventive method, PTTG carboxy-terminal-related polynucleotides or PTTG-C peptides or PTTG2-encoding polynucleotides or PTTG2 peptides are complexed with an uptake-enhancing agent. "Complexed" means that the polynucleotide or peptide is a constituent or member of a complex, mixture, or adduct resulting from chemical binding or bonding between and/or among the other constituents, including the cellular uptake-enhancing agent(s), and/or their moieties. Chemical binding or bonding can have the nature of a covalent bond, ionic bond, hydrogen bond, hydrophobic bond, or any combination of these bonding types linking the constituents of the complex at any of their parts or moieties, of which a constituent can have one or a multiplicity of moieties of various sorts. Not every constituent of a complex need be bound to every other constituent, but each constituent has at least one chemical bond with at least one other constituent of the complex. Constituents can include, but are not limited to, molecular compounds of a polar, non-polar, or detergent character; ions, including cations, such as, but not limited to, $Na^+$, $K^+$, $Li^+$, $Ca^{2+}$, $Mg^{2+}$, $Fe^{2+}$, $Fe^{3+}$, $Zn^{2+}$, $Cu^+$, $Cu^{2+}$, and/or $NH_4^+$, or anions, such as, but not limited to $Cl^-$, $Br^-$, $Fl^-$, $NO_3^-$, $NO_2^-$, $NO^-$, $HCO_3^-$, $CO_3^{2-}$, $SO_4^{2-}$, and/or $PO_4^{3-}$; biological molecules, such as proteins, oligopeptides, polypeptides, oligonucleotides, nucleic acids, nucleic acid constructs, plasmids, viral particles; an/or organic polymers and co-polymers.

PTTG carboxy-terminal-related polynucleotides or PTTG-C peptides or PTTG2-encoding polynucleotides or PTTG2 peptides can be, but are not necessarily, directly bound to the cellular uptake-enhancing agent. For example, the polynucleotide can be contained in an expression vector or other nucleic acid construct, which vector or other construct is bound to the uptake-enhancing agent at some moiety or part of he vector or construct not directly linked to the PTTG carboxy-terminal-related or PTTG2-encoding polynucleotide; for purposes of the present invention, the PTTG carboxy-terminal-related or PTTG2-encoding polynucleotide is still "complexed" with the uptake-enhancing agent, although not being directly bound to the uptake-enhancing agent by a chemical bond. As long as the polynucleotide and the uptake enhancing agent are both constituents or members of the same complex, an indirect chemical linkage suffices. An example with respect to PTTG-C or PTTG2 peptides, is an intervening third peptide sequence linking a first PTTG-C peptide segment or PTTG2 peptide segment with a second cell uptake-enhancing and/or importation-competent peptide segment. The first and second peptide segments, indirectly linked, are "complexed" for purposes of the invention.

Examples of uptake-enhancing agents usefully complexed with the polynucleotide include cationic or polycationic lipids, which can form cationic or polycationic lipid-DNA or liposome-DNA complexes ("lipoplexes"). Such lipoplexes can, optionally, also be coated with serum albumin or formulated as large-sized colloidally unstable complexes to further enhance transfection efficiency; the presence of calcium di-cations ($Ca^{2+}$) can also enhance lipid-based transfection efficiency. (E.g., Simoes, S. et al., *Human serum albumin enhances DNA transfection by lipoplexes and confers resistance to inhibition by serum*, Biochim. Biophys. Acta 1463(2):459–69 [2000]; Turek, J. et al., *Formulations which increase the size of lipoplexes prevent serum-associated inhibition of transfection*, J. Gene Med.

2(1):32–40 [2000]; Zudam, N. J. et al., *Lamellarity of cationic liposomes and mode of preparation of lipoplexes affect transfection efficiency*, Biochim. Biophys. Acta 1419 (2):207–20 [1999]; Lam, A. M. and Cullis, P. R., *Calcium enhances the transfection potency of plasmid DNA-cationic liposome complexes*, Biochim. Biophys. Acta 1463(2) :279–290 [2000]).

Inventive compositions can include negatively charged ternary complexes of cationic liposomes, transferrin or fusigenic peptide(s)or poly(ethylenimine). (E.g., Simoes, S. et al., *Gene delivery by negatively charged ternary complexes of DNA, cationic liposomes and transferrin or fusigenic peptides*, Gene Ther. 5(7):955–64 [1998]). Liposomal uptake-enhancing agents complexed with inventive polynucleotide(s) can also be encapsulated in polyethylene glycol (PEG), FuGENE6, or the like. (E.g., Saravolac, E. G., et al., *Encapsulation of plasmid DNA in stabilized plasmid-lipid particles composed of different cationic lipid concentration for optimal transfection activity*, J. Drug Target 7(6):423–37 [2000]; Yu, R. Z. et al., *Pharmacokinetics and tissue disposition in monkeys of an antisense oligonucleotide inhibitor of Ha-ras encapsulated in stealth liposomes*, Pharm. Res. 16(8):1309–15 [1999]; Tao, M. et al., *Specific inhibition of human telomerase activity by transfection reagent, FuGENE6-antisense phophorothioate oligonucleotide complex in HeLa cells*, FEBS Lett 454(3):312–6 [1999]).

In some embodiments, the uptake of antisense oligonucleotides is also enhanced by complexation with biocompatible polymeric or co-polymeric nanoparticles, for example, comprising alginate, aminoalkylmethacrylate, methylmethacrylate, polymethylmethacrylate, methylaminoethyl-methacrylate, polyalkylcyanoacrylate (e.g., polyhexylcyanoacrylate), or the like. (E.g., Aynie, I. et al., *Spongelike alginate nanoparticles as a new potential system for the delivery of antisense oligonucleotides*, Antisense Nucleic Acid Drug Dev. 9(3):301–12 [1999]; Zimmer, A., *Antisense oligonucleotide delivery with polyhexylcyanoacrylate nanoparticles as carriers*, Methods 18(3) :286–95, 322 [1999]; Berton, M. et al., *Highly loaded nanoparticulate carrier using an hydrophobic antisense oligonucleotide complex*, Eur. J. Pharm. Sci. 9(2): 163–70 [1999]; Zobel, H. P. et al., *Evaluation of aminoalkylmethacrylate nanoparticles as colloidal drug carrier systems. Part II: characterization of antisense oligonucleotides loaded copolymer nanoparticles*, Eur. J. Pharm. Biopharm. 48(1):1–12 [1999]; Fattal, E. et al., *Biodegradable polyalkylcyanoacrylate nanoparticles for the delivery of oligonucleotides*, J. Controlled Release 53(1–3):137–43 [1998]).

Other useful uptake-enhancing agents for complexing with polynucleotides include starburst polyamidoamine (PAMAM) dendrimers. (E.g., Yoo, H. et al., *PAMAM dendrimers as delivery agents for antisense oligonucleotides*, Pharm. Res. 16(12):1799–804 [1999]; Bielinska, A. U. et al., *Application of membrane-based dendrimer/DNA complexes for solid phase transfection in vitro and in vivo*, Biomaterials 21(9):877–87 [2000]; Bielinska, A. U. et al., *DNA complexing with polyamidoamine dendrimers: implications for transfection*, Bioconjug. Chem. 10(5):843–50 [1999]; Bielinska, A. U. et al., *Regulation of in vitro gene expression using antisense oligonucleotides or antisense expression plasmids transfected using starburst PAMAM dendrimers*, Nucleic Acid Res. 24(11):2176–82 [1996]; Kukowska-Latallo, J. F. et al., *Efficient transfer of genetic material into mammalian cells using Starburst polyamidoamine dendrimers*, Proc. Natl. Acad. Sci. USA 93(10):4897–902 [1996]; Delong, R. et al., *Characterization of complexes of oligonucleotides with polyamidoamine starburst dendrimers and effects on intracellular delivery*, J. Pharm. Sci. 86(6) :762–64 [1997]).

Other preferred uptake-enhancing agents include lipofectin, lipfectamine, DIMRIE C, Superfect, Effectin (Qiagen), unifectin, maxifectin, DOTMA, DOGS (Transfectam; dioctadecylamidoglycylspermine), DOPE (1,2-dioleoyl-sn-glycero-3-phosphoethanolamine), DOTAP (1,2-dioleoyl-3-trimethylammonium propane), DDAB (dimethyl dioctadecylammonium bromide), DHDEAB (N,N-di-n-hexadecyl-N,N-dihydroxyethyl ammonium bromide), HDEAB (N-n-hexadecyl-N,N-dihydroxyethylammonium bromide), polybrene, or poly (ethylenimine) (PEI), and/or peptides, such as polylysine, protamine, pK17, peptide K8, and peptide p2. (E.g., Ferkol, Jr. et. al., U.S. Pat. Nos., 5,972,900 and 5,972,901; Vaysse, L. and Arveiler, B., *Transfection using synthetic peptides: comparison of three DNA-compacting peptides and effect of centrifugation*, Biochim. Biophys. Acta 1474(2):244–50 [2000]; Ni, Y. H. et al., *Protamine enhance the efficiency of liposome-mediated gene transfer in a cultured human hepatoma cell line*, J. Formos. Med. Assoc. 98(8):562–66 [1999]; Banerjee, R. et al., *Novel series of non-glycerol-based cationic transfection lipids for use in liposomal gene delivery*, J. Med. Chem. 42(21):4292–99 [1999]; Godbey, W. T. et al., *Improved packing of poly(ethylenimine)/DNA complexes increases transfection efficiency*, Gene Ther. 6(8): 1380–88 [1999]; Kichler, A et al., *Influence of the DNA complexation medium on the transfection efficiency of lipospermine/DNA particles*, Gene Ther. 5(6):855–60 [1998]; Birchaa, J. C. et al., *Physico-chemical characterisation and transfection efficiency of lipid-based gene delivery complexes*, Int. J. Pharm. 183(2): 195–207 [1999]). These non-viral cellular uptake-enhancing agents have the advantage that they facilitate stable integration of xenogeneic DNA sequences into the vertebrate genome, without size restrictions commonly associated with virus-derived transfecting or transducing agents.

Another example, a viral cellular uptake-enhancing agent, is the adenovirus enhanced transferrin-polylysine-mediated gene delivery system has been described and patented by Curiel et al. (Curiel D. T., et al., *Adenovirus enhancement of transferrin-polylysine-mediated gene delivery*, PNAS USA 88: 8850–8854 (1991). The delivery of DNA depends upon endocytosis mediated by the transferrin receptor (Wagner et al., *Transferrin-polycation conjugates as carriers for DNA uptake into cells*, PNAS (USA) 87: 3410–3414 (1990). In addition this method relies on the capacity of adenoviruses to disrupt cell vesicles, such as endosomes and release the contents entrapped therein. This system can enhance the gene delivery to mammalian cells by as much as 2,000 fold over other methods.

A particularly useful uptake enhancing agent for delivery of polynucleotides to human T-lymphocytes is a "tamed" (i.e., lacking native viral genes required for immunodeficiency pathogenesis and/or virulence) Human Immunodeficiency Virus (HIV) vector, which mediates uptake via the CD4 molecule. A variety of such tamed viral vectors, binding with CD4 and/or with other T-lymphocyte markers, are also known in the art.

The amount of each component of the composition is chosen so that the gene modification, e.g., by transfection or transduction, of a mammalian cell is optimized. Such optimization requires no more than routine experimentation. The ratio of polynucleotide to lipid is broad, preferably about 1:1, although other effective proportions can also be utilized depending on the type of lipid uptake-enhancing agent and polynucleotide utilized. (E.g., Banerjee, R. et al. [1999], Jaaskelainen, I. et al., *A lipid carrier with a membrane active component and a small complex size are required for efficient cellular delivery of anti-sense phosphorothioate oligonucleotides*, Eur. J. Pharm. Sci. 10(3):187–193 [2000], Sakurai, F. et al., *Effect of DNA/liposome mixing ratio on the physicochemical characteristics, cellular uptake and intracellular trafficking of plasmid DNA/ cationic liposome complexes and subsequent gene expression*, J. Controlled Release 66(2–3):255–69 [2000]).

A suitable amount of the inventive polynucleotide to be delivered to the cells, in accordance with the method, preferably ranges from about 0.1 nanograms to about 1 milligram per gram of tumor tissue, in vivo, or about 0.1 nanograms to about 1 microgram per 5000 cells, in vitro. Suitable amounts for particular varieties of PTTG-C-related polynucleotides or PTTG2-encoding polynucleotides and/or cell types and/or for various mammalian subjects undergoing treatment, can be determined by routine experimentation. For example, malignant cell lines, such as MCF-7 or HeLa, typically are more efficiently transfected by the inventive PTTG-C-related polynucleotides than non-malignant cell lines. Also, those skilled in the art are aware that there is typically considerable variability among individual cancer patients to any single treatment regimen, therefore, the practitioner will tailor any embodiment of the inventive method to each individual patient as appropriate.

In some preferred embodiments, the polynucleotide can be delivered into the mammalian cell, either in vivo or in vitro using suitable expression vectors well-known in the art (e.g., retroviral vectors, such as lentiviral vectors, or adenovirus vectors, and the like). (See, e.g., Anderson, W. F., *Gene therapy scores against cancer*, Nat. Med. 6(8):862–63 [2000]). In addition, to inhibit the in vivo expression of PTTG, the introduction by expression vector of the antisense strand of a DNA encoding a PTTG-C peptide is contemplated.

Suitable expression vectors are well-known in the art, and include vectors capable of expressing DNA operatively linked to a regulatory sequence, such as a promoter region that is capable of regulating expression of such DNA. Thus, an expression vector refers to a recombinant DNA or RNA construct, such as a plasmid, a phage, recombinant virus or other vector that, upon introduction into an appropriate host cell, results in expression of the inserted DNA. Appropriate expression vectors are well known to those of skill in the art and include those that are replicable in eukaryotic cells and/or prokaryotic cells and those that remain episomal or those which integrate into the host cell genome.

Exemplary, eukaryotic expression vectors, include the cloned bovine papilloma virus genome, the cloned genomes of the murine retroviruses, and eukaryotic cassettes, such as the pSV-2 gpt system (described by Mulligan and Berg, 1979, Nature Vol. 277:108–114) the Okayama-Berg cloning system (Mol. Cell Biol. Vol. 2:161–170, 1982), pGAL4, pCI (e.g., pCI-neo), and the expression cloning vector described by Genetics Institute (Science Vol. 228:810–815, 1985), are available which provide substantial assurance of at least some expression of the protein of interest in the transformed mammalian cell.

Particularly preferred are vectors which contain regulatory elements that can be linked to the inventive PTTG-encoding DNAs, such as a PTTG-C-encoding DNA segment or PTTG2-encoding DNA segment, for transfection of mammalian cells. Examples are cytomegalovirus (CMV) promoter-based vectors such as pcDNA1 (Invitrogen, San Diego, Calif.), MMTV promoter-based vectors such as pMAMNeo (Clontech, Palo Alto, Calif.) and pMSG (Pharmacia, Piscataway, N.J.), and SV40 promoter-based vectors such as pSVβ (Clontech, Palo Alto, Calif.).

In one embodiment of the present invention, adenovirus-transferrin/polylysine-DNA (TfAdpl-DNA) vector complexes (Wagner et al., 1992, PNAS, USA, 89:6099–6103; Curiel et al., 1992, Hum. Gene Therapy, 3:147–154; Gao et al., 1993, Hum. Gene Ther., 4:14–24) are employed to transduce mammalian cells with heterologous PTTG-specific nucleic acid. Any of the plasmid expression vectors described herein may be employed in a TfAdpl-DNA complex.

In addition, vectors may contain appropriate packaging signals that enable the vector to be packaged by a number of viral virions, e.g., retroviruses, herpes viruses, adenoviruses, resulting in the formation of a "viral vector."

"Virus", as used herein, means any virus, or transfecting fragment thereof, which can facilitate the delivery of the polynucleotide into mammalian cells. Examples of viruses which are suitable for use herein are adenoviruses, adeno-associated viruses, retroviruses such as human immunedeficiency virus, lentiviruses, mumps virus, and transfecting fragments of any of these viruses, and other viral DNA segments that facilitate the uptake of the desired DNA segment by, and release into, the cytoplasm of germ cells and mixtures thereof A preferred viral vector is Moloney murine leukemia virus and the retrovirus vector derived from Moloney virus called vesicular-stomatitis-virus-glycoprotein (VSV-G)-Moloney murine leukemia virus. A most preferred viral vector is a pseudotyped (VSV-G) lentiviral vector derived from the HIV virus. (Naldini et al. [1996]). Also, the mumps virus is particularly suited because of its affinity for immature sperm cells including spermatogonia. All of the above viruses may require modification to render them non-pathogenic or less antigenic. Other known viral vector systems, however, are also useful within the confines of the invention.

Viral based systems provide the advantage of being able to introduce relatively high levels of the heterologous nucleic acid into a variety of cells. Suitable viral vectors for introducing inventive PTTG-specific polynucleotides into mammalian cells (e.g., vascular tissue segments) are well known in the art. These viral vectors include, for example, Herpes simplex virus vectors (e.g., Geller et al., 1988, Science, 241:1667–1669), Vaccinia virus vectors (e.g., Piccini et al., 1987, Meth. in Enzymology, 153:545–563); Cytomegalovirus vectors (Mocarski et al., in *Viral Vectors*, Y. Gluzman and S. H. Hughes, Eds., Cold Spring Harbor Laboratory, Cold Spring Harbor, N.Y., 1988, pp. 78–84), Moloney murine leukemia virus vectors (Danos et al., 1980, PNAS, USA, 85:6469), adenovirus vectors (e.g., Logan et al., 1984, PNAS, USA, 81:3655–3659; Jones et al., 1979, Cell, 17:683–689; Berkner, 1988, Biotechniques, 6:616–626; Cotten et al., 1992, PNAS, USA, 89:6094–6098; Graham et al., 1991, Meth. Mol. Biol., 7:109–127), adeno-associated virus vectors, retrovirus vectors (see, e.g., U.S. Pat. Nos. 4,405,712 and 4,650,764), and the like. Especially preferred viral vectors are the adenovirus and retroviral vectors.

As used herein, "retroviral vector" refers to the well-known gene transfer plasmids that have an expression cassette encoding an heterologous gene residing between two retroviral LTRs. Retroviral vectors typically contain appropriate packaging signals that enable the retroviral vector, or RNA transcribed using the retroviral vector as a template, to be packaged into a viral virion in an appropriate packaging cell line (see, e.g., U.S. Pat. No. 4,650,764). Retroviral vectors include lentiviral vectors, such as HIV-derived vectors.

Suitable retroviral vectors for use herein are described, for example, in U.S. Pat. Nos. 5,252,479, and in WIPO publications WO 92/07573, WO 90/06997, WO 89/05345, WO 92/05266 and WO 92/14829, incorporated herein by reference, which provide a description of methods for efficiently introducing nucleic acids into human cells using such retroviral vectors. Other retroviral vectors include, for example, the mouse mammary tumor virus vectors (e.g., Shackleford et al., 1988, PNAS, USA, 85:9655–9659), and the like.

A most preferred embodiment employs a pseudotyped retroviral vector system, which was developed for gene therapy. (Naldini, L., et al., *In vivo gene delivery and stable transduction of nondividing cells by a lentiviral vector*, Science 272: 263–267 [1996]), and which is used to transduce mammalian cells. This gene delivery system employs retroviral particles generated by a three-plasmid expression system. In this system a packaging construct contains the human cytomegalovirus (hCMV) immediate early promoter, driving the expression of all viral proteins. The construct's design eliminates the cis-acting sequences crucial for viral packaging, reverse transcription and integration of these transcripts. The second plasmid encodes a heterologous envelope protein (env), namely the G glycoprotein of the vesicular stomatitis virus (VSV-G). The third plasmid, the transducing vector (pHR'), contains cis-acting sequences of human immunodeficiency virus (HIV) required for packaging, reverse transcription and integration, as well as unique restriction sites for cloning heterologous complementary DNAs (cDNAs). For example, a genetic selection marker, such as green fluorescent protein (GFP), enhanced green fluorescent protein (EGFP), blue fluorescent protein, yellow fluorescent protein, β-galactosidase, and/or a gene encoding another preselected product is cloned downstream of the hCMV promoter in the HR'vector, and is operatively linked so as to form a transcriptional unit. A VSV-G pseudotyped retroviral vector system is capable of infecting a wide variety of cells including cells from different species and of integrating into the genome. Some retroviruses, i.e., lentiviruses, such as HIV, have the ability to infect non-dividing cells. Lentiviruses have a limited capacity for heterologous DNA sequences, the size limit for this vector being 7–7.5 kilobases (Verma, I. M. and Somia, N., *Gene Therapy—promises, problems and prospects*, Nature 389:239–242 [1997]). In vivo experiments with lentiviruses show that expression does not shut off like other retroviral vectors and that in vivo expression in brain, muscle, liver or pancreatic-islet cells, is sustained at least for over six months—the longest time tested so far (Verma and Somia [1997]; Anderson, W F., *Human Gene Therapy*, Nature (Suppl). 392:25–30 [1998]).

"Gene delivery (or transfection) mixture", in the context of this patent, means a selected PTTG carboxy-terminal-related polynucleotide, whether in sense or anti-sense orientation, together with an appropriate vector mixed, for example, with an effective amount of uptake-enhancing agent as described above. (E.g., Clark et al., *Polycations and cationic lipids enhance adenovirus transduction and transgene expression in tumor cells*, Cancer Gene Ther. 6(5):437–46 [1999]). For example, the efficiency of adenoviral-, retroviral-, or lentiviral-mediated transduction is enhanced significantly by including a cationic lipid, such as polybrene during the infection.

In some peptide-based embodiments of the inventive method of inhibiting neoplastic cellular proliferation and/or transformation, involves delivering an inventive composition comprising a PTTG carboxy-terminal peptide, which is interchangeably designated herein "PTTG-C" or "PTTG1-C" or "PTTG C-terminal peptide".

In other peptide-based embodiments a PTTG2 peptide, as further described herein, is delivered.

The terms "protein", "peptide", and "polypeptide" are used interchangeably herein. As used herein, the phrase "PTTG" refers to protein member of a mammalian family of PTTG proteins, formerly also known as "pituitary-tumor-specific-gene" (PTSG) proteins.

In vivo, PTTG1 proteins are further characterized by having the ability to induce tumor formation, for example, in nude mice (e.g., when transfected into NIH 3T3 and the like). PTTG proteins include naturally occurring allelic variants thereof encoded by mRNA generated by alternative splicing of a primary transcript, and further include fragments thereof which retain at least one native biological activity.

The term "biologically active" or "functional", when used herein as a modifier of inventive PTTG protein(s), peptide (s), or fragments thereof, refers to a polypeptide that exhibits at least one of the functional characteristics attributed to PTTG. For example, one biological activity of PTTG1 is the ability to transform cells in vitro (e.g., NIH 3T3 and the like). Another biological activity of PTTG1 is the ability to modulate the activation of mammalian T-lymphocytes, as described herein. Yet another biological activity of PTTG1 is the ability to induce neoplastic cellular proliferation (e.g., tumorigenesis) in nude mice (e.g., when transfected into NIH 3T3 cells and the like).

On the other hand, the inventive PTTG-C peptide, as distinct from the full length native PTTG protein, and PTTG2 peptides, as first disclosed herein, have the biological activity of inhibiting PTTG1-mediated transactivation and tumorigenesis in a dominant negative manner. "Dominant negative" is commonly used to describe a gene or protein which has a dominant effect similar to that described genetically, e.g., one copy of the gene gives a mutant phenotypic effect, and a negative effect in that it prevents or has a negative impact on a biological process such as a signal transduction pathway. Thus, PTTG carboxy-terminal peptides and PTTG2 peptides have the ability to downregulate intracellular PTTG1 expression and/or endogenous PTTG1 function.

The inventive method is not limited to any particular biochemical, genetic, and/or physiological mechanism(s) by which a PTTG-C or PTTG2 peptide exerts its biological activity on PTTG1 expression and/or PTTG1 function, and any or all such mechanism(s) can contribute to the biological activity of PTTG-C or PTTG2, in accordance with the invention.

Another biological activity of PTTG peptides or PTTG-C peptides is the ability to act as an immunogen for the production of polyclonal and monoclonal antibodies that bind specifically to a PTTG and/or PTTG-C. Thus, an inventive nucleic acid encoding a PTTG or a PTTG-C will encode a polypeptide specifically recognized by an antibody that also specifically recognizes (i.e., specifically binds) a particular PTTG protein as described herein. Such activity may be assayed by any method known to those of skill in the art. For example, a test-polypeptide encoded by a PTTG cDNA can be used to produce antibodies, which are then assayed for their ability to bind to the protein. If the antibody binds to the test-polypeptide and the protein with substantially the same affinity, then the polypeptide possesses the requisite biological activity with respect to immunogenicity.

In accordance with some embodiments of the inventive method of inhibiting neoplastic cellular proliferation and/or transformation of a mammalian breast or ovarian cell, whether in vitro or in vivo, useful PTTG-C peptides encompass also any fragment of a larger PTTG-C molecule, which fragment retains PTTG-C biological activity with respect to downregulating endogenous PTTG1 expression and/or endogenous PTTG1 function. Useful PTTG-C peptides are preferably, but not exclusively, about 15 to about 60 contiguous amino acid residues long and comprise one or more proline-rich regions, which are peptide segments having a PXXP motif, where the Xs between the proline (P) residues represent any amino acid residue, including proline. The proline-rich region(s) of the PTTG-C peptide is a potential SH3-binding site.

SH3 binding sites of PTTG1 protein molecules are useful targets for inhibiting intracellular PTTG1 expression and/or PTTG1 protein function. Downregulation or inhibition of intracellular PTTG1 expression and/or endogenous PTTG1 function can be accomplished by blocking specific binding to a SH3-binding site normally present on endogenous PTTG1 protein molecules, thus interfering with SH3-mediated signal transduction in the cell.

Most preferably, the PTTG-C peptide is derived from a human PTTG that is designated "hPTTG1" or "PTTG1" protein. The native human PTTG1 protein is 202 amino acids long, having the following amino acid sequence (Table 7 below; encoded by nucleotide positions 95 through 700 of human PTTG1 sequence SEQ. ID.NO.:3 and degenerate sequences). Other mammalian PTTG molecules sharing the biological activities of hPTTG1, for example rat PTTG and murine PTTG, are also considered to be in the category of PTTG1 proteins.

TABLE 7 hPTTG1 amino acid sequence.

| | | | | | |
|---|---|---|---|---|---|
| 1 | MATLIYVDKE | NGEPGTRVVA | KDGLKLGSGP | SIKALDGRSQ | VSTPRFGKTF (SEQ. ID. NO.:4) |
| 51 | DAPPALPKAT | RKALGTVNRA | TEKSVKTKGP | LKQKQPSFSA | KKMTEKTVKA |
| 101 | KSSVPASDDA | YPEIEKFFPF | NPLDFESFDL | PEEHQIAHLP | LSGVPLMILD |
| 151 | EERELEKLFQ | LGPPSPVKMP | SPPWESNLLQ | SPSSILSTLD | VELPPVCCDI |
| 201 | DI | | | | |

The human PTTG1 peptide is also encoded by any degenerate coding sequence encoding the amino acid sequence of SEQ. ID. NO.:4.

A preferred PTTG-C has the amino acid sequence corresponding to amino acid residues 147 through 202 of SEQ. ID. NO.:4 (Table 8 below; encoded by nucleotide positions 533 through 700 of SEQ. ID. NO.:3 or 1–168 of SEQ. ID. NO. :10 and degenerate sequences).

TABLE 8

Human PTTG-C amino acid sequence.

MILDEERELE KLFQLGPPSP VKMPSPPWES NLLQSPSSIL STLDVELPPV CCDIDI.   (SEQ. ID. NO.:9)

There are at least two proline-rich regions between amino acid residues 163–173 of SEQ. ID. NO.:4, which correspond to amino acid residues 17 through 27 of SEQ. ID. NO.:9, encoded by nucleotides 49 through 81 of SEQ. ID. NO.:10 and degenerate sequences. Proline-rich regions are found at amino acid residues 163–167 and 170–173 of SEQ. ID. NO.:4, corresponding to amino acid residues17–20 and 24–27 of SEQ. ID. NO.:9. Other useful smaller peptide fragments of SEQ. ID. NO.:9 are tested by routine means for their effectiveness in inhibiting neoplastic cellular proliferation and/or transformation of a cell.

Another example of a PTTG protein is a rat PTTG having the following amino acid sequence (Table 9 below; encoded by nucleotide positions 293–889 of SEQ. ID. NO.:1 and degenerate sequences).

TABLE 9

Rat PTTG amino acid sequence.

| | | | | | | | | | | | | | | | | |
|---|---|---|---|---|---|---|---|---|---|---|---|---|---|---|---|---|
| Met | Ala | Thr | Leu | Ile | Phe | Val | Asp | Lys | Asp | Asn | Glu | Glu | Pro | Gly | Ser | 16 (SEQ. ID. NO.:2) |
| Arg | Leu | Ala | Ser | Lys | Asp | Gly | Leu | Lys | Leu | Gly | Ser | Gly | Val | Lys | Ala | 32 |
| Leu | Asp | Gly | Lys | Leu | Gln | Val | Ser | Thr | Pro | Arg | Val | Gly | Lys | Val | Phe | 48 |
| Gly | Ala | Pro | Gly | Leu | Pro | Lys | Ala | Ser | Arg | Lys | Ala | Leu | Gly | Thr | Val | 64 |
| Asn | Arg | Val | Thr | Glu | Lys | Pro | Val | Lys | Ser | Ser | Lys | Pro | Leu | Gln | Ser | 80 |
| Lys | Gln | Pro | Thr | Leu | Ser | Val | Lys | Lys | Ile | Thr | Glu | Lys | Ser | Thr | Lys | 96 |
| Thr | Gln | Gly | Ser | Ala | Pro | Ala | Pro | Asp | Asp | Ala | Tyr | Pro | Glu | Ile | Glu | 112 |
| Lys | Phe | Phe | Pro | Phe | Asp | Pro | Leu | Asp | Phe | Glu | Ser | Phe | Asp | Leu | Pro | 128 |
| Glu | Glu | His | Gln | Ile | Ser | Leu | Leu | Pro | Leu | Asn | Gly | Val | Pro | Leu | Met | 144 |
| Ile | Leu | Asn | Glu | Glu | Arg | Gly | Leu | Glu | Lys | Leu | Leu | His | Leu | Asp | Pro | 160 |
| Pro | Ser | Pro | Leu | Gln | Lys | Pro | Phe | Leu | Pro | Trp | Glu | Ser | Asp | Pro | Leu | 176 |
| Pro | Ser | Pro | Pro | Ser | Ala | Leu | Ser | Ala | Leu | Asp | Val | Glu | Leu | Pro | Pro | 192 |
| Val | Cys | Tyr | Asp | Ala | Asp | Ile. | | | | | | | | | | 199 |

A rat PTTG-C peptide includes amino acid residues 144 through 199 of SEQ. ID. NO.:2, i.e., SEQ. ID. NO.:16 (Table 10 below; encoded by nucleotide positions 722 through 889 of SEQ. ID. NO.:1 or 1–168 of SEQ. ID. NO.:18 and degenerate sequences).

TABLE 10

Rat PTTG-C amino sequence.

| | | | | | | | | | | | | | | | | |
|---|---|---|---|---|---|---|---|---|---|---|---|---|---|---|---|---|
| Met | Ile | Leu | Asn | Glu | Glu | Arg | Gly | Leu | Glu | Lys | Leu | Leu | His | Leu | Asp | 16 SEQ. ID. NO.:16 |
| Pro | Pro | Ser | Pro | Leu | Gln | Lys | Pro | Phe | Leu | Pro | Trp | Glu | Ser | Asp | Pro | 32 |
| Leu | Pro | Ser | Pro | Pro | Ser | Ala | Leu | Ser | Ala | Leu | Asp | Val | Glu | Leu | Pro | 48 |
| Pro | Val | Cys | Tyr | Asp | Ala | Asp | Ile | | | | | | | | | 56 |

The amino acid sequence of SEQ. ID. NO.:16 includes proline-rich regions at amino acid residues 17–20, 24–27, and 34–37 (corresponding to amino acid residues 160–163, 167–170, and 177–180 of SEQ. ID. NO.:2).

Another example of a PTTG protein is a murine PTTG having the following amino acid sequence (Table 11 below; encoded by nucleotide positions 304 through 891 of SEQ. ID. NO.:15 and degenerate sequences).

TABLE 11

Murine PTTG amino acid sequence.

```
  1 MATLIFVDKD NEEPGRRLAS KDGLKLGTGV KALDGKLQVS TPRVGKVFNA    SEQ ID NO.:14

51 PAVPKASRKA LGTVNRVAEK PMKTGKPLQP KQPTLTGKKI TEKSTKTQSS

101 VPAPDDAYPE IEKFFPFNPL DFDLPEEHQI SLLPLNGVPL ITLNEERGLE

151 KLLHLGPPSP LKTPFLSWES DPLYSPPSAL STLDVELPPV CYDADI
```

A murine PTTG-C peptide includes amino acid residues 141 through 196 of SEQ. ID. NO.:14, i.e., SEQ. ID. NO.:17 (Table 12 below; encoded by nucleotide positions 724 through 891 of SEQ. ID. NO.:15 or 1–168 of SEQ. ID. NO.:19 and degenerate sequences).

NO.:64, 1–188 of SEQ. ID. NO.:64, 1–189 of SEQ. ID. NO.:64, and 1–190 of SEQ. ID. NO.:64). Also included among useful PTTG2 peptides are (B) a mammalian PTTG2 peptide having at least about 95% sequence homology with any peptide of (A). Importantly, the useful peptide com-

TABLE 12

Murine PTTG-C amino acid sequence.

ITLNEERGLE KLLHLGPPSP LKTPFLSWES DPLYSPPSAL STLDVELPPV CYDADI. 56 (SEQ. ID. NO.:17)

The amino acid sequence of SEQ. ID. NO.:17 includes a proline-rich region at amino acid residues 17–20 (corresponding to amino acid residues 157–160 of SEQ. ID. NO.:14).

Preferred PTTG-C peptides include:

(A) peptides having an amino acid sequence of (SEQ. ID. NO.:9), (SEQ. ID. NO.:16), or (SEQ. ID. NO.:17); or (B) mammalian PTTG-C peptides having at least about 60% sequence homology with any of the sequences in (A), or (C) peptide fragments of any of the sequences in (A) or (B) that comprise at least 15 contiguous amino acid residues and that function to downregulate endogenous PTTG expression and/or PTTG function. Most preferably, the fragment of (C) includes one or more proline-rich regions.

Those of skill in the art will recognize that in other useful PTTG-C peptides numerous residues of any of the above-described PTTG, PTTG1, or PTTG-C amino acid sequences can be substituted with other, chemically, sterically and/or electronically similar residues without substantially altering PTTG1 or PTTG-C biological activity. In addition, larger polypeptide sequences containing substantially the same coding sequences as in SEQ ID NO:2, SEQ. ID. NO.:4, SEQ. ID. NO.:9, SEQ. ID. NO.:14, SEQ. ID. NO.:16, or SEQ. ID. NO.:17 (e.g., splice variants) are contemplated.

The amino acid sequence of human PTTG2 protein (SEQ. ID. NO.:64) is listed below in Table 12a (GenBank Accession AF116538.2; encoded by SEQ. ID. NO.:63 or nucleotide positions 383–958 of SEQ. ID. NO.:62, and by degenerate sequences).

prises the proline-rich regions (i.e., PXXP motifs) of hPTTG2, which are found at nucleotide positions 163–166 of SEQ. ID. NO.:64 and nucleotide positions 170–173 of SEQ. ID. NO.:64.

As employed herein, the term "substantially the same amino acid sequence" refers to amino acid sequences having at least about 60% sequence homology or identity with respect to any of the amino acid sequences described herein ("reference sequences"), and retaining comparable functional and biological activity characteristic of the protein defined by the reference sequences described, particularly with respect to neoplastic cellular proliferation and/or transformation or its inhibition. More preferably, proteins having "substantially the same amino acid sequence" will have at least about 80%, still more preferably about 90% amino acid identity with respect to a reference amino acid sequence; with greater than about 95% amino acid sequence identity being especially preferred. It is recognized, however, that polypeptide containing less than the described levels of sequence identity arising as splice variants or that are modified by conservative amino acid substitutions are also encompassed within the scope of the present invention. The degree of sequence homology is determined by conducting an amino acid sequence similarity search of a protein data base, such as the database of the National Center for Biotechnology Information (NCBI; www.ncbi.nlm.nih.gov/BLAST/), using a computerized algorithm, such as PowerBLAST, QBLAST, PSI-BLAST, PHI-BLAST, gapped or ungapped BLAST, or the "Align" program through the Baylor College of Medicine server (www.hgsc.bcm.tmc.edu/seq_data). (E.g., Altchul, S. F., et al., *Gapped BLAST and PSI-BLAST: a new generation of*

TABLE 12a hPTTG2 amino acid sequence.

MATLIYVDKE IGEPGTRVAA KDVLKLESRP SIKALDGISQ VLTPRFGKTY 50 (SEQ. ID. NO.:64)

DAPSALPKAT RKALGTVNRA TEKSVKTNGP RKQKQPSFSA KKMTEKTVKT 100

KSSVPASDDA YPEIEKFFPF NLLDFESFDL PEERQIAHLP LSGVPLMILD 150

EEGELEKLFQ LGPPSPVKMP SPPWECNLFA VSFKHSVDPG C// 191

A preferred PTTG2 peptide is (A) a peptide consisting essentially of amino acid residues 1–191 of (SEQ. ID. NO.:64) or a functional fragment thereof comprising at least consecutive amino acid residues 1–180 of (SEQ. ID. NO.:64) (i.e., including peptides with consecutive amino acid residues 1–180 of SEQ. ID. NO.:64, 1–181 of SEQ. ID. NO.:64, 1–182 of SEQ. ID. NO.:64, 1–183 of SEQ. ID. NO.:64, 1–184 of SEQ. ID. NO.:64, 1–185 of SEQ. ID. NO.:64, 1–186 of SEQ. ID. NO.:64, 1–187 of SEQ. ID.

*protein database search programs*, Nucleic Acids Res. 25(17):3389–402 [1997]; Zhang, J., & Madden, T. L., *PowerBLAST: a new network BLAST application for interactive or automated sequence analysis and annotation*, Genome Res. 7(6):649–56 [1997]; Madden, T. L., et al., *Applications of network BLAST server*, Methods Enzymol. 266:131–41 [1996]; Altschul, S. F., et al., *Basic local alignment search tool*, J. Mol. Biol. 215(3):403–10 [1990]).

Also encompassed by the terms PTTG protein or PTTG-C peptide, respectively, are biologically functional or active peptide analogs thereof. The term peptide "analog" includes any polypeptide having an amino acid residue sequence substantially identical to a sequence specifically shown herein in which one or more residues have been conservatively substituted with a functionally similar residue and which displays the ability to mimic the biological activity of PTTG (PTTG1 or PTTG2) or PTTG-C, respectively, particularly with respect to neoplastic cellular proliferation and/or transformation or its inhibition, or with respect to immunosuppressing mammalian lymphocyte cells, as described herein above. Examples of conservative substitutions include the substitution of one non-polar (hydrophobic) residue such as isoleucine, valine, leucine or methionine for another, the substitution of one polar (hydrophilic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid for another.

The phrase "conservative substitution" also includes the use of a chemically derivatized residue in place of a non-derivatized residue, provided that such polypeptide displays the requisite biological activity.

"Chemical derivative" refers to a subject polypeptide having one or more residues chemically derivatized by reaction of a functional side group. Such derivatized molecules include, for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Also included as chemical derivatives are those peptides which contain one or more naturally occurring amino acid derivatives of the twenty standard amino acids. For example, 4-hydroxyproline may be substituted for proline; 5-hydroxylysine may be substituted for lysine; 3-methylhistidine may be substituted for histidine; homoserine may be substituted for serine; and ornithine may be substituted for lysine. The inventive polypeptide of the present invention also include any polypeptide having one or more additions and/or deletions of residues, relative to the sequence of a polypeptide whose sequence is shown herein, so long as the requisite PTTG or PTTG-C biological activity is maintained.

In accordance with peptide-based embodiments of the inventive method of inhibiting neoplastic cellular proliferation and/or transformation, the composition comprising the PTTG-C peptide is delivered to the cell. A suitable amount of the inventive PTTG-C peptide to be delivered to the cells, in accordance with the method, preferably ranges from about 0.1 nanograms to about 1 milligram per gram of tumor tissue, in vivo, or about 0.1 nanograms to about 1 microgram per 5000 cells, in vitro. Suitable amounts for particular varieties of PTTG-C peptide and/or cell types and/or for various individual mammalian subjects undergoing treatment, can be determined by routine experimentation.

Methods of delivering and importing peptides into target cells are known. For example, the composition preferably, but not necessarily, comprises in addition to the PTTG-C peptide, a complex in which the PTTG-C peptide is complexed with a cellular uptake-enhancing agent. For example, the PTTG-C peptide can be covalently linked in a complex to a cellular uptake-enhancing and/or importation-competent peptide segment for delivery of PTTG-C into the mammalian cell; in addition, a nuclear localization peptide can be included in the complex to direct the PTTG-C to the nucleus. (E.g., Lin et al., *Method for importing biologically active molecules into cells*, U.S. Pat. No. 6,043,339). An "importation-competent peptide," as used herein, is a sequence of amino acids generally of a length of about 10 to about 50 or more amino acid residues, many (typically about 55–60%) residues of which are hydrophobic such that they have a hydrophobic, lipid-soluble portion. The hydrophobic portion is a common, major motif of a signal peptide, and it is often recognizable as a central part of the signal peptide of a protein secreted from cells. A signal peptide is a peptide capable of penetrating through the cell membrane to allow the export of cellular proteins. Signal peptides useful in the present method are also "importation-competent," i.e., capable of penetrating through the cell membrane from outside the cell to the interior of the cell.

In preferred embodiments, a PTTG-C peptide or PTTG2 peptide forms a first PTTG-C peptide segment or PTTG2 peptide segment of a chimeric or fusion protein. The chimeric or fusion protein comprises at least the first PTTG-C peptide segment or PTTG2 peptide segment and a second cellular uptake-enhancing and/or importation-competent peptide segment. The second segment of the chimeric or fusion protein is a cellular uptake-enhancing and/or importation-competent peptide segment, such as a signal peptide, that allows the hybrid molecule to enter neoplastic cells that overexpress PTTG, whether in vitro or in vivo. The second peptide segment, such as the human immunodeficiency virus (HIV) TAT protein (Schwarze, S. R., et al., *In vivo protein transduction: delivery of a biologically active protein into the mouse*, Science 285:1569–72 [1999]), infiltrates the cells, and once within the cells, the PTTG-C peptide segment and/or PTTG2 peptide segment of the fusion protein becomes active within the cells to inhibit endogenous PTTG expression and/or PTTG function. Another example of a useful uptake-enhancing peptide segment is the signal peptide from Kaposi fibroblast growth factor (K-FGF). Other useful examples of uptake enhancing peptide segments are formed of ferritin peptides, or lactalbumin-α peptides, which latter is particularly useful for targeting cells of breast or mammary origin. But any cellular uptake-enhancing and/or importation-competent peptide segment, capable of translocating across the cell membrane into the interior of the selected target mammalian cell, can be used according to this invention. The chimeric or fusion protein can also include additional segments, such as a linker segment, that can be an intervening segment between the first and second segments. The additional segment can alternatively be a terminal segment, as appropriate.

In embodiments of the method involving the use of PTTG-C or PTTG2 chimeric or fusion proteins, the cellular uptake-enhancing and/or importation-competent peptide segment can be the uptake-enhancing agent. Alternatively, or in addition, the cellular uptake-enhancing agent can be a lipid or liposome uptake-enhancing agent as described herein above, such as lipofectin, lipofectamine, DOTAP, and others. Cationic (or polycationic) lipids or liposomes can also be complexed with a signal peptide and a negatively-charged biologically active molecule by mixing these components and allowing them to charge-associate. Anionic liposomes generally are utilized to encapsulate within the liposome the substances to be delivered to the cell. Procedures for forming cationic liposome-encapsulating substances are standard in the art and can readily be utilized herein by one of ordinary skill in the art to encapsulate the complex of this invention. For example, liposome uptake-enhancing agents complexed with inventive PTTG-C peptide fragments or PTTG2 peptides can be encapsulated in polyethylene glycol (PEG), FuGENE6, or the like.

With respect to delivery of the inventive composition (whether containing a PTTG-C-related polynucleotide or PTTG-C peptide or active fragment or PTTG2-encoding polynucleotide or PTTG2 peptide) to mammalian cells in vivo, the composition is administered to a mammalian subject in need of treatment, including a human subject, by any conventional delivery route. Preferably, the PTTG-C-related or PTTG2-encoding polynucleotide, or PTTG-C or PTTG2 peptide, whether or not complexed with cellular uptake-enhancing and/or importation-competent peptides (e.g., signal or localization peptides), is injected intravenously, intra-arterially, intraperitoneally, or by means of injection directly into a tumor or into a cell by microinjection. Direct injection of the inventive composition into the tumor is preferred for breast or ovarian tumors in vivo. Conventional stereotactic methods can be useful for direct injection into tumors or cells. Administration by nasal, rectal, or vaginal delivery routes can also be useful. Administration by catheter or stent can also be useful for delivering the composition containing the PTTG-C-related or PTTG2-encoding polynucleotide or PTTG-C or PTTG2 peptide.

In other preferred embodiments, controlled release formulations of biodegradable polymeric microspheres or nanospheres (e.g., polylactide-co-glycolide; PLGA) encapsulating the PTTG-C or PTTG2 peptide, or PTTG-C- or PTTG2-chimeric or fusion protein are administered to the mammalian subject orally. (E.g., Zhu, G. et al., *Stabilization of proteins encapsulated in injectable poly(lactide-co-glycolide)*, Nature Biotechnology 18:52–57 [2000]).

In some embodiments, isolated and crystallized PTTG-C or PTTG2 peptide can be cross-linked with a multifunctional crosslinking agent that inhibits proteolysis of the peptide in vivo. (Navia, M. A., *Method of protein therapy by orally administering crosslinked protein crystals*, U.S. Pat. No. 6,011,001).

Some useful embodiments of the method of inhibiting neoplastic cellular proliferation and/or transformation of mammalian breast or ovarian cells include further administering a cytotoxic chemotherapeutic agent to the cell simultaneously with or after delivering to the cell the PTTG carboxy-terminal-related polynucleotide (which in some embodiments is comprised in an expression vector), or the PTTG carboxy terminal (PTTG-C) peptide or the biologically functional fragment thereof. Because the presence of intracellular PTTG-C peptide hypersensitizes the cell to the cytotoxic chemotherapeutic agent, the practitioner can decrease the typical effective dose of the cytotoxic chemotherapeutic agent by about 10- to 100-fold, compared to the conventional dose, thereby minimizing damage to non-malignant tissue from cytotoxic chemotherapeutic agents.

Consequently, in other embodiments of the method that further comprise delivering the inventive composition containing the PTTG carboxy-terminal-related polynucleotide or the PTTG carboxy terminal (PTTG-C) peptide (or the biologically functional fragment thereof) to the cell in vivo within a subject, systemic toxic effects from anti-cancer medication are lessened in a particular subject receiving treatment with the lower effective dose of cytotoxic chemotherapeutic agent. Therefore, the quality of life and the likelihood of survival for the subject can be improved.

The cytotoxic chemotherapeutic agent includes but is not limited to paclitaxel (Taxol), 5-fluorouracil, cisplatin, carboplatin, methotrexate, daunorubicin, doxorubicin, vincristine, vinblastine, or a cytotoxic alkylating agent, such as, but not limited to, busulfan (1,4-butanediol dimethanesulphonate; Myleran, Glaxo Wellcome), chlorambucil, cyclophosphamide, melphalan, or ethyl ethanesulfonic acid. The cytotoxic chemotherapeutic agent is administered to the cell by conventional means, but in an effective dose about 10- to 100-fold lower than the conventional dose for a given cytotoxic chemotherapeutic agent. Administration of the cytotoxic chemotherapeutic agent can be simultaneous with or after delivery of the inventive composition as long as biologically active PTTG-C peptide is still present in the cell.

In accordance with the inventive method of inhibiting neoplastic cellular proliferation and/or transformation that is mediated by PTTG (PTTG1), the mammalian cell is a cell that overexpresses PTTG1, the gene that encodes a PTTG1 protein. Although detecting PTTG1 overexpression by the cell is not essential or necessary to the practice of the inventive method, the level of PTTG1 expression, including overexpression, is detectable by one skilled in the art. Detection of PTTG1 expression is accomplished by immunochemical assay for PTTG1 protein, for example, using the inventive anti-PTTG-C antibodies, described herein, or other anti-PTTG-specific antibodies. Alternatively, amplification of PTTG-specific mRNAs present in biological samples (e.g., tissue biopsy) can be used to detect PTTG1 expression. This is done by known molecular biological techniques of amplification and analysis of the amplification products for the presence or absence of PTTG1-specific amplification products. If PTTG1 gene-specific amplification products are present, the findings are indicative of expression of the PTTG1 gene and diagnostic of the presence of neoplastic cellular proliferation in the subject as defined herein.

However, for interpretation of negatives (no PTTG-specific amplification products) analysis is preferably carried out following a control amplification of nucleic acids specific for a housekeeping gene, for example, a gene encoding β-actin, phosphofructokinase (PFK), glyceraldehyde 3-phosphate dehydrogenase, or phosphoglycerate kinase. Only if expression of the housekeeping gene is detected in the sample, is the absence of PTTG gene expression reliably accepted. With increasing sensitivity of amplification and analysis methods employed, it becomes increasingly preferable to determine the level of PTTG gene expression relative to expression of a housekeeping gene, in order to better distinguish neoplastic, hyperplastic, cytologically dysplastic and/or premalignant cellular growth or proliferation from the detectable background of normal cellular division. The ratio of PTTG expression to housekeeping gene expression is determined, for example, by real-time PCR methods or densitometric measurement and analysis of electrophoretic bands after amplification. When the ratio of PTTG1 expression to housekeeping gene expression exceeds a normal cell standard range and/or approximates an abnormal (e.g., neoplastic) cell standard range, this indicates overexpression of PTTG1 gene product, characteristic of neoplastic, hyperplastic, cytologically dysplastic and/or premalignant cellular growth or proliferation.

PTTG-specific mRNAs in a biological sample are amplified by a suitable amplification method. For example, a reverse transcriptase-mediated polymerase chain reaction (RT-PCR) is employed to amplify PTTG-specific nucleic acids. Briefly, two enzymes are used in the amplification process, a reverse transcriptase to transcribe PTTG-specific cDNA from a PTTG-specific mRNA template in the sample, a thermal resistant DNA polymerase (e.g., Taq polymerase), and PTTG-specific primers to amplify the cDNA to produce PTTG gene-specific amplification products. The use of limited cycle PCR yields semi-quantitative results. (E.g., Gelfand et al., *Reverse transcription with thermostable DNA polymerase-high temperature reverse transcription*, U.S. Pat. Nos. 5,310,652; 5,322,770; Gelfand et al., *Unconventional nucleotide substitution in temperature selective RT-PCR*, U.S. Pat. No. 5,618,703).

Alternatively, single enzyme RT-PCR is employed to amplify PTTG gene-specific nucleic acids. Single enzymes now exist to perform both reverse transcription and polymerase functions, in a single reaction. For example, the Perkin Elmer recombinant *Thermus thermophilus* (rTth) enzyme(Roche Molecular), or other similar enzymes, are commercially available.

Real-time RT-PCR can be employed to amplify PTTG-specific nucleic acids. Briefly, this is a quantitative gene analysis based on the ratio of PTTG gene expression and the expression of a housekeeping gene, i.e., a gene that is expressed at about the same level in normal and abnormal (e.g., malignant) cells, for example, a gene encoding β-actin, phosphofructokinase, glyceraldehyde 3-phosphate dehydrogenase, or phosphoglyceratekinase. The the ratio of the PTTG and housekeeping genes' expressions is routinely established as a standard for normal and abnormal cells, which standard expression ratio(s) is (are) used for comparison in determining that expression of the PTTG gene relative to expression of the "housekeeping" gene in a given sample is either "normal" or "increased", the latter indicative of "overexpression" and diagnostic for the presence of neoplastic, hyperplastic, cytologically dysplastic and/or premalignant cellular growth or proliferation. In this embodiment, the ratio is the key to diagnosis and constitutes quantitative gene expression analysis. This embodiment utilizes so-called real-time quantitative PCR, carried out with commercially available instruments, such as the Perkin Elmer ABI Prism 7700, the so-called Light Cycler (Roche Molecular), and/or other similar instruments. Optionally, single enzyme RT-PCR technology, for example, employing rTth enzyme, can be used in a real-time PCR system. Preferably, amplification and analysis are carried out in an automated fashion, with automated extraction of mRNA from a urine sediment sample, followed by real-time PCR, and fluorescence detection of amplification products using probes, such as TaqMan or Molecular Beacon probes. Typically, the instrumentation includes software that provides quantitative analytical results during or directly following PCR without further amplification or analytical steps.

Alternatively, transcription-mediated amplification (TMA) is employed to amplify PTTG gene-specific nucleic acids. (E.g., K. Kamisango et al., *Quantitative detection of hepatitis B virus by transcription-mediated amplification and hybridization protection assay*, J. Clin. Microbiol. 37(2):310–14 [1999]; M. Hirose et al., *New method to measure telomerase activity by transcription-mediated amplification and hybridization protection assay*, Clin. Chem. 44(12) 2446–52 [1998]). Rather than employing RT-PCR for the amplification of a cDNA, TMA uses a probe that recognizes a PTTG-specific (target sequence) RNA; in subsequent steps, from a promoter sequence built into the probe, an RNA polymerase repetitively transcribes a cDNA intermediate, in effect amplifying the original RNA transcripts and any new copies created, for a level of sensitivity approaching that of RT-PCR. The reaction takes place isothermally (one temperature), rather than cycling through different temperatures as in PCR.

Other useful amplification methods include a reverse transcriptase-mediated ligase chain reaction (RT-LCR), which has utility similar to RT-PCR. RT-LCR relies on reverse transcriptase to generate cDNA from mRNA, then DNA ligase to join adjacent synthetic oligonucleotides after they have bound the target cDNA.

Amplification of a PTTG gene-specific nucleic acid segment of the subject can be achieved using PTTG gene-specific oligonucleotide primers and primer sets as provided herein.

Optionally, high throughput analysis may be achieved by PCR multiplexing techniques well known in the art, employing multiple primer sets, for example primers directed not only to PTTG gene-specific nucleic acids, but to amplifying expression products of housekeeping genes (controls) or of other potential diagnostic markers (e.g., oncogenes), as well, such as MAG or telomerase, to yield additional diagnostic information. (E.g., Z. Lin et al., *Multiplex genotype determination at a large number of gene loci*, Proc. Natl. Acad. Sci. USA 93(6):2582–87 [1996]; Demetriou et al., *Method and probe for detection of gene associated with liver neoplastic disease*, U.S. Pat. No. 5,866,329).

Hybridization analysis is a preferred method of analyzing the amplification products, employing one or more PTTG-specific probe(s) that, under suitable conditions of stringency, hybridize(s) with single stranded PTTG-specific nucleic acid amplification products comprising complementary nucleotide sequences. Hybridization refers to the binding of complementary strands of nucleic acid (i.e., sense:antisense strands or probe:target-DNA) to each other through hydrogen bonds, similar to the bonds that naturally occur in chromosomal DNA. The amplification products are typically deposited on a substrate, such as a cellulose or nitrocellulose membrane, and then hybridized with labeled PTTG-specific probe(s), optionally after an electrophoresis. Conventional dot blot, Southern, Northern, or fluorescence in situ (FISH) hybridization protocols, in liquid hybridization, hybridization protection assays, or other semi-quantitative or quantitative hybridization analysis methods are usefully employed along with the PTTG gene-specific probes of the present invention. Preferred probe-based hybridization conditions comprise a temperature of about 37° C., a formamide concentration of about 20%, and a salt concentration of about 5×standard saline citrate (SSC; 20×SSC contains 3 M sodium chloride, 0.3 M sodium citrate, pH 7.0). Such conditions will allow the identification of sequences which have a substantial degree of similarity with the probe sequence, without requiring perfect homology. The phrase "substantial similarity" refers to sequences which share at least 50% homology. Stringency levels used to hybridize a given probe with target-DNA can be readily varied by those of skill in the art. Preferably, hybridization conditions will be selected which allow the identification of sequences having at least about 60% homology with the probe, while discriminating against sequences which have a lower degree of homology with the probe.

As used herein, a "probe" is single-stranded DNA or RNA, or a nucleic acid analog. The inventive probe is preferably 7 to 500 nucleotides long, more preferably 14 to 150 nucleotides long, and most preferably at least 50 nucleotides long. The probe comprises, for at least part of its length, a PTTG-specific nucleotide sequence at least 7 to 15 contiguous nucleotides long, such that the probe hybridizes to a PTTG-specific single stranded nucleic acid of interest under suitably stringent hybridization conditions. Examples of PTTG-specific nucleotide sequences are set forth in any of SEQ. ID. NOS.: 1, 3, 10, 15, 18, 19, 62, 63, 65, 66, or 68 preferably, but not necessarily, including 5' and/or 3' coding regions thereof. In addition, the entire cDNA encoding region of an inventive PTTG-specific nucleotide sequence, or the entire sequence corresponding to SEQ. ID. NOS.: 1, 3, 10, 15, 18, 19, or nucleotide sequences complementary to any of these, can be used as a probe. For example, probes comprising inventive oligonucleotide primer sequences, such as, but not limited to, SEQ. ID. NO.:8, can be labeled for use as probes for detecting or analyzing PTTG-specific nucleic acid amplification products. Any of the inventive isolated PTTG-C-related polynucleotides can be used as probes or primers.

Alternatively, electrophoresis for analyzing amplification products is done rapidly and with high sensitivity by using any of various methods of conventional slab or capillary electrophoresis, with which the practitioner can optionally choose to employ any facilitating means of nucleic acid fragment detection, including, but not limited to, radionuclides, UV-absorbance or laser-induced fluorescence. (K. Keparnik et al., *Fast detection of a (CA) 18 microsatellite repeat in the IgE receptor gene by capillary electrophoresis with laser-induced fluorescence detection*, Electrophoresis 19(2);249–55 [1998]; H. Inoue et al., *Enhanced separation of DNA sequencing products by capillary electrophoresis using a stepwise gradient of electric field strength*, J. Chromatogr. A. 802(1):179–84 [1998]; N. J. Dovichi, *DNA sequencing by capillary electrophoresis*, Electrophoresis 18(12–13):2393–99 [1997]; H. Arakawa et al., *Analysis of single-strand conformation polymorphisms by capillary electrophoresis with laser induced fluorescence detection*, J. Pharm. Biomed. Anal. 15(9–10):1537–44 [1997]; Y. Baba, *Analysis of disease-causing genes and DNA-based drugs by capillary electrophoresis. Towards DNA diagnosis and gene therapy for human diseases*, J. Chromatgr B. Biomed. Appl. 687(2):271–302 [1996]; K. C. Chan et al., *High-speed electrophoretic separation of DNA fragments using a short capillary*, J. Chromatogr B. Biomed. Sci. Appl. 695(1): 13–15 [1997]). Probes can be labeled by methods well-known in the art.

As used herein, the terms "label", "tracer", and "indicating means" in their various grammatical forms refer to single atoms and molecules that are either directly or indirectly involved in the production of a detectable signal. Any label or indicating means can be linked to PTTG-specific probes, primers, or amplification products, or PTTG proteins, peptides, peptide fragments, or anti-PTTG antibody molecules. The label can be used alone or in conjunction with additional reagents. Such labels are themselves well-known in the art. The label can be a fluorescent labeling agent that chemically binds to antibodies or antigens without denaturation to form a fluorochrome (dye) that is a useful immunofluorescent tracer. A description of immunofluorescent analytic techniques is found in DeLuca, "Immunofluorescence Analysis", in Antibody As a Tool, Marchalonis et al., eds., John Wiley & Sons, Ltd., pp. 189–231 (1982), which is incorporated herein by reference. Any of diverse fluorescent dyes can optionally be used as a label, including but not limited to, SYBR Green I, Y1O-PRO-1, thiazole orange, Hex (i.e., 6-carboxy-2',4',7',4,7-hexachlorofluoroscein), pico green, edans, fluorescein, FAM (i.e., 6-carboxyfluorescein), or TET (i.e., 4,7,2',7'-tetrachloro-6-carboxyfluoroscein). (E.g., J. Skeidsvoll and P. M. Ueland, *Analysis of double-stranded DNA by capillary electrophoresis with laser-induced fluorescence detection using the monomeric dye SYBR green I*, Anal. Biochem. 231(20):359–65 [1995]; H. Iwahana et al., *Multiple fluorescence-based PCR-SSCP analysis using internal fluorescent labeling of PCR products*, Biotechniques 21(30:510–14, 516–19 [1996]).

The label can also be an enzyme, such as horseradish peroxidase (HRP), glucose oxidase, β-galactosidase, and the like. Alternatively, radionuclides are employed as labels. The linking of a label to a substrate, i.e., labeling of nucleic acid probes, antibodies, polypeptide, and proteins, is well known in the art. For instance, an invention antibody can be labeled by metabolic incorporation of radiolabeled amino acids provided in the culture medium. See, for example, Galfre et al., Meth. Enzymol., 73:3–46 (1981). Conventional means of protein conjugation or coupling by activated functional groups are particularly applicable. See, for example, Aurameas et al., Scand. J. Immunol., Vol. 8, Suppl. 7:7–23 (1978), Rodwell et al., Biotech., 3:889–894 (1984), and U.S. Pat. No. 4,493,795.

In accordance with yet another embodiment of the present invention, there are provided anti-PTTG antibodies having specific reactivity with PTTG polypeptides of the present invention. Antibody fragments, for example Fab, Fab', F(ab')$_2$, or F(v) fragments, that selectively or specifically bind a PTTG protein, PTTG-C peptide, or immunogenic fragment of PTTG-C, are also encompassed within the definition of "antibody".

Inventive antibodies can be produced by methods known in the art using PTTG polypeptide, proteins or portions thereof, such as PTTG-C peptide or immunogenic fragments of PTTG-C, as antigens. For example, polyclonal and monoclonal antibodies can be produced by methods well known in the art, as described, for example, in Harlow and Lane, *Antibodies: A Laboratory Manual* (Cold Spring Harbor Laboratory [1988]), which is incorporated herein by reference. Isolated or purified PTTG proteins, PTTG-C peptides, and immunogenic PTTG-C fragments can be used as immunogens in generating such specific antibodies.

PTTG proteins, PTTG-C peptides, or polypeptide analogs thereof, are purified or isolated by a variety of known biochemical means, including, for example, by the recombinant expression systems described herein, precipitation, gel filtration, ion-exchange, reverse-phase and affinity chromatography, and the like. Other well-known methods are described in Deutscher et al., *Guide to Protein Purification: Methods in Enzymology* Vol. 182, (Academic Press, [1990]), which is incorporated herein by reference. Isolated PTTG proteins or PTTG-C peptides are free of cellular components and/or contaminants normally associated with a native in vivo environment.

Isolated PTTG (PTTG, PTTG2, or PTTG3) proteins or PTTG-C peptides can also be chemically synthesized For example, synthetic polypeptide can be produced using Applied Biosystems, Inc. Model 430A or 431A automatic peptide synthesizer (Foster City, Calif.) employing the chemistry provided by the manufacturer. Alternatively, PTTG can be isolated or purified from native sources, and PTTG-C peptides can be isolated from PTTG (or from chimeric proteins) by the use of suitable proteases.

Alternatively, PTTG (e.g., PTTG1, PTTG2, or PTTG3) or PTTG-C polypeptides can be recombinantly derived, for example, produced by mammalian cells genetically modified to express PTTG-C-encoding polynucleotides in accordance with the inventive technology as described herein. Recombinant methods are well known, as described, for example, in Sambrook et al., supra., 1989). An example of the means for preparing the inventive PTTG or PTTG-C polypeptide(s) is to express nucleic acids encoding the PTTG protein or PTTG-C peptide of interest in a suitable host cell, such as a bacterial cell, a yeast cell, an amphibian cell (i.e., oocyte), or a mammalian cell, such as the inventive mammalian host cell described herein below, using methods well known in the art, and recovering the expressed polypeptide, again using well-known methods.

The immunogenicity of various PTTG-C fragments of interest is determined by routine screening. Alternatively, synthetic PTTG (e.g., PTTG1, PTTG2, or PTTG3) or PTTG-C polypeptides or fragments thereof can be prepared (using commercially available synthesizers) and used as immunogens. Amino acid sequences can be analyzed by methods well known in the art to determine whether they encode hydrophobic or hydrophilic domains of the corresponding polypeptide. Altered antibodies such as chimeric, humanized, CDR-grafted or bifunctional antibodies can also be produced by methods well known in the art. Such antibodies can also be produced by hybridoma, chemical synthesis or recombinant methods described, for example, in Sambrook et al., supra., and Harlow and Lane, supra. Both anti-peptide and anti-fusion protein antibodies can be used. (see, for example, Bahouth et al., *Trends Pharmacol. Sci.* 12:338 [1991]; Ausubel et al., *Current Protocols in Molecular Biology* (John Wiley and Sons, NY [1989] which are incorporated herein by reference).

Antibody so produced can be used, inter alia, in diagnostic or assay methods and systems to detect the level of PTTG protein, PTTG-C peptide, or immunogenic fragments thereof, present in a mammalian, preferably human, biological sample, such as tissue or vascular fluid. This is useful, for example, in determining the level of PTTG expression. Such antibodies can also be used for the immunoaffinity or affinity chromatography purification of the inventive PTTG proteins or PTTG-C peptides. In addition, methods are contemplated herein for detecting the presence of PTTG protein or PTTG-C peptide, either on the surface of a cell or within a cell (such as within the nucleus), which methods comprise contacting the cell with an antibody that specifically binds to PTTG protein or PTTG-C peptide, under conditions permitting specific binding of the antibody to PTTG protein or PTTG-C peptide, detecting the presence of the antibody bound to PTTG or PTTG-C, and thereby detecting the presence of PTTG or PTTG-C polypeptide on the surface of, or within, the cell. With respect to the detection of such polypeptide, the antibodies can be used for in vitro diagnostic or assay methods, or in vivo imaging methods.

Immunological procedures useful for in vitro detection of target PTTG or PTTG-C polypeptides in a sample include immunoassays that employ a detectable antibody. Such immunoassays include, for example, ELISA, immunofluorescence assay (IFA), Pandex microfluorimetric assay, agglutination assays, flow cytometry, serum diagnostic assays and immunohistochemical staining procedures which are well known in the art. An antibody can be made detectable by various means well known in the art. For example, a detectable marker can be directly or indirectly attached to the antibody. Useful markers include, for example, radionuclides, enzymes, fluorogens, chromogens and chemiluminescent labels.

Inventive anti-PTTG or anti-PTTG-C antibodies are also contemplated for use herein to modulate activity of the PTTG1 polypeptide in living animals, in humans, or in biological tissues or fluids isolated therefrom. Accordingly, compositions comprising a carrier and an amount of an antibody having specificity for PTTG polypeptide effective to block naturally occurring ligands or other PTTG-binding proteins from binding to invention PTTG polypeptide are contemplated herein. For example, a monoclonal antibody directed to an epitope of PTTG1 polypeptide molecules present on the surface of a cell and having an amino acid sequence substantially the same as an amino acid sequence for a cell surface epitope of an PTTG polypeptide including the amino acid sequence shown in SEQ ID NOS:2, 4, 9, 14, 16, or 17 can be useful for this purpose.

The present invention also relates to transfected, transduced, or otherwise transformed mammalian host cells, including lymphocyte and non-lymphocyte cells such as breast or ovarian cells, comprising any of the inventive PTTG-C-related polynucleotide-containing compositions as described herein above. The inventive cells are either contained in a mammalian subject or are cultured in vitro. Included among preferred embodiments are mammalian host cells containing an expression vector comprising the inventive PTTG-C-related polynucleotide in a transcriptional unit. Preferably, a product is expressed by the cell, which product, most preferably, but not necessarily, is a biologically active PTTG-C peptide that functions to down-regulate PTTG1-mediated neoplastic cellular proliferation and/or transformation. In vitro and in vivo methods of transfecting, transducing, or transforming suitable host cells are generally known in the art. Methods for culturing cells, in vitro, are also well known. Exemplary methods of transfection, transduction, or transformation include, e.g., infection employing viral vectors (see, e.g., U.S. Pat. Nos. 4,405,712 and 4,650,764), calcium phosphate transfection (U.S. Pat. Nos. 4,399,216 and 4,634,665), dextran sulfate transfection, electroporation, lipofection (see, e.g., U.S. Pat. Nos. 4,394,448 and 4,619,794), cytofection, microparticle bombardment, and the like. The heterologous nucleic acid can optionally include sequences which allow for its extra-chromosomal (i.e., episomal) maintenance, or heterologous DNA can be caused to integrate into the genome of the host (as an alternative means to ensure stable maintenance in the host cell).

The present invention further provides transgenic non-human mammals containing the inventive mammalian cells that are capable of expressing exogenous nucleic acids encoding PTTG polypeptides, particularly the inventive PTTG-C peptides and functional fragments thereof as described hereinabove. As employed herein, the phrase "exogenous nucleic acid" refers to nucleic acid sequence which is not native to the host, or which is present in the host in other than its native environment (e.g., as part of a genetically engineered DNA construct). Methods of producing transgenic non-human mammals are known in the art. Typically, the pronuclei of fertilized eggs are microinjected in vitro with foreign, i.e., xenogeneic or allogeneic DNA or hybrid DNA molecules, and the microinjected fertilized eggs are then transferred to the genital tract of a pseudopregnant female to gestate to term. (E.g., P. J. A. Krimpenfort et al., *Transgenic mice depleted in mature T-cells and methods for making transgenic mice*, U.S. Pat. Nos. 5,175,384 and 5,434,340; P. J. A. Krimpenfort et al., *Transgenic mice depleted in mature lymphocytic cell-type*, U.S. Pat. No. 5,591,669). Alternatively, methods for producing transgenic non-human mammals can involve genetic modification of female or male germ cells using an expression vector, which germ cells are then used to produce zygotes, which are gestated to term. The resulting offspring are selected for the desired phenotype. These offspring can further be bred or cloned to produce additonal generations of transgenic animals with the desired phenotype. The inventive transgenic non-human mammals, preferably, but not necessarily, are large animals such as bovines, ovines, porcines, equines, and the like, that produce relatively large quantities of PTTG-C peptides that can be harvested for use in practicing the method of inhibiting neoplastic cellular proliferation and/or transformation.

Most preferably, the transgenic non-human mammal is a female that produces milk into which the inventive PTTG-C peptides have been secreted. The PTTG-C peptides are then purified from the milk. (E.g., Christa, L., et al., *High expression of the human hepatocarcinoma-intestine-pancreas/pancreatic-associated protein (HIPPAP) gene in the mammary gland of lactating transgenic mice secretion into the milk and purification of the HIP/PAP lectin*, Eur. J. Biochem. 267(6):1665–71 [2000]; Sobolev, A. S. et al., *Receptor-mediated transfection of murine and ovine mammary glands in vivo*, J. Biol. Chem. 273(14):7928–33 [1998]; Zhang, K. et al., *Construction of mammary gland-specific expression vectors for human clottingfactor IX and its secretory expression in goat milk*, Chin. J. Biotechnol. 13(4):271–6 [1997]; Clark, A. J., *Gene expression in the mammary glands of transgenic animals*, Biochem. Soc. Symp. 63:133–40 [1998]; Niemann, H. et al., *Expression of human blood clottingfactor VIII in the mammary gland of transgenic sheep*, Transgenic Res. 8(3):237–47 [1999]).

Techniques for obtaining the preferred transgenic female mammals typically employ transfection with an expression vector in which, within a transcriptional unit regulated, for example, by a suitable β-lactoglobulin promoter, the PTTG-C peptide-encoding polynucleotide is chimerically linked with a polynucleotide encoding a mammary secretory signal peptide, such that mammary-specific expression yields a chimeric polypeptide from which the desired PTTG-C peptide segment is removed proteolytically and purified.

The present invention is also directed to a kit for the treatment of neoplastic cellular proliferation. The kit is useful for practicing the inventive method of inhibiting neoplastic cellular proliferation and/or transformation. The kit is an assemblage of materials or components, including at least one of the inventive compositions. Thus, in some embodiments the kit contains a PTTG-C-related polynucleotide and/or PTTG-C peptides, as described above. In other embodiments, the kit contains a polynucleotide comprising a DNA segment encoding a mammalian PTTG2 peptide, such as a peptide consisting essentially of amino acid residues 1–191 of (SEQ. ID. NO.:64) or a fragment thereof comprising at least amino acid residues 1–180 of (SEQ. ID. NO.:64), for example, a polynucleotide consisting of (SEQ. ID. NO.:63) or a degenerate sequence thereof, or a polynucleotide encoding a mammalian PTTG2 peptide having at least about 95% sequence homology with hPTTG2 or a functional fragment. Alternatively, the kit can contain a composition comprising a peptide consisting essentially of amino acid residues 1–191 of (SEQ. ID. NO.:64) or a fragment thereof comprising at least amino acid residues 1–180 of (SEQ. ID. NO.:64) or a mammalian PTTG2 peptide having at least about 95% sequence homology with hPTTG2 or a functional fragment thereof comprising at least amino acid residues 1–180 of (SEQ. ID. NO.:64).

The exact nature of the components configured in the inventive kit depends on its intended purpose. For example, some embodiments of the kit are configured for the purpose of treating cultured mammalian cells. Other embodiments are configured for the purpose of treating mammalian cells in vivo, i.e., for treating mammalian subjects in need of treatment, for example, subjects with malignant tumors. Preferred embodiments are directed to treating breast or ovarian cancers. In a most preferred embodiment, the kit is configured particularly for the purpose of treating human subjects. The embodiments containing PTTG2 peptides or PTTG2 peptide fragments or polynucleotides encoding PTTG2 peptides or fragments, the kit also includes instructions for the use of the composition for inhibiting neoplastic cellular proliferation and/or transformation.

Some embodiments of the kit include a kit for the treatment of neoplastic cellular proliferation of T-lymphocytes, which includes a composition comprising a tamed HIV vector operatively linked to a PTTG carboxy-terminal-related polynucleotide; and instructions for the use of said composition for inhibiting neoplastic cellular proliferation and/or transformation of T-lymphocytes.

Also included within the present invention is a kit for immunosuppressive therapy, which contains a composition comprising a tamed HIV vector operatively linked to a PTTG carboxy-terminal-related polynucleotide; and instructions for using the composition for inhibiting the activation of T-lymphocytes.

Instructions for use are included in the kit. "Instructions for use" typically include a tangible expression describing the reagent concentration or at least one assay method parameter, such as the relative amounts of reagent and sample to be admixed, maintenance time periods for reagent/sample admixtures, temperature, buffer conditions, and the like, typically for an intended purpose.

Optionally, the kit also contains other useful components, such as, diluents, buffers, pharmaceutically acceptable carriers, specimen containers, syringes, stents, catheters, pipetting or measuring tools, paraphernalia for concentrating, sedimenting, or fractionating samples, or the inventive antibodies, and/or primers and/or probes for controls.

The materials or components assembled in the kit can be provided to the practitioner stored in any convenient and suitable ways that preserve their operability and utility. For example the components can be in dissolved, dehydrated, or lyophilized form; they can be provided at room, refrigerated or frozen temperatures.

The components are typically contained in suitable packaging material(s). As employed herein, the phrase "packaging material" refers to one or more physical structures used to house the contents of the kit, such as invention nucleic acid probes or primers, and the like. The packaging material is constructed by well known methods, preferably to provide a sterile, contaminant-free environment.

The packaging materials employed in the kit are those customarily utilized in polynucleotide-based or peptide-based systems. As used herein, the term "package" refers to a suitable solid matrix or material such as glass, plastic, paper, foil, and the like, capable of holding the individual kit components. Thus, for example, a package can be a glass vial used to contain suitable quantities of an inventive composition containing nucleic acid or peptide components. The packaging material generally has an external label which indicates the contents and/or purpose of the kit and/or its components.

The invention will now be described in greater detail by reference to the following non-limiting examples, which unless otherwise stated were performed using standard procedures, as described, for example in Maniatis et al., *Molecular Cloning: A Laboratory Manual*, Cold Spring Harbor Laboratory Press, Cold Spring Harbor, N.Y., USA (1982); Sambrook et al., Molecular Cloning: A Laboratory Manual (2 ed.), Cold Spring Harbor Laboratory Press, Cold Spring Harbor, N.Y., USA (1989); Davis et al., *Basic Methods in Molecular Biology*, Elsevier Science Publishing, Inc., New York, USA (1986); or *Methods in Enzymology: Guide to Molecular Cloning Techniques* Vol.152, S. L. Berger and A. R. Kimmerl Eds., Academic Press Inc., San Diego, USA (1987).

EXAMPLES

Example 1

Isolation of PTTG cDNA

To clarify the molecular mechanisms involved in pituitary tumorigenesis, differential display PCR was used to identify mRNAs differentially expressed in pituitary tumor cells (see, e.g., Risinger et al., 1994, Molec. Carcinogenesis, 11:13–18; and Qu et al., 1996, Nature, 380:243–247). GC and $GH_4$ pituitary tumor cell lines (ATCC #CCL-82 and #CCL-82.1, respectively) and an osteogenic sarcoma cell line UM108 (ATCC #CRL-1663) were grown in DMEM supplemented with 10% fetal bovine serum. Normal Sprague-Dawley rat pituitaries were freshly excised. Total RNA was extracted from tissue cultured cells and pituitary tissue using RNeasy™ kit (Qiagen) according to manufacturer's instructions. Trace DNA contamination in RNA preparations was removed by DNase1 (GenHunter Corporation) digestion. cDNA was synthesized from 200 ng total RNA using MMLV reverse transcriptase (GenHunter Corporation), and one of the three anchored primers (GenHunter Corporation). The cDNA generated was used in the PCR display.

Three downstream anchored primers $AAGCT_{11}N$ (SEQ. ID. NO.:13; where N may be A, G, or C), were used in conjunction with 40 upstream arbitrary primers for PCR display. 120 primer pairs were used to screen mRNA expression in pituitary tumors versus normal pituitary. One tenth of the cDNA generated from the reverse transcriptase reaction was amplified using AmpliTaq DNA polymerase (Perkin Elmer) in a total volume of 20 µl containing 10 mM Tris, pH 8,4, 50 nM KCl, 1.5 mM $MgCl_2$, 0.001% gelatin, 2 µM dNTPs, 0.2 µM each primer and 1 µl [$^{35}S$]dATP. PCR cycles consisted of 30 seconds at 94° C., 2 minutes at 40° C., and 30 seconds 72° C. for 40 cycles. The products were separated on 6% sequencing gels, and dried gels were exposed to Kodak film for 24 to 48 hours.

After development, DNA fragments amplified from pituitary tumor and normal pituitary were compared. Bands unique to pituitary tumor were excised from the gel, and DNA extracted by boiling in 100 µl water and precipitated with ethanol in the presence of glycogen (GenHunter Corporation). DNA was reamplified using the original set of primers and the same thermal cycling conditions except that the dNTP concentration was increased to 20 µM. Reaction products were run on 1% agarose gel and stained with ethidium bromide. Bands were excised from the gel, eluted (Qiagen), cloned in to TA vectors (Invitrogen) and sequenced using sequenase (USB). Using 120 primer pairs in the above-described PCR assay, 11 DNA bands that appeared to be differentially expressed in pituitary tumor cells were identified. These bands were evaluated further by Northern blot analysis, using the PCR products as probes.

For Northern blot analysis, 20 µg of total RNA were fractionated on 1% agarose gel, blotted on to nylon membrane and hybridized with random primed probe using Quickhyb solutions (Stratagene). After washing, membranes were exposed to Kodak films for 6 to 72 hours. As a result of the Northern blot assay, pituitary tumor specific signals were detected for 2 bands. DNA sequence analysis revealed that one sequence was homologous with Insulin-induced growth response protein, while the another 396 base pair fragment (amplified using 5'-AAGCTTTTTTTTTTG-3' [SEQ. ID. NO.:11] as the anchored primer and 5'-AAGCTTGCTGCTC-3' [SEQ. ID. NO.:12] as an arbitrary primer) showed no homology to known sequences in the GenBank. This 396 bp fragment detected a highly expressed mRNA of about 1.3 kb in pituitary tumor cells, but not in normal pituitary nor in osteogenic sarcoma cells.

Example 2

Characterization of cDNA Sequence Encoding PTTG

To characterize this pituitary tumor-specific mRNA further, a cDNA library was constructed using mRNA isolated from rat pituitary tumor cells. Poly A+RNA was isolated from pituitary tumor $GH_4$ cells using messenger RNA isolation kit (Stratagene) according to manufacturer's instructions, and was used to construct a cDNA library in ZAP Express vectors (Stratagene). The cDNA library was constructed using ZAP Express™ cDNA synthesis and Gigapack III gold cloning kit (Stratagene) following manufacturer's instructions. The library was screened using the 396 bp differentially displayed PCR product (cloned into TA vector) as the probe. After tertiary screening, positive clones were excised by in vivo excision using helper phage. The resulting pBK-CMV phagemid containing the insert was identified by Southern Blotting analysis. Unidirectional nested deletions were made into the DNA insert using EXOIII/Mung bean nuclease deletion kit (Stratagene) following manufacturer's instructions. Both strands of the insert DNA were sequenced using Sequenase (USB).

Using the 396 bp PCR fragment described in Example 1 as a probe, a cDNA clone of 974 bp (SEQ. ID. NO.:1) was isolated and characterized. This cDNA was designated as pituitary tumor-specific gene (PTTG). The sequence of PTTG contains an open reading frame for 199 amino acids (SEQ ID NO:2). The presence of an in-frame stop codon upstream of the predicted initiation codon indicates that PTTG contains the complete ORF. This was verified by demonstrating both in vitro transcription and in vitro translation of the gene product as described in Example 3.

Example 3

In vitro Transcription and Translation of the PTTG

Sense and antisense PTTG mRNAs were in vitro transcribed using T3 and T7 RNA polymerase (Stratagene), respectively. The excess template was removed by DNase I digestion. The in vitro transcribed mRNA was translated in rabbit reticular lysate (Stratagene). Reactions were carried out at 30° C. for 60 minutes, in a total volume of 25 µl containing 3 µl in vitro transcribed RNA, 2 µl $^{35}S$-Methionine (Dupond) and 20 µl lysate. Translation products were analyzed by SDS-PAGE (15% resolving gel and 5% stacking gel), and exposed to Kodak film for 16 hours.

The results indicate that translation of in vitro transcribed PTTG sense mRNA results in a protein of approximately 25 KD on SDS-PAGE, whereas no protein was generated in either the reaction without added mRNA or when PTTG antisense mRNA was utilized.

Example 4

Northern Blot Analysis of PTTG mRNA Expression

A search of GenBank and a protein profile analysis (using a BLAST Program search of databases of the national center for Biotechnology Information) indicated that PTTG shares no homology with known sequences, and its encoded protein is highly hydrophilic, and contains no well recognized functional motifs. The tissue expression patten of PTTG mRNA was studied by Northern Blot analysis. A rat multiple tissue Northern blot was purchased from Clontech. Approximately 2 μg of poly A+ RNA per lane from eight different rat tissues (heart, brain, spleen, lung, liver, skeletal muscle, kidney, and testis) was run on a denaturing formaldehyde 1.2% agarose gel, transferred to nylon membrane and UV-cross linked. The membrane was first hybridized to the full length PTTG cDNA probe, and was stripped and rehybridized to a human β-actin cDNA control probe. Hybridization was performed at 60° C. for one hour in ExpressHyb hybridization solution (Clontech). Washing was twice 15 minutes at room temperature in 2×SSC, 0.05% SDS, and twice 15 minutes at 50° C. in 0.1% SSC, 0.1% SDS. Exposure time for PTTG probe was 24 hrs, and actin probe 2 hours.

The results of the Northern assay indicate that testis is the only tissue, other than pituitary tumor cells, that expresses PTTG mRNA, and the testis expression level is much lower (2 μg polyA+ mRNA, 24 hour exposure) than in pituitary tumor cells (20 μg total RNA, 6 hour exposure). Interestingly, the testicular transcript (about 1 Kb) is shorter than the transcript in pituitary tumors (1.3 Kb), indicating that the mRNA is differentially spliced in testis, and that the 1.3 Kb transcript is specific for pituitary tumor cells.

Example 5
Over-Expression of PTTG in NIH 3T3 Fibroblast Cells

Since PTTG mRNA is over-expressed in pituitary tumor cells, whether this protein exerts an effect on cell proliferation and transformation was determined. An eukaryotic expression vector containing the entire coding region of PTTG was stably transfected into NIH 3T3 fibroblasts.

The entire coding region of the PTTG was cloned in frame into pBK-CMV eukaryotic expression vector (Stratagene), and transfected into NIH 3T3 cells by calcium precipitation. 48 hrs after transfection, cells were diluted 1:10 and grown in selection medium containing 1 mg/ml G418 for two weeks in when individual clones were isolated. Cell extracts were prepared from each colony and separated on 15% SDS-polyacrylamide gels, and blotted onto nylon membrane. A polyclonal antibody was generated using the first 17 amino acids of PTTG as epitope (Research Genetics). The antibody was diluted 1:5000 and incubated with the above membrane at room temperature for 1 hour. After washing, the membrane was incubated with horseradish peroxidase-labeled secondary antibody for one hour at room temperature. The hybridization signal was detected by enhanced chemiluminescence (ECL detection system, Amersham).

Expression levels of the PTTG were monitored by immunoblot analysis using the above-described specific polyclonal antibody directed against the first 17 amino acids of the protein. Expression levels of individual clones varied, and clones that expressed higher protein levels were used for further analysis.

Example 6
Effect of PTTG Expression on Cell Proliferation

A non-radioactive cell proliferation assay was used to determine the effect of PTTG protein over-expression on cell proliferation (see, e.g., Mosmann, T., 1983, J. Immunol. Meth., 65:55–63; and Carmichael et al., 1987, Cancer Res., 47:943–946). Cell proliferation was assayed using CellTiter 96™ Non-radioactive cell proliferation assay kit (Promega) according to the manufacturer's instructions. Five thousand cells were seeded in 96 well plates (6 wells for each clone in each assay), and incubated at 37° C. for 24 to 72 hours. At each time point, 15 μl of the Dye solution were added to each well, and incubated at 37° C. for 4 hours. One hundred μl of the solubilization/stop solution were then added to each well. After one hour incubation, the contents of the wells were mixed, and absorbance at 595 nm was recorded using an ELISA reader. Absorbance at 595 nm correlates directly with the number of cells in each well.

Three independent experiments were performed. The cell growth rate of 3T3 cells expressing PTTG protein (assayed by cellular conversion of tetrazolium into formazan) was suppressed 25 to 50% as compared with 3T3 cells expressing the pCMV vector alone, indicating that PTTG protein inhibits cell proliferation (data not shown).

Example 7
PTTG Induction of Morphological Transformation and Soft-Agar Growth of NIH 3T3 Cells The transforming property of PTTG protein was demonstrated by its ability to form foci in manslayer cultures and show anchorage-independent growth in soft agar (Table 1). As primary pituitary cells are an admixture of multiple cell types and they do not replicate in vitro, NIH 3T3 cells were employed. For the soft agar assay (Schwab et al., 1985, Nature, 316:160–162), 60 mM tissue culture plates were coated with 5 ml soft-agar (20% 2× DEEM, 50% DEEM, 10% fetal bovine serum, 20% 2.5% agar, melted and combined at 45° C.). 2 ml cells suspended in medium were then combined with 4 ml agar mixture, and 1.5 ml of this mixture added to each plate. Cells were plated at a density of $10^4$ cells/dish and incubated for 14 days before counting the number of colonies and photography. Only colonies consisting of at least 40 cells were counted. Values shown in Table 1 are means±SEM of triplicates.

TABLE 13

Colony Formation by NIH 3T3 Cells Transfected with PTTG cDNA Constructs

| Cell line | Growth in Soft Agar | Efficiency of Colony formation in Soft Agar (%)* |
|---|---|---|
| No DNA | 0 | 0 |
| Vector only | 1.3 ± 0.7 | 0.013 |
| PTTG 3 | 26 ± 4.6 | 0.26 |
| PTTG 4 | 132 ± 26 | 1.32 |
| PTTG 8 | 33 ± 6.0 | 0.33 |
| PTTG 9 | 72 ± 13 | 0.72 |
| PTTG 10 | 92 ± 18 | 0.92 |

*Efficiency of colony formation was calculated as percentage of number of colonies divided by total number of cells.

The results indicate that NIH 3T3 parental cells and 3T3 cells transfected with pCMV vector do not form colonies on soft agar, whereas 3T3 cells transfected with PTTG form large colonies. In addition, focal transformation is observed in cells over-expressing PTTG protein, but cells expressing pCMV vector without the PTTG insert showed similar morphology to the parental 3T3 cells.

Example 8
Assay to Determine Whether PTTG is Tumorigenic in vivo

To determine whether PTTG is tumorigenic in vivo, PTTG-transfected 3T3 cells were injected subcutaneously into athymic nude mice. 3×10$^5$ cells of either PTTG or pCMV vector-only transfected cells were resuspended in PBS and injected subcutaneously into nude mice (5 for each group). Tumors were excised from sacrificed animals at the end of the 3rd week and weighed. All injected animals developed large tumors (1–3 grams) within 3 weeks. The results are shown in Table 14 below. No mouse injected with vector-only transfected cells developed tumors. These results clearly indicate that PTTG is a potent transforming gene in vivo.

TABLE 14

In vivo Tumorigenesis by NIH 3T3 Cells Transfected with PTTG cDNA Expression Vector

| Cell line | No. Animals injected | Tumor formation |
|---|---|---|
| Vector only | 5 | 0/5 |
| PTTG 4 | 5 | 5/5 |

Example 9
Human Carcinoma Cell Lines Express PTTG

The pattern of expression of PTTG in various human cell lines was studied employing a multiple human cancer cell line Northern blot (Clontech). The specific cell lines tested are shown in Table 15 below.

TABLE 15

Human Carcinoma Cell Lines Tested

| | Cell Line | PTTG Expression |
|---|---|---|
| 1 | Promyelocytic Leukemia HL-60 | + |
| 2 | HeLa Cell S3 | + |
| 3 | Chronic Myelogenous Leukemia K-562 | + |
| 4 | Lymphoblastic Leukemia MOLT-4 | + |
| 5 | Burkitt's lymphoma Raji | + |
| 6 | Colorectal Adenocarcinoma SW 480 | + |
| 7 | Lung Carcinoma A549 | + |
| 8 | Melanoma G361 | + |

About 2 μg polyA RNA from each of the 8 cell lines indicated in Table 3 above were placed on each lane of a denaturing formaldehyde 1.2% agarose gel, separated by denaturing gel electrophoresis to ensure intactness, transferred to a charge-modified nylon membrane by Northern blotting, and fixed by UV irradiation. Lanes 1 to 8 contained RNA from promyelocytic leukemia HL-60, HeLa cell line S3, human chronic myelogenous leukemia K-562, lymphoblastic leukemia MOLT-4, Burkitt's lymphoma Raji, colorectal adenocarcinoma SW 480, lung carcinoma A549 and melanoma G361, respectively. RNA size marker lines at 9.5, 7.5, 4.4, 2.4, and 1.35 kb were indicated in ink on the left margin of the blot, and utilized as sizing standards, and a notch was cut out from the lower left hand corner of the membrane to provide orientation. Radiolabeled human β-actin cDNA was utilized as a control probe for matching of different batches of polyA RNAs. A single control band at 2.0 kb in all lanes spotted is confirmatory.

The blots were probed with the full length rat PTTG cDNA probe (SEQ. ID No: 1; 974 bp) at 60° C. for 1 hr. in ExpressHyb hybridization solution (Clontech) as described by Sambrook et al., the relevant section of which reference is incorporated herein by reference. See, Sambrook et al., Molecular Cloning: A Laboratory Manual, 2nd. Ed, Cold Spring Harbor Laboratory Press, Cold Spring Harbor, N.Y. (1989). The blots were then washed twice for 15 min at room temperature in 2×SSC, 0.05% SDS, and twice for 15 min at 50° C. in 0.1% SSC, 0.1% SDS. A more detailed description of the remaining experimental procedures masy be found in Pei & Melmed, the relevant section of which is incorporated herein by reference. (See, Pei & Melmed, Endocrinology 4: 433–441 [1997]).

All cells tested by the Northern blot analysis as described above evidenced expression of human PTTG (i.e., PTTG1), including lymphoma, leukemia, melanoma and lung carcinomas, among others.

Example 10
Molecular Cloning of Human PTTG cDNA

A human fetal liver cDNA library (Clontech, Palo Alto, Calif.) was screened as described by Maniatis et al. (Maniatis et al, Molecular cloning, Cold Spring Harbor Press, 1989), using a radioactively labeled cDNA fragment of the entire rat PTTG coding region as a probe. The cDNA inserts from positive clones were subcloned into plasmid pBluescript-SK (Stratagene, La Jolla, Calif.), and subjected to sequence analysis using Sequenase kit (U.S. Biochemical Corp., Cleveland, Ohio).

A complete open reading frame containing 606 bp was found in the positive clones. The homology between the nucleotide sequences of the open reading frame and the coding region of rat PTTG is 85%. Amino acid sequence comparison between the translated product of this open reading frame and rat PTTG protein reveals 77% identity and 89% homology. The cDNAs obtained from these clones represents human homologies of rat PTTG. No other cDNA fragments with higher homology were detected from the library.

Example 11
Tissue Distribution of Human PTTG mRNA

Total RNA was prepared using Trizol Reagent (Gibco-BRL, Gaithersburg, Md.) from normal human pituitary glands (Zoion Research Inc. Worcester, Mass.) and fresh human pituitary tumors collected at surgery and frozen in liquid nitrogen. 20 mg total RNA were used for 1% agarose gel electrophoresis. RNA blots (Clontech, Palo Alto, Calif.) derived from normal adult and fetal tissues as well as from malignant tumor cell lines, were hybridized with radioactively labeled human cDNA fragment containing the complete coding region. The RNA isolated from each cell line was transferred onto a nylon membrane (Amersham, Arlington Heights, Ill.), and hybridized with radioactively labeled probe at 55° C. overnight in 6×SSC, 2× Denhardt's solution, 0.25% SDS. The membranes were washed twice at room temperature for 15 minutes each, and then for 20 minutes at 60° C. in 0.5×SSC, 0.1% SDS, and autoradiographed. The autoradiography was carried out using Kodak BIOMEX-MR film (Eastman Kodak, Rochester, N.Y.) with an intensifying screen. The blots were stripped by washing for 20 minutes in distilled water at 95° C. for subsequent probing.

The results from the Northern blot analysis indicated that PTTG is expressed in liver, but not in brain, lung, and kidney of human fetal tissue. In addition, PTTG is strongly expressed in testis, modestly expressed in thymus, and weakly expressed in colon and small intestine of normasl human adult tissue. No expression was detected by Northern analysis in brain, heart, liver, lung, muscle, ovary, placenta, kidney, and pancreas.

The expression of PTTG in several human carcinoma cell lines was also analyzed by Northern blots. In every carcinoma cells examined, PTTG was found highly expressed. The human tumor cell lines tested are listed in Table 16 below.

TABLE 16

Tested Human Tumor Cell Lines

Promyelocytic leukemia HL-60
Epitheloid carcinoma HeLa cell S3
Chronic myelogenous leukemia K-562
Lymphoblastic leukemia MOLT-4
Burkitt's lymphoma Raji TABLE 16-continued Tested Human Tumor Cell Lines Colorectal adenocarcinoma SW 480
Lung carcinoma A549
Melanoma G361
Hepatocellular carcinoma Hep 3B
Thyroid carcinoma TC-1
Breast adenocarcinoma MCF-7
Osteogenic sarcoma U2 OS
Placenta choriocarcinoma JAR
Choriocarcinoma JEG-3

Example 12
Human PTTG Expression in Normal Pituitary and Pituitary Tumors

RT-PCR was performed as follows. 5 mg total RNA were treated with 100 U RNase-free DNase I at room temperature for 15 minutes. DNase I was inactivated by incubation at 65° C. for 15 minutes. The sample was then used for reverse transcription using oligo-dT primer and SuperScript II reverse transcriptase (Gibco-BRL, Gaithersburg, Md.). After reverse transcription, the sample was subjected to PCR amplification with PCR SuperMix (Gibco-BRL, Gaithersburg, Md.) using hPTTG-specific primers and human cyclophilin A-specific primers as an internal control.

Northern blot analysis indicated that the level of expression of PTTG is quite low in normal pituitary as well as in pituitary tumors. Therefore, comparative RT-PCR was used to study the expression of PTTG quantitatively in normal pituitary and pituitary tumors. The results of this study showed that in most of pituitary tumors tested, including non-functioning tumors, GH-secreting tumors, and prolactinomas, the expression level of PTTG was higher than that of normal pituitary.

Example 13
Stable Transfection of Human PTTG into NTH 3T3 Cells

The complete coding region of hPTTG cDNA was subcloned in reading frame into the mammalian expression vector pBK-CMV (Stratagene, La Jolla, Calif.), and transfected into NIH 3T3 fibroblast cells by Lipofectamine (Gibco-BRL, Gaithersburg, Md.) according to manufacturer's protocol. 24 hours after transfection, the cells were serially diluted and grown in selection medium containing 1 mg/ml G418 for 2 weeks. Individual clones were isolated and maintained in selection medium. Total RNA was isolated from hPTTG-transfected cell lines as well as from control cells in which blank vector pBK-CMV had been transfected. Northern blot was performed to confirm overexpression of hPTTG in transfected cell lines. These cell lines were used in subsequent cell proliferation assay as well as in vitro and in vivo transformation assay.

Example 14
Cell Proliferation Assay

A cell proliferation assay was performed using the Cell-Titer 96 non-radioactive cell proliferation assay kit (Promega Medicine, Wisconsin) according to the manufacturer's protocol. 5,000 cells were seeded in 96-well plates and incubated at 37° C. for 24–72 hours. Eight wells were used for each clone in each assay. At each time point, 15 ml of dye solution was added to each well and the cells were incubated at 37° C. for 4 hours. After incubation, 100 ml solubilization/stop solution were added to each well, and the plates incubated overnight at room temperature. The absorbance was determined at 595 nm using an ELISA plate reader.

Control and hPTTG-overexpressing NIH 3T3 cells were used to perform this assay. The results indicated that the growth of cells transfected with the PTTG-expressing vector was suppressed by 30–45% as compared with cells transfected with blank vector. These results clearly show that the PTTG protein inhibits cell proliferation.

Example 15
In vitro and in vivo Transformation Assay
(a) In vitro Transformation Assay Control and hPTTG-transfected cells were tested for anchorage-independent growth in soft agar. 3 ml of soft agar (20% of 2×DMEM, 50% DMEM, 10% fetal bovine serum, and 20% of 2.5% agar, melted and mixed at 45° C.) were added to 35 mm tissue dishes. 10,000 cells were mixed with 1 ml soft agar and added to each dish, and iincubated for 2 weeks until colonies could be counted and photographed.
(b) In vivo Transformation Assay $5 \times 10^5$ cells containing either a blank vector or hPTTG-expressing cells were injected into nude mice. The mice were sacrificed two weeks after injection, and the tumors formed near the injection sites examined.

When the NIH 3T3 cells stably transfected with the PTTG-expressing vector were tested in an anchorage-independent growth assay, these cells caused large colony formation on soft agar, suggesting the transforming ability of PTTG protein.

When the NIH 3T3 cells were injected into nude mice, they caused in vivo tumor formation within 2 weeks after injection. These data indicate that human PTTG, as its rat homologue, is a potent transforming gene.

Example 16
Inhibition of Cell Transformation/Tumor Formation by PTTG C-Terminal Polypeptide
Cell Lines NIH 3T3 cells were maintained in high glucose (4.5 g/L) DMEM (Gibco-BRL) supplemented with 10% fetal bovine serum. HeLa cells were maintained in low glucose (1 g/L) DMEM (Gibco-BRL) supplemented with 10% fetal bovine serum (FBS). T-47D and MCF-7 cells were maintained in high glucose DMEM (Gibco-BRL) supplemented with 10% fetal bovine serum and 0.01 mg/mL bovine insulin (Sigma). All cell lines were obtained from American Type Culture Collection (ATCC).
Site-directed Mutagenesis and Stable Transfection of Human and Mutant PTTG into NIH 3T3 Cells Point mutations on the proline-rich domain(s) of wild type human PTTG polypeptide (wtPTTG) were generated by PCR-based site-directed mutagenesis. Two synthetic oligonucleotides,
5'-GATGCTCTCCGCACTCTGGGAATCCAATCTG-3' (SEQ. ID. NO.:5) and
5'-TTCACAAGTTGAGGGGCGCCCAGCTGAAACAG-3' (SEQ. ID. NO.:6), which cause point mutations that result in amino acid sequence changes P163A, S165Q, P166L, P170L, P172A, and P173L in the wtPTTG protein, were used to amplify human PTTG cDNA cloned into pBlue-Script-SK vector (Stratagene). Amplified mutated cDNA (mutPTTG) was then cloned into mammalian expression vector pCI-neo (Promega). Overexpression of mutPTTG in transfected cells was confirmed by Northern analysis and RT-PCR followed by direct sequence analysis. wtPTTG and mutPTTG were subdloned into pCI-neo, and the vector was used to transfect NIH 3T3 cells as described in Zhang, X., et al. [1999a].
Transactivation Assay wtPTTG cDNA was fused in frame with pGAL4 (Stratagene), designated pGAL4-wtPTTG and was used as template for deletion and mutation analysis; mutPTTG cDNA was also fused in frame with pGAL4 and designated pGAL4-mutPTTG. pGAL4-VP 16 was used as a positive control. Experimental plasmids; were co-transfected with pLUC and pCMV-β-Gal (as internal control). Cell lysates were prepared 48 hours after transfection and assayed for luciferase activity as described (Wang, Z. and Melmed, S. [2000]; Sambrook, J., et al., *Molecular Cloning: A Laboratory Manual*, 2d Ed. Cold Spring Harbor Laboratory, Cold Spring Harbor, N.Y., 10.2.1–10.2.6[1989]).

Constructions of Expression Vectors for Wild Type and Mutant Human PTTG C-terminal Polypeptides To generate wtPTTG and mutPTTG C-terminal polypeptide expression vector, the internal Xba I site of wtPTTG and mutPTTG cDNA and the 3'-portions of these cDNAs were cloned into pCI-neo (Promega, Madison, Wis.) via Xba I and Not I sites. In these clone, the ATG for M147 of full-length PTTG is used as an initiation codon, generating a polypeptide of 56 amino acid residues corresponding to nucleotide positions 147 through 202 of full-length wtPTTG.

Stable Transfection of Human PTTG C-terminal Peptide into Tumor Cells

Wild type and mutant PTTG C-terminal expression constructs were transfected into HeLa, MCF-7, and T47-D cells with Lipofectin (GIBCO-BRL) according to the manufacturer's protocol. Twenty-four hours after transfection, cells were serially diluted and selected with G418 (1 mg/mL) for 2 weeks. Individual clones were isolated and maintained in selection medium (respective high or low glucose DMEM with 10% FBS, as described above, and G148 [1 mg/mL]), and total RNA was extracted from transfected cells. Expression of wild-type and mutated PTTG-C terminal was confirmed by RT-PCR using two synthetic oligonucleotides, with one specific to the 5'-nontranslational region from vector pCI-neo, 5'-GGCTAGAGTACTTAATACGACTCACTATAGGC-3' (SEQ. ID. NO.:7), and the other to the 3'-translational region of PTTG1 cDNA, 5'-CTATGTCACAGCAAACAGGTGGCAATTCAAC-3' (SEQ. ID. NO.:8), followed by direct sequence analysis.

In Vitro Colony Formation and in vivo Tumorigenesis

NIH 3T3 stable transfectants were tested in vivo as described in Zhang, X., et al. [1999a]. Transfected cells were tested for anchorage-independent growth in soft agar as described Zhang, X., et al. [1999a]. HeLa cells were incubated for 3 weeks and MCF-7 (breast carcinoma) and T-47D (breast carcinoma) cells for 2 weeks. For in vivo assays of tumorigenesis, $1 \times 10^7$ MCF-7 stable transfectants were resuspended in 500 µL MATRIGEL basement membrane matrix (Becton Dickinson, Bedford, Mass.) and were injected subcutaneously into nude mice (three mice for each group). After four weeks, animals were photographed and tumors were excised and weighed.

ELISA of Basic Fibroblast Growth Factor (bFGF) in Conditioned Medium

The concentration of basic fibroblast growth factor (bFGF) concentration in HeLa cell culture medium was assayed using Quantikine HS Human FGF Basic Immunoassay Kit (R&D Systems, Minneapolis, Minn.) according to the manufacturer's protocol. Cells ($1 \times 10^5$) were plated in 100-mm cell culture dishes. After 72 hours, the culture medium was collected and 200 mL was used for ELISA assay.

Effects of Wild Type Human PTTG and Mutant PTTG Overexpression on Tumor Induction It was previously demonstrated that NIH 3T3 cells overexpressing wild type PTTG formed large colonies in an anchorage-independent growth assay and formed tumors when injected into athymic nude mice, while point mutations in the proline-rich region (P163A, P170L, P172A, and P173L) abrogated formation of colonies and tumors (Zhang, X., et al. [1999a]). Overexpression of wtPTTG and mutPTTG (P163A, S165Q, P166L, P170L, P172A, and P173L) in each transfectant cell line was confirmed by Northern analysis and RT-PCR followed by direct sequence analysis (not shown).

It was further shown that overexpressing PTTG transfectants injected into athymic nude mice caused tumor formation within 2 weeks in all injected animals. Five mice in each of three groups were injected subcutaneously with $3 \times 10^5$ NIH 3T3 cells transfected with: (1) control cell line (transfected with pGAL4 vector alone); (2) wild type PTTG-overexpressing (wtPTTG); or (3) mutant PTTG-overexpressing (mutPTTG [P163A, S165Q, P166L, P170L, P172A, and P173L]). After 2 weeks, mice were sacrificed and tumors were excised and weighed. In the mice injected with control transfectants or mutPTTG transfectants, no tumors developed. but mice injected with transfectant cells bearing wtPTTG developed tumors without exception. Tumor weights ranged from 470 to 1500 mg (Table 17).

TABLE 17

Tumor formation by PTTG-expressing NIH 3T3 Cells in Athymic Nude Mice.

| Vector | Tumor weight (mg) wtPTTG | mutPTTG |
|---|---|---|
| none* | 1500 | none |
| none | 770 | none |
| none | 1250 | none |
| none | 550 | none |
| none | 470 | none |

*none = no detectable tumor.

PTTG Exhibits Transcriptional Activation

Vector pGal4 alone (negative control) did not activate the luciferase (luc) reporter, and a known activation domain, VP 16, significantly increased reporter activity about 28-fold. pGAL4-wtPTTG exhibited transactivation properties and induced reporter activity about 22-fold (FIG. 1).

Transcriptional activity of pGAL4-mutPTTG (mutated proline region [P163A, S165Q, P166L., P170L, P172A, and P173L]), other point mutations, as well as a separate deletions (d) of wtPTTG were also tested as indicated in Table 18. In Table 18, the indicated plasmids were co-transfected with pLuc and pCMV-P-Gal into NIH 3T3 cells, and luciferase assays were performed, with β-Gal serving as the internal control. Each value represents triplicate wells from two independent experiments (±SEM); transactivation by wtPTTG was designated 100%. pGAL4-mutPTTG exhibited about 95% transactivating activity compared to pGAL4-wtPTTG, thus confirming the importance of the wtPTTG proline-rich motif for transactivation.

TABLE 18

Transactivation assay of hPTTG mutants.

| Mutant | activation activity (%)(±SEM) |
|---|---|
| pGAL4-wtPTTG | 100 |
| 163 Pro → Ala | 100 ± 10 |
| 166 Pro → Ala | 45 ± 5* |
| 170 Pro → Ala | 100 ± 10 |
| 182 Pro → Ala | 100 ± 10 |

TABLE 18-continued

Transactivation assay of hPTTG mutants.

| Mutant | activation activity (%)(±SEM) |
|---|---|
| 152 Glu → Gln | 100 ± 10 |
| 192 Glu → Gln | 50 ± 3* |
| 165 Ser → Ala | 30 ± 3* |
| 165 Ser → Leu | 20 ± 2* |
| 176 Ser → Ala | 100 ± 10 |
| 183 Ser → Ala | 100 ± 10 |
| 184 Ser → Ala | 100 ± 10 |
| d(1–100) | 100 ± 10 |
| d(180–202) | 100 ± 10 |
| mutPTTG | 6 ± 1* |

*p < 0.01

Human PTTG C-terminal Peptide Expression Blocks Cell Transformation

The critical role of the proline-rich region in transactivation, transformation and tumor formation, as described above, implies that PTTG functions through SH3-mediated signal transduction. If human PTTG1 protein mediates the SH3-related signal cascade, it probably contains at least two functional domains interacting with upstream and downstream signal molecule(s), respectively. A mutant protein containing only one such functional domain could then act in a dominant-negative manner to abrogate wild-type protein function and disrupt signal transduction.

Based on this hypothesis, a truncated PTTG1 mutant peptide, lacking N-terminal amino acid residues 1–146, was introduced into human carcinoma cells. An expression construct was used expressing a PTTG-C peptide corresponding to residues 147–202 of the full-length protein, under the control of a CMV promoter. This polypeptide contains the proline-rich domain(s) (residues 163–173; Zhang, X., et al. [1999a]), and when the coding sequence was fused to glutathione S-transferase (GST), it was expressed in *Escherichia coli* as an intact protein with the appropriate molecular weight (data not shown). Mutant expression vector pCIneo-mutPTTG (mutated proline region [P163A, S165Q, P166L., P170L, P172A, and P173L]), as well as the empty vector pCI-neo alone as control, were stably transfected into HeLa, MCF-7, and T-47D human carcinoma cell lines.

Figure 2A:
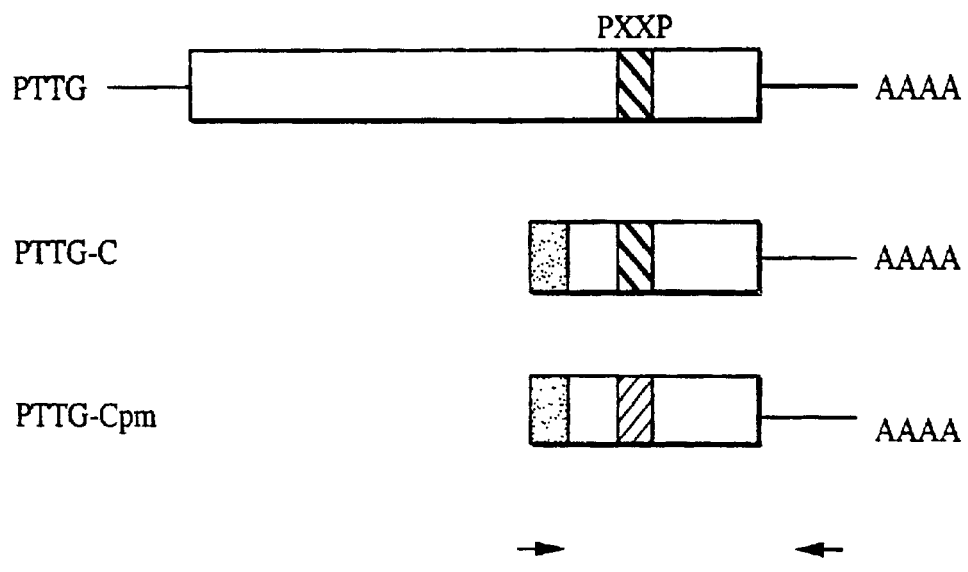
FIG. 2A illustrates expression construct which express a C-terminal peptide of human PTTG protein (PTTGC), corresponding to amino acid residues 147–202 of SEQ. ID. NO.:4 (i.e., SEQ. ID. NO.:9), under the control of the CMV promoter (black bar). PXXP represents the proline-rich region(s) of the PTTG-C. A mutant expression vector (PTTG-Cpm), contained point mutations P163A, S165Q, P166L, P170L, P172A, and P173L.
Figure 2B:
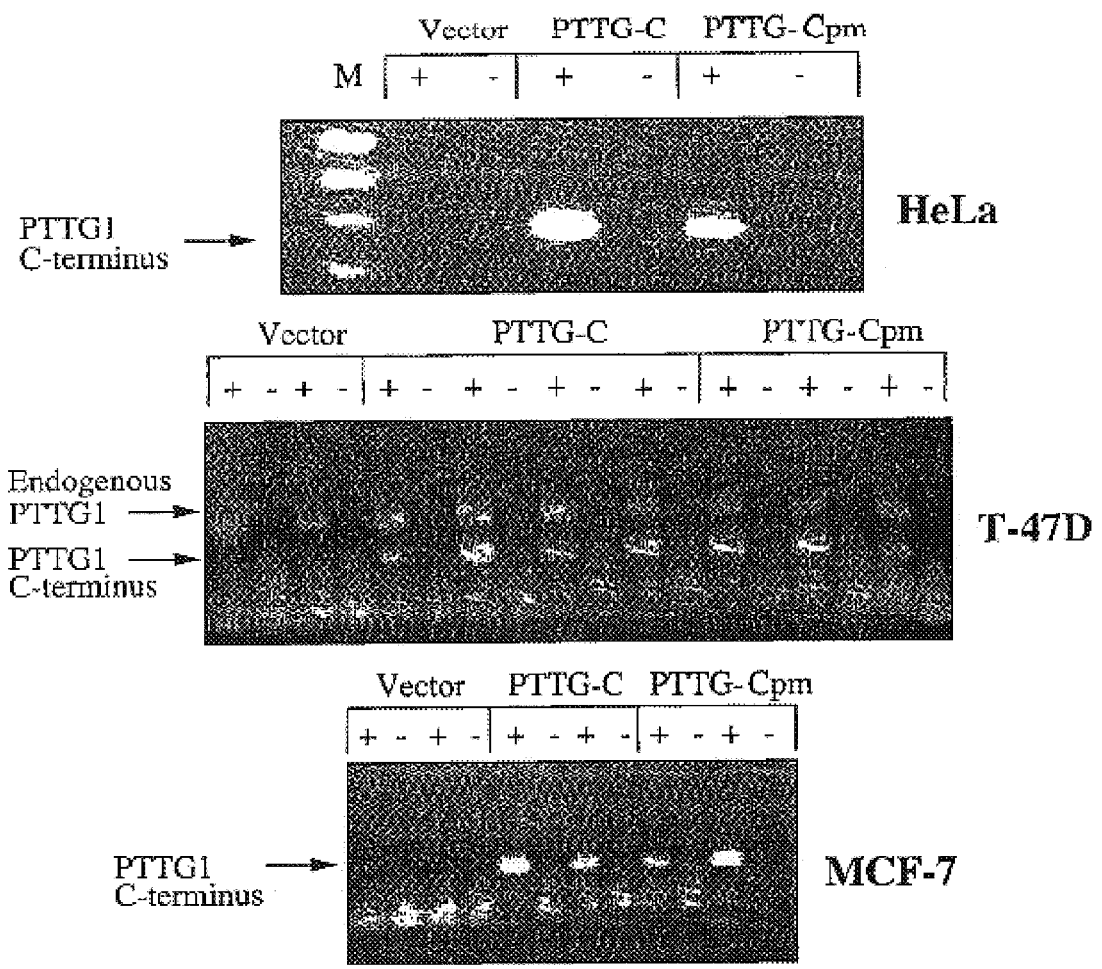
FIG. 2B includes representative 1% agarose gels of RT-PCR products of HeLa (top panel), T-47D (middle panel), and MCF-7 cells (bottom panel), showing PTTG-C and PTTG-Cpm expression. Products from reverse transcription carried out in the presence (+) or absence (−) of RT were used as template in PCR reactions.
Figure 2C:
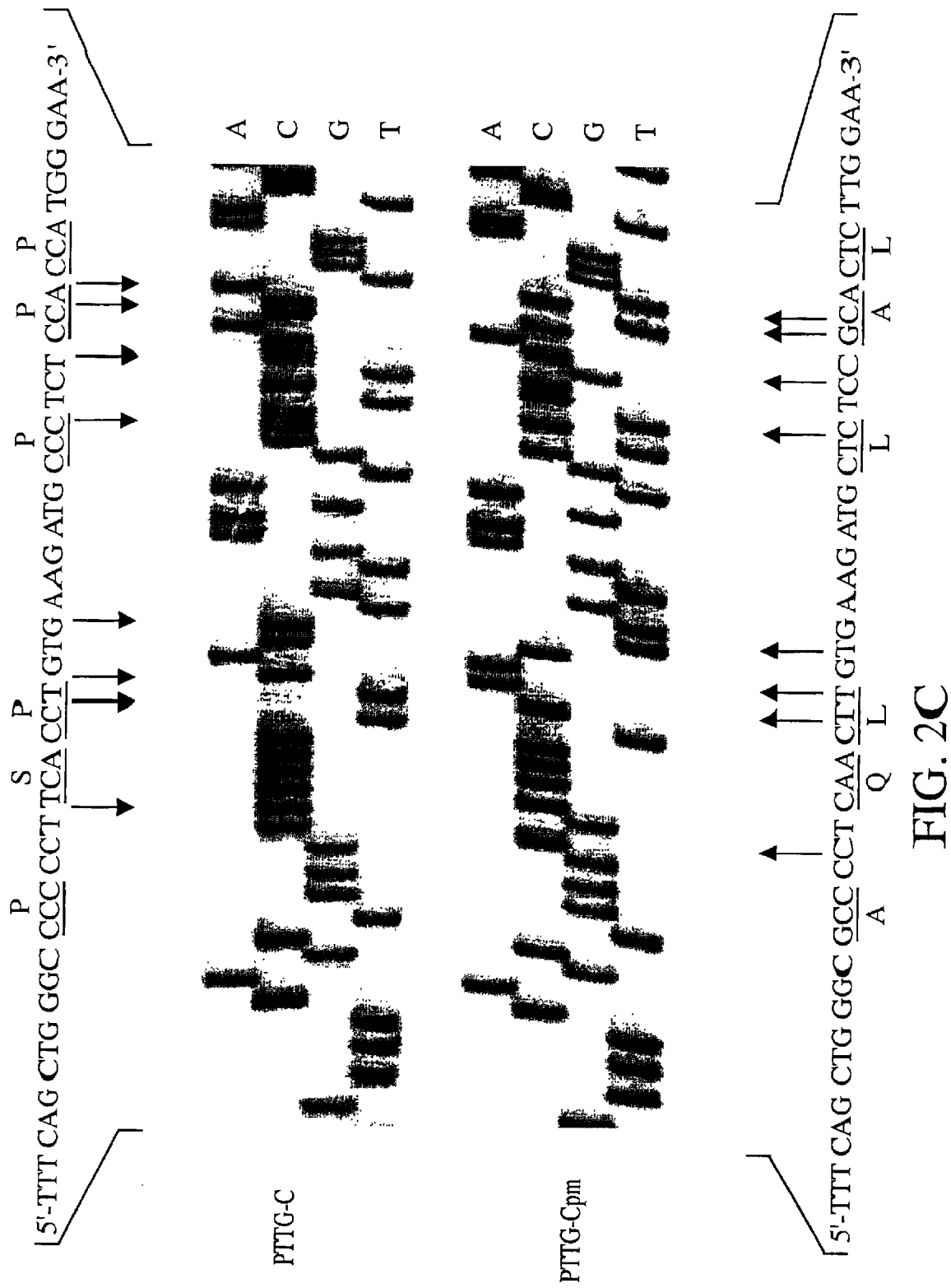
FIG. 2C shows a representative sequencing gel from RT-PCR followed by direct sequencing analysis showing PTTG-C and PTTG-Cpm expression in respective transfectants. Arrows point to nucleotide changes.
Figure 3:
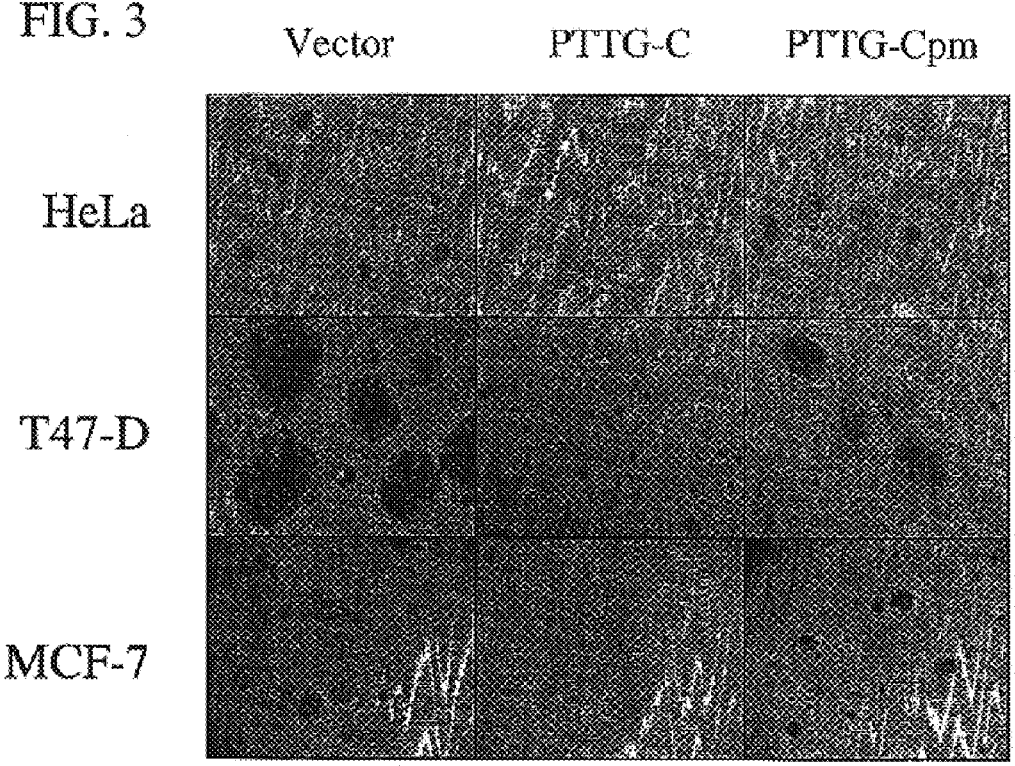
FIG. 3 shows colony formation of HeLa (top row), T-47D (middle row), and MCF-7 (bottom row) cells transfected with PTTG-C or PTTG-Cpm expression vectors on soft agar. "Vector" (left column) shows cells transfected with vector pCI-neo alone; "PTTG-C" (middle column) shows cells transfected with vector pCI-neo containing PTTG C-terminal encoding cDNA; "PTTG-Cpm" (right column) shows cells transfected with vector pCI-neo containing mutant PTTG C-terminal cDNA (P163A, S165Q, P166L, P170L, P172A, and P 173L).

Transfectants expressing wild-type PTTG carboxy-terminal peptide (PTTG-C), PTTG C-terminal mutated in several proline residues (PTTG-Cpm; mutated proline region [P163A, S165Q, P166L., P170L, P172A, and P173L]), and vector (V), were isolated. Expression of each transfectant line was confirmed by RT-PCR, using a primer directed to the 5'-nontranslational region of the expression vector and a primer directed to the 3'-translational region of PTTG mRNA, followed by direct sequence analysis (FIGS. 2A, 2B, and 2C). Transforming abilities of all three of these stably transfected cell lines were tested in an anchorage-independent growth assay, PTTG-Cpm cells were observed to form large colonies, as did control V cells containing the same expression vector but lacking either wild type or mutant C-terminal polypeptide. Each transfectant cell line was plated in three different plates. HeLa was scored on the 21st day and T-47D and MCF-7 on the 14th day. Colonies consisting of 60 or more cells were scored. However, the number and size, of colonies formed by cells expressing PTTG-C were markedly reduced (p<0.01) (FIG. 3). Table 19 (below) summarizes the soft agar colony formation for each cancer cell type.

TABLE 19

Colony Formation by PTTG I C-terminal (PTTG-C) and mutant PTTG C-terminal (PTTG-Cpm) Expressing Cells in Soft Agar.

| Cell Line | Vector | Colonies/$10^4$ Cells (mean ± SEM) |
|---|---|---|
| HeLa | Vector alone | 1465 ± 54 |
| | Vector alone | 2392 ± 55 |
| | PTTG-C | 11 ± 2* |
| | PTTG-C | 6 ± 1* |
| | PTTG-C | 48 ± 3* |
| | PTTG-C | 3 ± 1* |
| | PTTG-Cpm | 1169 ± 77 |
| | PTTG-Cpm | 1097 ± 79 |
| | PITG-Cpm | 2615 ± 76 |
| T-47D | Vector alone | 135 ± 4 |
| | PTTG-C | 46 ± 5* |
| | PTTG-C | 52 ± 2* |
| | PTTG-Cpm | 193 ± 5 |
| | PTTG-Cpm | 106 ± 5 |
| MCF-7 | Vector alone | 287 ± 3 |
| | PTTG-C | 9 ± 3* |
| | PTTG-C | 34 ± 4* |
| | PTTG-Cpm | 236 ± 11 |
| | PTTG-Cpm | 206 ± 4 |

* P < 0.01

Human PTTG C-terminal Polypeptide-expressing MCF-7 Breast Carcinoma Cells Fail to Develop Tumors in vivo Stably transfected MCF-7 breast carcinoma cell lines were injected ($1\times10^7$ cells/per mouse in 500 µL MATRIGEL basement membrane matrix) subcutaneously into athymic nude mice. After four weeks, mice were photographed, killed, and their tumors were excised and weighed. Three mice injected with cells transfected with control vector only developed visible tumors in 4 weeks, while three mice injected with PTTG-C-transfected cells failed to generate tumors. At autopsy, absence of subcutaneous or other peripheral tumor formation was confirmed in the mice receiving PTTG-C transfected cells. Three mice injected with PTTG-Cpm-transfected cells also developed tumors after 4 weeks, which were similar in size to those developed in mice injected with control vector-transfected cells, indicating that the mutated PTTG-C-terminal polypeptide lost its ability to abrogate endogenous PTTG function (Table 20).

TABLE 20

Tumor formation by PTTG-C expressing MCF-7 Breast Carcinoma Cells in Athymic Nude Mice.

| | Tumor weight (mg) | |
|---|---|---|
| Vector | PTTG-C | PTTG-Cpm |
| 212 | none* | 185 |
| 235 | none | 196 |
| 209 | none | 203 |

*none = no detectable tumor.

Figure 4:
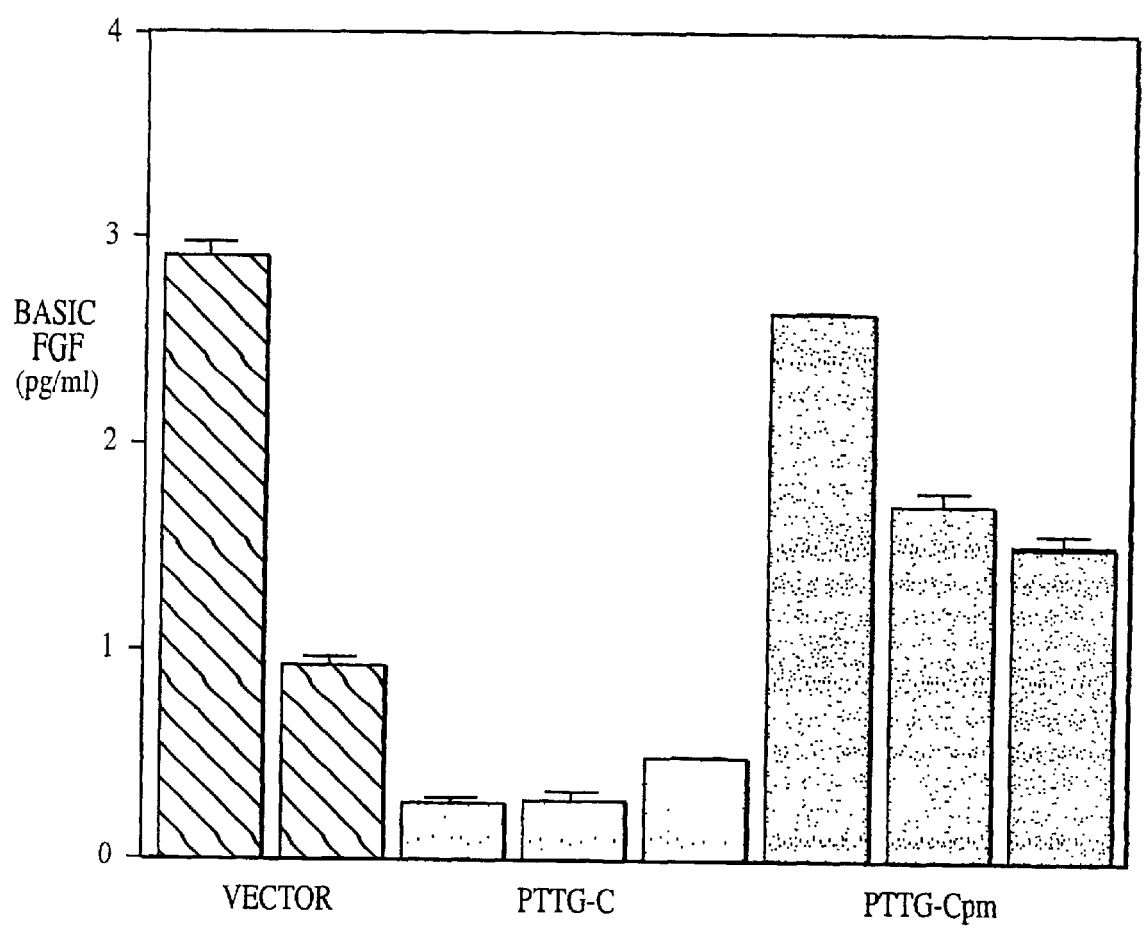
FIG. 4 shows suppression of bFGF secretion by HeLa cells expressing PTTG-C peptide. The concentration of bFGF in conditioned medium derived from transfectants cultured for 72 h as measure by ELISA. "Vector" (two left-most bars) indicates medium conditioned by cells transfected with vector pCI-neo alone; "PTTG-C" (three middle bars) indicates medium conditioned by cells transfected with vector pCI-neo containing wtPTTG-C-terminal encoding cDNA; "PTTG-Cpm" (three right-most bars) indicates medium conditioned by transfected with vector pCI-neo containing mutant PTTG C-terminal encoding cDNA (P163A, S165Q, P166L, P170L, P172A, and P173L).

These results show that overexpression of the PTTG C-terminal peptide caused cancer cells to lose their abilities for in vitro cell transformation and ex vivo tumor growth. Also, the importance of proline-rich regions is further confirmed here, since PTTG C-terminal peptide containing point mutations of these proline residues failed to interfere with transforming activity or tumor-forming activity in vivo. Suppression of bFGF Secretion and PRL Expression by PTTG-C Peptide As cells expressing wild-type human PTTG-C terminal peptide had markedly reduced colony forming ability on soft agar and were also unable to induce solid tumor growth in vivo, expression of bFGF was tested in HeLa transfectants. An enzyme-linked immunoabsorbent assay (ELISA) was performed to examine bFGF levels in conditioned medium derived from 72-hour cultures of HeLa transfectants. As shown in FIG. 4, bFGF levels were markedly decreased in conditioned medium derived from PTTG-C DNA-transfected cells than those derived from vector-only and PTTG-Cpm-transfected cells, indicated a suppression of bFGF secretion resulting from the presence of PTTG carboxy-terminal peptide.

Since, the growth rate of solid tumors is directly related to activation of angiogenesis and recruitment of new blood vessels, this shows that, in accordance with the inventive method, the ability for new blood vessel growth can be impaired by the inventive PTTG-C peptides, providing an additional mechanism leading to the failure of in vivo neoplastic cellular proliferation and tumor growth. Experimental tumors do not grow more than 1 or 2 mm in diameter in the absence of angiogenesis. (Folkman, J., N. Engl. J. Med. 285:1182–1186 [1971]; Folkman, J., and Klagsburn, M. (1987) Science 235:442–447 [1987]). The human cancer cell lines used in this study form prominent solid tumors (>2 mm in diameter) indicating active angiogenesis.

Moreover, these results imply that additional hormonal regulatory cascades can be affected by the inventive PTTG-C peptides, because reduced bFGF secretion can result in altered expression of bFGF-mediated pathways, for example prolactin (PRL) expression. For example, expression of the same human wild-type PTTG-C-terminal peptide (amino acid residues 147–202 of SEQ. ID. NO.:4) in rat prolactin (PRL)- and growth hormone (GH)-secreting GH3 cells caused markedly reduced PRL promoter activity (about 16-fold decrease), PRL mRNA expression (about 10-fold decrease), and prolactin protein expression (about 72-fold decrease) in comparison to rat GH3 cells transfected with control vector alone or GH3 cells expressing a mutated PTTG1 C-terminal fragment (P163A, S165Q, P166L, P170A, P172A, and P173L; data not shown). Furthermore, a compensatory increase in GH mRNA (about 13-fold increase) and protein (about 37-fold increase) were observed in the PTTG-C-terminal expressing GH3 cells. These observations demonstrate that PTTG carboxy-terminal peptide expressed in GH3 cells alters the hormonal secretory pattern by silencing PRL-gene expression and augmenting GH expression.

Example 17
Expression of PTTG in Normal and Leukemic T-Lymphocyte Cells
Cell Culture T-lymphocytes were prepared by positive selection of mononuclear cells from fresh peripheral venous blood of healthy human adults. In some experiments leukopack preparations of American Red Cross anonymous donors were used. Mononuclear blood cells were isolated by gradient centrifugation using Lymphoprep™ KIT (Nycomed Pharma AS, Oslo, Norway). When leukopack preparations were used, the isolated mononuclear cells were first frozen in 90% fetal bovine serum (FBS) supplemented with 10% DMSO. These cells were thawed and washed and grown in RPMI-1640 medium supplemented with 10% FBS. Human Jurkat leukemia T cell and human HL-60 promyelocytic leukemia cells were grown in the same medium.

Double T cell selection was performed using immunomagnetic beads (Dynal CD2™ CELLection™ KIT, Dynal AS, Oslo, Norway), and cells were further activated by culturing in Petri dishes containing immobilized anti-human monoclonal CD3 antibody (PharMingen International, Becton Dickinson Co.). Antibody immobilization was achieved by 90 min incubation (37° C.) of fresh 60 mm plastic Petri dishes filled with 1 mL of anti-CD3 solution (10 $\mu$g/mL) in phosphate buffered saline (PBS). KIT protocols provided by the manufacturers were used during isolation and activation of T-cells. In some experiments, resting T-cells were activated using phytohemagglutinin (PHA, 5 $\mu$g/mL, Gibco-BRL). In each experiment, cells were labeled with triple fluorochrome-labeled anti-CD3/CD19/CD45 antibodies (Caltag Laboratories, Inc., Burlingame, Calif.) and then were studied using flow cytometry (Becton-Dickinson FACScan) in order to check relative amounts of anti-CD3-labeled T-lymphocytes in the cell population. Samples containing 95–97% of T cells and 0–0.05% of B cells were used in the experiments. Cells were also treated with sodium salt of hydrocortisone 21-hemisuccinate (0.1–1 $\mu$M, Sigma, St.Louis, Mo.), cyclosporin A (1 $\mu$g/mL, Calbiochem, SanDiego, Calif.), TGF beta1 (10 ng/mL, R & D Systems, Inc., Minneapolis, Minn.), aphidicolin (1 $\mu$g/mL, Calbiochem), nocodazole (500 ng/mL, Calbiochem) beginning from zero time after the starting of cell activation. Control experiments for dissolvants (0.1% $C_2H_5OH$ (aphidicolin) and 0.2% DMSO (nocodazole)) did not evidence an effect on PTTG mRNA expression.

Northern Blot Analysis

Total RNA was isolated using TRIzol Reagent (Gibco-BRL, Grand Island, N.Y.); RNA (about 5 $\mu$g for T cells and 20 $\mu$g for Jurkat cells) was electrophoresed in 1% agarose-formaldehyde gel and blotted onto Hybond-N membranes (Amersham International, UK). The membranes were UV-cross-linked, prehybridized for 1 hour at 68° C. in QuickHyb solution (Stratagen, La Jolla, Calif.), and then were hybridized for 3 hours at 68° C. in the same solution supplemented with random-primed $^{32}$P-labeled human PTTG cDNA ($2\times10^6$ cpm/mL) and sonicated and denaturated salmon sperm DNA (Stratagen). When IL-2 mRNA expression was studied, sequences of oligonucleotide sense and anti-sense primers for PCR preparation of IL-2 cDNA probe (sized 457 base pairs) were as previously reported. (Butch, A W et al., *Cytokine exression bygerminal center cells*, J Immunol.150:39–47. [1993]). Cyclophilin cDNA probe was from Ambion, Inc. (Austin, Tex.). The membranes were washed twice (20 min each time) in 1xSSC and 0.1% SDS at room temperature, followed by one wash (30 min) in 0.2xSSC and 0.1% SDS at 60° C. After washing membrane was exposed to X-ray film (Kodak, Rochester, N.Y.) overnight.

Western Blot Analysis

Cells were harvested in Eppendorf tubes and lysed for 15 min on ice in lysis buffer: 50 mM HEPES, 150 mM NaCl, 10 mM EDTA, 10 mM $Na_4P_2O_7$, 100 mM NaF, 2 mM sodium orthovanadate, pH 7.4, supplemented before use with 1% Triton X-100, 1 mM phenylmethylsulfonyl fluoride (PMSF), 1 $\mu$g/mL aprotinin, 2 mM leupeptin. Protein concentration was determined in the lysed cells' supernatants, and aliquots containing 50 $\mu$g of protein were diluted in SDS-PAGE sample buffer, boiled for 5 min, cooled, centrifuged and separated in 10% SDS-PAGE. Proteins were transferred onto PVDF Immobilon-P membrane (Millipore, Bedford, Mass.). Membrane was incubated with polyclonal rabbit antiserum against human PTTG polypeptide fragment (1:3,000 dilution) at 4° C. overnight, followed by incubation with peroxidase-linked secondary antibody (Santa Cruz Biotechnology, Santa Cruz. Calif.). Blots were visualized using ECL Western Blotting Detection Reagent (Amersham).

FACS Analysis

To study cell cycle patterns cells were pelleted by centrifugation, washed in cold (4° C.) phosphate-buffered saline (PBS), resuspended in 1 mL of PBS, and then 2 mL of cold methanol was slowly added for cell fixation.

500 μL of propidium iodide (500 μg/mL PBS) together with 1 μL of ribonuclease A (10 units/μL) were added and cell suspension was vortexed. After incubation for 1 hour at 4° C., cell samples were analyzed by flow cytometry, performed on Becton-Dickinson FACScan. Analysis regions contained a minimum of 10,000 events. Cell cycle analysis was then performed on these data on Modfit software using Macintosh computer.

Cell labeling with triple mouse anti-CD3/CD19/CD45 flourochrome-labeled antibodies was performed using manufacturer protocol (Caltag Laboratories, Inc., Burlingame, Calif.). Shortly 15 μL of Caltag triple antibody was added to 100 μL of cell suspension, and then 180 μL of PBS was added and gently mixed. Tubes were incubated at room temperature for 15 min in the dark, cells were fixed using Cal-Lyse Lysing Solution (Caltag Laboratories, Inc.), washed with 3 mL of deionized water, pelleted by centrifugation and resuspended in 1 mL of cold PBS. Flow cytometry was done using a Becton-Dickinson FACScan.

All experiments were repeated at least 3 times, and the results of a typical experiment are presented immediately below.

PTTG Expression was Upregulated Upon T-cell Activation

It is known that T-cell activation needs a complex interaction between T lymphocyte and antigen-presenting cell. (Crabtree G R, Clipstone N A, *Signal transmission between the plasma membrane and nucleus of T lymphocytes*, Annu Rev Biochem. 63:1045–1083 [1994]). T cell receptor interaction with major histocompatibility complex generates the most important signals for T-cell activation, although some adhesive interactions as well as costimulatory molecules are also of great significance here. T-cell surface molecules appear to provide costimulatory signals in two ways: either quantitatively by augmenting the second messenger generated by TCR/CD3 complex (for example, CD2), or qualitavely (for example, CD28) by generating intracellular biochemical signals distinct from those generated by TCR/CD3 complex. The procedure which we used for positive T-cell included T-cell binding to anti-CD2-coated immunomagnetic beads followed by cell culturing in anti-CD3-coated dishes. Although immunomagnetic beads themselves were not able to activate T-cells (no increase in PTTG mRNA expression and in cell cycling was observed) they could serve as a co-stimulator for T-cells. As an indirect argument for this suggestion could be our observation (data are not presented in this study) that T-cells isolated using cell sorter could not be activated neither with immobilized anti-CD3-antibodies, nor with PHA.

Figure 5:
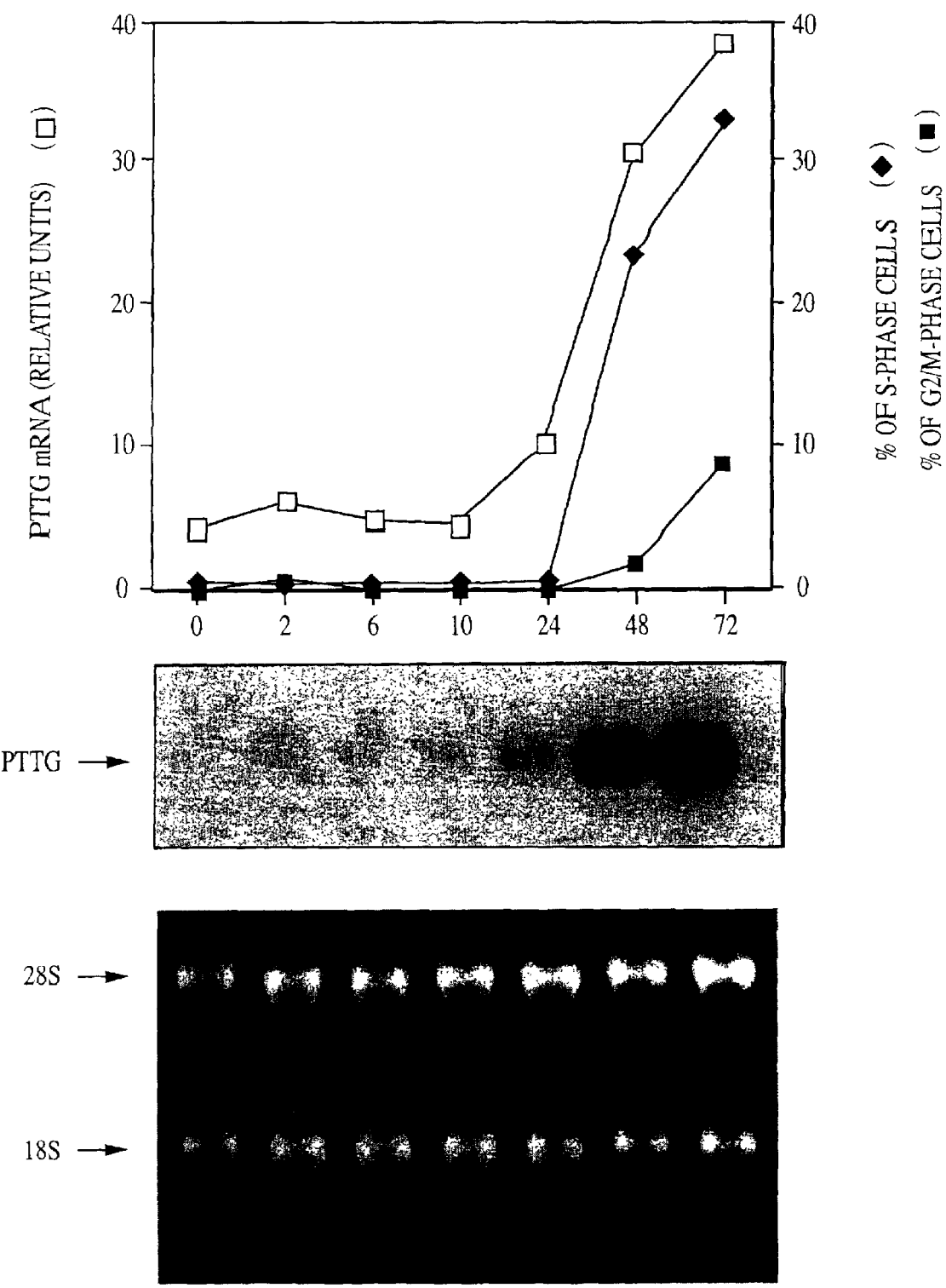
FIG. 5 shows PTTG mRNA expression in normal adult human T-cells treated with mitogen anti-CD3 antibody. T-cells were isolated and stimulated with anti-CD3 antibody for 72 hours. PTTG mRNA PTTG was measured with northern blotting (middle panel) and percentage of cells in S or G2/M phase was determined by FACS.
Figure 6:
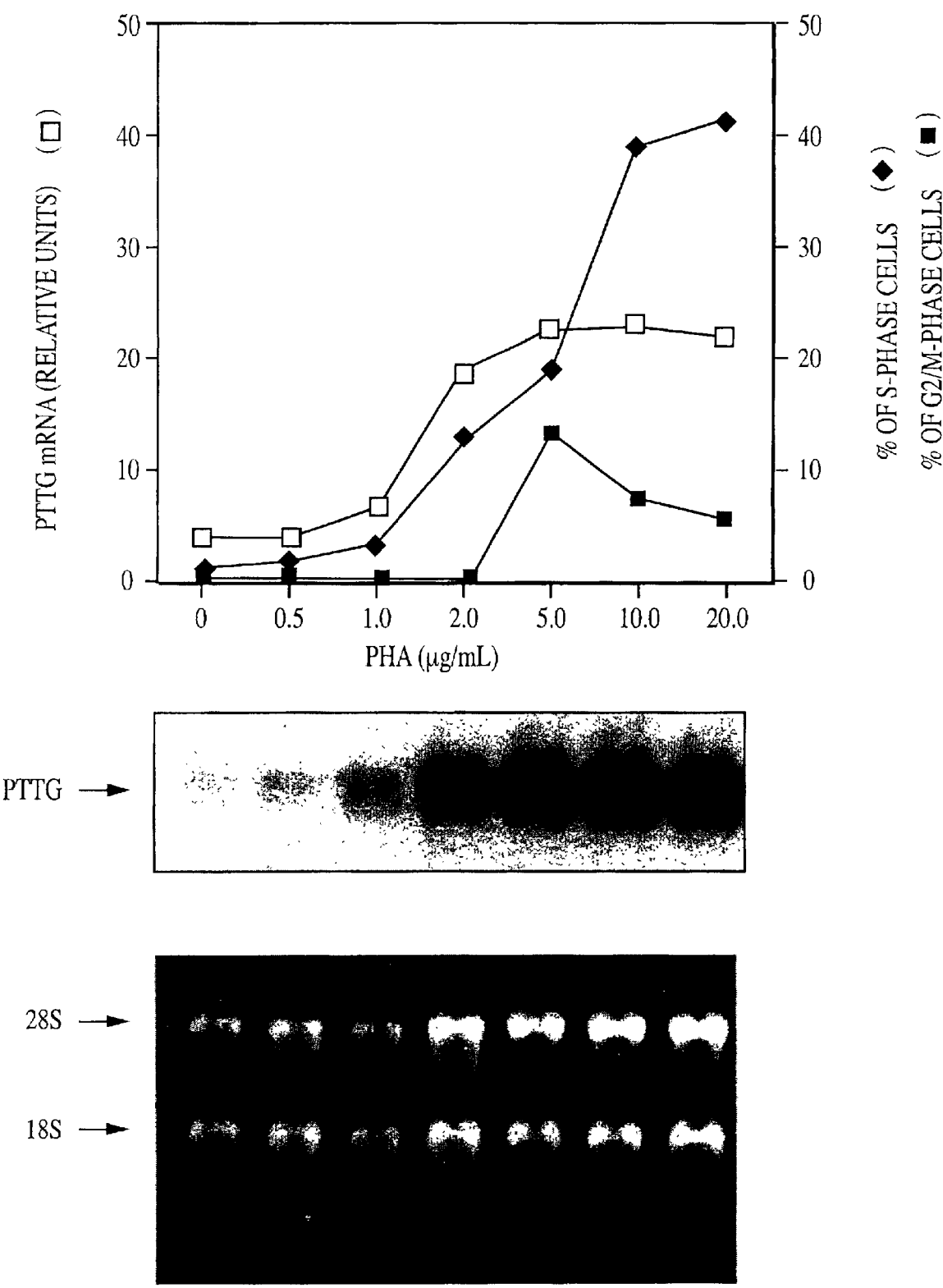
FIG. 6 shows PTTG mRNA expression in normal adult human T-cells treated with mitogen phytohemagglutinin (PHA). T-cells were isolated and stimulated with increasing concentrations of PHA for 72 hours. PTTG mRNA was measured with northern blotting (middle panel) and percentage of cells in S or G2/M phase was determined by FACS.

After resting human T cells were treated with a T-cell mitogen CD3 antibody, T-cells began to proliferate as shown by cells sequentially entering S phase and G2/M phase (FIG. 5). PTTG mRNA expression was practically non-existent in resting T-cells but it was dramatically increased as percentage of cells in S and G2/M phase became substantial. After resting T-lymphocyte cells were stimulated with another mitogen (phytohemagglutinin [PHA]), a similar time course was seen for both T-cell proliferation and PTTG expression (data not shown). T-cell proliferation and PTTG expression after 3 days of PHA stimulation were similarly dependent on PHA concentration up to 5 μg/mL (FIG. 6). Higher concentrations of PHA further increased S phase but decreased G2/M phase, but had no further effect on PTTG expression.

IL-2 is the most important early T cell activation gene. (Crabtree, G. R. and Clipstone, N. A., *Signal transmission between the plasma membrane and nucleus of T lymphocytes*, Annu Rev Biochem. 63:1045–1083 [1994]; Weiss A., *T lymphocyte activation*. In: Paul W E, ed. Fundamental Immunology. 3rd Edition. New York: Raven Press, Ltd. [1993] pp. 467–497; Kronke, M. et al., *Cyclosporine A inhibits T-cell growth factor gene expression at the level of mRNA transcription*, Proc Nat Acad Sci USA. 1984;81:5214–5218 [1984]).

In contrast to the expression of PTTG, which was upregulated at later time, interleukin 2 (IL-2) expression was increased early and before cell proliferation (FIG. 7). IL-2 expression was first increased 6 hours after induction by immobilized anti-CD3 antibody application, long before any cells were in S or G2/M phase, suggesting this phase of IL-2 expression was independent of cell proliferation. At that time neither PTTG mRNA expression, nor significant amount of S-phase could be seen. Another phase of IL-2 elevated expression occurred 48 hours after the beginning of T cell activation, after T-cells had begun to proliferate. At that time considerable amount of PTTG mRNA and both S- and G2/M-phase cells were observed, which implies that IL-2 mRNA was already produced by proliferating T cells.

Figure 8:
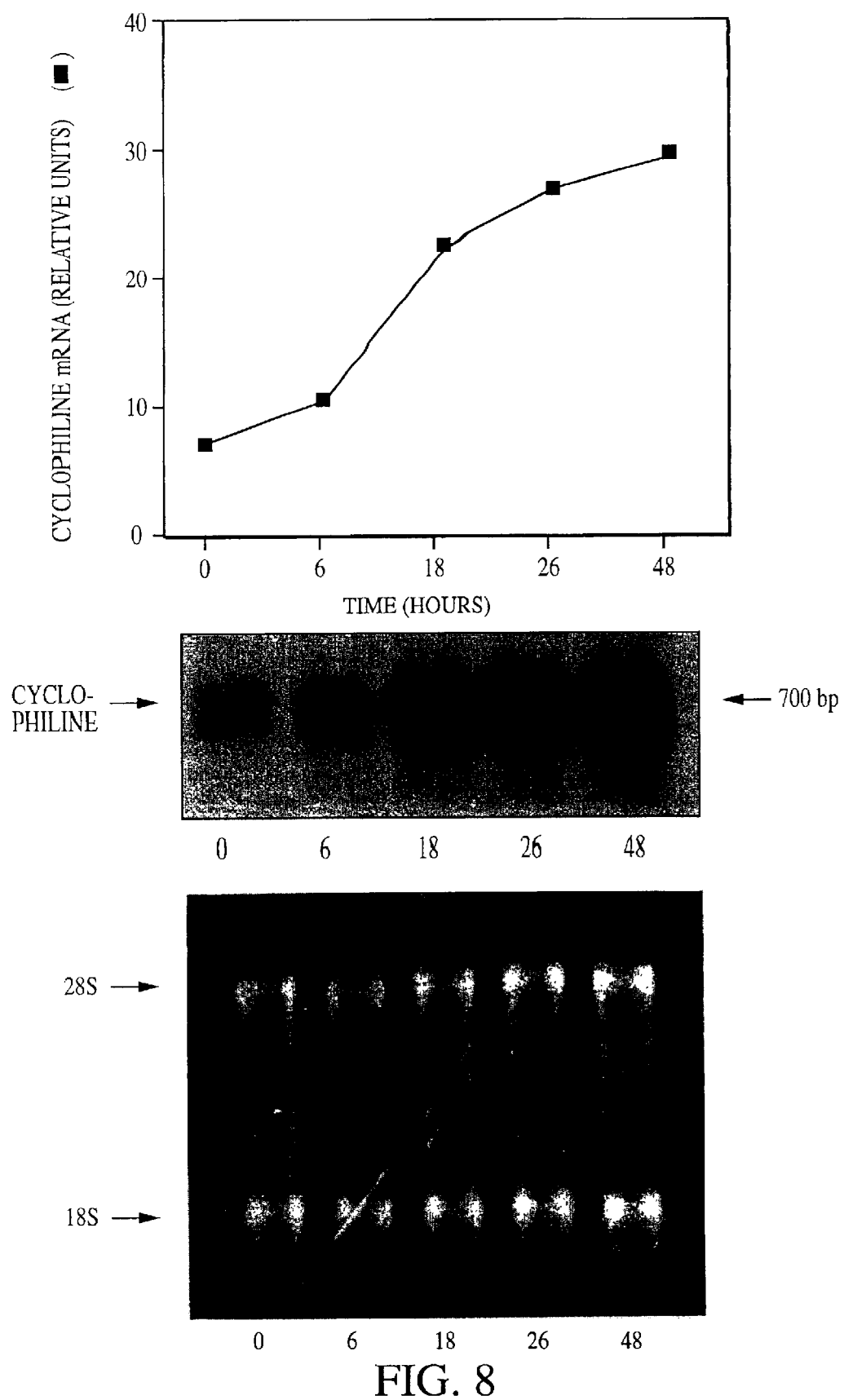
FIG. 8 shows cyclophilin mRNA expression in normal adult human T cells treated with mitogen anti-CD3 antibody. T cells were isolated and stimulated with anti-CD3 antibody for 48 hours. Cyclophiline mRNA (middle panel) was measured with northern blotting.

Cyclophilin, a house-keeping gene that also is an intracellular cyclosporin A-binding protein, was also increased as T-cells were activated by PHA (FIG. 8). It is known that cyclophilins serve as intracellular cyclosporin A-binding proteins. (Crabtree G R and Clipstone N A, Signal transmission between the plasma membrane and nucleus of T lymphocytes. Annu Rev Biochem. 63:1045–1083 [1994]). Cyclophilins possess peptidyl prolyl-cis-trans isomerase activity involved in the catalysis of the cis-trans isomerization of proline residues in polypeptide substrates. This enzymatic activity may play some role in T-cell signal transduction cascade, perhaps by catalyzing the correct folding of an inactive signaling intermediate into an active form. However, strong arguments exist that this simplified model is not the main mechanism of cyclosporin A action. It was shown that cyclosporin A-cyclophilin complex can block the action of calcineurin (calcium/calmodulin-regulated serine/threonine protein phosphatase) via regulating nuclei entry of transcription factor NF-AT (nuclear factor-activated T cells) which in its turn regulates T cell specific IL-2 gene expression. (Crabtree G R and Clipstone N A, Signal transmission between the plasma membrane and nucleus of T lymphocytes. Annu Rev Biochem. 63:1045–1083 [1994]). We found that the level of cyclophilin mRNA expression is significantly increasing after PHA-induced T cell activation, which implies that the activated T-cells should be more sensitive to the action of cyclosporin A than the resting T-cells because they have higher cyclophilin levels.

It is known that both IL-2 (Crabtree and Clipstone [1994]) and PTTG (Kakar S S, *Molecular cloning, genomic organization, and identification of the promoter for the human pituitary tumor transforming gene*, Gene. 240:317–324 [1999]) gene promoter contain AP-1 binding regions which suggests the existence of common regulators of expression of these two genes. It is also accepted that a known immunosuppressor cyclosporin A exerts its inhibitory action towards T lymphocytes via IL-2 gene suppression and this leads to the inhibition of DNA synthesis in T cells. (Crabtree and Clipstone [1994]; Kronke M et al., *Cyclosporine A inhibits T-cell growth factor gene expression at the level of mRNA transcription*, Proc Nat Acad Sci USA. 81:5214–5218 [1984]).

Figure 10:
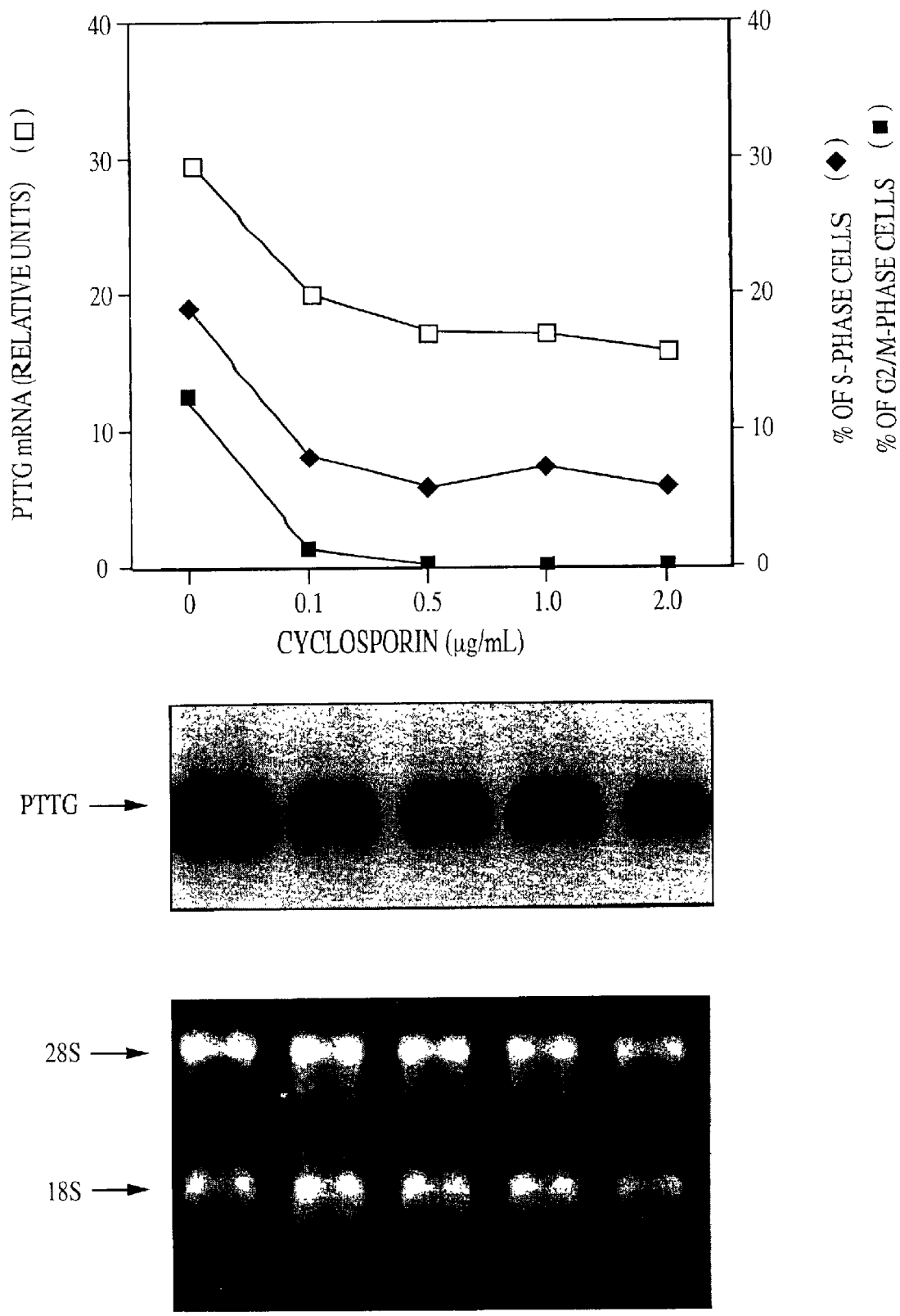
FIG. 10 shows PTTG mRNA expression and cyclosporin. PHA (5 μg/ml)-stimulated normal adult human T cells were treated with cyclosporin for 72 h. PTTG mRNA was measured with northern blotting (middle panel) and percentage of cells in S or G2/M phase was determined by FACS.

Although glucocorticoids have different (from cyclosporin A) intracellular receptors, they were also shown to suppress IL-2 and interferon-gamma production and to favor the production of IL-4 in T cells. (Clerici M, Trabattoni D, Piconi S et at. *A possible role for the cortisol/ anticortisols imbalance in the progression of human immune deficiency virus.* Pssychoneuroendocrinology. 22 Suppl 1:S27–S31 [1997]). Another mechanism previously described for glucocorticoids' action is based on the induction of T cell apoptosis. (Cidlowski J A et al., *The biochemistry and molecular biology of glucocorticoid-induced apoptosis in the immune system*, Recent Prog Horm Res. 51:457–490 [1996]). We found dose-dependent inhibition by hydrocortisone of both PTTG mRNA expression and the amount of S- and G2/M-phase T cells, although in low doses (final concentration 20 nM) this steroid hormone slightly increased these indexes. Immunosuppressants hydrocortisone (FIG. 9) and cyclosporin A (FIG. 10) inhibited PHA-stimulated T cell proliferation and PTTG expression. The inhibitory effect of cyclosporin A was much stronger, while hydrocortisone action was even slightly stimulatory at low doses and was inhibitory at concentrations higher than 100 nM. These results further implied that PTTG expression is associated with T-cell proliferation. In general, even in the presence of very high hydrocortisone doses one can observe some PTTG expression and T cell cycling, while cyclosporin A suppresses T-cell functions in a much stronger manneer. It should be also noted that hydrocortisone did not inhibit PTTG expression in Jurkat leukemia T cell line (see below).

PTTG Expression in Leukemic Cells

Human leukemia cell lines HL-60 and Jurkat grow in 10%-FBS-supplemented RPMI-1640 medium without CD3 or PHA as shown by the presence of S phase cells (FIG. 11). The abundance of PTTG mRNA in BL-60 and Jurkat cells was comparable to that in the activated T-cells by PHA or CD3 antibody. Among three immunomodulators used (cyclosporin A, hydrocortisone, and TGF-β1), only cyclosporin A acted in similar way on PTTG mRNA expression and cell cycling in both normal T-cells and Jurkat T cells, while the effects of hydrocortisone and TGF-β1 were specific for each of these two experimental models.

Cell Cycle-dependent PTTG Expression

We have shown that PTTG mRNA expression was cell-cycle dependent with peak expression at G2/M in a tumor cell line. We found a similar dependence of PTTG expression on cell cycle in T cells. This dependence was much more prominent in the case of normal T cells (FIG. 12) than in the case of Jurkat T-cell leukemia line (FIG. 13). Although the direction of revealed changes in the amount of S-phase cells and level of PTTG mRNA expression in normal T cells and Jurkat T cell line were mostly similar, the amplitude of these changes was found to be lower in the malignant Jurkat cells probably because of Jurkat cells' immortality and high basal levels of PTTG.

Figure 12:
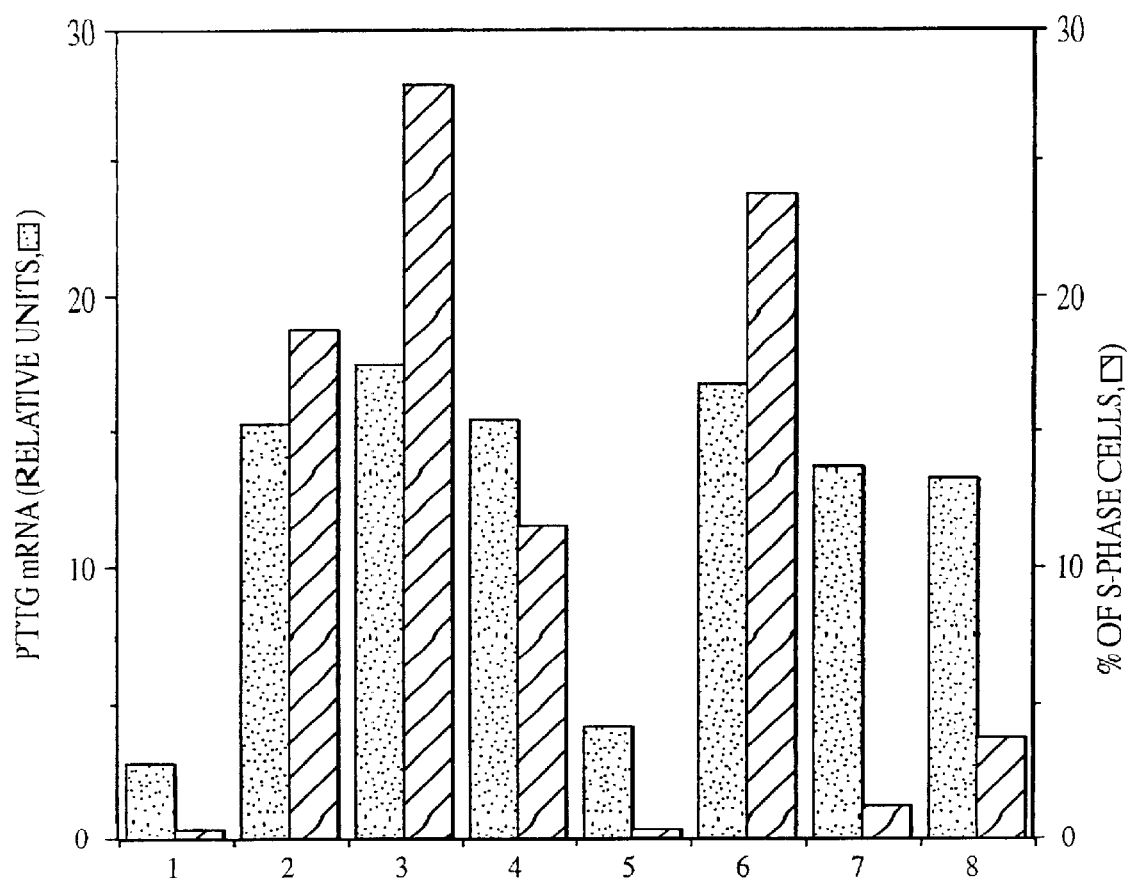
FIG. 12 shows PTTG mRNA expression and cell cycle in T cells. T cells were treated with the following conditions and PTTG mRNA and percentage of S phase were compared. (1) resting cells; (2) PHA (5 μg/mL)-stimulated; (3) anti-CD3-stimulated; (4) anti-CD3+hydrocortisone (100 nM); (5) anti-CD3+cyclosporine A (1 μg/mL); (6) anti-CD3+aphidicolin (1 μg/mL); (7) anti-CD3+nocodazole (500 ng/mL); (8) anti-CD3+TGF-β1 (10 ng/mL).
Figure 13:
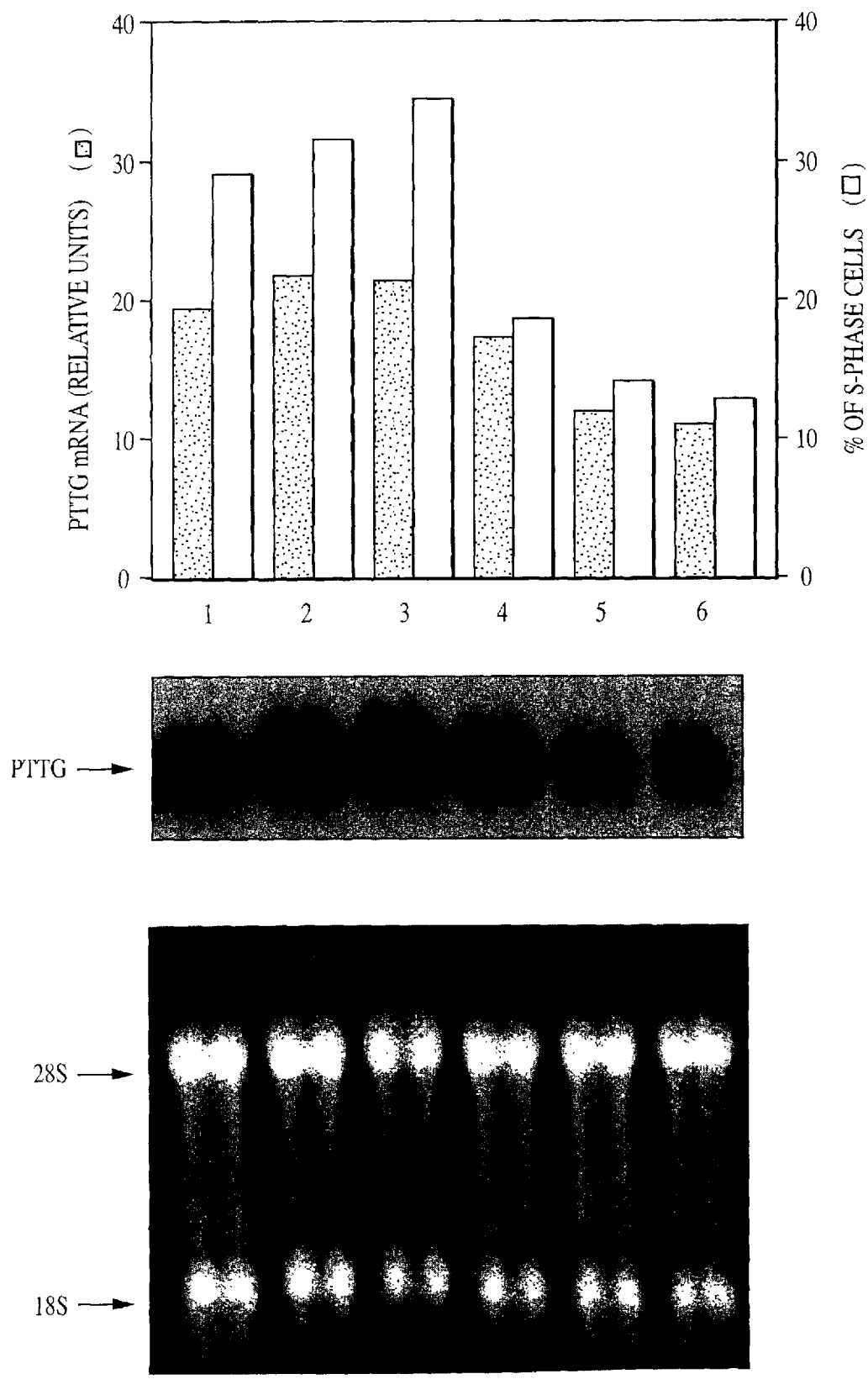
FIG. 13 shows PTTG mRNA expression in human Jurkat T cell leukemia line. Jurkat T cells were treated as described below. (1) cells kept for 48 h in 1% FBS-supplemented culture medium; (2) cells after medium change for fresh 1% FBS-supplemented; (3) cells after medium change for 10% FBS-supplemented; (4) phytohemagglutinin (PHA; 1 μg/mL)+phorbol-12-meristate-13-acetate (PMA; 50 ng/mL) in 1% FBS; (5) (PHA+PMA)+cyclosporine A (1 μg/mL); (6) (PHA+PMA)+TGF-β1 (10 ng/mL). PTTG mRNA was measured with northern blotting (middle panel) and percentage of cells in S phase was determined by FAGS.

We found that CD3 antibody-induced activation of T-cells was inhibited to different extents by cyclosporin A, hydrocortisone, aphidicolin (S phase inhibitor), or nocodazole (G2/M phase blocker), while TGF-β1 (10 ng/mL final concn) had no significant effect neither on PTTG mRNA nor on the amount of S- or G2/M-phase cells (FIG. 12). At the same time, neither fresh 1% or 10% FBS nor a mixture of phytohemagglutinin (PHA) and phorbol-12-meristate-13-acetate (PMA) [i.e., PHA+PMA mixture] considerably elevated PTTG level in Jurkat T-cell line and this mixture even decreased it. Jurkat cells were used for comparison and they were treated with PHA+PMA mixture which is used for its mitogenic action for Jurkat T cells after being cultured for 48 hours in 1% FBS-supplemented medium. Changes in the amount of S-phase cells were also parallel to changes in the level of PTTG mRNA expression. Cyclosporin A and TGF-β1 decreased both PTTG mRNA level and the amount of S-phase Jurkat cells, while hydrocortisone did not change these indexes even used in 10 μM final concentration (data are not shown).

It should be noted that TGF-β1 is well known for its bi-directional action on cell functions including cell proliferation which strongly depends on the properties of cell targets and the conditions of their treatment. At the same time when Jurkat T cells were used we detected TGF-β1-triggered inhibition of both PTTG mRNA expression and cell cycling. Although this effect was not observed in the presence of fresh FBS added to culture medium (data are not shown) and could be seen only after Jurkat cells' treatment with PHA+PMA mixture.

These results show that the expression of PTTG can be easily regulated in normal T-cells. It is induced to high level by both non-specific (PHA) and specific (anti-CD3 antibodies) T-cell activators, and this induction can be inhibited by known immunosuppressors—cyclosporin A and hydrocortisone. Importantly, preliminary data showed that the transfection of PHA-activated T cells with DNA encoding PTTG C-terminal region caused a decrease in the amount of S-phase cells and their accumulation in G2/M-phase of cell cycle.

Interestingly, hydrocortisone did not inhibit PTTG expression in Jurkat T cell line widely used for studying of T-cell functions, while another immunomodulator, TGF-β1 did not affect PTTG expression in normal T-cells, but decreased it in Jurkat cells. Thus, the results of study of PTTG functioning in Jurkat T cell line cannot be directly applied for normal T-cells, probably because of high basic level of expression of PTTG oncogene in the malignant cells.

Normal T cells and Jurkat T-cell line also possessed different sensitivity to the action of cell cycle inhibitors (aphidicolin and nocodazole). Aphidicolin stopped Jurkat cells in S-phase, decreasing the amount of G2/M-phase, while no significant changes in PTTG mRNA level were observed (data not shown). Nocodazole stopped these cells in G2/M-phase and S-phase cells were poorly detected in its presence, while some increase in PTTG mRNA expression was observed after nocodazole treatment of Jurkat cells. Probably, normal T-cells are more sensitive to the toxic effect of cell cycle inhibitors and in their presence both PTTG mRNA level and the amount of cycling cells were decreased.

The results presented herein show that targeting PTTG and PTTG expression is useful both for anti-neoplastic therapy and also for immunosuppressive therapy.

While the present invention is not committed to or dependent any particular mechanism of action, PTTG mRNA induction and parallel S-phase increase during normal T-cell activation imply that the mechanism of PTTG cell transforming action could be in its overexpression and resulting increase in cell cycling rather than in its misregulating effect on chromatide separation and resulting aneuploidy.

Example 18

PTTG1 Expression in Breast and Ovarian Tumor Tissues

Patients and Tissues

Separate samples of breast (n=13) and ovarian (n=15) tumors were obtained from consecutive unselected patients after surgical resection and either immersed in liquid nitrogen and stored at −70° C., or fixed in 10% formalin for analysis. Normal breast (n=14) and ovarian (n=9) postmortem tissues were obtained from the Brain & Tissue Banks for Developmental Disorders at The University of Maryland, Baltimore (mean±SEM age; 44±7.2 yr.). Non-degraded RNA was obtained from 25 of the 28 tumor tissues and 20 of the 23 normal tissues and used for further analysis. Twelve cases of breast carcinoma (mean±SEM age; 60±3.5 yr.) and thirteen cases of ovarian cancer (mean±SEM age; 56±4.9 yr.) (Table 21) were studied. Histologic evaluation was independently recorded by a pathologist.

Cell Cultures

MCF-7 (breast cancer), MDA-MB231 (estrogen receptor [ER]-negative breast cancer cells) and SKOV-3 (ovarian cancer) cells obtained from ATCC were maintained in phenol red-free DMEM with 10% FCS, pretreated with dextran-coated charcoal (CSS) for 3 days, prior to treatment with diethylstilbestrol ($10^{-8}$ M and $10^{-10}$ M), and/or ICI-182780 (Tocris) ($10^{-7}$ M and $10^{-8}$ M) for 48 h as previously described (Heaney, A. P. et al. [1999]).

Northern Blot Analysis

Total RNA was extracted from cell cultures ($\sim 3 \times 10^7$ cells) and excised tissues with TRIzol. RNA derived from JEG-3 choriocarcinoma cells served as a positive control for PTTG1 expression. Electrophoresed RNA was transferred to Hybond-N nylon membranes (Amersham International, Buckinghamshire, UK), and hybridized at 68° C. with human PTTG cDNA as previously described (Heaney, A. P. et al. [1999]). PTTG1 mRNA expression was normalized to β-actin expression and expressed as fold-increase relative to either matched normal mucosa from the same individual (8 breast cases), or the mean PTTG/actin ratio measured in normal breast (n=13) and ovarian tissue (n=7).

Western Blot Analysis

Proteins were prepared from breast and ovarian tissues using RIPA buffer (Heaney, A. P. et al. [1999]), denatured in loading buffer, and soluble proteins (50 μg by Bradford assay) were separated by electrophoresis (12% SDS-PAGE), transferred to PVDF membranes (Amersham), incubated in 5% non-fat milk in PBS-0.05% Tween solution, followed by incubation with antibodies to PTTG (1:5000), and β-actin (1:2500; Sigma). Blots were washed, incubated with appropriate horse radish peroxidase-conjugated anti-IgGs, washed and complexes were then visualized by ECL chemiluminescence detection.

Differences were assessed by ANOVA or the unpaired t-test when appropriate.

Results

PTTG1 is Overexpressed in Breast and Ovarian Tumors

Figures 14A, 14B:
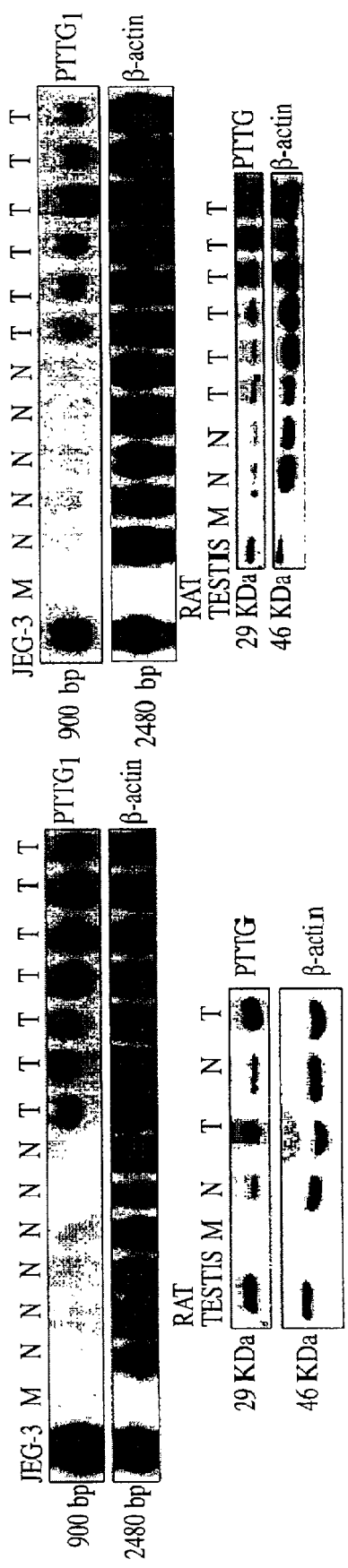
(FIG. 14a) normal (N) and breast tumor (T; n=12) tissues.
(FIG. 14b) normal (N) and ovarian tumor (T; n=13) tissues, depicting expression of PTTG1 mRNA and PTTG1 protein. Hybridization with [α-$^{32}$P] dCTP probes for either PTTG1 or β-actin or blotting with anti-PTTG1 antibody (1:5000) revealed PTTG overexpression in breast and ovarian carcinomas in comparison to adjacent normal tissue. JEG-3 choriocarcinoma cells served as a positive control. Left margins, molecular size; right margins, positions of mRNA products.
Figure 16A:
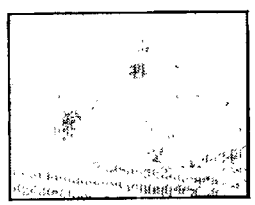
FIG. 16 demonstrates that wt-hPTTG C-terminus peptide inhibits colony formation in agar and sensitzies breast cancer cells to Taxol. MCF-7 cells (about 5,000) transfected with vector alone (a,b,c,d) or vector containing wt-hPTTG C-terminus-encoding DNA (e,f,g,h) were plated in agar containing vehicle only (a, e) or Taxol 10-11 M (b, f), 10-10 M (c,g) or 10-9 M (d,h) (magnification×200).
Figure 16E:
Figure 16B:
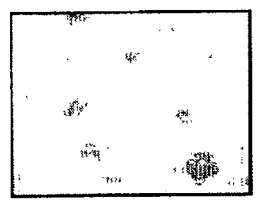
Figure 16F:
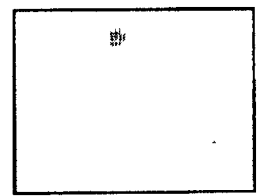
Figure 16C:
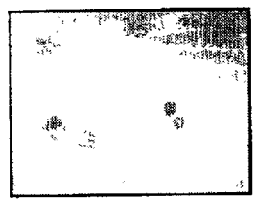
Figure 16G:
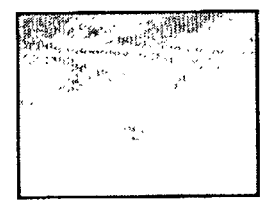
Figure 16D:
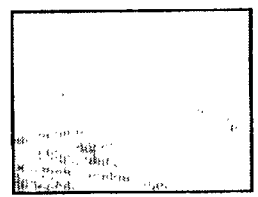
Figure 16H:
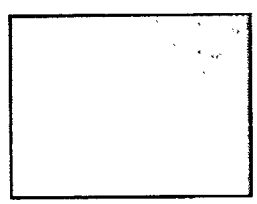

Increased PTTG1 mRNA expression was observed in 12 of 12 breast and 12 of 13 ovarian carcinomas (breast carcinoma exhibited 2.5±0.3 fold increase; ovarian carcinoma exhibited 3.5±0.6 fold increase) in comparison to normal breast or ovarian tissue respectively (Table 21; FIG. 14). Highest PTTG mRNA expression was detected in breast and ovarian tumors which invaded surrounding lymphatic or vascular structures (breast tumor exhibited 3.5±0.45 fold increase; ovarian tumor exhibited 3.8±0.7 fold increase) compared to tumors confined to the breast or ovary (breast tumor exhibited 1.9±0.35 fold increase; ovarian tumor exhibited 3.2±1.0 fold increase), although this difference was only statistically significant in the breast tumors (p=0.03).

TABLE 21

PTTG1 expression in breast and ovarian carcinomas.

| No. Patient Age | | Diagnosis | Lymph node invasion | PTTGexpression (fold-increase) |
|---|---|---|---|---|
| Breast Tumors: | | | | |
| 1 | 49 | CAI[a] | NA | 2.7 |
| 2 | 58 | CAI | −ve | 1.3 |
| 3 | 83 | infiltrating ductal Ca[b] | −ve | 2.3 |
| 4 | 42 | invasive ductal Ca | −ve | 1.0 |
| 5 | 80 | infiltrating ductal Ca | −ve | 1.3 |
| 6 | 56 | invasive Ca (mucinous) | −ve | 2.0 |
| 7 | 53 | invasive Ca (tubular) | −ve | 1.2 |
| 8 | 67 | infiltrating ductal Ca | −ve | 3.9 |
| 9 | 56 | invasive duct cell Ca | −ve[c] | 3.8 |
| 10 | 65 | invasive ductal Ca | +ve | 4.1 |
| 11 | 52 | infiltrating ductal Ca | +ve | 2.2 |
| 12 | 62 | infiltrating ductal Ca | +ve | 4.0 |
| | | | | 2.5 ± 0.3 (Mean ± SEM) |
| Ovarian Tumors: | | | | |
| 13 | 18 | Sertoli Leydig cell tumor | −ve | 1.9 |
| 14 | 45 | endometroid Ca | −ve | 0.9 |
| 15 | 62 | endometroid Ca[d] | −ve | 2.2 |
| 16 | 57 | Serous Cystadenoma | −ve | 4.9 |
| 17 | 62 | Mullerian Papillary Adeno Ca (HG)[e] | −ve | 6.3 |
| 18 | 50 | Mucinous Cystadeno Ca | +ve | 1.1 |
| 19 | 47 | Cystadenocarcinoma (HG)[e] | +ve | 1.8 |
| 20 | 67 | Serous Papillary Ca (HG) | +ve | 3.3 |
| 21 | 67 | Serous Papillary Ca (HG) | +ve | 3.3 |
| 22 | 82 | Adeno Ca (HG) | +ve | 3.8 |
| 23 | 48 | Mullerian Serous Papillary Ca | +ve | 4.2 |
| 24 | 51 | Mullerian Adeno Ca (HG) | +ve | 5.1 |
| 25 | 78 | Mullerian Serous papillary Adeno Ca (HG) | +ve | 7.6 |
| | | | | 3.5 ± 0.6 (Mean ± SEM) |

[b]Ca = carcinoma
[c]Lymphovascular invasion present
[d]bilateral involvement
[e]HG = high grade Estrogen-regulation of PTTG and its overexpression in breast and ovarian tumors from the mostly post-menopausal women in this study may seemingly appear a paradox. However, estrogens are an important growth factor in both pre- and post-menopausal women and the prevalence of hormone-dependent breast cancer increases with age, as does the incidence of breast cancer. After menopause, peripheral tissues produce sufficient estradiol concentrations to stimulate tumor growth, and about 80% of postmenopausal women with ER-positive breast tumors respond to antiestrogen-treatment, and adjuvant tamoxifen is standard therapy for postmenopausal women (Weidner, N. et al., Tumor angiogenesis: a new significant and independent prognostic factor in early-stage breast carcinoma, J. Natl. Cancer Inst. 1992; 84:1875–87 [1992]).

Estrogen Regulates PTTG1 Expression in Breast and Ovarian Cancer Cells in vitro and Correlates with Tumor Estrogen Receptor Expression Estrogen (diethylstilbestrol $10^{-8}$ M to $10^{-10}$ M) induced about a 2–9 fold-increase in PTTG1 mRNA expression in MCF-7 breast cancer cells (FIG. 15a; p<0.01), and in ovarian cancer cells (FIG. 15b, inset). Estrogen-mediated induction of PTTG1 was partially abrogated or blocked by co-incubation with the antiestrogen ICI-182780 ($10^{-7}$ M to $10^{-8}$M) (FIG. 15, p<0.01). PTTG1 mRNA expression was unaltered following treatment of estrogen receptor (ER)- negative MDA-MB231 breast cancer cells with estradiol (data not shown), confirming the requirement of the ER for estrogen-mediated PTTG1 mRNA induction.

PTTG regulates bFGF secretion (Pei, L and Melmed, S., *Isolation and characterisation of apituitary tumor-transforming gene (PTTG)*, Mol. Endocrinol. 11:433–441 [1997]) and in turn bFGF regulates PTTG in NIH 3T3 fibroblasts. Therefore, the incomplete suppression of estrogen-induced PTTG by ICI-182780 observed here may be due to medium-derived growth factors whose action may not be altered by antiestrogens. Breast and ovarian cancers are epithelial in origin and as stromal/epithelial components of normal and tumor tissue may differ, care must be exercised in interpretation. As stroma is poor in cellularity, and contributes little to the total DNA or RNA content in specimens (Orr-Weaver, T. L., *The difficulty in separating sisters*, Science. 285:344–345 [1999]), the detection of abundant PTTG expression in breast and ovarian tumors in comparison to expression in normal breast tissue, using Northern and Western blot analysis appears appropriate and is validated by other studies (Orr-Weaver [1999]).

Example 19

PTTG-C Hapersensitizes Cancer Cells to Treatment with Cytotoxic Anti-Cancer Drugs.

Figure 17:
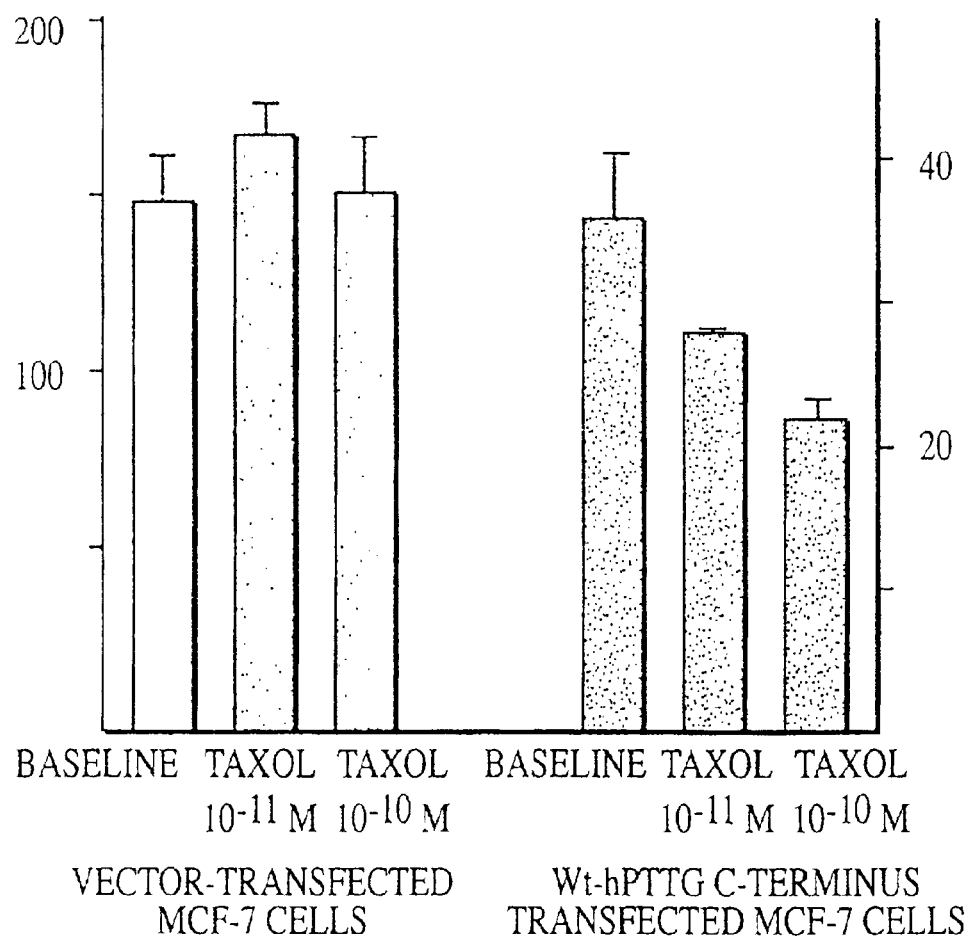
FIG. 17 shows the number of colonies formed by vector-transfected and vector plus wt-hPTTG C-terminus DNA-transfected MCF-7 cells in agar following treatment (10 days) with vehicle only or Taxol ($10^{-11}$ M to $10^{-10}$ M).

Co-expression of PTTG-C (wtPTTG C-terminus) in cancer cells, disrupts PTTG-mediated signaling, prevents colony formation in soft agar and in vivo tumor formation in nude mice. (See, Example 16 hereinabove). Furthermore, expression of PTTG-C in cancer cells, such as but not limited to breast and ovarian cancer cells, hypersensitizes the cells to treatment with cytotoxic anti-cancer drugs, such as paclitaxel (Taxol). For example, FIGS. 16 and 17 show that treatment of wtPTTG C-terminus-transfected MCF-7 (stable transfection) breast cancer cells with paclitaxel inhibited colony formation at lower doses ($10^{-11}$ M to $10^{-10}$ M) than those necessary to inhibit colony formation in the control vector-transfected cells ($10^{-9}$ M). (FIGS. 16 and 17).

Example 20

Modulation of Angiogensis by PTTG

Materials

Rat tail collagen type I was obtained from Sigma Chemical Co. (St. Louis, Mo.), and the modified Boyden chamber, and Transwells®, from Corning Costar (Cambridge, Mass.). Human recombinant, anti-bFGF antibody, and pre-immune goat IgG were purchased from R&D systems (Minneapolis, Minn.), growth factor reduced Matrigel basement membrane matrix (GFR Matrigel) from Becton Dickinson (Bedfold, Mass.), and fertilized White Leghorn chicken eggs from Chino Valley Ranchers (Arcadia, Calif.). All standard chemicals used were of the highest available commercial grade.

Cell Culture

NIH-3T3 cells were cultured in low glucose DMEM (GIBCO-BRL) supplemented with 10% bovine calf serum (BCS) and antibiotics. HUVECs (Clonetics San Diego, Calif.), were grown in EGM medium according to the vendor's instructions, and were grown to less than ten passages for all experiments.

Stably transfected NIH-3T3 cells ($2 \times 10^6$) expressing wild type, mutant hPTTG, or vector alone, as previously described (Zhang, X. et al., *Structure, expression, and function of human pituitary tumor-transforming gene (PTTG)*, Mol Endocrinol. 13:156–166 [1999]), were plated in 100-mm gelatinized dishes. Western blot analysis confirmed that equivalent amounts of PTTG protein were expressed in both wild type-PTTG and mutant-PTTG transfected cells. After 24 hours, the maintenance medium was replaced with 10 mL serum-free DMEM and the cells incubated a further 48 hours. This conditioned medium (CM) was then harvested from wild type hPTTG (WT-hPTTG-CM), mutant hPTTG (M-hPTTG-CM), and vector alone (C-CM) transfected NIH-3T3 cells and from non-transfected NIR-3T3 cells (N-CM), each CM type being filtered separately through a sterile 0.2 µm pore filter to remove debris and then being stored until further study.

bFGF ELISA

Conditioned medium (1 mL) was lyophilized with Speed-Vac (Savant, Farmingdale, N.Y.), resuspended in 100 mL phosphate-buffered saline (PBS), and bFGF concentration was assayed (Quantikine HS Human FGF basic Immunoassay Kit, R&D).

Endothelial Cell Proliferation Assay

HUVECs were plated onto 48-well gelatinized culture plates at about 5000 cells/well for 24 hours. Medium was then replaced with equal aliquots of CM derived from cultures of transfected or non-transfected NIH-3T3 cells as described previously. As a positive control, DMEM was enriched with 1 ng/mL of recombinant human bFGF, and as a negative control, serum-free DMEM was used. To investigate activity of bFGF in each CM, 100 ng/ml anti-bFGF antibody or pre-immune goat IgG was first added to each CM. After 48 hours, HUVEC cells were trypsinized and counted with a Coulter Counter (Coulter Electronics, Hialeah, Fla.). All experiments were performed in triplicate.

Wound Migration assay

The wound assay was performed as previously described with some modifications (Sato, Y and Rifkin, D B., *Autocrine activities of basic fibroblast growth factor: regulation of endothelial cell movement, plasminogen activator synthesis, and DNA synthesis*, J Cell Biol. 107:1199–1205 [1988]). Confluent monolayers of HUVECs in 35-mm gelatinized culture dishes were wounded by pressing a razor blade to cut the cell sheets and mark the plate. The blade was gently moved to one side to remove part of the sheet. Cells were then washed twice with PBS. The transfected-3T3 cell-derived CM described above was applied and the HUVECs incubated in CM for a further 16 hours. Cells were then fixed with absolute methanol, stained with Giemsa and photographed. Migration was quantified by counting cells in 100 µM×2500 µM sections from the cut edge under microscopy with an ocular grid. The values represent the mean derived from 3 random fields. All experiments were repeated in triplicate.

Modified Boyden Chamber Migration Assay

Migration was also measured with 6.5-mm, 8.0 µm Transwells® as previously described with some modifications (Leavesley, D I et al., *Integrin beta 1- and beta 3-mediated endothelial cell migration is triggered through distinct signaling mechanisms*, J Cell Biol. 121:163–170 [1993]). The polycarbonate membrane was coated with 0.1% gelatin (1 h at 37° C.). 600 µL of each CM sample was added to the lower chamber and incubated at 37° C. for 30 min. Sub-confluent HUVECs which had been cultured in the growth factor-free medium for 16 h were harvested, washed, resuspended in serum-free DMEM (100 µL) and added to the upper chamber. After 24-h incubation, all non-migrant cells were removed from the upper face of the membrane with a cotton swab and migrant cells on the lower face were fixed with absolute methanol, stained with Giemsa and photographed. For quantitative analysis, stained cells were subsequently extracted with 10% acetic acid, and absorbance determined at 595 nm.

Tube Forming Assay

Assay of capillary tube-like structure formation of HUVEC was performed with commercial GFR Matrigel. 24-well plates were thickly coated with 300 μL GFR Matrigel (11 mg/mL) and incubated at 37° C. for 30 min to promote gelling. HUVECs suspended in 500-μL aliquots of sample CM were added to each well to bring the final culture to about $5 \times 10^4$ cells per well. After 24-h incubation, tube-formation was evaluated by phase-contrast microscopy and photographed by spot color digital camera (W. Nuhsbaum, Inc., McHenry, Ill.). Digital images were skeletonized with NIH-image software, and pixel numbers counted as previously described (Wojta, J., et al., *Hepatocyte growth factor increases expression of vascular endothelial growth factor and plasminogen activator inhibitor-1 in human keratinocytes and the vascular endothelial growth factor receptor flk-1 in human endothelial cells*, Lab Invest. 79:427–438 [1999]). All experiments were repeated in triplicate.

Chrorio-Allantoic Membrane (CAM) Assay

To investigate angiogenic activity of each CM in vivo, fertilized White Leghorn chicken eggs were incubated at 37° C. without $CO_2$ in a humidified incubator (Brooks, P C, et al., *Use of the 10-day-old chick embryo model for studying angiogenesis*, Methods Mol Biol. 129:257–269 [1999]). After 3-day incubation, a round window was opened in the shell and 3 mL albumin were removed to detach the CAM from the shell. 10 mL of CM from WT-hPTTG, M-HPTTG, vector transfected and untransfected 3T3 cells were lyophilized separately with (SpeedVac) and each was resuspended in 100 μL PBS. 1 μg of bFGF in 5 μL PBS was used as a positive control and similarly concentrated serum-free DMEM was used as a negative control. On day 9, 5 μL of either concentrated CM, or the positive or negative controls were applied to 0.5 mg rat tail collagen type I sponge. Sample-soaked sponges were then placed onto the CAM. On day 13, shell windows were carefully extended and the sponge and surrounding CAM area photographed. For quantitative analysis, the number of blood vessels entering the collagen sponges was counted under stereomicroscopy at 25× magnification. Three eggs were used for each sample and experiments were repeated in triplicate.

Statistical Analysis

Statistical analyses were performed using the Student's t test. All P values were two-tailed, and those less than 0.05 were considered significant.

Results bFGF Concentration in Conditioned Media

Figure 18:
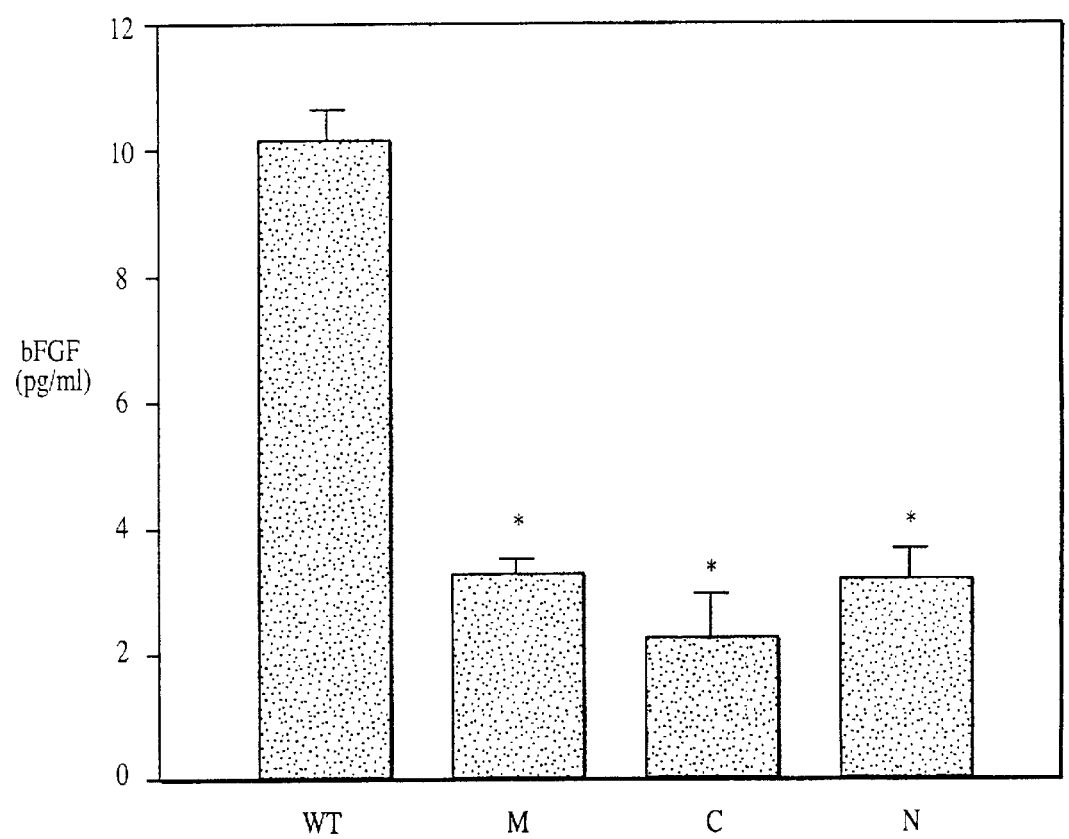
FIG. 18 shows bFGF concentrations in conditioned media derived from transfected and non-transfected NIH3T3 cells. Wild type PTTG, mutant hPTTG or vector alone-transfected or non-transfected NIH-3T3 cells were incubated in serum-free DMEM for 48 hours and aliquots of the conditioned media collected. bFGF concentration was measured by ELISA. WT, WT-hPTTG-CM; M, Mut-hPTTG-CM; C, C-CM; N, N-CM. The data shown is the mean±SD of three separate experiments. *, p<0.01 versus WT-hPTTG-CM.

As hPTTG regulates bFGF secretion (Zhang, X. et al., *Structure, expression, and function of human pituitary tumor-transforming gene (PTTG)*, Mol Endocrinol. 13:156–166 [1999]), we measured bFGF concentration in conditioned medium derived from stably transfected cells (about $2 \times 10^6$) after 48-hour culture in serum-free medium (FIG. 18). The bFGF concentration in CM harvested from WT-hPTTG transfectants, was 10.5±0.56 pg/mL, markedly higher than bFGF levels in CM derived from other transfected cell lines ([pg/mL] Mut-hPTTG, 3.3±0.27; Ctr-vector, 2.3±0.72; normal 3T3 cells 3.3±0.56; p<0.01). The bF concentration in CM from mut-hPTTG, Ctr-vector-transfected and normal 3T3 cells did not differ. Total cell number and protein concentration at the time of CM collection were similar for each independent cell line or transfectant.

Endothelial Cell Proliferation Assay

Figure 19:
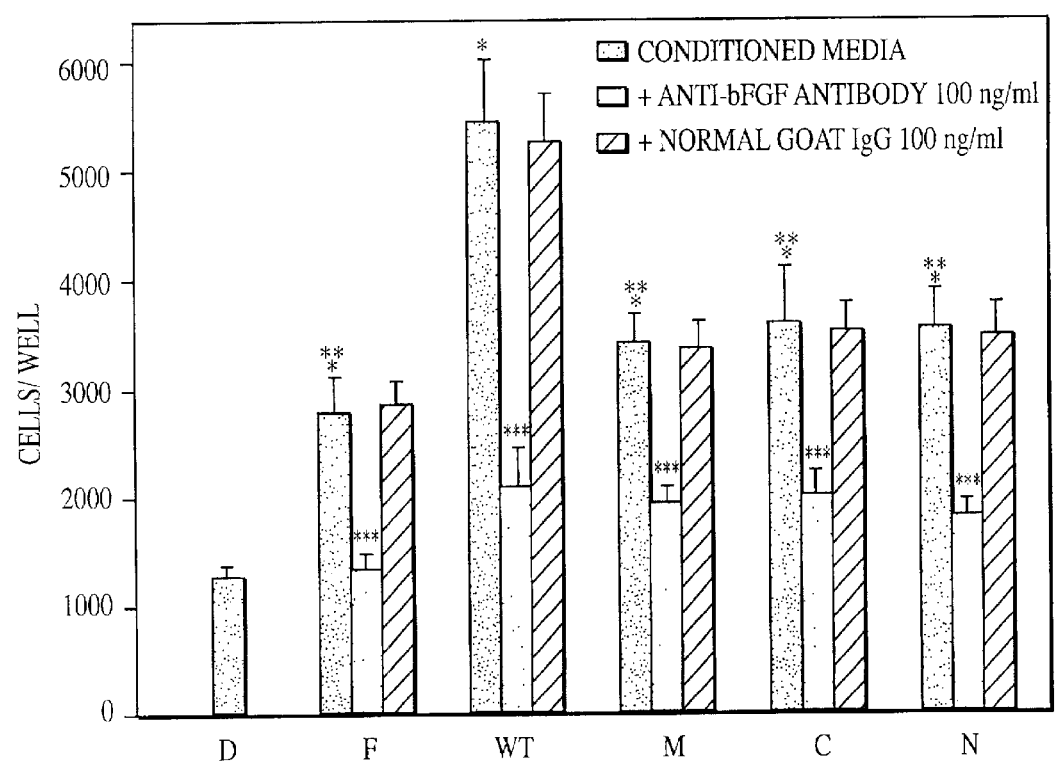
FIG. 19 demonstrates endothelial cell proliferation. HUVECs were cultured on 48-well culture plates in 500 ml conditioned media derived from transfected or non-transfected NIH3T3 cells. Cell numbers were determined after 48 hours incubation. The depicted results are the mean±SD of three separate experiments. From left to right: D, serum-free DMEM; F, 1 ng/mL bFGF in DMEM; WT, WT-hPTTG-CM; M, M-hPTTG-CM; C, C-CM; N, N-CM. p<0.01 versus* serum-free DMEM,  WT-hPTTG-CM, * respective conditioned media alone.

HUVECs were cultured in each CM for 48 hours after which the cell number was determined (FIG. 19). As expected CM derived from all cell lines exhibited proliferative activity in comparison with serum-free DMEM. CM from WT-hPTTG-transfected cells induced significantly higher cell proliferation than CM derived from Mut-hPTTG, Vector-transfected and normal 3T3 cells (p<0.01). Addition of anti-bFGF antibody to each CM suppressed proliferation activity by 62%, WT-hPTTG-CM; 43%, M-hPTTG-CM; 44%, C-CM; and by 49%, N-CM. However, cell proliferation after adding goat anti-bFGF antibody was still higher than in serum-free DMEM alone. Proliferation of HUVECs was not altered by adding pre-immune goat IgG to each CM, confirming that the induced proliferation was mediated by bFGF.

Endothelial Migration in Wound Assay and Boyden Chamber Assay

Figures 1, 2, 3, 4, 5, 20B:
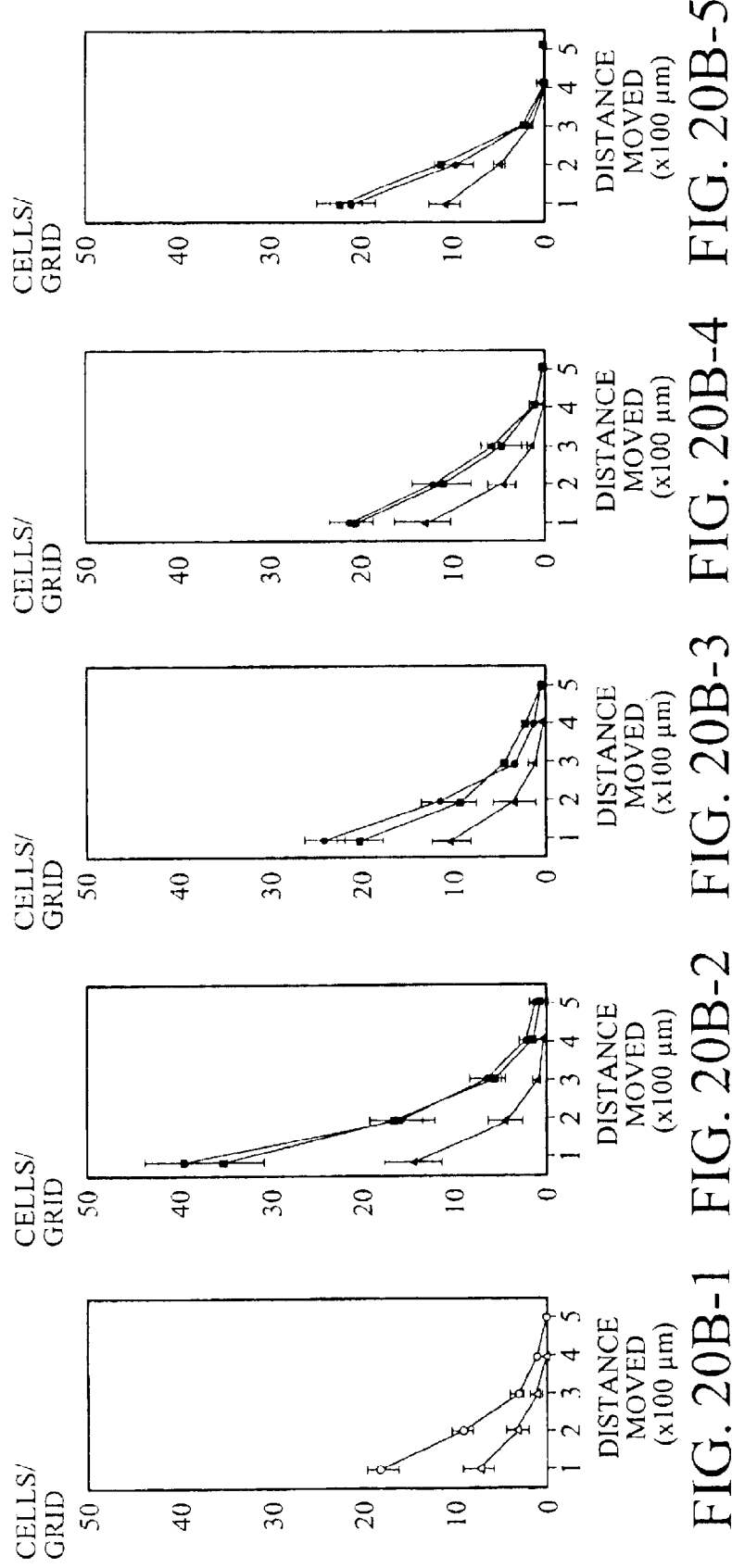
FIG. 2 shows PTTG-C and PTTG-Cpm expression in transfected tumor cells.
Figure 21B:
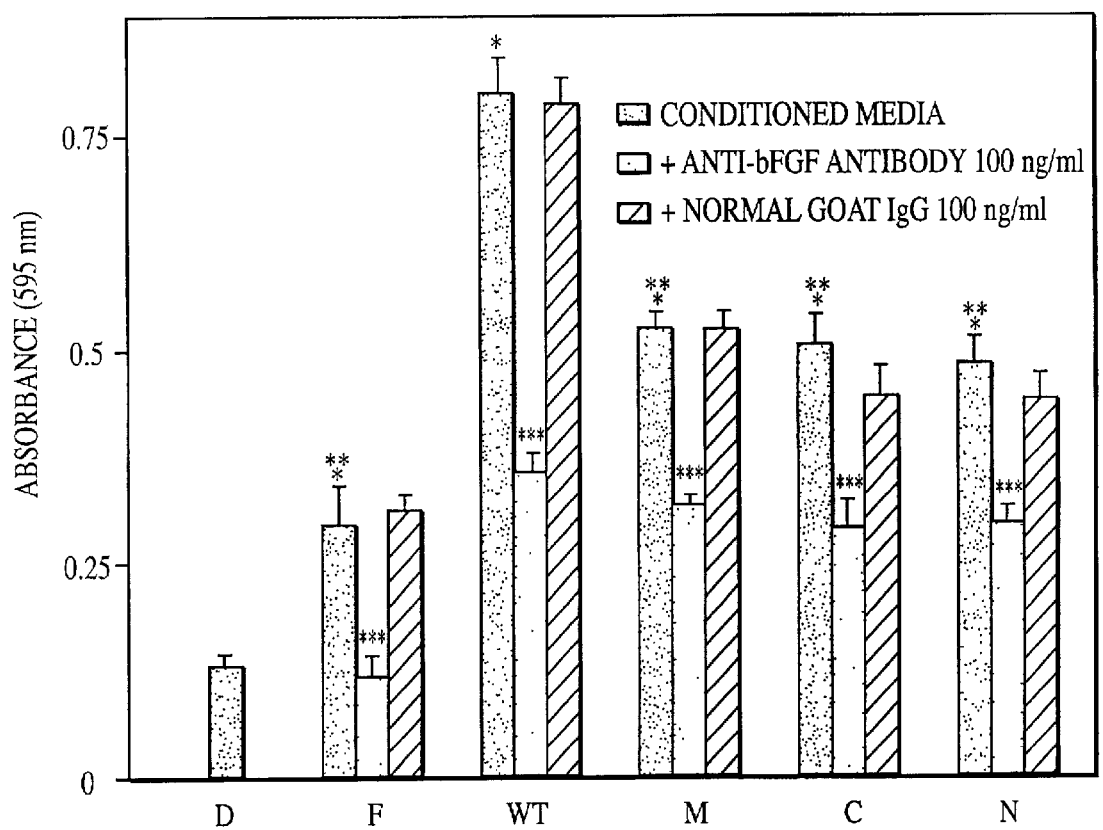
FIG. 21B shows quantification of migrated cells. Stained cells were extracted with 10% acetic acid and absorbance of extracted solution determined. The data shown is the mean±SD of three separate experiments. D, serum-free DMEM; F, 1 ng/ml of bFGF in DMEM; WT, WT-hPTTG-CM; M, M-hPTTG-CM; C, C-CM; N, N-CM. p<0.01 versus * DMEM,  WT-hPTTG-CM, * respective conditioned media (CM) alone.

Endothelial Cell proliferation and migration were tested by using the wound healing assay and modified Boyden chamber assay In the wound assay (FIG. 20), migration was quantified by counting the number of HUVECs which migrated into the non-wounded region with a grid marked in 100-μm increments. HUVECs that had been incubated (48 h) in WT-hPTTG-CM migrated farther and in greater numbers than HUVECs that had been incubated in CM from the other cell lines, harboring Mut-PTTG, vector alone or untransfected 3T3 cells. Goat anti-bFGF antibody suppressed activity in all cell lines, but pre-immune goat IgG had no effect. Using the modified Boyden chamber assay conditioned medium from Wt-hPTTG transfectants induced HUVEC cell migration through membrane pores (FIG. 21; p<0.01). Similar results were obtained when transfected or non-transfected NIH-3T3 cells were plated in the lower chambers and HUVECs plated in the upper chamber in a co-culture manner, (data not shown). Anti-bFGF antibody suppressed migration activity in all cell lines similarly to what was observed in the wound assay. Suppressive effects by anti-bFGF antibody of WT-hPTTG-CM, M-hPTTG-CM, C-CM and N-Cm were, in the same order, 55%, 40%, 43% and 39%. Inhibitory effects of the anti-bFGF antibody on CM mediated angiogenesis were more evident in WT-hPTTG-CM than in CM derived from the other cell lines. Thus, angiogenic activity of WT-hPTTG-CM is abrogated by neutralizing bFGF antibody. Addition of neutralizing bFGF antibody did not completely reverse the angiogenic effects of CM from wtPTTG-transfected cells, implying that some PTTG-directed angiogenesis is probably due to other CM-derived factors.

Similar angiogenic activity was observed using M-hPTTG-CM to C-CM and N-CM, and these were all significantly lower than angiogenic activity mediated by Wt-hPTTG-CM, demonstrating that WT-hPTTG-CM induces strong angiogenic activity. These results also imply that the proline-rich domains of the PTTG carboxy terminal end of PTTG peptide are important, not only with respect to transforming activity, but also for PTTG-mediated angiogenic properties.

Tube Forming Assay

Figure 22B:
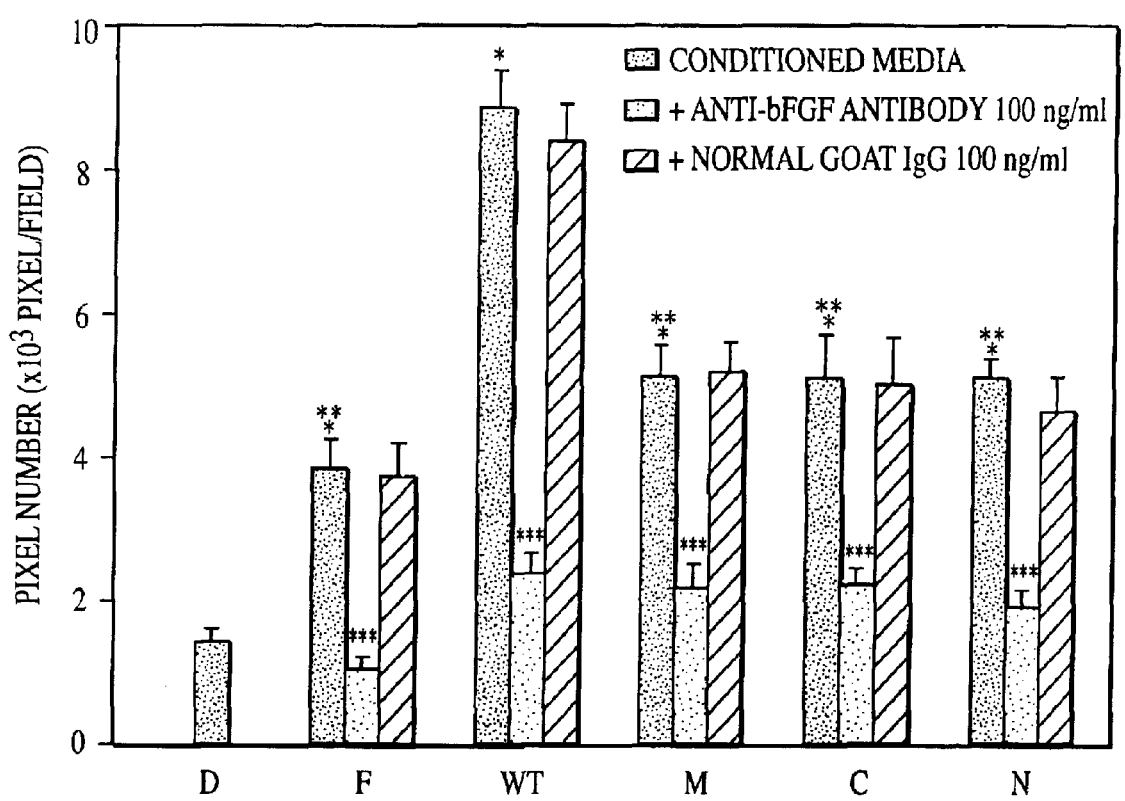
FIG. 22B shows quantification of tube-formation. Tube length was quantified as described in "Materials and Methods". The mean pixel number±SD of three separate experiments is expressed. From left to right: D, serum-free DMEM; F, 1 ng/ml bFGF in DMEM; WT, WT-hPTTG-CM; M, M-hPTTG-CM; C, C-CM; N, N-CM. $p<0.01$ versus * DMEM,  WT-hPTTG-CM, * respective conditioned medium (CM) alone.

Matrigel is useful for studying HUVEC attachment and differentiation. Since Matrigel itself induces HUVEC differential activity, we used GFR Material to reduce the effect of growth factors from the Matrigel itself. As shown in FIG. 22A, when HUVECs adhered on GFR Material, they aligned with one another and formed tubes resembling a capillary plexus under the influence of differential activity in the CM. Quantitative analysis of HUVEC tube formation (Denekamp J., *Review article: angiogenesis, neovascular proliferation and vascular pathophysiology as targets for cancer therapy*, Br J Radiol. 66:181–196 [1993]) revealed that WT-hPTTG-CM enhanced HUVEC tube formation compared to that observed when HUVECs were incubated in CM derived from other cell lines (FIG. 22B; p<0.01). The morphologic changes resembling capillary formation were suppressed by adding anti-bFGF antibody to each CM. Suppressive effects of anti-bFGF antibody of WT-hPTTG-CM, M-hPTTG-CM, C-CM and N-CM were, in the same order, 74%, 58%, 57%, and 62%.

The results of the assay of tube-formation of HUVEC cells further demonstrated that WT-hPTTG-CM induces strong angiogenic activity. As similar angiogenic activity was observed using M-hPTTG-CM to C-CM and N-CM, and these were all significantly lower than angiogenic activity mediated by Wt-hPTTG CM, it appears that the proline-rich domains of PTTG are important not only for transforming action, but also for PTTG- mediated angiogenic properties.

CAM Assay

Figures 1, 23A:
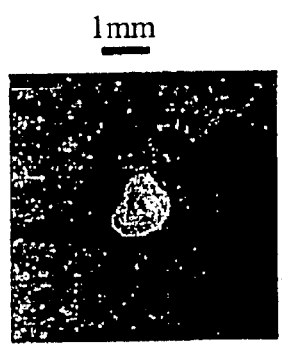
Figures 2, 23A:
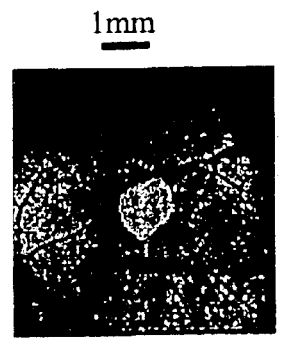
Figures 3, 23A:
Figures 4, 23A:
Figures 5, 23A:
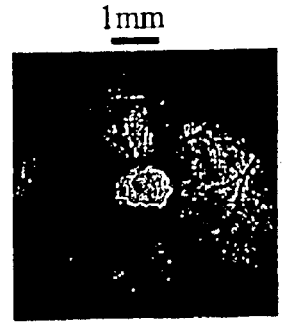
Figures 6, 23A:
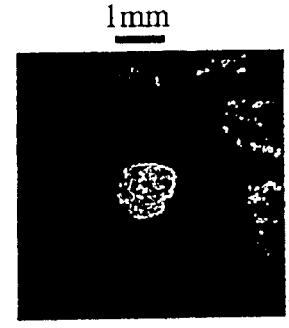
Figure 23B:
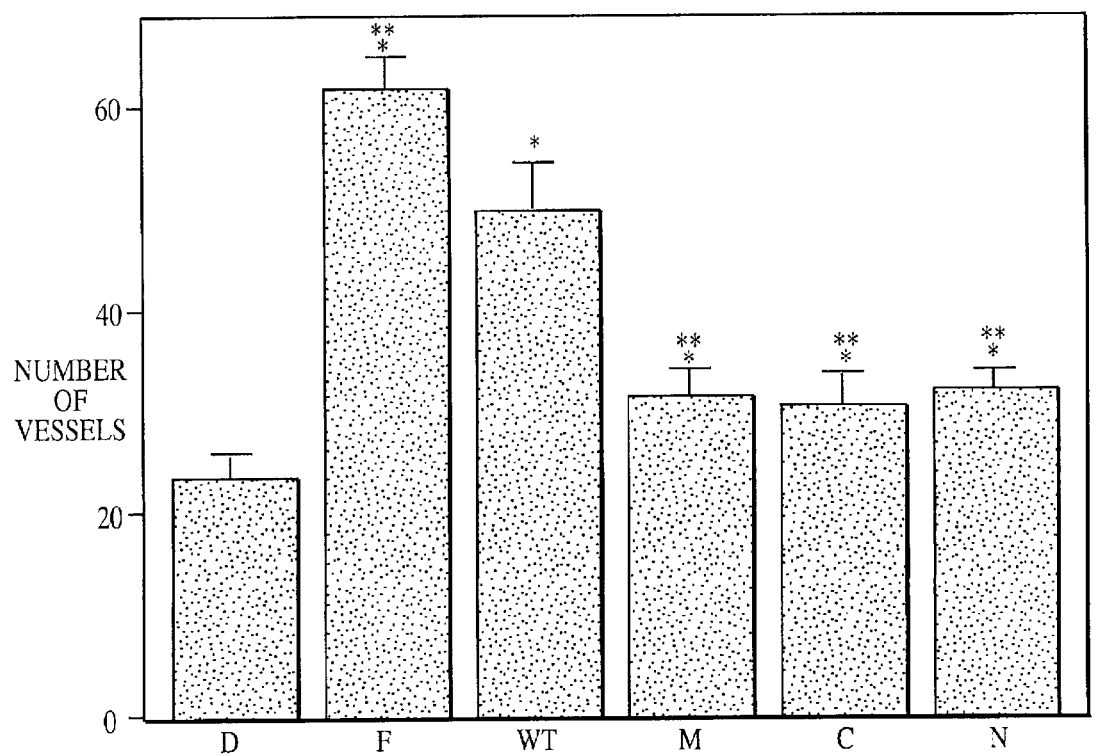
FIG. 23 demonstrates vascular reactions of CAM to conditioned media. Test samples, positive or negative control in collagen sponges were loaded on CAM of 9-day-old chick embryos. After 4 days, CAMs were photographed. (A) photographs of representative CAMs of 13-day-old chick embryo. 1, serum-free DMEM; 2, 1 ng/ml bFGF in DMEM; 3, WT-hPTTG-CM; 4, M-hPTTG-CM; 5, C-CM; 6, N-CM. (B) Quantification of induced vessels. Number of blood vessels entering the collagen sponges was counted under stereomicroscopy. The data shown is the mean±SD of three separate experiments. D, serum-free DMEM; F, 1 ng/ml of bFGF in PBS; WT, WT-hPTTG-CM; M, M-hPTTG-CM; C, C-CM; N, N-CM. $p<0.01$ versus* PBS, ** WT-hPTTG-CM.

PTTG-mediated angiogenic activity was also examined in vivo by CAM assay. Chick CAM provides an ideal microenvironment to induce new vessel development from pre-existing vessels. We observed that CM from WT-hPTTG-transfected cells induced a spoke-wheel like appearance on the CAM and this effect was more marked than that observed with CM derived from other cell lines. Vessel growth of CAM was tested in vivo using 9-day-old chick egg embryos. Sample-soaked collagen sponges were loaded on CAM and neovascularization of surrounding collagen sponges evaluated after 4 days incubation. As shown in FIG. 23A, application of sponges presoaked in WT-HPTTG-CM induced a spoke-wheel like appearance which was more evident than CAM vessel formation after application of sponges immersed in the other CMs. The number of detectable blood vessels entering the collagen sponges were counted under stereomicroscopy, (FIG. 23B), and as predicted, all CM samples derived from both transfected and non-transfected NIH-3T3 cells induced stronger angiogenic responses than did serum-free DMEM alone p<0.01).

Application of sponges containing WT-hPTTG-CM to the CAM induced highest angiogenic activity (p<0.01), although higher angiogenic activity was observed when recombinant bFGF (1 µg/egg) was added to the CAM. In contrast to the in vitro assays, quantitative angiogenic activity of sponges soaked in WT-hPTTG derived CM was weaker than that observed after application of a sponge soaked in added bFGF (1 µg/egg). However, bFGF bioavailability in the recombinant peptide-soaked sponge and the CM-soaked sponge may differ accounting for this discrepancy.

Example 21

PTTG2 Overexpression Inhibits PTTG1 Biological Activity

Polymerase chain reaction (PCR). PCR was performed with Expand High Fidelity PCR system (Roche Molecular Biochemicals, Indianapolis, Ind.) or Advantage Genomic Polymerase mix (Clontech, Palo Alto, Calif.), and the primers (Gibco, Grand Island, N.Y.) listed in Table 22 below.

TABLE 22

PCR Primers. PCR primer sequences from the sense (F) and antisense (R) orientations are listed. Introduced restriction enzyme sites are underlined.

| Forward Primer | Nucleotide Sequence | |
|---|---|---|
| 34a | 5' GGAGAACCAGGCACCCGTGTG | (SEQ. ID. NO.:20) |
| C106F | 5' AAGGATGGGCTGAAGCTGG | (SEQ. ID. NO.:21) |
| C124F | 5' GGGTCTGGACCTTCAATCAAAGC | (SEQ. ID. NO.:22) |
| 2-14F | 5' AATGTGGCTGTTGAGAGCG | (SEQ. ID. NO.:23) |
| 3-88F | 5' GGCATCCTTGTGGCTACA | (SEQ. ID. NO.:24) |
| 4-7F | 5' AGAGAGAGGCATGGATCAG | (SEQ. ID. NO.:25) |
| -5F | 5' CCAGAATGGCTACTCTGATC | (SEQ. ID. NO.:26) |
| 462F | 5' CCCCTTGAGTGGAGTGCCTC | (SEQ. ID. NO.:27) |
| C550F | 5' ATGCCCTCTCCACCATGG | (SEQ. ID. NO.:28) |
| G1-253F | 5' TTTAATATTACACGATCCTAG | (SEQ. ID. NO.:29) |
| G1-245F | 5' TACACGATCCTAGTTTTTTCTTCC | (SEQ. ID. NO.:30) |
| G1-213F | 5' GTGCCACAAAGTTTGCAAGA | (SEQ. ID. NO.:31) |
| G1-145F | 5' TCTACTTGGTGACCACGCC | (SEQ. ID. NO.:32) |
| G1-115F | 5' CTCCTGGGCGGAAGAGCC | (SEQ. ID. NO.:33) |
| G1-83F | 5' TTGTGGTTTAAACCAGGAGT | (SEQ. ID. NO.:34) |
| G2-62F | 5' AAATATAAAGTGGGACCAC | (SEQ. ID. NO.:35) |
| G2-53F | 5' GTGGGACCACGGTCTTAG | (SEQ. ID. NO.:36) |
| G2-49F | 5' GACCACGGTCTTAGATGAAT | (SEQ. ID. NO.:37) |
| G3-33F | 5' CTTAAATCTGGTCGAGAGCG | (SEQ. ID. NO.:38) |

TABLE 22-continued

PCR Primers. PCR primer sequences from the sense (F) and antisense (R) orientations are listed. Introduced restriction enzyme sites are underlined.

| | | |
|---|---|---|
| PTTG1S | 5' GGATCCGTAAGCTTATGGCTACTCTGATCTATG | (SEQ. ID. NO.:39) |
| PTTG2S | 5' GGATCCGTGCTACTCTGATCTACGTTG | (SEQ. ID. NO.:40) |
| PTTG3S | 5' GGATCCGTGCTACTCTGATCTATGTTG | (SEQ. ID. NO :41) |
| PTTG1-F | 5' CGGGGATCCGTGCTACTCTGATCTATGTTG | (SEQ. ID. NO.:42) |
| pBIND-3'F | 5' TGAGGTACCTGAAGATCTAAGGCC | (SEQ. ID. NO.:43) |
| pTargeT-3'F | 5' TAAATCTTTCCCGGGGGTACC | (SEQ. ID. NO.:44) |
| PTTG3-5'F | 5' CGGGGATCCGTGCTACTC | (SEQ. ID. NO.:45) |

| Reverse Primer | Nucleotide Sequence | |
|---|---|---|
| 601b | 5' CTATGTCACAGCAAACAGGTGGC | (SEQ. ID. NO.:46) |
| C233R | 5' GCCTTTCTGGTAGCTTTAGGTAA | (SEQ. ID. NO.:47) |
| C481R | 5' GAGGCACTCCACTCAAGGGG | (SEQ. ID. NO.:48) |
| C525R | 5' CTGAAACAGCTTTTCAAGCT | (SEQ. ID. NO.:49) |
| 2-306R | 5' GCTTGGCTGTTTTTGTTTTCT | (SEQ. ID. NO.:50) |
| 3-434R | 5' AGGTCAAAACTCTCGAAGC | (SEQ. ID. NO.:51) |
| 4-282R | 5' TCCGTTGATCTTTACTCACG | (SEQ. ID. NO.:52) |
| 653R | 5' TAAATATCTATGTCACAGCAAACAGG | (SEQ. ID. NO.:53) |
| G3-679R | 5' CACAAACTCTAAAGCACTAAG | (SEQ. ID. NO.:54) |
| PTTG1AS | 5' GGTACCTTAAATATCTATGTCACAGC | (SEQ. ID. NO.:55) |
| PTTG2AS | 5' GGTACCACATCCAGGGTCGACAGAATG | (SEQ. ID. NO.:56) |
| PTTG3AS | 5' GGTACCAATATCTATGTCACAGCAAAC | (SEQ. ID. NO.:57) |
| pBIND-5'R | 5' CACGGATCCCCGGGAATTC | (SEQ. ID. NO.:58) |
| G2-Ctail.R | 5' GCTTGAAGGAGATCTCAAAACAG | (SEQ. ID. NO.:59) |
| PTTG2-R | 5' TCAGGTACCTCAACATCCAGGGTC | (SEQ. ID. NO.:60) |
| PTTG3-R | 5' TCAGGTACCTCAAATATCTATGTC | (SEQ. ID. NO.:61) |

Radiation Hybrid (RH) Mapping of the PTTG Gene Family Members

The G3 RH mapping panel (Research Genetics, Huntsville, Ala.) was amplified with PTTG primers, as in (Prezant, T. R. et al., *An intronless homolog of human proto-oncogene hPTTG is expressed in pituitary tumors: evidence for hPTTG family*, J. Clin. Endocrinol. Metab. 84:1149–1152 [1999]), for 40 cycles of 94° C., 30 sec; 56° C., 30 sec; 72° C., 30 sec (PTTG3, PTTG4) or 2.5 min (PTTG2–4). Results were submitted electronically to the Stanford Human Genome Center website for linkage determination. PTTG relatedness was confirmed by sequencing.

PTTG3

The 34a/601b PCR product amplified from thymus DNA from individual UMB61 was sequenced. Gene-specific primers (3–88F/3–434R) were then designed to amplify the putative PTTG3 sequence from the G3 RH panel.

PTTG4

The common primers C106F/C525R amplified a cDNA-sized product in G3 RH panel members previously negative for PTTG2 and PTTG3. These PCR products were gel isolated (QIAEX II, QIAGEN, Valencia, Calif.) and sequenced. The G3 RH panel was then amplified with PTTG4-specific primers (4–7F/4–282R).

Confirmation of Chromosomal Localizations

Hamster-human monochromosomal DNAs containing human chromosomes 4 (NA10115), 5 (NA10114), 8 (NA10156B) or 11 (NA10927A), and Chinese hamster DNA (NA10658) were from Coriell Institute for Medical Research (Camden, N.J.). 10 ng DNAs were amplified with 3-88F/3-434R (PTTG3) or 4-7F/4-282R (PTTG4). 10 µg DNAs were digested with BamHI for Southern blot analysis.

Tissues and Cell Lines

Frozen tissues included normal human pituitary (Zoion Diagnostics, New York, N.Y.; National Neurological Research Specimen Bank, Los Angeles, Calif.) and thymus (UMB61), normal breast and ovarian tissues (Brain and Tissue Bank for Developmental Disorders, University of Maryland, Baltimore, Md.). Cell lines were from American Type Culture Collection (Manassas, Va.) or Dr. H. Phillip Koeffler. Pituitary tumors were obtained by the GCRC of Cedars-Sinai Medical Center (Los Angeles, Calif.), and colon, breast and ovarian tumor samples were obtained from the pathology department, all according to institutional guidelines.

RNA and DNA Isolations

Tissues or cell pellets were homogenized in TRIZOL reagent (Gibco) for RNA isolation, as in (Prezant, T. R. et al., *An intronless homolog of human proto-oncogene hPTTG is expressed in pituitary tumors: evidence for hPTTG family*, J. Clin. Endocrinol. Metab. 84:1149–1152 [1999]). DNAs were isolated from the TRIZOL interphase, re-extracted with proteinase K and phenol/chloroform and ethanol precipitated, or further purified with the QIAamp tissue kit (QIAGEN, Valencia, Calif.).

Primer Extension Analysis

PTTG-4 cDNAs were reverse transcribed from DNase-treated RNA (amplification grade DNAse I, from Gibco or Roche; SuperScript II from Gibco) and amplified with primers C106F/C525R or C124F/C481R. Nested PCR reactions (C106F/C525R primers, then C124F/C481R primers) were used for Clontech multiple tissue panel cDNAs (adult panels I and II, fetal panel I) and Marathon RACE-ready pituitary cDNA. ~1 ng PCR product in molten SeaPlaque agarose (FMC BioProducts, Rockland, Me.) was added to 6 µl primer extension mix, containing: ThermoSequenase enzyme, 1× buffer and 0.5 µl of [alpha-$^{33}$P]ddATP (Amersham, Piscataway, N.J.), 5 pmol primer C233R, and 2.5 µM dCTP, dGTP and TTP (Gibco). After 40 cycles of: 95° C., 15 sec; 62° C., 30 sec; 72° C., 1 min, reactions were denatured with formamide dye, electrophoresed in 8% sequencing gels (National Diagnostics, Atlanta, Ga.), and autoradiographed on Kodak BioMax MR film. C233R-primed sequencing ladder of PTTG3 was the size marker. Negative controls were –RT reactions (tumors and tissues) or PCR water blank (Clontech cDNAs). Densitometric analysis was performed on a Macintosh computer using the public domain NIH Image 1.61 program (developed at the NIH, available at rsb.info.nih.gov/nih-image).

Sequence Analysis

5' chromosomal walking (Clontech) used C525R/AP1 primers for the primary PCR, and primers AP2 with 2–306R (PTTG2), 3–434R (PTTG3) or C233R (PTTG4), for secondary PCRS. 3' chromosomal walking used AP1 plus 2–14F (PTTG2), 3–88F (PTTG3), or 4–7F (PTTG4) for primary PCRS, and AP2 plus primer C106F (PTTG2) or C124F (PTTG3,4) for secondary amplifications. PCR products were gel isolated (QIAEX II, Qiagen) or cloned into pCR2.1-TOPO (Invitrogen, Carlsbad, Calif.). ThermoSequenase reactions with [alpha-$^{33}$P]ddNTPs (Amersham) were electrophoresed through 6% acrylamide/8.3 M urea gels (National Diagnostics), and exposed to Kodak BioMax MR film. Sequences were assembled using GCG programs (Madison, Wis.), and analyzed for repeat elements with RepeatMasker (University of Washington, through the Baylor College of Medicine Sequence Utilities website).

Mapping Approximate Transcriptional Start Sites

The 5' ends of PTTG1–3 mRNAs were narrowed down by RT-PCR experiments. Reactions included genomic DNA (positive control), and DNased normal pituitary RNA treated with RT (test sample) or without RT (negative control). For PTTG1, the downstream primer was C233R, and the upstream primers were G1-253F, -245F, -213F, -145F, -115F and -83F. PCR products of the expected sizes for G1-213F/C233R and G1-145F/C233R were sequenced. For PTTG2, the downstream primer was 2-306R, and the upstream primers were G2-62F, -53F, -49F and 2-14F. For PTTG3, the downstream primer was 3-434R, and the upstream primers were G3-33F and 3-88F.

Southern Blots

~5 µg of BamHI-digested genomic DNAs were electrophoresed through 0.8% agarose in TBE, transferred to Hybond N+ (Amersham) membranes (Sambrook, J. et al., *Molecular cloning, a laboratory manual, Second edition*, Cold Spring Harbor Laboratory Press, Cold Spring Harbor, N.Y. [1989]), and hybridized at 68° C. for 2 hours (Quik-Hyb, Stratagene). The probe was a mixture of PTTG1–3 PCR products (-5F/653R), random-prime labelled (RadPrime, Gibco; [alpha-$^{32}$P]dCTP, New England Nuclear, Boston, Mass.). The stringent wash contained 0.1×SSC, 0.1% SDS at 60° C. Blots were exposed on Kodak BioMax MR film. Probe HHH202, from STS marker D17S33 on chromosome 17 (gift of M. Bragg) was used for normalization.

Northern Blots

10 µg total RNA was electrophoresed in 1% agarose gels containing morpholinopropanesulfonic acid buffer and 6% formaldehyde (Sambrook, J. et al. [1989]), transferred to Hybond N+ (Amersham), hybridized with PTTG1–3 probe mixture in Quik-Hyb solution (Stratagene) and washed as for Southern blots, above. Random prime labelled 18S cDNA (Ambion, Houston, Tex.) was used for loading normalization.

pTargeT Plasmids

PTTG coding sequences were PCR-amplified and TA-cloned into pTargeT (Promega, Madison, Wis.), using primers -5F/653R for PTTG1–2 and -5F/G3-679R for PTTG3. Templates were: PTTG1-cDNA clone 9C (Zhang, X. et al., *Structure, expression and function of human pituitary tumor transforming gene (PTTG)*, Mol. Endocrinol., 13: 156–166, [1999]), PTTG2-NA10115 (Coriell Institute), PTTG3-G3 RH panel member #6 (Research Genetics). PTTG2ΔC was generated by PCR mutagenesis of pTargeT-PTTG2 with primer pair Gene2-Ctail.F/-Ctail.R, followed by kinase and intramolecular ligation (RapidLigase, Roche; transformation into SURE2 cells, Stratagene).

pBIND Plasmids

PTTG coding sequences were amplified with PTTG-S/PTTG-AS primers, subcloned into pCR2.1 (Invitrogen), digested with BamHI and KpnI, and directionally cloned into pBIND-GAL4 (Stratagene). In-frame DBD-PTTG fusions were confirmed by sequencing. Identical junction sequences were later made by re-amplification, enzyme digestion, and ligation. PTTG1 used PTTG1-F/pBIND-5'R and BamHI; PTTG2 used PTTG2-R/pBIND3'F and KpnI, PTTG3 used PTTG3-5'F/PTTG3-R (pTargeT-PTTG3 template), BamHI+KpnI, subcloned into pBIND; pBIND-PTTG2ΔL used Gene2-Ctail.R/pBIND-3'F, and KpnI. PTTG2ΔS arose as a PCR artifact. The 1 base deletion, at nucleotide 466 after the ATG, results in 156 amino acids of PTTG2, followed by 10 out-of-frame amino acids, and no PXXP motifs.

Transcriptional Activation Assays

Maxi or miniprep DNAs (Qiagen) were co-transfected into NIH 3T3 cells (Lipofectamine PLUS, Gibco) in triplicate wells, in at least three experiments. Per well, DNA concentrations were: 1 µg pBIND plasmids, 0.125 µg reporter pG5/Luc, and 0.1 µg pCMV/βgal. Cytoplasmic extracts were prepared 2–3 days after transfections for luciferase assays (Ray, D. W. et al., *Leukemia inhibitory factor (LIF) stimulates proopiomelanocortin (POMC) expression in a corticotroph cell line. Role of STAT pathway*, J. Clin. Invest. 97:1852–1859 [1996]), which were normalized to β-galactosidase (Invitrogen). Experimental means +/- SEMs were analyzed by One-way ANOVA, Bonferroni's Multiple Comparison Test, and Prism 3.0 analytical software.

Transcriptional Inhibition Assays 2.5 μg competitor plasmid [pTargeT plasmids (no insert control, or PTTG1–3 inserts), or pCI-neo plasmids (PTTG1-C'WT, -C'Mut)] was co-transfected with 0.5 μg pBIND plasmid, 0.125 μg pG5ALuc, and 0.1 μg pCMV/Bgal, into each of three wells of NIH 3T3 cells. The 1:5 dilution of pTargeT-PTTG2 used 0.5 μg plasmid and 2.0 μg of pTargeT, for a total concentration of 2.5 μg competitor DNA mix. Lysates were harvested and assayed for luciferase and β-galactosidase activities, as above. In one experiment, DNA was prepared from half the cells after harvesting into phosphate buffered saline (Gibco), centrifuging, and resuspending in TRIZOL (Gibco). DNAs were isolated from the interphase, denatured for "dot blot" analysis, and probed with LacZ.

Results: Identifying the PTTG Gene Family

PTTG1 and PTTG2: The chromosomal location of PTTG1 on 5q33 (Zhang, X. et al., *Structure, expression and function of human pituitary tumor transforming gene (PTTG)*, Mol. Endocrinol. 13:156–166 [1999a]) and the discovery and localization of intronless PTTG2 at 4p12 have been described (Prezant, T. R. et al., *An intronless homolog of human proto-oncogene hPTTG is expressed in pituitary tumors: evidence for hPTTG family*, J. Clin. Endocrinol. Metab. 84:1149–1152 [1999]). Using PCR-ELISA with gene-specific oligonucleotides (GSOs), it was shown that PTTG2 is transcribed at low levels in spleen, liver and leukocytes (Prezant, T. R. et al. [1999]). PTTG2 mRNA comprised a significant proportion of total PTTG in different pituitary tumor subtypes. In the process of sequencing genomic DNA for PTTG2, two additional PTTG family members were discovered.

PTTG3: In examining a case control, we found an unusual "PTTG2" sequence, containing 37 homozygous sequence changes (Prezant, T. R. et al. [1999]). Whether this represented a third (intronless) PTTG gene was tested by amplifying the G3 RH mapping panel with PCR primers specific to the putative PTTG3 sequence. The human PTTG3 genomic sequence (SEQ. ID.NO.:65; GenBank Accession AY028471) is listed below in Table 23. The underlined sequence (SEQ. ID. NO.:66), beginning at the transcriptional start site at nucleotide positions 339–341 and extending through the stop codon at nucleotide positions 945–947 is the coding sequence for an hPTTG3 protein (SEQ. ID. NO.:67).

TABLE 23 hPTTG3 gene sequence.

```
   1 ccagatttct ggaaataaag atctactaag aaatgaagag cacttgaaatagtaacaaca    (SEQ. ID. NO.:65)
  61 gaactaaaca tattttgatt ttttaataat ttaaatctct aaaagttaacaaacaagaat
 121 agtaataact tatggtgggt ttatatctaa tgtatcagta aaatatatgacaacagtatt
 181 ataaaagcta gcattagaga catggaagta taccattgta agacatatcctataagtgta
 241 agtattctat aagtgatgtg gtataattca aatgaagata gactgtaataaattaaagat
 301 atatacttaa atctggtcga gagcggcaat aatccagaat ggctactctgatctatgttg
 361 ataaggaaaa cgaagaacca ggcatccttg tggctacaaa ggatgggctgaagctggggt
 421 ctggaccttc aatcaaagcc ttagatggga gatctcaagt ttcaatatcatgttttggca
 481 aaacattcga tgctcccaca tccttaccta aagctaccag aaaggctttgggaactgtca
 541 acagagctac agaaaagtca gtaaagacca atggaccect caaacaaaaacagccaagct
 601 tttctgccaa aaagatgact gagaagactg ttaaagcaaa aaactctgttcctgcctcag
 661 atgatggcta tccagaaata gaaaaattat ttcccttcaa tcctctaggcttcgagagtt
 721 ttgacctgcc tgaagagcac cagattgcac atctcccctt gagtgaagtgcctctcatga
 781 tacttgatga ggagagagag cttgaaaagc tgtttcagct gggccccccttcacctttga
 841 agatgccctc tccaccatgg aaatccaatc tgttgcagtc tcctttaagcattctgttga
 901 ccctggatgt tgaattgcca cctgtttgct ctgacataga tatttaaatttcttagtgct
 961 ttagagtttg tgtatatttc tattaataaa gcattatttg tttaacagaaaaaagatat
1021 atacttaaat cctaaaataa aataaccatt aaaaggaaaa acaggagttataactaataa
1081 gggaacaaag gacataaaat gggataataa tgcttaatcc aaaataaagcagaaaatgaa
1141 gaaaaatgaa atgaagaaca gataaataga aaacaaatag caatatgaaagacaaacttg
1201 accgggtgtg gtggctgatg cctgtaatcc cagcactgtg ggaggctgaggcaggcggat
1261 cacctgaggt cgggagtctg agaccagcct caccaacatg gagaa//
```

The corresponding PTTG3 amino acid sequence encoded by (SEQ. ID. NO.:66) is in Table 24 below.

TABLE 24 hPTTG3 amino acid sequence.

| | | | | | |
|---|---|---|---|---|---|
| MATLIYVDKE | NEEPGILVAT | KDGLKLGSGP | SIKALDGRSQ | VSISCFGKTF | 50 (SEQ. ID. NO.:67) |
| DAPTSLPKAT | RKALGTVNRA | TEKSVKTNGP | LKQKQPSFSA | KKMTEKTVKA | 100 |
| KNSVPASDDG | YPEIEKLFPF | NPLGFESFDL | PEEHQIAHLP | LSEVPLMILD | 150 |
| EERELEKLFQ | LGPPSPLKMP | SPPWKSNLLQ | SPLSILLTLD | VELPPVCSDI | 200 |
| DI// | 202 | | | | |

PTTG3 was localized 15 cRads from marker SHGC-12833 on chromosome 8q22, with a LOD score of 10.47. This chromosomal localization was confirmed by Southern blot analysis (see below) and PCR analysis (not shown), using DNA from a hamster/human hybrid line containing only human chromosome 8.

The open reading frames of PTTG2 and PTTG3 were determined by chromosomal walking and sequence analysis. The PCR and GSO primers from our previous study (Prezant, T. R. et al. [1999]) have greater homology to PTTG1 and PTTG2, than to PTTG3 cDNA. The encoded proteins are 90% identical to PTTG1 protein, with both PXXP motifs conserved. These family members share greater overall homology to PTTG1 protein than do the rodent PTTG proteins (FIG. 24). However, PTTG2 has a +T insertion at nucleotide position 534 of SEQ. ID. NO.:63 that changes the reading frame, resulting in a putative truncated protein of 191 amino acids (SEQ. ID. NO.:64), with homology to PTTG1 protein ending at amino acid 179. The sequence for PTTG2 in (Chen, L. et al., *Identification of the human pituitary tumor transforming gene (hPTTG) family: molecular structure, expression, and chromosomal localization*, Gene 248: 41–50 [2000]) differs from ours, since it does not contain the +T insertion. Our PTTG2 partial coding sequence was available through GenBank, with the accession number AF116538.1, and the sequence was confirmed.

Segments of the hPTTG2, hPTTG3, and hPTTG4 genomic sequences share close homology with the hPTTG1 open reading frame sequence (at nucleotide positions 95 through 700 of SEQ. ID. NO.:3). In particular, when aligned beginning with nucleotide position 99 of SEQ. ID. NO.:3, there is close homology with hPTTG2 at nucleotide positions 387–1065 of SEQ. ID. NO.:62; with hPTTG3 at nucleotide positions 343–1019 of SEQ. ID. NO.:65; and with hPTTG4 at nucleotide positions 418–1091 of SEQ. ID. NO.:68.

RT-PCR experiments were performed to determine whether the open reading frames of PTTG2 and PTTG3 are completely transcribed. Oligo(dT)-primed PTTG2 cDNA is amplified from normal pituitary with upstream primers beginning at −32, −49, and −53, but not at −62 from the ATG transcription start site, and PTTG3 cDNA is amplified with an upstream primer beginning at −33 from the ATG transcription start site. Thus, both genes are transcribed and potentially translated.

The location of the transcriptional start site for PTTG1 was similarly determined. RT-PCR products were obtained from normal pituitary, using upstream PCR primers at −83, −115, −145, −213, and −245, but not beginning at −253 from the ATG transcription start site. The sequence was confirmed for −213/C233R and −145/C233R RT-PCR products. Interestingly, this transcribed region of human PTTG overlaps the rat PTTG promoter. (Pei, L., *Genomic organization and identification of an enhancer element containing binding sites for multiple proteins in rat pituitary tumor-transforming gene*, J. Biol. Chem., 273:5219–5225 [1998]).

Our PTTG1 gene structure of six exons and five introns (Zhang, X. et al. [1999a]) differs from that of (Chen, L. et al. [2000]). Chen et al. (2000) used primer extension analysis, without sequencing the extension product, and RNAse protection, using a probe that spans the intron 1/exon 2 junction; they concluded that PTTG1 mRNA starts at −37 nucleotides upstream of the ATG transcription start site. The promoter of Chen et al. (2000), therefore, contains intron 1. Our laboratory has consistently amplified RT-PCR products that do not retain this intron.

PTTG4: To simultaneously distinguish expression of all three PTTG cDNAs, we identified a region amenable to primer extension analysis, and tested new PCR "common" primers for the RT-PCR (C106F/C525R) and the primer extension (C233R) reactions, with genomic DNA derived from the individual in whom we discovered PTTG3. Table 25 shows a human PTTG4 pseudogene and flanking genomic sequence (SEQ. ID. NO.:68; GenBank Accession AY028473).

TABLE 25 hPTTG4 sequence.

| | | | | | |
|---|---|---|---|---|---|
| 1 | aaaaacatta | aagctgaagg | ggcaacttca | aatacctcct | ttattaagataaacaaaagt (SEQ. ID. NO.:68) |
| 61 | agtttttcca | actacttaga | aatgtaatgt | ctcaaattct | actcttttcatcattcaggg |
| 121 | gtatgtcatg | ggttgaattg | tggccccaaa | aaagatatag | tgaagtcctcagaatgtgac |
| 181 | catgtttgga | aataggcttg | ttagagatgt | gattagtcag | gataaggtcctactggagca |

TABLE 25-continued hPTTG4 sequence.

```
 241 gagtgggccc ctaacccaat atgactggtg tccatacaag aagacacagacacacaggaa 301 gaacaccata tggagatgga acactgcaga gacgcatcca caagccaaggaatgcctggg 361 gctactagaa gcaaagagag aggcatggat cagattctcc cccagaagga acccaccctg 421 ctctgatcta tgttgataag gagaatggag aaccaggtat ccatgcagctcctaaagata 481 ggctgaagct gggatctgga ccttcaatca aagccttaga ggggagatctcaagtttcag 541 caccacgtgt tggcaaaatg tccaatgctt taccagcctt acctaaagctaccagaaagt 601 cttttggaac tgtcaacagg gctacagaaa cgtgagtaaa gatcaacggactcctcaaac 661 taaaacaccc aaatttctct gccgaaaaga tgaccaggaa gactgttaaagcaaaaagct 721 ctgttccttc ctcagataat gcctacccag aaatagaaaa attatttcacttcaatcttc 781 tagattttga gagttttaac caacctgaag tgcaccagat tgcaggcctccccttgagtg 841 gagtgcctct tatgatcctt gataaggaga gagagcttga aaagctgtttcagctgggcc 901 cgccttcgcc tgtgaagatg ccctctccgc catgggaacc caatctgttgcagtgtcctt 961 caaccettct gttgaccctg gatgttgaat tgccacctgt ttactatgacataaatattt 1021 aaatttcttc atgctttagg gtttgtgtgt atttgtayta ataaagcattctttaacagg 1081 aaaaaaaaaa ctcaccctgc taacacctta atttggaact tccacctcca gactgtgaga 1141 ca
```

The complex sequence (SEQ. ID. NO.:68) had 12 of 168 nucleotides that differed from both PTTG2 and PTTG3 sequences. These surprising results suggested two possibilities: either or both of the alleles of PTTG2 and/or PTTG3 had multiple sequence changes; or additional intronless PTTG homolog(s) are present.

To test these hypotheses, we re-amplified the radiation hybrid (RH) panel mapping with the new primers, C106F/C525R, and found identical sequences with 11 of the 12 nucleotide changes, in 7 panel members that were previously negative for PTTG2 and PTTG3. Thus, the existence of an intronless PTTG4 gene was confirmed, which gene maps to a different locus from other genes of the PTTG family. RH mapping with PTTG4-specific primers localized it to chromosome 11q12–13 (LOD score of 14.00, at 14 cRs from marker D11S4205). Additional sequence data imply that PTTG4 is a pseudogene, since it lacks homology to exon 2 of PTTG1, which contains the ATG transcription start site. Furthermore, no long open reading frame was found, although there is overall 89% homology to PTTG1 in 673 bp overlap.

Figure 25:
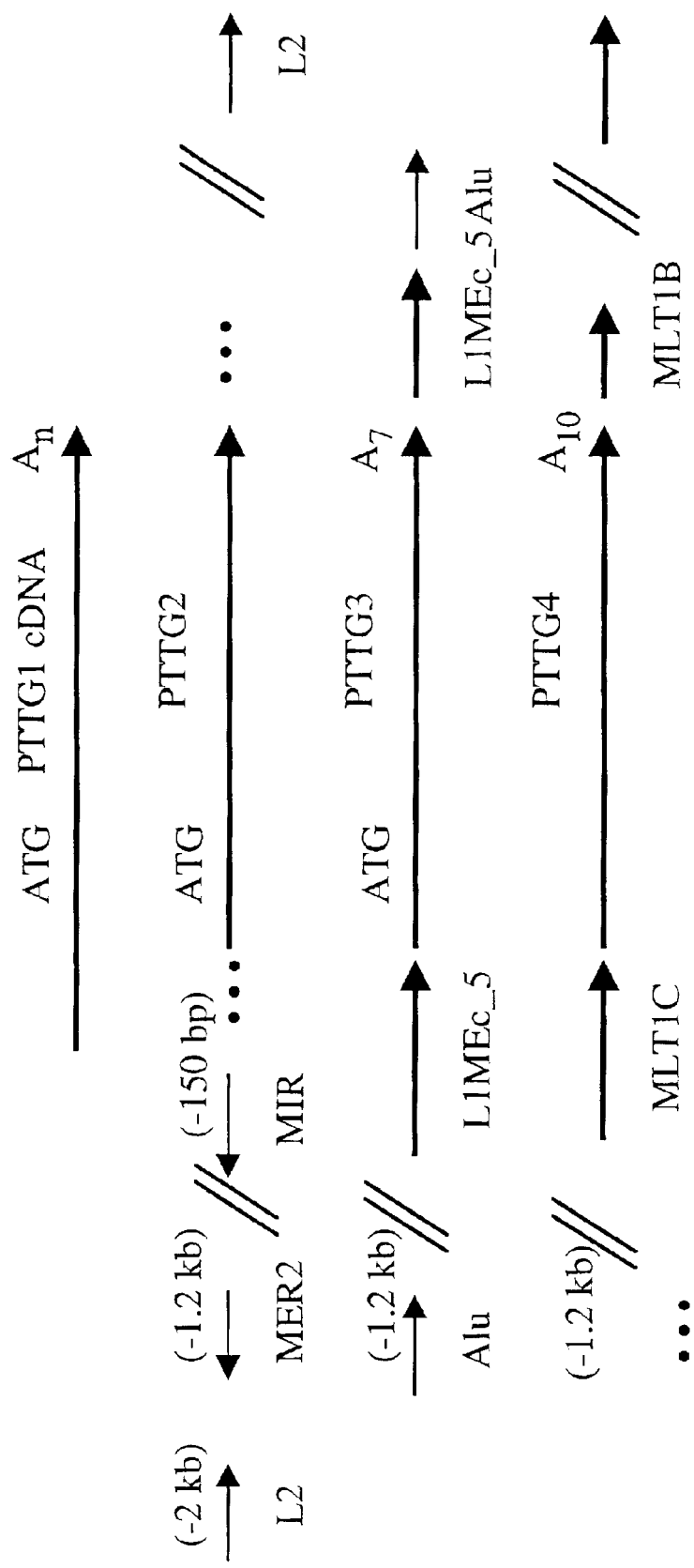
FIG. 25 shows the genomic structure of the human PTTG gene family. The intronless PTTG homologs, PTTG2–4, are shown beneath the cDNA of PTTG1, to indicate relative sizes and common features. PTTG2 and PTTG3 each contain an in-frame ATG, which is lacking in PTTG4. Flanking repeat elements that could be associated with retrotransposition events are shown.

FIG. 25 shows the genomic structures of the PTTG family. PTTG3 and PTTG4 appear to be classic intronless genes, in that they are flanked by direct repeats and contain short stretches of poly(A) at the location corresponding to the poly(A) tail of PTTG1 mRNA (Brosius, J., *RNAs from all categories generate retrosequences that may be exapted as novel genes or regulatory elements*, Gene 238:115–134 [1999]). PTTG3 is flanked by Line1 family repeats, while PTTG4 is surrounded by LTRs. PTTG2 has L2b repeats more than 1 kb away, and has no vestigial poly(A) tail. The lack of retroposon hallmarks and the divergent carboxy terminal encoding sequence may reflect an older age for the retrotransposition event for PTTG2.

The PTTG family members localize to four different chromosomes and have distinct tissue specific expression patterns. PTTG3 was alluded to in Prezant et al. (Prezant, T. R. et al., *An intronless homolog of human proto-oncogene hPTTG is expressed in pituitary tumors: evidence for hPTTG family*, J. Clin. Endocrinol. Metab. 84:1149–1152 [1999]), and subsequently described by Chen et al. (Chen, L. et al., *Identification of the human pituitary tumor transforming gene (HPTTG) family: molecular structure, expression, and chromosomal localization*, Gene, 248:41–50 [2000]). Minor differences (5q33 vs. 5q35.1, 4p12 vs. 4p15.1, 8q22 vs. 8q13.1) in the reported chromosomal localizations of PTTG1–3, presumably are due to different methodologies (RH mapping used herein, vs. FISH used by Chen et al. In addition, under permissive PCR conditions, the PTTG4 pseudogene is herein described, centromeric to men 1 on chromosome 11. The chromosomal assignments described herein were confirmed by Southern blot analysis.

Expression Pattern of the PTTG Family in Normal Tissues

Figure 26:
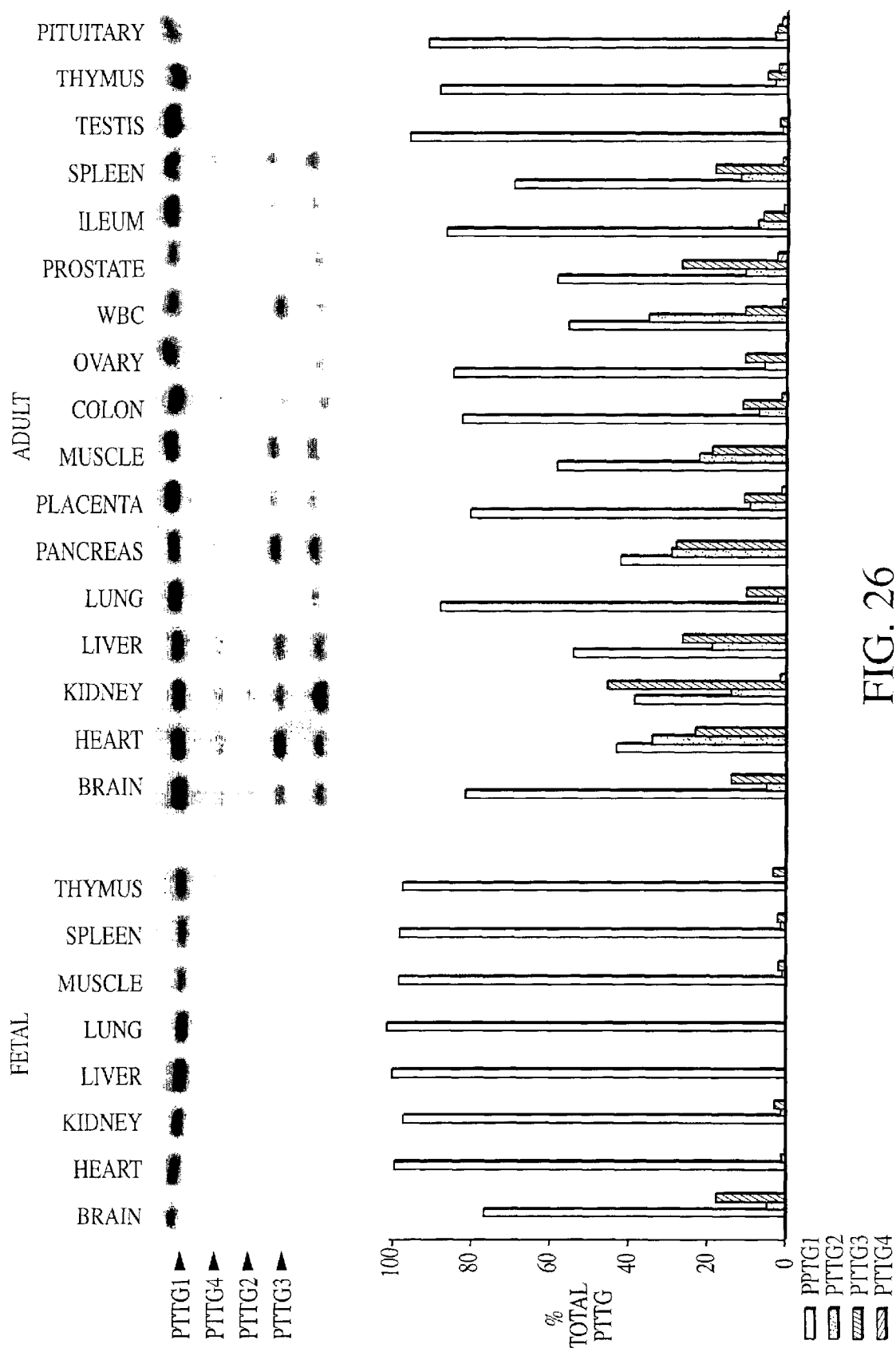
FIG. 26 illustrates primer extension analysis of PTTG in normal human fetal and adult tissues. PTTG cDNAs were amplified by nested PCR from Clontech's fetal multiple tissue panel (a), and adult multiple tissue panels I and II (b), and subjected to primer extension analysis to determine relative proportions of the PTTG gene family members. Top: autoradiograms; Bottom: densitometry results.

Primer extension analysis of normalized RT-PCR products distinguishes the expression of PTTG1 and the three intronless PTTG2, PTTG3 and PTTG4 genes. FIG. 26 shows that PTTG1 is the predominant form in most fetal and adult tissues, although only adult testis, thymus, spleen, colon, placenta and brain and fetal liver have detectable PTTG mRNA in Northern blots. (Zhang, X. et al. [1999a]). We found that the proportion of PTTG2 mRNA is highest in colon, leukocytes, liver and heart, and PTTG3 is highest in colon, prostate, pancreas and kidney. PTTG4 is not significantly transcribed. The relative proportions of the four PTTG cDNAs, as derived from densitometric analysis, are depicted graphically (FIG. 26).

The primer extension method we employed is PCR-based, and required nested reactions for most tissues in which PTTG expression was low (Zhang, X. et al. [1999a]), because the Clontech cDNAs were quite dilute (0.2 ng/$\mu$l). Therefore, these results relate the relative expression of the gene family members within samples.

PTTG1 mRNA comprises the highest proportion of total PTTG mRNA in nine fetal tissues and in most adult tissues. For some tissues where PTTG is detectable by Northern blot, the new family members are also expressed: PTTG2 in spleen and colon, and PTTG3 in colon. PTTG2 and/or PTTG3 cDNAs are also detectable in several tissues with low PTTG expression (both genes in wbc, breast, ovary; PTTG2 in liver and heart, PTTG3 in kidney, prostate and pancreas). Since PTTG4 is not significantly transcribed, and also lacks an in-frame ATG codon, it appears to be a pseudogene.

The tissue distribution patterns for PTTG2 and PTTG3 mRNA differ from those described in (Chen et al. [2000]). Their results are concordant with ours for PTTG2: (+) spleen and colon, and (−) thymus, and PTTG3: (−) spleen, thymus, testis, ovary, small intestine, but discordant for PTTG2: (+) prostate, testis, ovary, small intestine, and (−) wbc and PTTG3: (+) only ovarian tumors and (−) prostate, colon, wbc. The discrepancies are not simply due to different RNA sources, since both groups used Clontech Northern blots or the corresponding multiple tissue panels, but could be due to methodological differences. For example, their PTTG2 oligonucleotide probe used in Northern blot analysis might detect an unrelated gene, since no mRNA size information is provided. Also, the sequence of one of each primer pair used for PTTG2 and PTTG3 RT-PCRs in their study differs from our determinations. Their negative results with the PTTG3 Northern blot are likely due to the three sequence differences in their antisense oligonucleotide probe.

Expression Pattern of the PTTG Family in Cancers

Figure 27A:
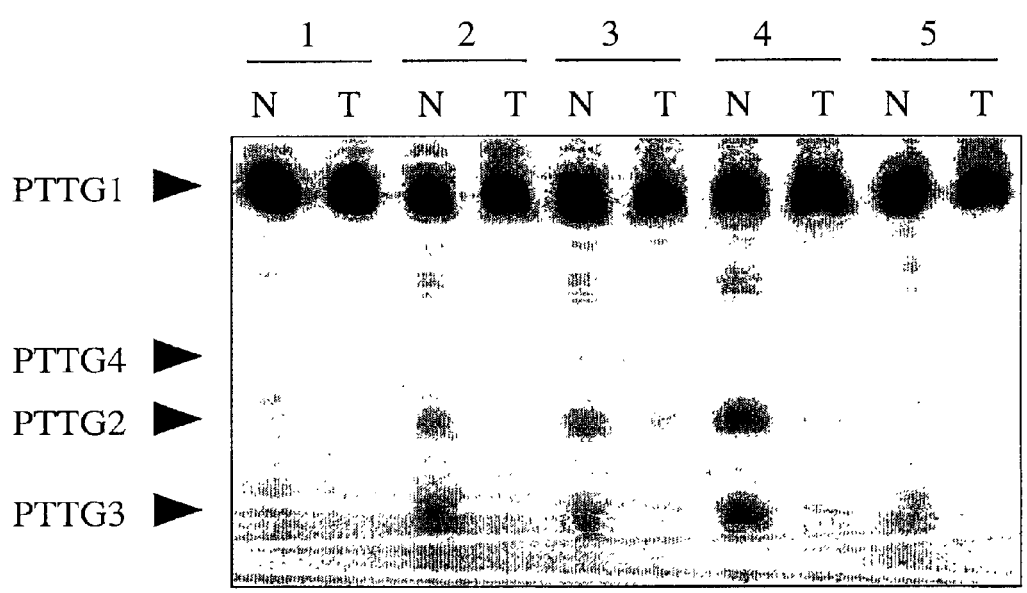
FIG. 27 demonstrates primer extension analysis of human PTTG in normal and neoplastic colon (FIG. 27A), breast (FIG. 27B) and ovary (FIG. 27C). PTTG RT-PCR products were normalized and subjected to primer extension analysis to determine the relative expression levels of PTTG1–4. Panels: (A) PTTG cDNAs from paired normal and tumorous colon tissues derived from five patients, (B) normal and tumorous breast, (C) normal and tumorous ovarian tissues. T=tumor, N=normal tissue.
Figure 28:
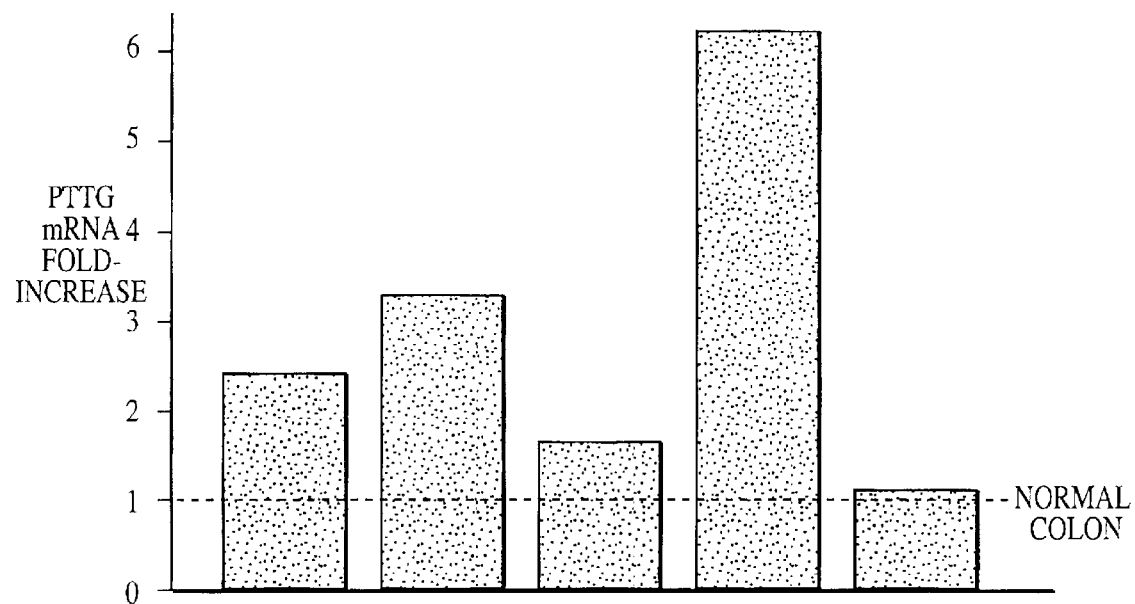
FIG. 28 shows relative PTTG mRNA expression in cells of the five colon tumors in FIG. 27A compared to adjacent normal colon cells.

We assessed the relative contributions of the PTTG family members to the 5–10 fold increases of PTTG mRNA observed in colon, breast and ovarian carcinomas. The primer extension assays utilized normalized RT-PCR products (using similar amounts of cDNA product in the primer extension). FIG. 27A shows that while PTTG1 is the predominant form in normal colon, PTTG2 and PTTG3 are also transcribed. However, the proportion of PTTG1 mRNA was selectively increased in 5 colon tumors, compared to matched normal tissue samples (FIG. 28). Thus, in primary colon neoplasias, as in cancer cell lines, the increased PTTG mRNA levels are mostly due to PTTG1.

Figure 27B:
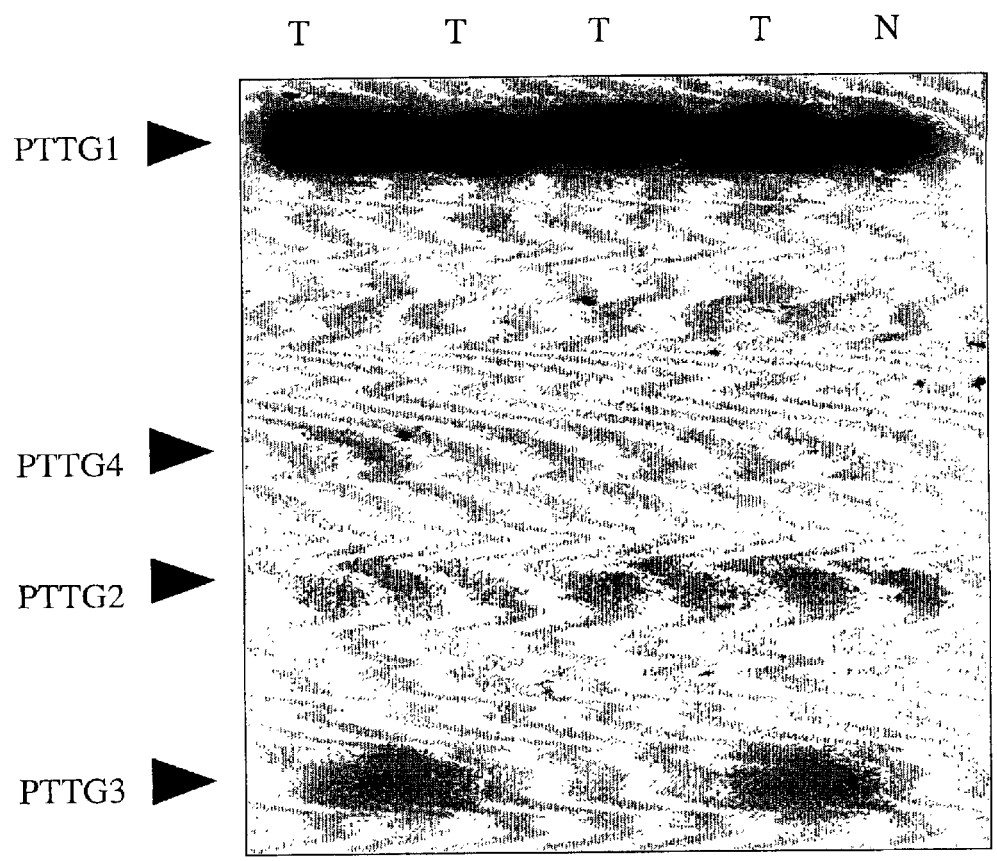
Figure 27C:
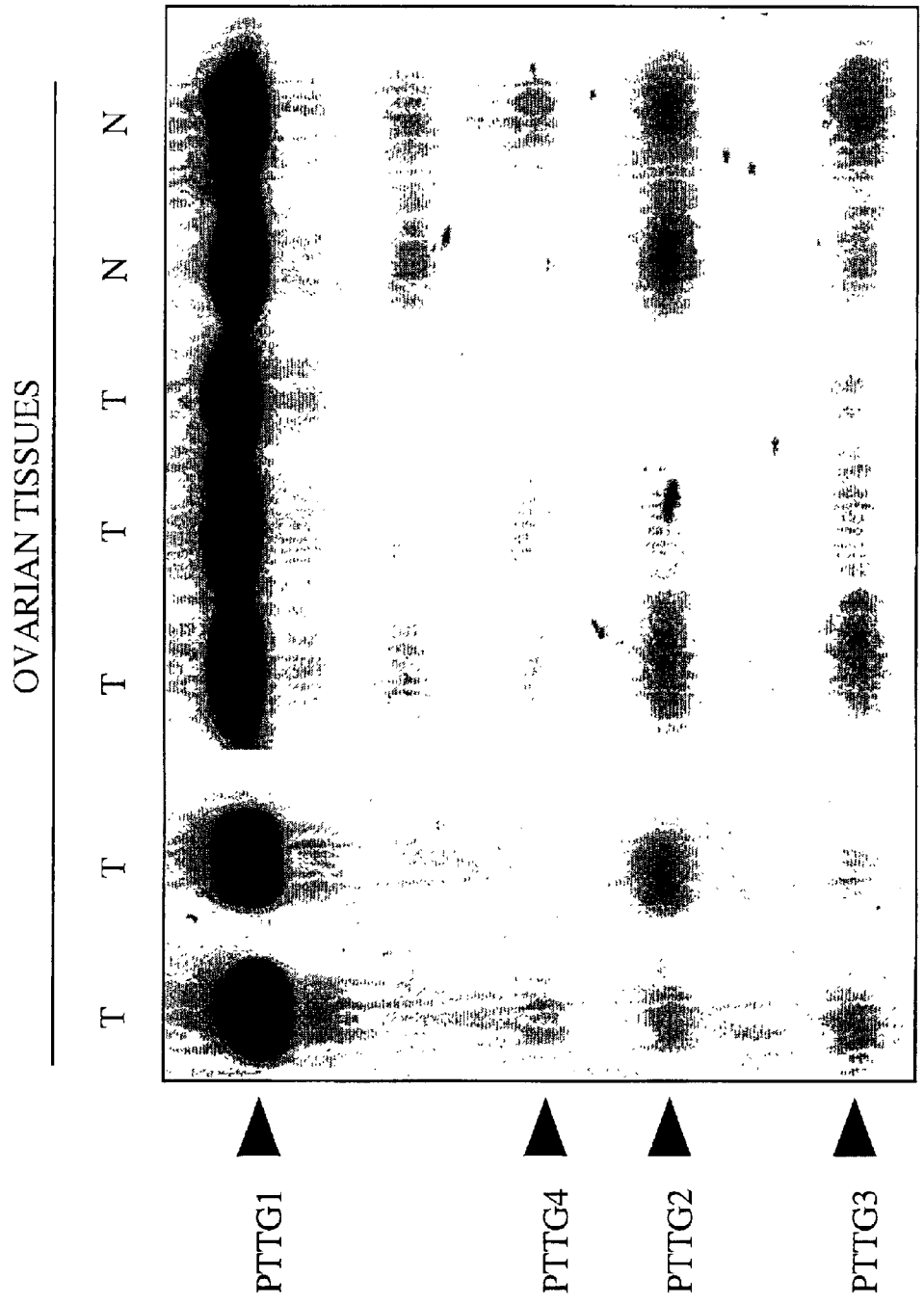

PTTG1 mRNA was also the predominant species in leukemia cell lines (n=3, not shown), breast cancer (n=4, FIG. 27B), and ovarian cancer (n=5, FIG. 27C). PTTG1 mRNA is clearly the major contributor to the high levels of PTTG expression in ovarian cancer, representing >95% of total PTTG mRNA in four of five tumors, shown in FIG. 27C. PTTG1 mRNA is proportionally the most highly expressed family member in both ovarian and breast cancers. PITG3 transcript was undetectable in normal breast, but was moderately expressed in 2 of 4 breast tumors. Low levels of PTTG2 cDNA were similar in normal breast and in four breast tumors. PTTG2 and PTTG3 cDNAs were detected in all of five ovarian cancers, but their ratios were not higher than in the normal ovarian controls. Unlike Chen et al. [2000], we did not observe an ovarian tumor-specific expression pattern for PTTG3, since it is expressed proportionally higher in normal ovary, and 4 of 5 ovarian tumors and the ovarian cancer cell line SKOV3 (not shown) expressed mostly the PTTG1 transcript.

Figure 29:
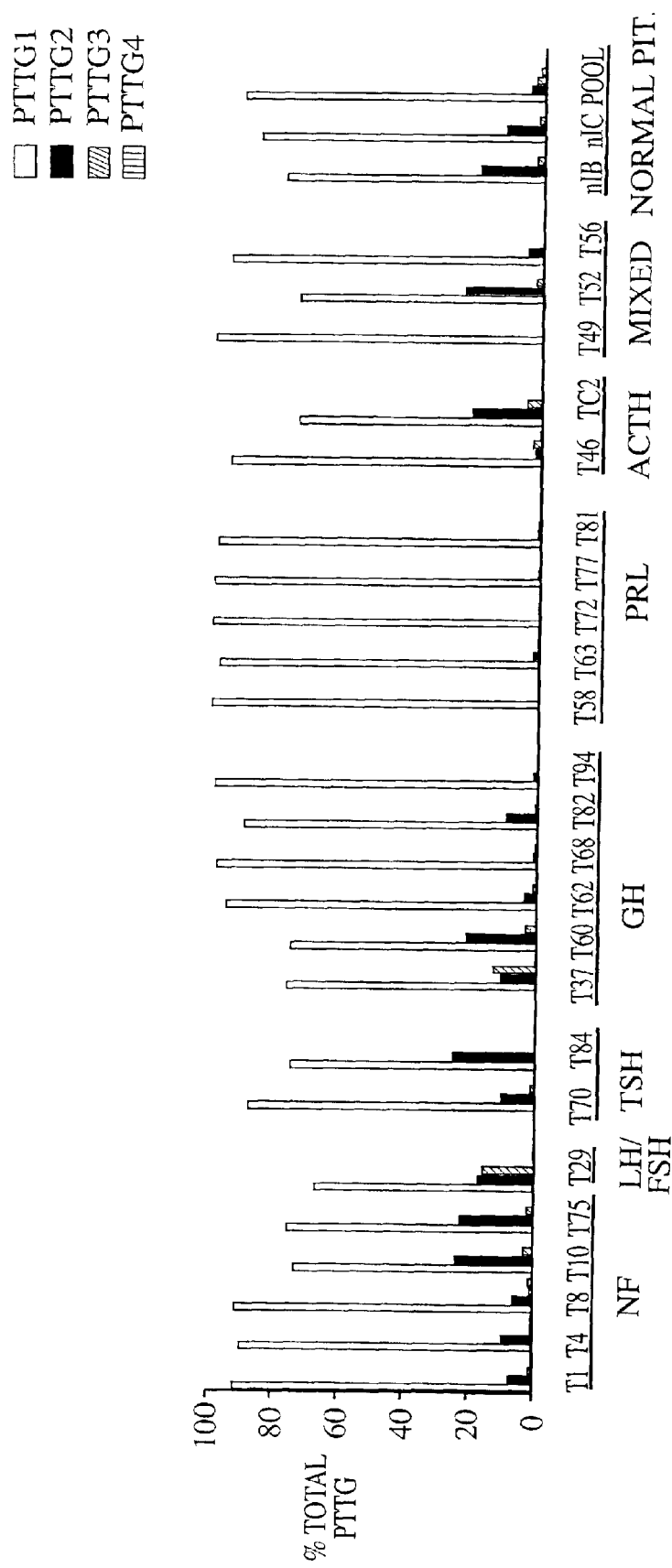
FIG. 29 shows primer extension analysis of human PTTG in pituitary tumors. Primer extension reactions using normalized PTTG cDNA from human pituitary adenomas or normal pituitary were analyzed densitometrically and shown graphically. Normal pituitary samples included two individual postmortem biopsies and cDNA from a pool of 18 normal pituitaries (Clontech). Tumor subtypes: NF—nonfunctional; hormone secreting: PRL—prolactin, GH—growth hormone, ACTH—adrenocorticotropic hormone, LH/FSH—luteinizing hormone and follicle-stimulating hormone, αsu—immunopositive for alpha subunit. The three mixed tumors were immunopositive for the following hormones: T-49: FSH/LH/ACTH, T-52: GH/PRL/αsu, T-56: PRL/ACTH.

Primer extension results for pituitary adenomas are summarized in FIG. 29. While PTTG2 cDNA was readily detectable in 15 of 24 adenomas, PTTG3 was weakly expressed in only 5 of 24 tumors. Five of five prolactinomas examined did not express PTTG2. Preferential PTTG1 expression in prolactinomas might be due to regulation by estrogen. (Heaney, A. P. et al., *Early involvement of estrogen-induced pituitary tumor transforming gene and fibroblast growth factor expression in prolactinoma pathogenesis*, Nature Med. 5: 1317–1321 [1999]). The higher proportion of PTTG2 mRNA in other pituitary tumor subtypes may be associated with the generally benign outcome of these adenomas.

Table 26 summarizes the chromosomal locations, homology and expression patterns of the PTTG family members.

TABLE 26

Human PTTG Gene Family. Homology: identical nucleotide (nt) or amino acid (aa) sequence: similarity to hPTTG1: conservative amino acid changes. Chromosomal loci were determined by radiation hybrid (RH) mapping. Expression patterns summarize the results from primer extension analyses in FIGS. 26–29.

| Gene | DNA | Protein | Locus | Expression Pattern |
|---|---|---|---|---|
| PTTG1 | (100) | (100) | 5q33 | highest expression in testis, detectable by Northern blot in thymus, spleen, colon, brain, placenta, fetal liver, major form in other normal tissues, increased in cancer cell lines, colon, breast and ovarian tumors |
| PTTG2 | 93 (620 nt) | 90 (179/191 aa) 93% similarity | 4p12 | normal colon, ovary, wbc, spleen, liver, heart, low in normal breast and pituitary, higher in some pituitary tumors |
| PTTG3 | 94 (632 nt) | 90 (202 aa) 94% similarity | 8q22 | normal colon, breast, ovary, kidney, prostate, pancreas, wbc, higher in some breast tumors |
| PTTG4 | 89 (673 nt) | — | 11q12-13 | — |

Absence of PTTG Gene Amplifications in Cancers

Figure 30A:
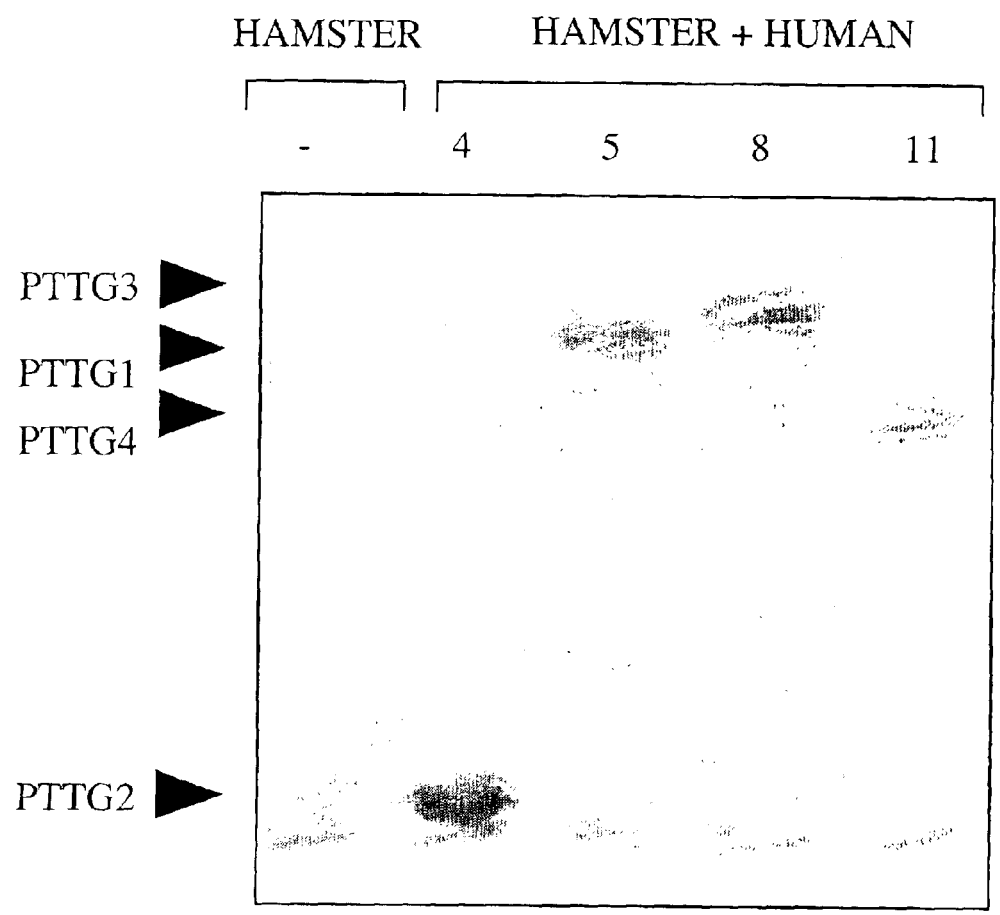
FIG. 30A shows Southern blot analysis of PTTG gene family to confirm chromosomal localizations. BamHI-digested DNAs from hamster/human monochromosomal hybrid cell lines were electrophoresed and subjected to Southern blot analysis with a PTTG cDNA probe to identify the origin of each hybridizing band in human genomic DNA.
Figure 30B:
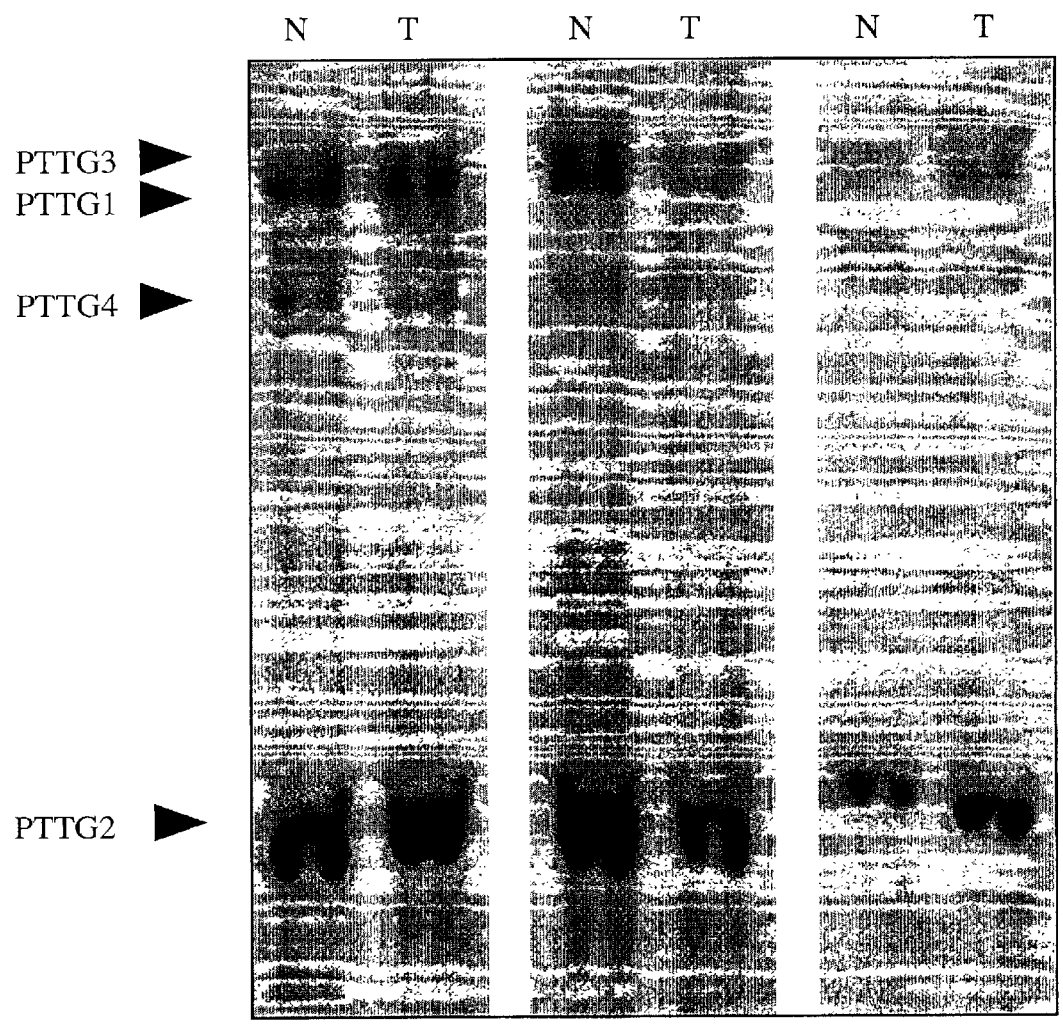
FIG. 30B shows Southern blot analysis of BamHI-digested human genomic DNA from three colon tumors and matched normal tissue, probed with PTTG1–3 PCR products. Each lane pair was derived from a different patient. T=tumor, N=normal tissue.

Whether PTTG gene family members are rearranged and/or amplified in colon neoplasms and cancer cell lines was investigated, using Southern blot analysis. Initially, it was determined that BamHI digests outside of the coding region and yields distinguishable bands for the four PTTG genes (FIG. 30A), with DNAs from hamster/human monochromosomal hybrids. Despite at least 5–10 fold increases in PTTG nRNA expression, no chromosomal amplifications or rearrangements were observed in three pairs of matched colon tumors compared to adjacent normal tissue samples (FIG. 30B).

Figure 30C:
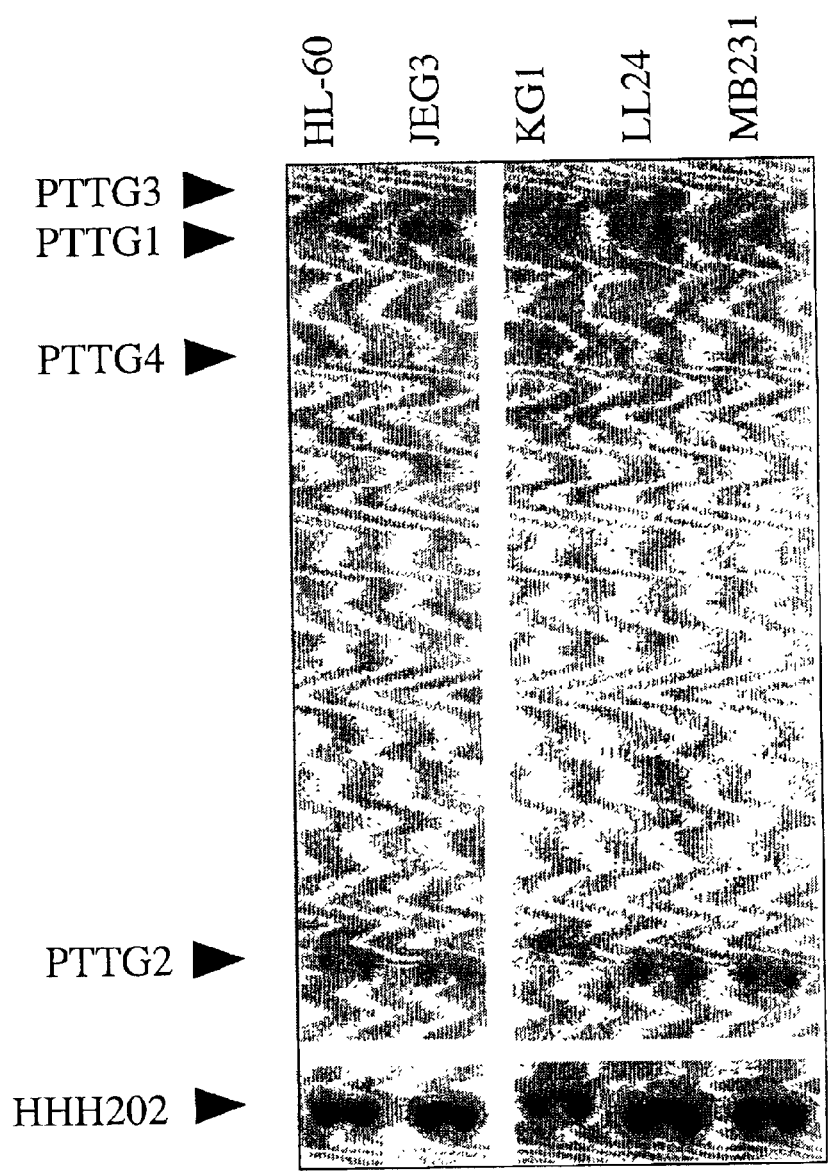
FIG. 30C shows Southern blot analysis of BamHI-digested genomic DNAs, which were electrophoresed and subjected to Southern blot analysis, with a probe mixture of PTTG1 cDNA and PTTG2 and PTTG3 genomic PCR products. Cell lines were: HL-60, JEG3, KG1, LL24 and MB231. Hybridization to a chromosome 17 probe, HHH202, is depicted below.
Figure 30D:
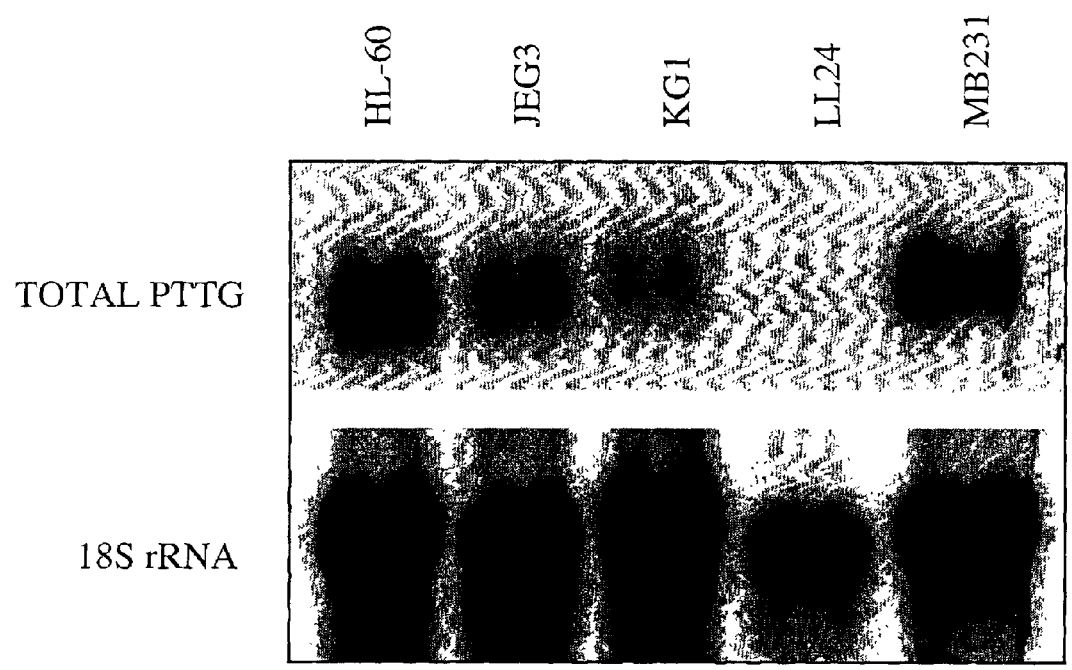
FIG. 30D shows Northern blot analysis of PTTG in cancer cell lines.

The myeloid cell line HL-60, which abundantly expresses PTTG in the Clontech cancer RNA panel, possesses an interstitial deletion of chromosomal region 5q11-q31 (31), in close proximity to the PTTG1 locus. (Zhang, X. et al. [1999a]). This deletion is observed in myelodysplastic syndrome (MDS) and acute myeloid leukemia (AML). (Mitelman, F. et al, *A breakpoint map of recurrent chromosomal rearrangements in human neoplasia*, Nature Genet., 15: special issue, [April 1997]; Horrigan, S. K. et al., *Delineation of a minimal interval and identification of 9 candidates for a tumor suppressor gene in malignant myeloid disorders on 5q31*, Blood 95:2372–2377 [2000]). We found that the dosage of the PTTG1-sized BamHI restriction fragment was decreased in two lymphoid cell lines, HL-60 and KG-1, compared to a primary epithelial cell line, LL24 (FIG. 30C). Shown below is the same blot hybridized with a single gene probe from chromosome 17. The corresponding Northern blot for these cell lines is shown in FIG. 30D.

Functional Analysis of the PTTG Family

Transcriptional Activation

Figure 31:
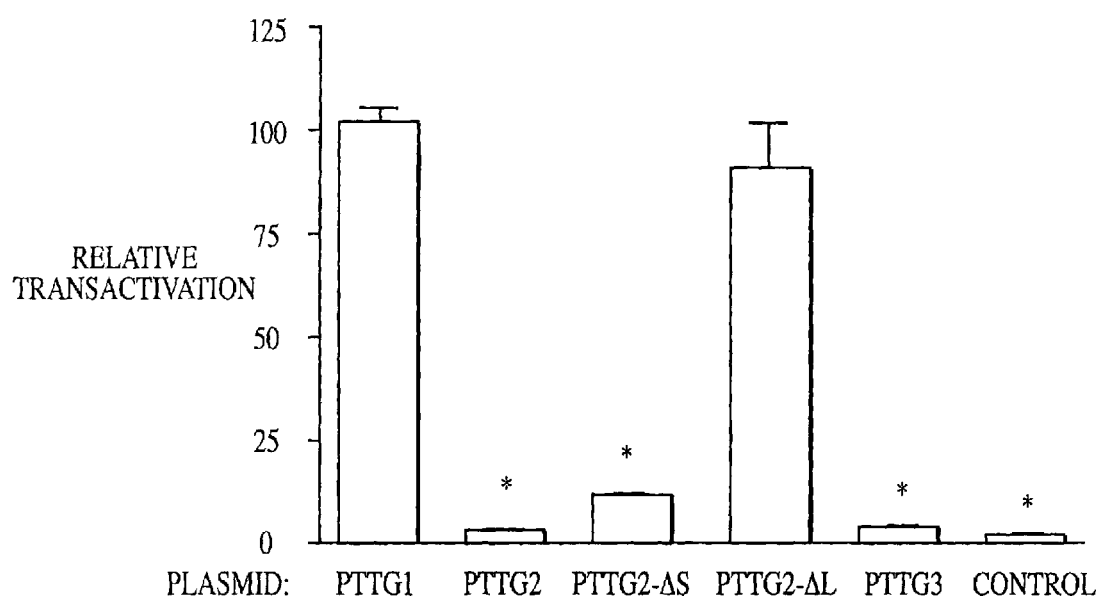
FIG. 31 shows transcriptional activation mediated by human PTTG1, PTTG2 and PTTG3. The GAL4-DBD plasmids: pBIND (no insert control), and pBIND-PTTG1, -PTTG2, -PTTG2ΔS, -PTTG2ΔL, or -PTTG3 were transfected into NIH3T3 cells for transactivation assays, as described herein. PTTG2ΔL-encodes a truncated PTTG2, lacking the divergent carboxy terminal tail after amino acid 179. PTTG2ΔS has a frameshift mutation after codon 156, that results in a truncated protein with 10 out-of-frame amino acids and no PXXP domains. Luciferase levels were normalized to β-galactosidase activities. Results show means +/− SEM from three separate experiments.

PTTG1 protein is a transcriptional activator in yeast and mammalian two-hybrid systems (Dominguez, A. et al., *PTTG, a human homologue of rat PTTG, is overexpressed in hematopoietic neoplasms. Evidence for a transcriptional activation function of PTTG*, Oncogene 17:2187–2193 [1998]; Wang, Z. and Melmed, S., *Pituitary tumor transforming gene (PTTG) transforming and transactivation activity*. J. Biol. Chem., 275: 7459–7461 [2000]). The transactivation functions of PTTG1, PTTG2 and PTTG3 were compared in a mammalian two-hybrid system. The chimeric GAL4 DNA binding domain (DBD) fused with PTTG1 caused a 54-fold increase in expression of the luciferase reporter plasmid compared to transfection with the DBD control plasmid. PTTG2 and PTTG3 inserts induced 1.8-fold and 5.5-fold increases of luciferase expression, respectively. Thus, while PTTG2 and PTTG3 are highly homologous to PTTG1, their coding sequences, if expressed, may have different biological functions in vivo. PTTG2, with its divergent carboxy terminal end, has the least transcriptional activity. Deletion of the segment encoding the entire carboxy terminal end (PTTG2ΔL) increases transactivation of PTTG2 26-fold, implying that this region is inhibitory to transcription, while a shorter truncation lacking the PXXP motifs (PTTG2ΔS) is not transcriptionally active. The results of three experiments are shown in FIG. 31.

PTTG2 Inhibits PTTG1 Transactivation Activity

Figure 32A:
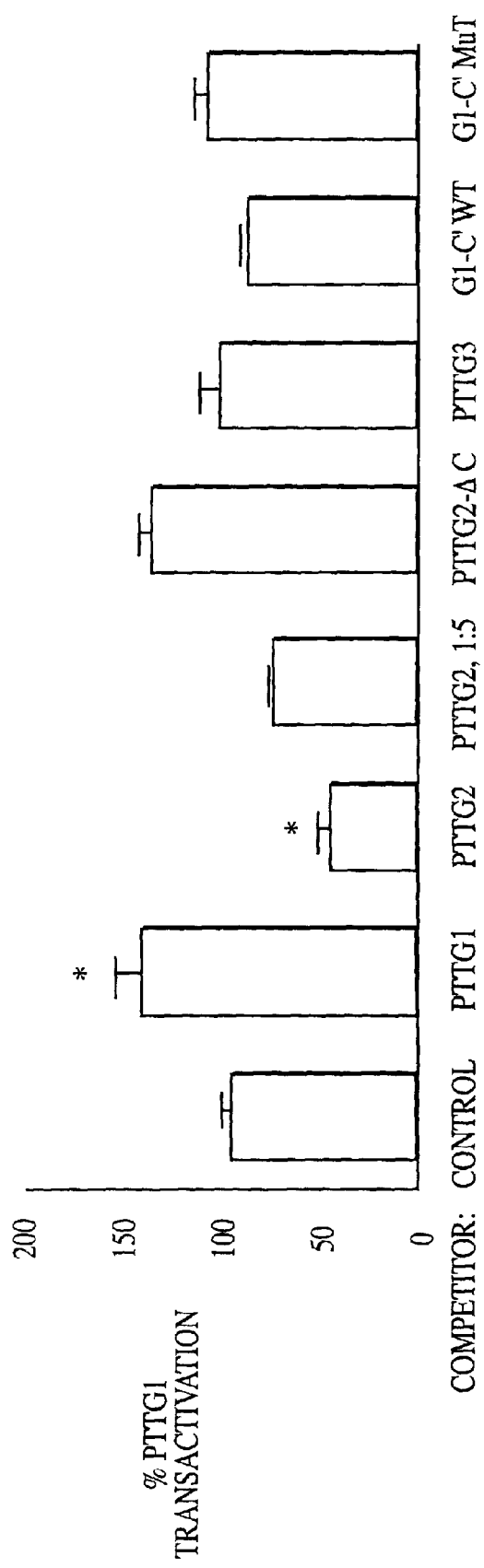
FIG. 32A demonstrates that PTTG1 transactivation function is inhibited by overexpression of PTTG2. A five-fold excess of plasmids overexpressing PTTG1–3, the PTTG1 carboxy terminus (wild type or mutated in SH3 domains), or truncated (PTTG2ΔC), the control pTargeT plasmid (no insert), was co-transfected into NIH3T3 cells with pBIND-G1, pG5/Luc and pCMV/Bgal, as described herein. Luciferase levels were normalized to beta-galactosidase activities, and are expressed as percent control relative to co-transfections with the pTargeT plasmid. Results are means +/− SEM from at least three experiments. C'=carboxy-terminal end.
Figure 32B:
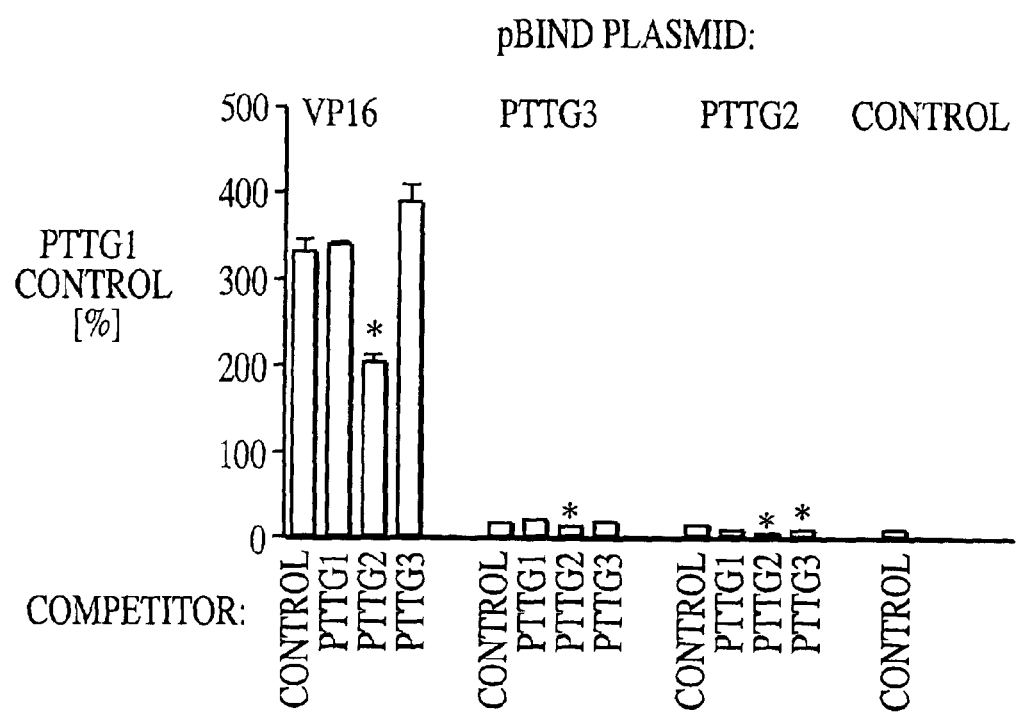
FIG. 32B shows transactivation functions of VP16, PTTG3, and PTTG2 are inhibited by overexpression of PTTG2. A five-fold excess of plasmids overexpressing PTTG1–3, or the control pTargeT plasmid (no insert), was co-transfected into NIH3T3 cells with the transactivation plasmids, and assayed as described. Results are means +/− SEM from triplicate wells. Relative to PTTG1, transactivation activities were: VP16 (331%), PTTG3 (15.4%), PTTG2 (9.87%), pBIND control plasmid (4.65%).

Whether PTTG2 and/or PTTG3 is a dominant negative inhibitor of PTTG1 was tested. A five-fold molar excess of PTTG-containing plasmid (without the DBD domain) was co-transfected for transactivation assays, with both plasmids transcriptionally controlled by CMV promoters. FIG. 32A shows that PTTG2 overexpression potently inhibits transactivation by PTTG1 (48% decrease, p<0.001). This inhibition is dose-dependent, but not gene-specific, as PTTG2 also inhibits transactivation for DBD plasmids containing VP16, PTTG3 and PTTG2 (FIG. 32B). In contrast, overexpression of PTTG1 does not reverse the reduced transactivation function of PTTG2.

To determine whether inhibition is mediated by the two SH3-binding domains in the carboxy terminus which are required for transactivation activity, wild type and mutant C-terminal fragments of PTTG1 were tested in the competition assay. The wild type C-terminus of PTTG1 only modestly reduced transactivation. This implies that the unique C-terminal of PTTG2 is responsible for transactivation inhibition, and a mutant PTTG2 plasmid, encoding a truncated PTTG2 protein (aa 1–179; confirmed by immunocytofluorescence [not shown]), no longer inhibited PTTG1 transactivation (FIG. 32B).

PTTG protein localizes to the nucleus (Chien, W. and Pei, L., *A novel binding factor facilitates nuclear translocation and transcriptional activation function of the pituitary tumor-transforming gene product*, J. Biol. Chem. 275:19422–19427 [2000]; Yu, R. et al., *Pituitary tumor transforming gene (PTTG) regulates placental JEG-3 cell division and survival: evidence from live cell imaging*, Mol. Endocrinol. 14:1137–1146 [2000]), where it participates in chromosome segregation (Zou, H. et al., *Identification of a vertebrate sister-chromatid separation inhibitor involved in transformation and tumorigenesis*, Science 285:418–422 [1999]). PTTG protein can also function as a transcriptional activator. (Dominguez, A. et al., *PTTG, a human homologue of rat PTTG, is overexpressed in hematopoietic neoplasms. Evidence for a transcriptional activation function of PTTG*, Oncogene, 17: 2187–2193 [1998]; Wang, Z. and Melmed, S., *Pituitary tumor transforming gene (PTTG) transforming and transactivation activity*, J. Biol. Chem., 275: 7459–7461, [2000]). To begin the functional characterization of the PTTG gene family, the open reading frames encoded by PTTG2 and PTTG3 were tested for transactivation function in mammalian cells. Despite 90% amino acid identity, PTTG3 protein has 10-fold lower transactivation activity than PTTG1, possibly due to amino acid differences (E175K, D124G) in residues shown hereinabove by structure/function analysis of murine PTTG1 to be critical for transactivation.

While the encoded PTTG2 protein is 90% identical to PTTG1 protein for 179 amino acids, its carboxy terminal end is non-homologous for an additional 12 amino acids. This divergent carboxy terminus likely accounts for the 30-fold decrease in transactivation activity, since PTTG2 protein retains the critical residues identified in murine PTTG, corresponding to P145, S165, E175, and amino acids 123–130 in human PTTG1. The carboxy terminal region is critical for murine PTTG function, since a variant PTTG transcript, encoding a different carboxy terminus, lost both transactivation function and transforming ability. Removal of the carboxy terminal segment of PTTG2 resulted in a 26-fold increase in transactivation function, implying that this region of PTTG2 has an inhibitory effect on transactivation.

We tested whether PTTG2 and/or PTTG3 proteins inhibit transactivation function by PTTG1 protein. Plasmids overexpressing these genes were co-transfected in transactivation assays, using a five-fold molar excess of the "free" PTTG genes compared to the DBD plasmid. Overexpression of PTTG2 reduced PTTG1 transactivation activity by nearly half, while PTTG3 had no significant effect in this system. Inhibition by PTTG2 was dose-dependent, and reproduced with different preparations of DNA in multiple experiments. We found that PTTG2 overexpression also inhibited transactivation activities of PTTG3 and PTTG2, and the unrelated gene VP16. Unexpectedly, overexpression of free PTTG1 enhanced transactivation activity of DBD-PTTG1. This enhancement was gene-specific, as the transactivation activities of VP16, PTTG2 and PTTG3 were unchanged. One interpretation is that PTTG1 forms oligomers during transactivation.

Since wildtype PTTG1-C terminus overexpression had only a slight inhibitory effect on PTTG1 transactivation, the significant decrease in transactivation caused by PTTG2 overexpression clearly requires more than the two SH3 binding domains. We tested whether the distinct carboxy terminal tail of PTTG2 protein is responsible for its dominant negative inhibitory effects, by creating a plasmid encoding a truncated PTTG2. Overexpression of mutant PTTG2 protein (confirmed by immunocytofluorescence; not shown) does not inhibit transactivation by PTTG1. Therefore, the inhibitory function of PTTG2 depends on its divergent carboxy terminal end.

The PTTG family differs from other oncogene families in two significant ways. First, only PTTG1 is overexpressed in most cancers, including tumors of the colon, breast, ovary and myeloid lineages. This is in contrast to ras and myc, in which multiple homologs are proto-oncogenes, although their activation might correspond to tissue-specific cancers.

A second distinction of the PTTG family is that its different homologs can have opposing intracellular functions. PTTG1 activates transcription, while PTTG2 inhibits transactivation in a dose-dependent, albeit non-specific manner. The inhibitory domain is mapped to the divergent PTTG2 carboxy terminal end. Although the present invention does not depend on a particular molecular mechanism, several models may account for this transcriptional inhibition, such as nonproductive binding to the transcription machinery, sequestering of transcription factors, or formation of inactive heterodimers. It is noteworthy that of all the tumors studied, pituitary tumors, which rarely metastasize, generally have proportionally higher levels of expression.

We claim:

1. A method of inhibiting neoplastic cellular proliferation or transformation of both, in vitro is comprising:

providing a mammalian cell, in vitro, that endogenously overexpresses PTTG1; and delivering to a mammalian cell a composition comprising an expression vector comprising a promoter and a polynucleotide, said polynucleotide comprising a first DNA segment encoding a mammalian PTTG2 peptide consisting of amino acid residues 1–191 of SEQ ID NO:64, said polynucleotide being operatively linked to the promoter in a transcriptional unit, said expression vector being complexed with a cellular uptake-enhancing agent, in an amount and under conditions sufficient to enter the cell, such that the PTTG2 peptide is expressed in the cell, whereby neoplastic cellular proliferation or transformation or both, of the cell is inhibited.

2. The method of claim 1, wherein the polynucleotide further comprises a second DNA segment encoding an uptake-enhancing and/or importation-competent, or both, peptide segment.

3. The method of claim 2, wherein the cellular uptake-enhancing or importation-competent, or both, peptide segment is a human immunodeficiency virus TAT-derived peptide segment, a signal peptide from Kaposi fibroblast growth factor, ferritin peptide, or lactalbumin-α peptide.

4. The method of claim 1, wherein the cell is of human origin.

5. The method of claim 1, wherein the cell exhibits neoplastic, hyperplastic, cytologically dysplastic, or premalignant cellular growth or proliferation.

6. The method of claim 1, wherein the cell is a malignant cell.

7. The method of claim 1, wherein the the cell is pituitary cell, a colon cell, leukocyte, a breast cell, or an ovarian cell.

8. The method of claim 1, wherein said uptake-enhancing agent comprises a lipid agent.

9. The method of claim 1, wherein the composition in vitro that endogenously overexpresses PTTG1, and in which neoplastic cellular proliferation or transformation, or both, is inhibited, comprising:

a composition comprising an expression vector comprising a promoter and a polynucleotide, said polynucleotide comprising a first DNA segment encoding a mammalian PTTG2 peptide consisting of amino acid residues 1–191 of SEQ ID NO:64, said polynucleotide being operatively linked to the promoter in a transcriptional unit, said expression vector being complexed with a cellular uptake-enhancing agent, in an amount and under conditions sufficient to enter the cell, such that the PTTG2 peptide is expressed in the cell.

10. The mammalian cell of claim 9, wherein the polynucleotide further comprises a second DNA segment encoding an uptake-enhancing or importation-competent, or both, peptide segment.

11. The mammalian cell of claim 10, wherein the cellular uptake-enhancing or importation-competent, or both, peptide segment is a human immunodeficiency virus TAT-derived peptide segment, a signal peptide from Kaposi fibroblast growth factor, ferritin peptide, or lactalbumin-α peptide.

12. The mammalian cell of claim 9, wherein the cell is of human origin.

13. The method of claim 9, wherein the cell exhibits neoplastic, hyperplastic, cytologically dysplastic, or premalignant cellular growth or proliferation.

14. The mammalian cell of claim 9, wherein the cell is a malignant cell.

15. The mammalian cell of claim 9, wherein the cell is a pituitary cell, a colon cell, a leukocyte cell, a breast cell, or a ovarian cell.

16. The mammalian cell of claim 9, wherein said uptake-enhancing agent comprises a lipid agent.

* * * * *

SEQUENCE LISTING

<160> NUMBER OF SEQ ID NOS: 68

<210> SEQ ID NO 1
<211> LENGTH: 974
<212> TYPE: DNA
<213> ORGANISM: Rattus rattus

<400> SEQUENCE: 1

```
aattcggcac gagccaacct tgagcatctg atcctcttgg cttctccttc ctatcgctga      60
gctggtaggc tggagacagt tgtttgggtg ccaacatcaa caaacgattt ctgtagttta     120
gcgtttatga ccctggcgtg aagatttaag gtctggatta agcctgttga cttctccagc     180
tacttctaaa tttttgtgca taggtgctct ggtctctgtt gctgcttagt tcttccagcc     240
ttcctcaatg ccagttttat aatatgcagg tctctcccct cagtaatcca ggatggctac     300
tctgatcttt gttgataagg ataacgaaga gccaggcagc cgtttggcat ctaaggatgg     360
attgaagctg ggctctggtg tcaaagcctt agatgggaaa ttgcaggttt caacgccacg     420
agtcggcaaa gtgttcggtg ccccaggctt gcctaaagcc agcaggaagg ctctgggaac     480
tgtcaacaga gttactgaaa agccagtgaa gagtagtaaa cccctgcaat cgaaacagcc     540
gactctgagt gtgaaaaaga tcaccgagaa gtctactaag acacaaggct ctgctcctgc     600
tcctgatgat gcctacccag aaatagaaaa gttcttcccc ttcgatcctc tagattttga     660
gagttttgac ctgcctgaag agcaccagat ctcacttctc cccttgaatg gagtgcctct     720
catgatcctg aatgaagaga gggggcttga gaagctgctg cacctggacc cccttcccc      780
tctgcagaag cccttcctac cgtgggaatc tgatccgttg ccgtctcctc ccagcgccct     840
ctccgctctg gatgttgaat tgccgcctgt tgttacgat gcagatattt aaacgtctta     900
ctcctttata gtttatgtaa gttgtattaa taaagcattt gtgtgtaaaa aaaaaaaaaa     960
aaactcgaga gtac                                                       974
```

<210> SEQ ID NO 2
<211> LENGTH: 199
<212> TYPE: PRT
<213> ORGANISM: Rattus rattus

<400> SEQUENCE: 2

```
Met Ala Thr Leu Ile Phe Val Asp Lys Asp Asn Glu Glu Pro Gly Ser
 1               5                  10                  15

Arg Leu Ala Ser Lys Asp Gly Leu Lys Leu Gly Ser Gly Val Lys Ala
            20                  25                  30

Leu Asp Gly Lys Leu Gln Val Ser Thr Pro Arg Val Gly Lys Val Phe
        35                  40                  45

Gly Ala Pro Gly Leu Pro Lys Ala Ser Arg Lys Ala Leu Gly Thr Val
    50                  55                  60

Asn Arg Val Thr Glu Lys Pro Val Lys Ser Ser Lys Pro Leu Gln Ser
65                  70                  75                  80
```

```
Lys Gln Pro Thr Leu Ser Val Lys Lys Ile Thr Glu Lys Ser Thr Lys
                85                  90                  95
Thr Gln Gly Ser Ala Pro Ala Pro Asp Asp Ala Tyr Pro Glu Ile Glu
            100                 105                 110
Lys Phe Phe Pro Phe Asp Pro Leu Asp Phe Glu Ser Phe Asp Leu Pro
        115                 120                 125
Glu Glu His Gln Ile Ser Leu Leu Pro Leu Asn Gly Val Pro Leu Met
    130                 135                 140
Ile Leu Asn Glu Glu Arg Gly Leu Glu Lys Leu Leu His Leu Asp Pro
145                 150                 155                 160
Pro Ser Pro Leu Gln Lys Pro Phe Leu Pro Trp Glu Ser Asp Pro Leu
                165                 170                 175
Pro Ser Pro Pro Ser Ala Leu Ser Ala Leu Asp Val Glu Leu Pro Pro
            180                 185                 190
Val Cys Tyr Asp Ala Asp Ile
        195

<210> SEQ ID NO 3
<211> LENGTH: 779
<212> TYPE: DNA
<213> ORGANISM: Homo sapiens

<400> SEQUENCE: 3
atggccgcga gttgtggttt aaaccaggag tgccgcgcgt ccgttcaccg cggcctcaga       60
tgaatgcggc tgttaagacc tgcaataatc agaatggct actctgatct atgttgataa      120
ggaaaatgga gaaccaggca cccgtgtggt tgctaaggat gggctgaagc tggggtctgg     180
accttcaatc aaagccttag atgggagatc tcaagtttca acaccacgtt ttggcaaaac     240
gttcgatgcc ccaccagcct tacctaaagc tactagaaag gctttgggaa ctgtcaacag     300
agctacagaa aagtctgtaa agaccaaggg acccctcaaa caaaaacagc caagcttttc     360
tgccaaaaag atgactgaga agactgttaa agcaaaaagc tctgttcctg cctcagatga     420
tgcctatcca gaaatagaaa aattctttcc cttcaatcct ctagactttg agagttttga     480
cctgcctgaa gagcaccaga ttgcgcacct ccccttgagt ggagtgcctc tcatgatcct     540
tgacgaggag agagagcttg aaaagctgtt tcagctgggc ccccctcac ctgtgaagat      600 gccctctcca ccatgggaat ccaatctgtt gcagtctcct tcaagcattc tgtcgaccct     660
ggatgttgaa ttgccacctg tttgctgtga catagatatt taaatttctt agtgcttcag     720
agtttgtgtg tatttgtatt aataaagcat tctttaacag ataaaaaaaa aaaaaaaa      779

<210> SEQ ID NO 4
<211> LENGTH: 202
<212> TYPE: PRT
<213> ORGANISM: Homo sapiens

<400> SEQUENCE: 4

Met Ala Thr Leu Ile Tyr Val Asp Lys Glu Asn Gly Glu Pro Gly Thr
1               5                   10                  15
Arg Val Val Ala Lys Asp Gly Leu Lys Leu Gly Ser Gly Pro Ser Ile
                20                  25                  30
Lys Ala Leu Asp Gly Arg Ser Gln Val Ser Thr Pro Arg Phe Gly Lys
            35                  40                  45
Thr Phe Asp Ala Pro Pro Ala Leu Pro Lys Ala Thr Arg Lys Ala Leu
        50                  55                  60
Gly Thr Val Asn Arg Ala Thr Glu Lys Ser Val Lys Thr Lys Gly Pro
```

-continued

```
                65                  70                  75                  80
Leu Lys Gln Lys Gln Pro Ser Phe Ser Ala Lys Lys Met Thr Glu Lys
                    85                  90                  95

Thr Val Lys Ala Lys Ser Ser Val Pro Ala Ser Asp Asp Ala Tyr Pro
                100                 105                 110

Glu Ile Glu Lys Phe Phe Pro Phe Asn Pro Leu Asp Phe Glu Ser Phe
            115                 120                 125

Asp Leu Pro Glu Glu His Gln Ile Ala His Leu Pro Leu Ser Gly Val
    130                 135                 140

Pro Leu Met Ile Leu Asp Glu Glu Arg Glu Leu Glu Lys Leu Phe Gln
145                 150                 155                 160

Leu Gly Pro Pro Ser Pro Val Lys Met Pro Ser Pro Pro Trp Glu Ser
                165                 170                 175

Asn Leu Gln Ser Pro Ser Ser Ile Leu Ser Thr Leu Asp Val Glu
            180                 185                 190

Leu Pro Pro Val Cys Cys Asp Ile Asp Ile
        195                 200

<210> SEQ ID NO 5
<211> LENGTH: 31
<212> TYPE: DNA
<213> ORGANISM: Artificial Sequence
<220> FEATURE:
<223> OTHER INFORMATION: Synthetic oligonucleotide.

<400> SEQUENCE: 5
gatgctctcc gcactctggg aatccaatct g                                    31

<210> SEQ ID NO 6
<211> LENGTH: 32
<212> TYPE: DNA
<213> ORGANISM: Artificial Sequence
<220> FEATURE:
<223> OTHER INFORMATION: Synthetic oligonucleotide.

<400> SEQUENCE: 6
ttcacaagtt gagggcgcc cagctgaaac ag                                    32

<210> SEQ ID NO 7
<211> LENGTH: 32
<212> TYPE: DNA
<213> ORGANISM: Artificial Sequence
<220> FEATURE:
<223> OTHER INFORMATION: Synthetic oligonucleotide specific to pCI-neo
      plasmid. vector.

<400> SEQUENCE: 7
ggctagagta cttaatacga ctcactatag gc                                   32

<210> SEQ ID NO 8
<211> LENGTH: 31
<212> TYPE: DNA
<213> ORGANISM: Homo sapiens

<400> SEQUENCE: 8
ctatgtcaca gcaaacaggt ggcaattcaa c                                    31

<210> SEQ ID NO 9
<211> LENGTH: 56
<212> TYPE: PRT
<213> ORGANISM: Homo sapiens
```

```
<400> SEQUENCE: 9

Met Ile Leu Asp Glu Glu Arg Glu Leu Glu Lys Leu Phe Gln Leu Gly
 1               5                  10                  15

Pro Pro Ser Pro Val Lys Met Pro Ser Pro Pro Trp Glu Ser Asn Leu
            20                  25                  30

Leu Gln Ser Pro Ser Ser Ile Leu Ser Thr Leu Asp Val Glu Leu Pro
        35                  40                  45

Pro Val Cys Cys Asp Ile Asp Ile
    50                  55

<210> SEQ ID NO 10
<211> LENGTH: 168
<212> TYPE: DNA
<213> ORGANISM: Homo sapiens

<400> SEQUENCE: 10
atgatccttg acgaggagag agagcttgaa aagctgtttc agctgggccc cccttcacct      60
gtgaagatgc cctctccacc atgggaatcc aatctgttgc agtctccttc aagcattctg     120
tcgaccctgg atgttgaatt gccacctgtt tgctgtgaca tagatatt                  168

<210> SEQ ID NO 11
<211> LENGTH: 16
<212> TYPE: DNA
<213> ORGANISM: Artificial Sequence
<220> FEATURE:
<223> OTHER INFORMATION: Anchored primer sequence.

<400> SEQUENCE: 11
aagctttttt tttttg                                                      16

<210> SEQ ID NO 12
<211> LENGTH: 13
<212> TYPE: DNA
<213> ORGANISM: Artificial Sequence
<220> FEATURE:
<223> OTHER INFORMATION: Arbitrary primer sequence.

<400> SEQUENCE: 12
aagcttgctg ctc                                                         13

<210> SEQ ID NO 13
<211> LENGTH: 16
<212> TYPE: DNA
<213> ORGANISM: Artificial Sequence
<220> FEATURE:
<223> OTHER INFORMATION: n = a, g, or c; Anchored primer sequence.

<400> SEQUENCE: 13
aagctttttt tttttn                                                      16

<210> SEQ ID NO 14
<211> LENGTH: 194
<212> TYPE: PRT
<213> ORGANISM: Mus musculus

<400> SEQUENCE: 14

Met Ala Thr Leu Ile Phe Val Asp Lys Asp Asn Glu Glu Pro Gly Arg
 1               5                  10                  15

Arg Leu Ala Ser Lys Asp Gly Leu Lys Leu Gly Thr Gly Val Lys Ala
            20                  25                  30

Leu Asp Gly Lys Leu Gln Val Ser Thr Pro Arg Val Gly Lys Val Phe
```

```
                35                  40                  45
Asn Ala Pro Ala Val Pro Lys Ala Ser Arg Lys Ala Leu Gly Thr Val
     50                  55                  60
Asn Arg Val Ala Glu Lys Pro Met Lys Thr Gly Lys Pro Leu Gln Pro
 65                  70                  75                  80
Lys Gln Pro Thr Leu Thr Gly Lys Lys Ile Thr Glu Lys Ser Thr Lys
                 85                  90                  95
Thr Gln Ser Ser Val Pro Ala Pro Asp Asp Ala Tyr Pro Glu Ile Glu
            100                 105                 110
Lys Phe Phe Pro Phe Asn Pro Leu Asp Phe Asp Leu Pro Glu Glu His
        115                 120                 125
Gln Ile Ser Leu Leu Pro Leu Asn Gly Val Pro Leu Ile Thr Leu Asn
    130                 135                 140
Glu Glu Arg Gly Leu Glu Lys Leu Leu His Leu Gly Pro Pro Ser Pro
145                 150                 155                 160
Leu Lys Thr Pro Phe Leu Ser Trp Glu Ser Asp Pro Lys Pro Pro Ser
                165                 170                 175
Ala Leu Ser Thr Leu Asp Val Glu Leu Pro Pro Val Cys Tyr Asp Ala
            180                 185                 190
Asp Ile

<210> SEQ ID NO 15
<211> LENGTH: 945
<212> TYPE: DNA
<213> ORGANISM: Mus musculus

<400> SEQUENCE: 15
tcttgaactt gttatgtagc aggaggccaa atttgagcat cctcttggct tctctttata      60
gcagagattg taggctggag acagttttga tgggtgccaa cataaactga tttctgtaag     120
agttgagtgt tttatgaccc tggcgtgcag atttaggatc tggattaagc ctgttgactt     180
ctccagctac ttataaattt ttgtgcatag gtgccctggg taaagcttgg tctctgttac     240
tgcgtagttt ttccagccgt ctcaatgcca atattcaggc tctctccctt agagtaatcc     300
agaatggcta ctcttatctt tgttgataag gataatgaag aacccggccg ccgtttggca     360
tctaaggatg ggttgaagct gggcactggt gtcaaggcct tagatgggaa attgcaggtt     420
tcaacgcctc gagtcggcaa agtgttcaat gctccagccg tgcctaaagc cagcagaaag     480
gctttgggga cagtcaacag agttgccgaa aagcctatga agactggcaa accctccaa      540
ccaaaacagc cgaccttgac tgggaaaaag atcaccgaga gtctactaa  acacaaagc      600
tctgttcctg ctcctgatga tgcctaccca gaaatagaaa agttcttccc tttcaatcct     660
ctagattttg acctgcctga ggagcaccag atctcacttc tccccttgaa tggcgtgcct     720
ctcatcaccc tgaatgaaga gagggctg gagaagctgc tgcatctggg ccccctagc       780
cctctgaaga caccctttct atcatgggaa tctgatccgc tgtactctcc tcccagtgcc     840
ctctccactc tggatgttga attgccgcct gtttgttacg atgcagatat ttaaacttct     900
tacttctttg tagtttctgt atgtatgttg tattaataaa gcatt                    945

<210> SEQ ID NO 16
<211> LENGTH: 56
<212> TYPE: PRT
<213> ORGANISM: Rattus rattus

<400> SEQUENCE: 16
```

```
Met Ile Leu Asn Glu Glu Arg Gly Leu Glu Lys Leu Leu His Leu Asp
 1               5                  10                  15

Pro Pro Ser Pro Leu Gln Lys Pro Phe Leu Pro Trp Glu Ser Asp Pro
                20                  25                  30

Leu Pro Ser Pro Ser Ala Leu Ser Ala Leu Asp Val Glu Leu Pro
            35                  40                  45

Pro Val Cys Tyr Asp Ala Asp Ile
    50                  55
```

<210> SEQ ID NO 17
<211> LENGTH: 56
<212> TYPE: PRT
<213> ORGANISM: Mus musculus

<400> SEQUENCE: 17

```
Ile Thr Leu Asn Glu Glu Arg Gly Leu Glu Lys Leu Leu His Leu Gly
 1               5                  10                  15

Pro Pro Ser Pro Leu Lys Thr Pro Phe Leu Ser Trp Glu Ser Asp Pro
                20                  25                  30

Leu Tyr Ser Pro Pro Ser Ala Leu Ser Thr Leu Asp Val Glu Leu Pro
            35                  40                  45

Pro Val Cys Tyr Asp Ala Asp Ile
    50                  55
```

<210> SEQ ID NO 18
<211> LENGTH: 168
<212> TYPE: DNA
<213> ORGANISM: Rattus rattus

<400> SEQUENCE: 18

```
atgatcctga atgaagagag ggggcttgag aagctgctgc acctggaccc cccttcccct    60
ctgcagaagc ccttcctacc gtgggaatct gatccgttgc cgtctcctcc cagcgccctc   120
tccgctctgg atgttgaatt gccgcctgtt tgttacgatg cagatatt                168
```

<210> SEQ ID NO 19
<211> LENGTH: 168
<212> TYPE: DNA
<213> ORGANISM: Mus musculus

<400> SEQUENCE: 19

```
atcaccctga atgaagagag agggctggag aagctgctgc atctgggccc ccctagccct    60
ctgaagacac cctttctatc atgggaatct gatccgctgt actctcctcc cagtgccctc   120
tccactctgg atgttgaatt gccgcctgtt tgttacgatg cagatatt                168
```

<210> SEQ ID NO 20
<211> LENGTH: 21
<212> TYPE: DNA
<213> ORGANISM: Artificial Sequence
<220> FEATURE:
<223> OTHER INFORMATION: Forward primer 34a

<400> SEQUENCE: 20

```
ggagaaccag gcacccgtgt g                                              21
```

<210> SEQ ID NO 21
<211> LENGTH: 19
<212> TYPE: DNA
<213> ORGANISM: Artificial Sequence
<220> FEATURE:
<223> OTHER INFORMATION: Forward primer C106F

```
<400> SEQUENCE: 21
aaggatgggc tgaagctgg                                                   19

<210> SEQ ID NO 22
<211> LENGTH: 23
<212> TYPE: DNA
<213> ORGANISM: Artificial Sequence
<220> FEATURE:
<223> OTHER INFORMATION: Forward primer C124F

<400> SEQUENCE: 22
gggtctggac cttcaatcaa agc                                              23

<210> SEQ ID NO 23
<211> LENGTH: 19
<212> TYPE: DNA
<213> ORGANISM: Artificial Sequence
<220> FEATURE:
<223> OTHER INFORMATION: Forward primer 2-14F

<400> SEQUENCE: 23
aatgtggctg ttgagagcg                                                   19

<210> SEQ ID NO 24
<211> LENGTH: 18
<212> TYPE: DNA
<213> ORGANISM: Artificial Sequence
<220> FEATURE:
<223> OTHER INFORMATION: Forward primer 3-88F

<400> SEQUENCE: 24
ggcatccttg tggctaca                                                    18

<210> SEQ ID NO 25
<211> LENGTH: 19
<212> TYPE: DNA
<213> ORGANISM: Artificial Sequence
<220> FEATURE:
<223> OTHER INFORMATION: Forward primer 4-7F

<400> SEQUENCE: 25
agagagaggc atggatcag                                                   19

<210> SEQ ID NO 26
<211> LENGTH: 20
<212> TYPE: DNA
<213> ORGANISM: Artificial Sequence
<220> FEATURE:
<223> OTHER INFORMATION: Forward primer -5F

<400> SEQUENCE: 26
ccagaatggc tactctgatc                                                  20

<210> SEQ ID NO 27
<211> LENGTH: 20
<212> TYPE: DNA
<213> ORGANISM: Artificial Sequence
<220> FEATURE:
<223> OTHER INFORMATION: Forward primer 462F

<400> SEQUENCE: 27
ccccttgagt ggagtgcctc                                                  20

<210> SEQ ID NO 28
```

```
<211> LENGTH: 18
<212> TYPE: DNA
<213> ORGANISM: Artificial Sequence
<220> FEATURE:
<223> OTHER INFORMATION: Forward primer C550F

<400> SEQUENCE: 28
atgccctctc caccatgg                                                 18

<210> SEQ ID NO 29
<211> LENGTH: 21
<212> TYPE: DNA
<213> ORGANISM: Artificial Sequence
<220> FEATURE:
<223> OTHER INFORMATION: Forward primer G1-253F

<400> SEQUENCE: 29
tttaatatta cacgatccta g                                             21

<210> SEQ ID NO 30
<211> LENGTH: 24
<212> TYPE: DNA
<213> ORGANISM: Artificial Sequence
<220> FEATURE:
<223> OTHER INFORMATION: Forward primer G1-245F

<400> SEQUENCE: 30
tacacgatcc tagttttttc ttcc                                          24

<210> SEQ ID NO 31
<211> LENGTH: 20
<212> TYPE: DNA
<213> ORGANISM: Artificial Sequence
<220> FEATURE:
<223> OTHER INFORMATION: Forward primer G1-213F

<400> SEQUENCE: 31
gtgccacaaa gtttgcaaga                                               20

<210> SEQ ID NO 32
<211> LENGTH: 19
<212> TYPE: DNA
<213> ORGANISM: Artificial Sequence
<220> FEATURE:
<223> OTHER INFORMATION: Forward primer G1-145F

<400> SEQUENCE: 32
tctacttggt gaccacgcc                                                19

<210> SEQ ID NO 33
<211> LENGTH: 18
<212> TYPE: DNA
<213> ORGANISM: Artificial Sequence
<220> FEATURE:
<223> OTHER INFORMATION: Forward primer G1-115F

<400> SEQUENCE: 33
ctcctgggcg gaagagcc                                                 18

<210> SEQ ID NO 34
<211> LENGTH: 20
<212> TYPE: DNA
<213> ORGANISM: Artificial Sequence
<220> FEATURE:
<223> OTHER INFORMATION: Forward primer G1-83F

<400> SEQUENCE: 34
```
ttgtggttta aaccaggagt 20

<210> SEQ ID NO 35
<211> LENGTH: 19
<212> TYPE: DNA
<213> ORGANISM: Artificial Sequence
<220> FEATURE:
<223> OTHER INFORMATION: Forward primer G2-62F

<400> SEQUENCE: 35
aaatataaag tgggaccac 19

<210> SEQ ID NO 36
<211> LENGTH: 18
<212> TYPE: DNA
<213> ORGANISM: Artificial Sequence
<220> FEATURE:
<223> OTHER INFORMATION: Forward primer G2-53F

<400> SEQUENCE: 36
gtgggaccac ggtcttag 18

<210> SEQ ID NO 37
<211> LENGTH: 20
<212> TYPE: DNA
<213> ORGANISM: Artificial Sequence
<220> FEATURE:
<223> OTHER INFORMATION: Forward primer G2-49F

<400> SEQUENCE: 37
gaccacggtc ttagatgaat 20

<210> SEQ ID NO 38
<211> LENGTH: 20
<212> TYPE: DNA
<213> ORGANISM: Artificial Sequence
<220> FEATURE:
<223> OTHER INFORMATION: Forward primer G3-33F

<400> SEQUENCE: 38
cttaaatctg gtcgagagcg 20

<210> SEQ ID NO 39
<211> LENGTH: 33
<212> TYPE: DNA
<213> ORGANISM: Artificial Sequence
<220> FEATURE:
<223> OTHER INFORMATION: Forward primer PTTG1S

<400> SEQUENCE: 39
ggatccgtaa gcttatggct actctgatct atg 33

<210> SEQ ID NO 40
<211> LENGTH: 27
<212> TYPE: DNA
<213> ORGANISM: Artificial Sequence
<220> FEATURE:
<223> OTHER INFORMATION: Forward primer PTTG2S

<400> SEQUENCE: 40
ggatccgtgc tactctgatc tacgttg 27

<210> SEQ ID NO 41
<211> LENGTH: 27
<212> TYPE: DNA

```
<213> ORGANISM: Artificial Sequence
<220> FEATURE:
<223> OTHER INFORMATION: Forward primer PTTG3S

<400> SEQUENCE: 41
ggatccgtgc tactctgatc tatgttg                                              27

<210> SEQ ID NO 42
<211> LENGTH: 30
<212> TYPE: DNA
<213> ORGANISM: Artificial Sequence
<220> FEATURE:
<223> OTHER INFORMATION: Forward primer PTTG1-F

<400> SEQUENCE: 42
cggggatccg tgctactctg atctatgttg                                           30

<210> SEQ ID NO 43
<211> LENGTH: 24
<212> TYPE: DNA
<213> ORGANISM: Artificial Sequence
<220> FEATURE:
<223> OTHER INFORMATION: Forward primer pBIND-3'F

<400> SEQUENCE: 43
tgaggtacct gaagatctaa ggcc                                                 24

<210> SEQ ID NO 44
<211> LENGTH: 21
<212> TYPE: DNA
<213> ORGANISM: Artificial Sequence
<220> FEATURE:
<223> OTHER INFORMATION: Forward primer pTargeT-3'F

<400> SEQUENCE: 44
taaatctttc ccgggggtac c                                                    21

<210> SEQ ID NO 45
<211> LENGTH: 18
<212> TYPE: DNA
<213> ORGANISM: Artificial Sequence
<220> FEATURE:
<223> OTHER INFORMATION: Reverse primer 601b

<400> SEQUENCE: 45
cggggatccg tgctactc                                                        18

<210> SEQ ID NO 46
<211> LENGTH: 23
<212> TYPE: DNA
<213> ORGANISM: Artificial Sequence
<220> FEATURE:
<223> OTHER INFORMATION: Reverse primer 601b

<400> SEQUENCE: 46
ctatgtcaca gcaaacaggt ggc                                                  23

<210> SEQ ID NO 47
<211> LENGTH: 23
<212> TYPE: DNA
<213> ORGANISM: Artificial Sequence
<220> FEATURE:
<223> OTHER INFORMATION: Reverse primer C233R

<400> SEQUENCE: 47
gcctttctgg tagctttagg taa                                                  23
```

<210> SEQ ID NO 48
<211> LENGTH: 20
<212> TYPE: DNA
<213> ORGANISM: Artificial Sequence
<220> FEATURE:
<223> OTHER INFORMATION: Reverse primer C481R

<400> SEQUENCE: 48
gaggcactcc actcaagggg                                           20

<210> SEQ ID NO 49
<211> LENGTH: 20
<212> TYPE: DNA
<213> ORGANISM: Artificial Sequence
<220> FEATURE:
<223> OTHER INFORMATION: Reverse primer C525R

<400> SEQUENCE: 49
ctgaaacagc ttttcaagct                                           20

<210> SEQ ID NO 50
<211> LENGTH: 21
<212> TYPE: DNA
<213> ORGANISM: Artificial Sequence
<220> FEATURE:
<223> OTHER INFORMATION: Reverse primer 2-306R

<400> SEQUENCE: 50
gcttggctgt ttttgttttc t                                         21

<210> SEQ ID NO 51
<211> LENGTH: 19
<212> TYPE: DNA
<213> ORGANISM: Artificial Sequence
<220> FEATURE:
<223> OTHER INFORMATION: Reverse primer 3-434R

<400> SEQUENCE: 51
aggtcaaaac tctcgaagc                                            19

<210> SEQ ID NO 52
<211> LENGTH: 20
<212> TYPE: DNA
<213> ORGANISM: Artificial Sequence
<220> FEATURE:
<223> OTHER INFORMATION: Reverse primer 4-282R

<400> SEQUENCE: 52
tccgttgatc tttactcacg                                           20

<210> SEQ ID NO 53
<211> LENGTH: 26
<212> TYPE: DNA
<213> ORGANISM: Artificial Sequence
<220> FEATURE:
<223> OTHER INFORMATION: Reverse primer 653R

<400> SEQUENCE: 53
taaatatcta tgtcacagca aacagg                                    26

<210> SEQ ID NO 54
<211> LENGTH: 21
<212> TYPE: DNA
<213> ORGANISM: Artificial Sequence
<220> FEATURE:

<223> OTHER INFORMATION: Reverse primer G3-679R

<400> SEQUENCE: 54
cacaaactct aaagcactaa g     21

<210> SEQ ID NO 55
<211> LENGTH: 26
<212> TYPE: DNA
<213> ORGANISM: Artificial Sequence
<220> FEATURE:
<223> OTHER INFORMATION: Reverse primer PTTG1AS

<400> SEQUENCE: 55
ggtaccttaa atatctatgt cacagc     26

<210> SEQ ID NO 56
<211> LENGTH: 27
<212> TYPE: DNA
<213> ORGANISM: Artificial Sequence
<220> FEATURE:
<223> OTHER INFORMATION: Reverse primer PTTG2AS

<400> SEQUENCE: 56
ggtaccacat ccagggtcga cagaatg     27

<210> SEQ ID NO 57
<211> LENGTH: 27
<212> TYPE: DNA
<213> ORGANISM: Artificial Sequence
<220> FEATURE:
<223> OTHER INFORMATION: Reverse primer PTTG3AS

<400> SEQUENCE: 57
ggtaccaata tctatgtcac agcaaac     27

<210> SEQ ID NO 58
<211> LENGTH: 19
<212> TYPE: DNA
<213> ORGANISM: Artificial Sequence
<220> FEATURE:
<223> OTHER INFORMATION: Reverse primer pBIND-5'R

<400> SEQUENCE: 58
cacggatccc cgggaattc     19

<210> SEQ ID NO 59
<211> LENGTH: 23
<212> TYPE: DNA
<213> ORGANISM: Artificial Sequence
<220> FEATURE:
<223> OTHER INFORMATION: Reverse primer G2-Ctail.R

<400> SEQUENCE: 59
gcttgaagga gatctcaaaa cag     23

<210> SEQ ID NO 60
<211> LENGTH: 24
<212> TYPE: DNA
<213> ORGANISM: Artificial Sequence
<220> FEATURE:
<223> OTHER INFORMATION: Reverse primer PTTG2-R

<400> SEQUENCE: 60
tcaggtacct caacatccag ggtc     24

```
<210> SEQ ID NO 61
<211> LENGTH: 24
<212> TYPE: DNA
<213> ORGANISM: Artificial Sequence
<220> FEATURE:
<223> OTHER INFORMATION: Reverse primer PTTG3-R

<400> SEQUENCE: 61
tcaggtacct caaatatcta tgtc                                              24

<210> SEQ ID NO 62
<211> LENGTH: 1231
<212> TYPE: DNA
<213> ORGANISM: Homo sapiens

<400> SEQUENCE: 62
ataaattaga aaatgcaata acggcagaaa tctttcttta ttggttgctc tgccctttac        60
ctaagtggtt tttgaccatt taacaatgtg taagagttgg gttttacctc cattttatgg       120
atgtggaaat agggcttgga tgttagctaa cttgcccaaa tcttacagct aacagaaagt       180
ggtactcccg agattcctac ccaggtttgt ctgacctcag gcctgtgctc tttatatgag       240
ttcatgctaa ctctcagatg atgtgctagg cacaaaaatt agatattaca ccaatttcca       300
ctatagttaa cattctatct aaatataaag tgggaccacg gtcttagatg aatgtggctg       360
ttgagagcgg caataatcca gaatggctac tctgatctac gttgataagg aaattggaga       420
accaggcacc cgtgtggctg ccaaggatgt gctgaagctg gagtctagac cttcaatcaa       480
agcattagat gggatatctc aagttttaac accacgtttt ggcaaaacat acgatgctcc       540
atcagcctta cctaaagcta ccagaaaggc tttgggcact gtcaacgagc tacagaaaa       600 gtcagtaaag accaatggac ccagaaaaca aaaacagcca gcttttctg ccaaaaagat       660 gaccgagaag actgttaaaa caaaaagttc tgttcctgcc tcagatgacg cctatccaga       720
aatagaaaaa ttctttccct tcaatcttct agactttgag agttttgacc tgcctgaaga       780
gcgccagatt gcacacctcc ccttgagtgg agtgcctctc atgatccttg atgaggaggg       840
agagcttgaa aagctgtttc agctgggccc cccttcacct gtgaaaatgc cctctccacc       900
atgggaatgc aatctgtttg cagtctcctt caagcattct gtcgaccctg atgttgaat       960 tgccagctgt ttgctatgac atagatattt aaatttctta gtgctttgga gtttgtgtgt      1020
acttgtatta ataaagcatt atttgtttaa caacataata aatacataaa tataaagtgg      1080
gtcatattcc tctttatgtg catctgtctc agctgtccct tgtttctata tttcttccat      1140
actacagccc gtactctttg gggatatgtc aacatgattt acttctgtag agaaacagga      1200
gacaggaaat agcaaaggat aaaggagaaa a                                     1231

<210> SEQ ID NO 63
<211> LENGTH: 576
<212> TYPE: DNA
<213> ORGANISM: Homo sapiens

<400> SEQUENCE: 63
atggctactc tgatctacgt tgataaggaa attggagaac caggcacccg tgtggctgcc       60
aaggatgtgc tgaagctgga gtctagacct tcaatcaaag cattagatgg gatatctcaa      120
gttttaacac cacgttttgg caaaacatac gatgctccat cagccttacc taaagctacc      180
agaaaggctt tgggcactgt caacagagct acagaaagt cagtaaagac caatggaccc      240
agaaaacaaa aacagccaag cttttctgcc aaaaagatga ccgagaagac tgttaaaaca      300
```

| | |
|---|---|
| aaaagttctg ttcctgcctc agatgacgcc tatccagaaa tagaaaaatt ctttcccttc | 360 |
| aatcttctag actttgagag ttttgacctg cctgaagagc gccagattgc acacctcccc | 420 |
| ttgagtggag tgcctctcat gatccttgat gaggagggag agcttgaaaa gctgtttcag | 480 |
| ctgggccccc cttcacctgt gaaaatgccc tctccaccat gggaatgcaa tctgtttgca | 540 |
| gtctccttca agcattctgt cgaccctgga tgttga | 576 |

```
<210> SEQ ID NO 64
<211> LENGTH: 191
<212> TYPE: PRT
<213> ORGANISM: Homo sapiens

<400> SEQUENCE: 64

Met Ala Thr Leu Ile Tyr Val Asp Lys Glu Ile Gly Glu Pro Gly Thr
 1               5                  10                  15
Arg Val Ala Ala Lys Asp Val Leu Lys Leu Glu Ser Arg Pro Ser Ile
            20                  25                  30
Lys Ala Leu Asp Gly Ile Ser Gln Val Leu Thr Pro Arg Phe Gly Lys
        35                  40                  45
Thr Tyr Asp Ala Pro Ser Ala Leu Pro Lys Ala Thr Arg Lys Ala Leu
    50                  55                  60
Gly Thr Val Asn Arg Ala Thr Glu Lys Ser Val Lys Thr Asn Gly Pro
65                  70                  75                  80
Arg Lys Gln Lys Gln Pro Ser Phe Ser Ala Lys Lys Met Thr Glu Lys
                85                  90                  95
Thr Val Lys Thr Lys Ser Ser Val Pro Ala Ser Asp Asp Ala Tyr Pro
            100                 105                 110
Glu Ile Glu Lys Phe Phe Pro Phe Asn Leu Leu Asp Phe Glu Ser Phe
        115                 120                 125
Asp Leu Pro Glu Glu Arg Gln Ile Ala His Leu Pro Leu Ser Gly Val
    130                 135                 140
Pro Leu Met Ile Leu Asp Glu Glu Gly Glu Leu Glu Lys Leu Phe Gln
145                 150                 155                 160
Leu Gly Pro Pro Ser Pro Val Lys Met Pro Ser Pro Pro Trp Glu Cys
                165                 170                 175
Asn Leu Phe Ala Val Ser Phe Lys His Ser Val Asp Pro Gly Cys
            180                 185                 190

<210> SEQ ID NO 65
<211> LENGTH: 1305
<212> TYPE: DNA
<213> ORGANISM: Homo sapiens

<400> SEQUENCE: 65
```

| | |
|---|---|
| ccagatttct ggaaataaag atctactaag aaatgaagag cacttgaaat agtaacaaca | 60 |
| gaactaaaca tattttgatt ttttaataat ttaaatctct aaaagttaac aaacaagaat | 120 |
| agtaataact tatggtgggt ttatatctaa tgtatcagta aaatatatga caacagtatt | 180 |
| ataaaagcta gcattagaga catggaagta taccattgta agacatatcc tataagtgta | 240 |
| agtattctat aagtgatgtg gtataattca atgaagata gactgtaata aattaaagat | 300 |
| atatacttaa atctggtcga gagcggcaat aatccagaat ggctactctg atctatgttg | 360 |
| ataaggaaaa cgaagaacca ggcatccttg tggctacaaa ggatgggctg aagctggggt | 420 |
| ctggaccttc aatcaaagcc ttagatggga gatctcaagt tcaatatca tgttttggca | 480 |
| aaacattcga tgctcccaca tccttaccta agctaccag aaaggctttg ggaactgtca | 540 |

```
acagagctac agaaaagtca gtaaagacca atggacccct caaacaaaaa cagccaagct        600
tttctgccaa aaagatgact gagaagactg ttaaagcaaa aaactctgtt cctgcctcag        660
atgatggcta tccagaaata gaaaaattat tcccttcaa tcctctaggc ttcgagagtt         720
ttgacctgcc tgaagagcac cagattgcac atctcccctt gagtgaagtg cctctcatga       780
tacttgatga gggagagag cttgaaaagc tgtttcagct gggcccccct tcacctttga         840
agatgccctc tccaccatgg aaatccaatc tgttgcagtc tcctttaagc attctgttga       900
ccctggatgt tgaattgcca cctgtttgct ctgacataga tatttaaatt tcttagtgct       960
ttagagtttg tgtatatttc tattaataaa gcattatttg tttaacagaa aaaagatat       1020 atacttaaat cctaaaataa aataaccatt aaaaggaaaa acaggagtta taactaataa      1080
gggaacaaag gacataaaat gggataataa tgcttaatcc aaaataaagc agaaaatgaa      1140
gaaaaatgaa atgaagaaca gataaataga aaacaaatag caatatgaaa gacaaacttg      1200
accgggtgtg gtggctgatg cctgtaatcc cagcactgtg ggaggctgag gcaggcggat      1260
cacctgaggt cgggagtctg agaccagcct caccaacatg gagaa                      1305

<210> SEQ ID NO 66
<211> LENGTH: 609
<212> TYPE: DNA
<213> ORGANISM: Homo sapiens

<400> SEQUENCE: 66
atggctactc tgatctatgt tgataaggaa aacgaagaac caggcatcct tgtggctaca         60
aaggatgggc tgaagctggg gtctggacct tcaatcaaag ccttagatgg gagatctcaa       120
gtttcaatat catgttttgg caaaacattc gatgctccca tccttacc taaagctacc         180 agaaaggctt tgggaactgt caacagagct acagaaaagt cagtaaagac caatggaccc       240
ctcaaacaaa aacagccaag cttttctgcc aaaaagatga ctgagaagac tgttaaagca       300
aaaaactctg ttcctgcctc agatgatggc tatccagaaa tagaaaaatt atttcccttc      360
aatcctctag gcttcgagag ttttgacctg cctgaagagc accagattgc acatctcccc      420
ttgagtgaag tgcctctcat gatacttgat gaggagagag agcttgaaaa gctgtttcag      480
ctgggccccc cttcaccttt gaagatgccc tctccaccat ggaaatccaa tctgttgcag      540
tctcctttaa gcattctgtt gaccctggat gttgaattgc cacctgtttg ctctgacata      600
gatatttaa                                                               609

<210> SEQ ID NO 67
<211> LENGTH: 202
<212> TYPE: PRT
<213> ORGANISM: Homo sapiens

<400> SEQUENCE: 67

Met Ala Thr Leu Ile Tyr Val Asp Lys Glu Asn Glu Glu Pro Gly Ile
  1               5                  10                  15

Leu Val Ala Thr Lys Asp Gly Leu Lys Leu Gly Ser Gly Pro Ser Ile
                 20                  25                  30

Lys Ala Leu Asp Gly Arg Ser Gln Val Ser Ile Ser Cys Phe Gly Lys
             35                  40                  45

Thr Phe Asp Ala Pro Thr Ser Leu Pro Lys Ala Thr Arg Lys Ala Leu
         50                  55                  60

Gly Thr Val Asn Arg Ala Thr Glu Lys Ser Val Lys Thr Asn Gly Pro
 65                  70                  75                  80
```

```
Leu Lys Gln Lys Gln Pro Ser Phe Ser Ala Lys Lys Met Thr Glu Lys
                85                  90                  95

Thr Val Lys Ala Lys Asn Ser Val Pro Ala Ser Asp Asp Gly Tyr Pro
            100                 105                 110

Glu Ile Glu Lys Leu Phe Pro Phe Asn Pro Leu Gly Phe Glu Ser Phe
        115                 120                 125

Asp Leu Pro Glu Glu His Gln Ile Ala His Leu Pro Leu Ser Glu Val
130                 135                 140

Pro Leu Met Ile Leu Asp Glu Glu Arg Glu Leu Glu Lys Leu Phe Gln
145                 150                 155                 160

Leu Gly Pro Pro Ser Pro Leu Lys Met Pro Ser Pro Pro Trp Lys Ser
                165                 170                 175

Asn Leu Leu Gln Ser Pro Leu Ser Ile Leu Leu Thr Leu Asp Val Glu
            180                 185                 190

Leu Pro Pro Val Cys Ser Asp Ile Asp Ile
        195                 200

<210> SEQ ID NO 68
<211> LENGTH: 1142
<212> TYPE: DNA
<213> ORGANISM: Homo sapiens

<400> SEQUENCE: 68
aaaaacatta aagctgaagg ggcaacttca aatacctcct ttattaagat aaacaaaagt      60
agttttccaa actacttaga aatgtaatgt ctcaaattct actcttttca tcattcaggg    120
gtatgtcatg ggttgaattg tggccccaaa aaagatatag tgaagtcctc agaatgtgac    180
catgtttgga aataggcttg ttagagatgt gattagtcag gataaggtcc tactggagca    240
gagtgggccc ctaacccaat atgactggtg tccatacaag aagacacaga cacacaggaa    300
gaacaccata tggagatgga acactgcaga gacgcatcca caagccaagg aatgcctggg    360
gctactagaa gcaaagagag aggcatggat cagattctcc cccagaagga acccacccctg   420
ctctgatcta tgttgataag gagaatggag aaccaggtat ccatgcagct cctaaagata    480
ggctgaagct gggatctgga ccttcaatca agccttaga ggggagatct caagtttcag     540
caccacgtgt tggcaaaatg tccaatgctt taccagcctt acctaaagct accagaaagt    600
cttttggaac tgtcaacagg gctacagaaa cgtgagtaaa gatcaacgga ctcctcaaac    660
taaaacaccc aaatttctct gccgaaaaga tgaccaggaa gactgttaaa gcaaaaagct    720
ctgttccttc ctcagataat gcctacccag aaatagaaaa attatttcac ttcaatcttc    780
tagattttga gagttttaac caacctgaag tgcaccagat gcaggcctc ccccttgagtg    840
gagtgcctct tatgatcctt gataaggaga gagagcttga aaagctgttt cagctgggcc    900
cgccttcgcc tgtgaagatg ccctctccgc catgggaacc caatctgttg cagtgtcctt    960
caacccttct gttgaccctg gatgttgaat gccacctgt ttactatgac ataaatattt     1020
aaatttcttc atgctttagg gtttgtgtgt atttgtayta ataaagcatt ctttaacagg    1080
aaaaaaaaaa ctcaccctgc taacaccta atttggaact tccacctcca gactgtgaga    1140
ca                                                                  1142
```